US011603570B2

(12) United States Patent
Armstrong

(10) Patent No.: US 11,603,570 B2
(45) **Date of Patent: *Mar. 14, 2023**

(54) METHODS FOR THE DETECTION AND TREATMENT OF LEUKEMIAS THAT ARE RESPONSIVE TO DOT1L INHIBITION

(71) Applicant: MEMORIAL SLOAN KETTERING CANCER CENTER, New York, NY (US)

(72) Inventor: Scott A. Armstrong, New York, NY (US)

(73) Assignee: MEMORIAL SLOAN KETTERING CANCER CENTER, New York, NY (US)

( * ) Notice: Subject to any disclaimer, the term of this patent is extended or adjusted under 35 U.S.C. 154(b) by 398 days.

This patent is subject to a terminal disclaimer.

(21) Appl. No.: 16/565,422

(22) Filed: Sep. 9, 2019

(65) Prior Publication Data

US 2020/0239963 A1 Jul. 30, 2020

Related U.S. Application Data

(63) Continuation of application No. 14/909,713, filed as application No. PCT/US2014/049641 on Aug. 4, 2014, now Pat. No. 10,407,732.

(60) Provisional application No. 61/885,947, filed on Oct. 2, 2013, provisional application No. 61/861,923, filed on Aug. 2, 2013.

(51) Int. Cl.

| | |
|---|---|
| ***C07H 21/04*** | (2006.01) |
| ***C12Q 1/6886*** | (2018.01) |
| ***A61K 31/5377*** | (2006.01) |
| ***A61K 31/7064*** | (2006.01) |

(52) U.S. Cl.

CPC ........ *C12Q 1/6886* (2013.01); *A61K 31/5377* (2013.01); *A61K 31/7064* (2013.01); *C12Q 2600/106* (2013.01); *C12Q 2600/156* (2013.01); *C12Q 2600/158* (2013.01)

(58) Field of Classification Search

None

See application file for complete search history.

(56) References Cited

FOREIGN PATENT DOCUMENTS

| | | | |
|---|---|---|---|
| WO | WO 2007/087015 | A1 | 8/2007 |
| WO | WO-2012/075381 | A1 | 6/2012 |

OTHER PUBLICATIONS

Hollink et al., "NUP98/NSD1 characterizes a novel poor prognostic group in acute myeloid leukemia with a distinct HOX gene expression pattern," Blood, vol. 118, No. 13, pp. 3645-3656 (Aug. 2, 2011).

Mullighan et al., "Pediatric acute myeloid leukemia with NPM1 mutations is characterized by a gene expression profile with dysregulated HOXgene expression distinct from MLL-rearranged leukemias," Leukemia, (21), pp. 2000-2009 (Jun. 28, 2007).

Chen et al., "Abrogation of MLL-AF10 and CALM-AF10-mediated transformation through genetic inactivation or pharmacological inhibition of the H3K79 methyltransferase Dot1L," Leukemia, vol. 27, No. 4, pp. 813-822 (Nov. 9, 2012).

Krivtsov et al., "MLL translocations, histone modifications and leukemia stem-cell development," Nature Reviews—Cancer, vol. 7, No. 11, pp. 823-833 (Nov. 1, 2007).

Daigle et al., "Potent inhibition of DOT1L as treatment of MLL-fusion leukemia," Blood, vol. 122, No. 6, pp. 1017-1025 (Jun. 25, 2013).

Chen et al., "Abrogation of MLL-AF10 and CALM-AF10-mediated transformation through genetic inactivation or pharmacological inhibition of the H3K79 methyltransferase Dot1L," Blood; $54^{th}$ Annual Meeting and Exposition of the American Society of Hematology (Atlanta, GA), vol. 120, No. 21, pp. 1-2 (Nov. 1, 2012).

Brunangelo et al., "Acute myeloid leukemia with mutated nucleophosmin (NPM1): is it a distinct entity?," Blood, pp. 1109-1120, DOI: 10.1182/blood-2010-, retrieved from http://www.bloodjournal.org/content/bloodjournal/117/4/1109.full.pdf (Jan. 1, 2011).

International Search Report and Written Opinion, PCT/US2014/049641, Memorial Sloan Kettering Cancer Center (dated Aug. 4, 2014).

Daigle et al., "Selective killing of mixed lineage leukemia cells by a potent small-molecule DOT1L inhibitor", Cancer, 20(1):53-65 (Jul. 2011).

Bernt et al., "A role for DOT1L in MLL-rearranged leukemias", Epigenomics, 3(6):667-70 (Dec. 2011).

Deshpande et al., "Leukemic transformation by the MLL-AF6 fusion oncogene requires the H3K79 methyltransferase DOT1L", Blood, 121 (13):2533-41 (Mar. 2013).

(Continued)

*Primary Examiner* — Celine X Qian

(74) *Attorney, Agent, or Firm* — Foley & Lardner LLP

(57) ABSTRACT

Disclosed are: (i) methods for identifying leukemia patients who (or leukemia cells that) do not exhibit an MLL-translocation, rearrangement or MLL-partial tandem duplication but who are nonetheless susceptible to treatment with DOT1L inhibitors; and (ii) methods for treating leukemia patients who (or inhibiting proliferation or inducing apoptosis of leukemia cells that) do not exhibit an MLL-translocation, rearrangement or MLL-partial tandem duplication with DOT1L inhibitors. The patients identified as susceptible and the patients (or cells) treated exhibit elevated expression of a IIOX cluster gene or of a HOX cluster-associated gene. Elevated expression of such genes can be measured, e.g., by quantitating the relevant RNA and comparing it to that of a healthy individual (or cell) or to a predetermined standard or it can be inferred by determining whether the patient or cell possesses a mutation that is associated with elevated HOX cluster gene or HOX cluster associated gene expression and thereby inferring that the relevant expression with be elevated.

9 Claims, 11 Drawing Sheets

Specification includes a Sequence Listing.

(56) References Cited

OTHER PUBLICATIONS

Hollink et al., "NUP98/NSD1 characterizes a novel poor prognostic group in acute myeloid leukemia with a distinct HOX gene expression pattern", Blood, 118(13):3645-56 (Sep. 2011).
Deshpande; et al., "Chromatin modifications as therapeutic targets in MLL-rearranged leukemia", Trends Immunol., 33(11):563-70 (Nov. 2012).

FIG. 6A
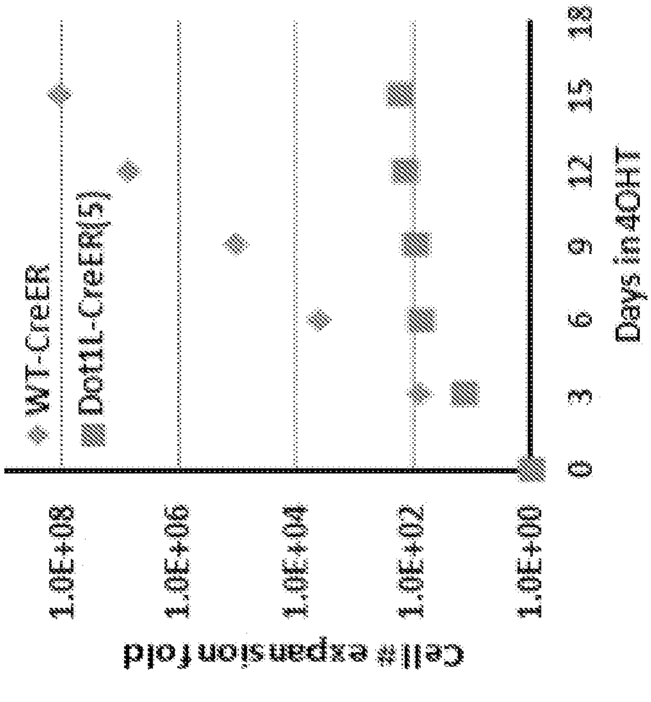
FIG. 6B
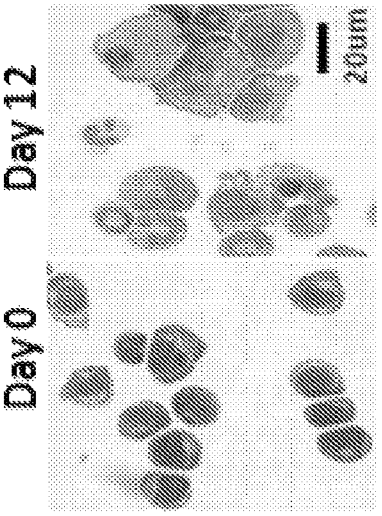
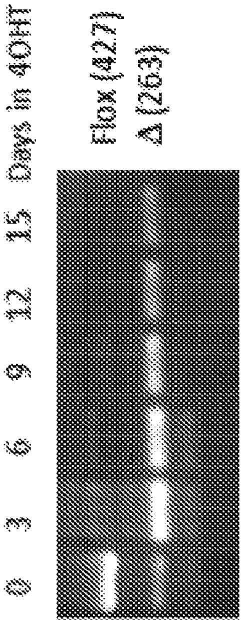
FIG. 6C

FIG. 9
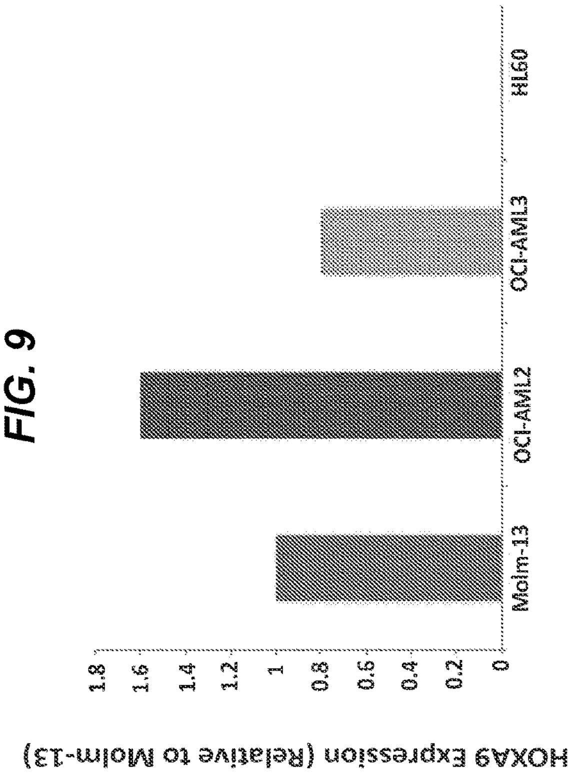
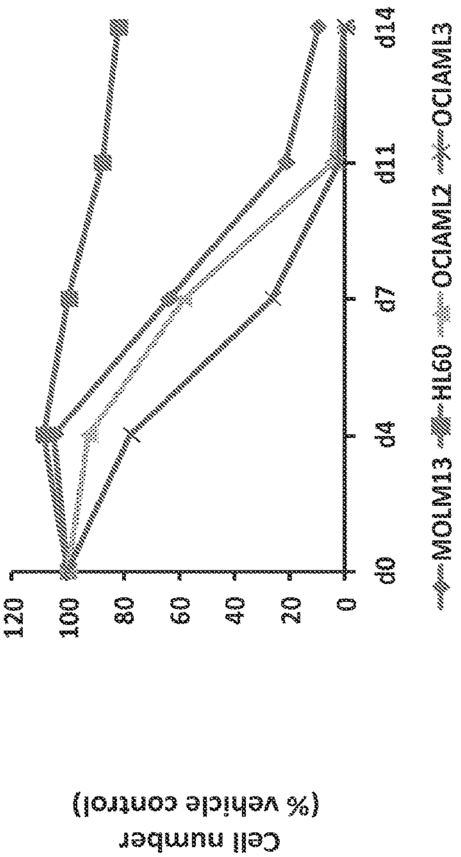
FIG. 10

FIG. 13A
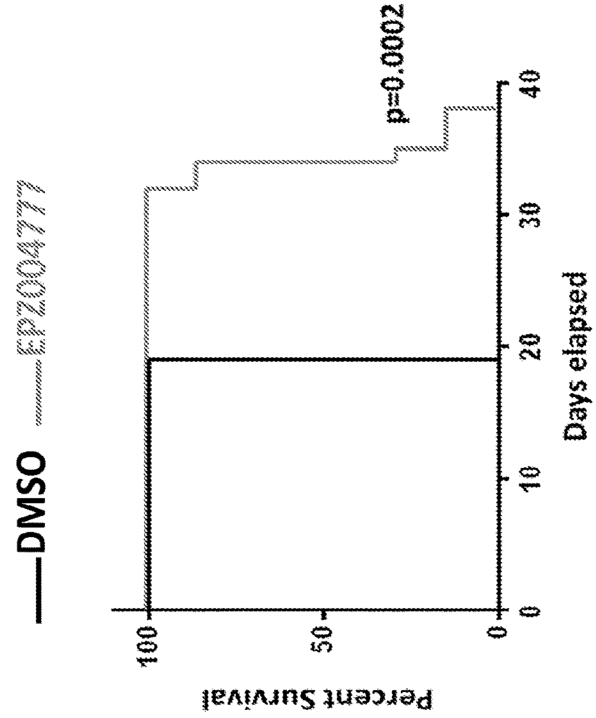
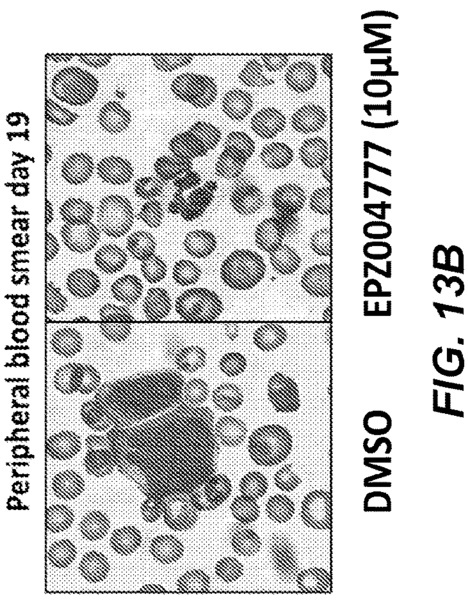
FIG. 13B
FIG. 13C
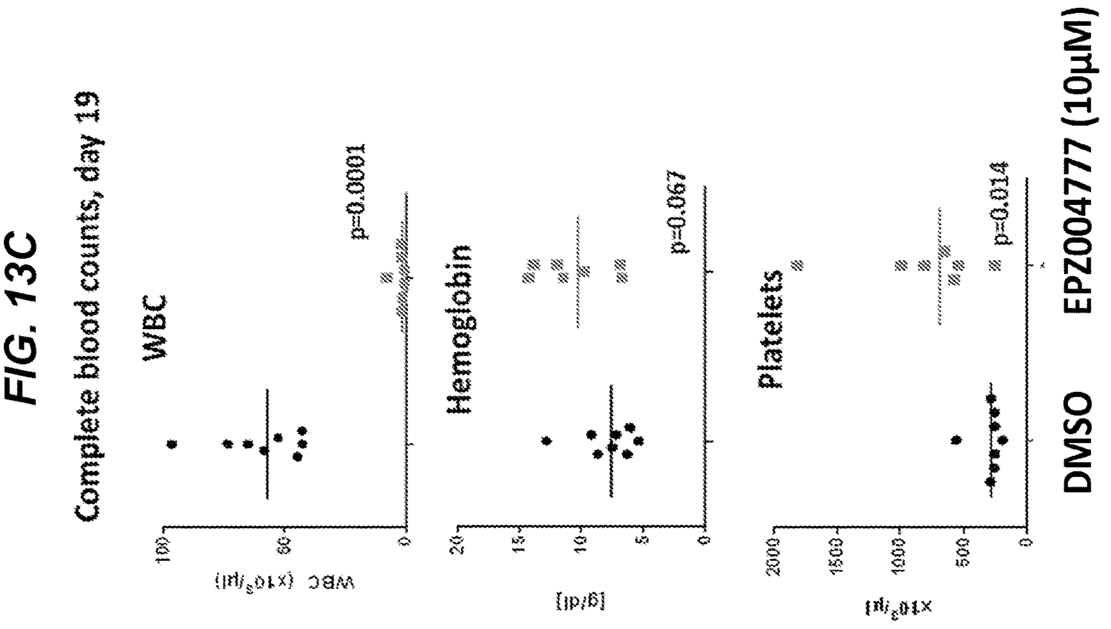

$Npm1^{cA/+}Rosa^{SB/+}$ AML $Npm1^{cA/+}Flt3^{ITD/+}$ AML

SEQUENCE LISTING

<160> NUMBER OF SEQ ID NOS: 48

<210> SEQ ID NO 1
<211> LENGTH: 2561
<212> TYPE: DNA
<213> ORGANISM: Homo sapiens

<400> SEQUENCE: 1

```
attcatatca tttttcttct ccggccccat ggaggaagtg agaaagttgg cacagtcacg     60
ccgggcttcg caggaccagg tcactcagtg acagatggac aatgcaagaa tgaactcctt    120
cctggaatac cccatactta gcagtggcga ctcggggacc tgctcagccc gagcctaccc    180
ctcggaccat aggattacaa ctttccagtc gtgcgcggtc agcgccaaca gttgcggcgg    240
cgacgaccgc ttcctagtgg gcagggggt gcagatcggt tcgccccacc accaccacca     300
ccaccaccat caccaccccc agccggctac ctaccagact tccgggaacc tgggggtgtc    360
ctactcccac tcaagttgtg gtccaagcta tggctcacag aacttcagtg cgccttacag    420
cccctacgcg ttaaatcagg aagcagacgt aagtggtggg tacccccagt gcgctcccgc    480
tgtttactct ggaaatctct catctcccat ggtccagcat caccaccacc accagggtta    540
tgctgggggc gcggtgggct cgcctcaata cattcaccac tcatatggac aggagcacca    600
gagcctggcc ctggctacgt ataataactc cttgtcccct ctccacgcca gccaccaaga    660
agcctgtcgc tcccccgcat cggagacatc ttctccagcg cagacttttg actggatgaa    720
agtcaaaaga aaccctccca aaacagggaa agttggagag tacggctacc tgggtcaacc    780
caacgcggtg cgcaccaact tcactaccaa gcagctcacg gaactggaga aggagttcca    840
cttcaacaag tacctgacgc gcgcccgcag ggtggagatc gctgcatccc tgcagctcaa    900
cgagacccaa gtgaagatct ggttccagaa ccgccgaatg aagcaaaaga aacgtgagaa    960
ggagggtctc ttgcccatct ctccggccac cccgccagga aacgacgaga aggccgagga   1020
atcctcagag aagtccagct cttcgccctg cgttccttcc ccggggtctt ctacctcaga   1080
cactctgact acctcccact gaggcggctc cagccccaga caacagccca ggcatctcct   1140
tgggctggga cttcttaccc aaagcacatg cttagcttat ctttctttcc atttacagtc   1200
tctttcttcc tttctaatcc tatctgggga gctcctggcc aggataatat atttgcagat   1260
```

```
aattctggac cagagacttg gtgcggggtt aacaccttca tccagattgg gtgccagcat   1320

acattttctg gtgggcctta acatccctcc tgcttttagg agaattcaca gaacctactg   1380

ttcctttcag atgacctttt ggaaaatagt tccctttgcc aacagaaaca tgccagaagg   1440

aatcttctca tcttttatct aactatatgt acagctctcc cctcccttgt ccttgaaagt   1500

aggatatagc gaaaggcgag tccaggagct caggaagaag agatgcacta tatgtttaca   1560

caattaattc atcccttaat ttaagtcatt ttcatgtgtg tgagtttgct ggttgtaaat   1620

actttgtcct aagagattta tctttataca gattttctag aaatgtttag gttactaaaa   1680

cagggtgggc aaactctcta aactggtaca attttatagg tgaaagaaaa aattccctca   1740

tttaaaccca atcagatgcc tcagagggta gccttgattt gttcttacag ttaagaagcc   1800

ctgcagagca caaacttcag aaacccggct tcctgtgcta agtctttccc aatctctacc   1860

cctttcttct cgggccaccc tctgtttaaa atttgtgctg ggttattcag aacctaaaag   1920

tattattcaa accaatttct tccttccaca gttatcttag ctggatataa tgtattttca   1980

gctcaattgt taatgtgatg gatggcacaa tgaatgtata ttttgtgtta ttcgtgaata   2040

gtcttttgca tgtcgcacaa tgtttgatgt ccccaaagta ccacactgag ttctatcagt   2100

tatcctttgt gagcctatga tattccccat ttcctgtaca atcatgaaca gctctgagat   2160

cctggagtga tatgatccag agcagagttt acgggtctta ggatgtctgt aataaataaa   2220

tatactcaag tttcaggtat gcttaagcat ccgtgtattt ggctgggcta caatttgtta   2280

attcctatga agttggcaca tttcatgagg ggaaagggag aagggtggta aatattttca   2340

aagagatggg cctttttcttg aataaaagtt aataacagct cctttattat aatcaaagct   2400

cataatggaa aaaaagactg atgaagaaat ttatgaagca gatttatttt tgaaacaaac   2460

atggatactt cctgggtcaa gtgctaacct tttcacctcc aactggatgt tgacgtatat   2520

ataaacagaa ctcccttcaa aagccaaaaa aaaaaaaaaa a                        2561
```

<210> SEQ ID NO 2
<211> LENGTH: 1791
<212> TYPE: DNA
<213> ORGANISM: Homo sapiens

<400> SEQUENCE: 2

```
tcttttgatt aaagcccaaa ttgtcattgg gcagaagcaa tcatgtgaca gccaattcgg     60

tccaatttca accttgtctc catgaattca atagtttaat agtagcgcgg tccccatacg    120

gctgtaatca gtgaattaga aaaaaaacac cctagcagcg atattctatg atagattttt    180

tttcctctgc gctcgccttt ttcctaggcc ttgccccccc aaagcccctc caaaagaggg    240

aactttttct ctgagggggc tccaaggaga aggccatgaa ttacgaattt gagcgagaga    300

ttggttttat caatagccag ccgtcgctcg ctgagtgcct gacatctttt ccccctgtcg    360

ctgatacatt tcaaagttca tcaatcaaga cctcgacgct ttcacactcg acactgattc    420

ctcctccttt tgagcagacc attcccagcc tgaaccccgg cagtcaccct cgccacggcg    480

ctggcggccg ccccaagccg agccccgcgg gcagccgcgg cagcccggtg cccgccggcg    540

ccctgcagcc gcccgagtac ccctggatga aggagaagaa ggcggccaag aaaaccgcac    600

ttctgccggc cgccgccgcc gccgccaccg ccgcagccac cggccctgct tgcctcagcc    660

acaaagaatc cctggaaatc gccgatggca gcggcggggg atcgcggcgc ctgagaactg    720

cttacaccaa cacacagctt ctagagctgg aaaaagaatt tcatttcaac aagtaccttt    780
```

```
gcagaccccg aagggtggag attgcagcgc tgctggattt gactgagaga caagtgaaag    840
tgtggtttca gaaccggagg atgaagcaca agaggcagac ccagtgcaag gaaaaccaaa    900
acagcgaagg gaaatgtaaa agccttgagg actccgagaa agtagaggag gacgaggaag    960
agaagacgct ctttgagcaa gcccttagcg tctctggggc ccttctggag agggaaggct   1020
acacttttca gcaaaatgcc ctctctcagc agcaggctcc caatggacac aatggcgact   1080
cccaaagttt cccagtctcg cctttaacca gcaatgagaa aaatctgaaa cattttcagc   1140
accagtcacc cactgttccc aactgcttgt caacaatggg ccagaactgt ggagctggcc   1200
taaacaatga cagtcctgag gcccttgagg tcccctcttt gcaggacttt agcgttttct   1260
ccacagattc ctgcctgcag ctttcagatg cagtttcacc cagtttgcca ggttccctcg   1320
acagtcccgt agatatttca gctgacagct tagacttttt tacagacaca ctcaccacaa   1380
tcgacttgca gcatctgaat tactaaaaac attaaagcaa aacaaagcat caccaaacaa   1440
aaactccttt gaccaggtgg ttttgccttc ttttatttgg gagtttattt tttattttct   1500
tcttgaccta ccccttccct cctttaagtg ttgaggattt tctgtttagt gattccctga   1560
cccagtttca aacagagcca tcttttacag attattttgg agttttagtt gttttaaacc   1620
taactcaaca accctttatg tgattcctga gagcagtatg aggcctgcaa gaaagtgatc   1680
atataattgt atcttcactt tctttttatt tttgtattac attgggatgc attgtcatgc   1740
atattttttg tagaataaat tctcctttgc tataagtaaa aaaaaaaaaa a            1791
```

<210> SEQ ID NO 3
<211> LENGTH: 3396
<212> TYPE: DNA
<213> ORGANISM: Homo sapiens

<400> SEQUENCE: 3

```
ttcttgcaaa taatgtggtc tcaggcaagg acacagcatc ttggctgtct gctaaaaaaa     60
aaaaatgcct agactctcag tggaaattga gtgtcaagct gcaaaatctc aaatggcaga    120
ctatcatcat ttaagagcgc ctggacaccg gaaaaggcga ttccctgagc gcctggagtt    180
ggagacaatt cctggttcag aatttaaaca tctttctagg tctgcgcggg gcggccattg    240
gcggcggagt gtcacgtgac cgcgggggcg tgccaatgtg cgccctcacg ggtgtcaaac    300
ccctgtcaga gtgtgcgatc aagatcgtga aacaacgcga tgcaaaaagc gacctactac    360
gacagctcgg cgatctacgg tggctacccc taccaggcag ccaacgggtt cgcttataat    420
gccaatcagc agccgtaccc ggcgtccgcc gctttgggcg ccgacggcga gtaccaccga    480
cccgcctgct ccctccagtc tccctccagc gccgggggcc accccaaggc acacgaactg    540
agtgaggcgt gcctgcgcac cctgagcgcc ccacctagcc agcctccaag cctgggagag    600
ccgcccctgc acccgccgcc gccccaggcc gcgcccccctg ccccacagcc gcctcagccc    660
gcacctcagc cccctgcacc taccccctgcc gcgcccccgc ctccctcttc tgcctcccct    720
cctcagaatg ccagcaacaa ccctacccct gccaacgcgg ccaagagccc cctgctcaac    780
tcacccacag tggccaaaca aatcttcccc tggatgaaag agtctcgaca aaacacaaag    840
cagaaaacca gcagctccag ctcaggcgaa agctgcgctg gcgacaagag cccgccgggg    900
caggcttcgt ccaagcgcgc gcgcacggcc tacacgagcg cgcagctggt ggagctggag    960
aaagagttcc acttcaaccg ctacctgtgc cggccgcgcc gggtggagat ggccaatctg   1020
ctgaacctca ctgagcgcca gatcaagatc tggttccaga atcgccgcat gaagtacaaa   1080
aaggatcaga agggcaaggg catgctaacg tcatcggggg gccagtctcc aagtcgcagc   1140
```

cccgtgcccc ccggagccgg tggctatctg aactctatgc attcgctggt caacagcgtc 1200
ccgtatgagc cccagtcgcc cccgcccttc tccaagcccc cccagggtac ctacgggctg 1260
ccccccgcct cctaccctgc gtccctgccc agctgcgcac ccccgccacc cccacagaag 1320
cgctacacgg cggcaggggc gggcgcaggg ggcacccccg actatgaccc gcacgctcat 1380
ggcctgcagg gcaacggcag ctatgggacc ccacacatac agggaagccc cgtcttcgtg 1440
gggggcagct atgtggagcc catgagcaac tccgggccag ccctctttgg tctaactcac 1500
ctcccccacg ctgcctcggg cgccatggac tatgggggtg ccgggccgct gggcagcggc 1560
caccaccacg ggccggggcc tggggagccg caccccacct acacggacct taccggccac 1620
catccttctc agggaagaat tcaggaagca cccaagctca cccacctgtg atagtgggct 1680
tggggctacg cgccaggaga gtctcccccc acccaccttt tttctttggt tgcttttttt 1740
ttttttttt tttaggttct tcctgccctt tccttccttc cttttctctc ttctccgccc 1800
cgcactccgt ttcccggttt ccccccctcgt tggtaaggcg tttttatagt ttatgtgacg 1860
tagcaatctt ggttgctgga atggctgtat catagcgata tttatctctt cctgctcctc 1920
gataggccac tggccctgca ccctttacct tctccactct ttgatcagaa acagggtata 1980
tgaacaaatt ttctagtcga gttttcaatg tgaatttgtt cttacattat ggctcccgag 2040
gggaagcgat tacttttttt aattttaaat ttttttttta attgcacttc ttgtaaagag 2100
tgagaaaaaa aatcaaaggc gctttgaaac aggggctctc tgtgcaagga tgactaagtg 2160
tacgtctttc cgtgtgtgta tgctggtgaa cagtcagatt tatttatatt tttttgcaag 2220
cattgaataa tctaagtttt aaatattatt tatccccatc cgttcgtatt tatattaaag 2280
aattctgtac cctgatggtt cagaagggtt cttgggcctt ttgttcaatt gtgtattggc 2340
gtacttagaa tttttttttat ttgaaagaga aatataattc ctttaaacgg taacgataca 2400
ataaaaccag agaagatcca gcttttgaaa acagtgattt aggtttgtaa catccggcaa 2460
aactgaaaaa aaaaatctgt aaacgcgaaa aatactagat ttgttttgag agttcttcat 2520
tccttgctgc tcacattctg agaaacaaaa agaaataaag tttttattct gaataatatc 2580
cgtgttaaga aggggttctt tggccgaaga cgtgggtctg cgtggaattc aggccgaggc 2640
gagccggcag agcaggccgg acgcagcagc cctctggctc cagcatgggg cctggccagg 2700
ctattcgcct ggaagctcgg cgaattctca ggatggcggc tggggctcca ggcggctgcg 2760
gcagctctgg taacgccgtg cggcgggcca gctgggctgc ccggttccca gctgctgcgg 2820
aggcaggctg agggcgcagg ggctgccgag tgctgtgcac ggaagaaaca aagacatccc 2880
ggcccaaggc gcagcgggag cgcacaggtg ccccgcggcc cagccggggg ataacgcagg 2940
gcggtcttct gctccatgct cttcctcggg tcaaagcgga ccaactaacg cctaaacctc 3000
ggtattagcc agccgcgcag aggatgccga gcactttccg ggagcaatcg gactcctggt 3060
ctcctccggg gatgcttcgc ggtctgttat cgcgtcagga ggaaagaatt gctccaaaaa 3120
tctgcacgcg gagcgaaaca gtttgaaagg gactgaggct cacccaggtc tccagcaaac 3180
ggaggactga actggggaga gtcaccctga gccagccctt ccctggactg ccggaatccc 3240
agcattagct tcctgctgaa tgtagtattt ggcattctct gaatttattt cctctccttc 3300
ccccacccag ctttcttttt atggccccag ggggaggggg agagagcaag gagatcggta 3360
tctttgtaat aaaactgcaa ttttataaat ttttca 3396

<210> SEQ ID NO 4

-continued

<211> LENGTH: 1728
<212> TYPE: DNA
<213> ORGANISM: Homo sapiens

<400> SEQUENCE: 4

```
aaaacgacaa cgcgagaaaa attagtattt ttgcacttca caaattaatg accatgagct     60

cgtttttgat aaactccaac tacatcgagc ccaagttccc tcccttcgag gagtacgcgc    120

agcacagcgg ctcgggcggc gcagacggcg gcccgggcgg gggccccggc taccagcagc    180

ccccagcgcc cccgacccag cacctgccgc tgcagcagcc ccagctccct cacgcgggcg    240

gcggccgaga gcccactgcc tcctactacg cgccgcggac cgcccgcgag cccgcctacc    300

ctgctgccgc gctgtacccc gcgcatgggg ccgcggacac cgcctacccc tatggctacc    360

gcggcggcgc cagccccggg cggccgcccc agcccgagca gcccccggcg caagccaagg    420

gcccagcgca cggcctgcat gcgagccacg tcctgcagcc ccagctgccg ccgcccctgc    480

agcctcgcgc cgtgcccccca gcggccccgc ggcgctgcga ggcggccccc gccaccccag    540

gcgtcccggc agggggcagc gcccccgcgt gcccgctgct cttggccgac aagagcccgc    600

tgggcctgaa gggcaaggag cccgtggtgt accccctggat gaagaagatc catgtcagcg    660

ccgttaaccc cagttataac ggaggggagc ctaagcgctc tcgaaccgcc tacacccggc    720

agcaggtctt ggagctggag aaggagttcc acttcaatcg atacctgacc cggcggcgcc    780

gcatcgagat cgcccacacg ctctgtttgt ctgagcgcca ggtcaagatc tggtttcaga    840

accggaggat gaagtggaag aaagaccaca aactgcccaa caccaagatg cgatcctcca    900

attcggcctc ggcctctgcc ggcccaccag ggaaagcaca aactcagagc ccacacctcc    960

atccccaccc ccacccgagc acctccacac ccgttccctc ctccatataa tcttctagag   1020

atcttaacca gtttctatcc cttacctgct tttctcttct cttctcctgc tccgttcctc   1080

atccacccct ccccatctgg accataatag acaccaaaac aaacccaaat tggtgaaaag   1140

aataatcaaa aagaagacat tatccggtta agagtctgtg ctggttgcca cccaagagag   1200

aacagttgtc caggatgctg gctggtggaa caacctgctg gcccgaaaca aggctgccag   1260

gtgtggatac ctgagaagga ctacttggta tcaaatactt ttgagatggc tacagtcagc   1320

tagctggaca gcccatgctg agtggggaca tacacttgca tctttgttga aagcagaaga   1380

agacagaccc tttccccacc ttccttacct cctcttcccc cattaaggca gctcatccaa   1440

gcttgtattt aactgaataa atgagtagac attgtggacc tcacaagatt atttaattct   1500

taagatgtgt agaccttgat ggtaggtgtg acatgttagt ttttcttact tgcatttatt   1560

taagacactg ttacagagat actgttgtcc ccttctgggg cacggtcttt ggggagaggg   1620

gagtgcattt agacttatgt ggaactgtac aaattgtgat gtggctacat agaaagccat   1680

gtgctaagaa taaactccat ttaaaaaaca ttaaaaatct aagattca                1728
```

<210> SEQ ID NO 5
<211> LENGTH: 1657
<212> TYPE: DNA
<213> ORGANISM: Homo sapiens

<400> SEQUENCE: 5

```
gggtgctata gacgcacaaa cgaccgcgag ccacaaatca agcacacata tcaaaaaaca     60

aatgagctct tattttgtaa actcattttg cggtcgctat ccaaatggcc cggactacca    120

gttgcataat tatggagatc atagttccgt gagcgagcaa ttcagggact cggcgagcat    180

gcactccggc aggtacggct acggctacaa tggcatggat ctcagcgtcg gccgctcggg    240
```

-continued

```
ctccggccac tttggctccg gagagcgcgc ccgcagctac gctgccagcg ccagcgcggc    300
gcccgccgag cccaggtaca gccagccggc cacgtccacg cactctcctc agcccgatcc    360
gctgccctgc tccgccgtgg ccccctcgcc cggcagcgac agccaccacg gcgggaaaaa    420
ctccctaagc aactccagcg gcgcctcggc cgacgccggc agcacccaca tcagcagcag    480
agaggggggtt ggcacggcgt ccggagccga ggaggacgcc cctgccagca gcgagcaggc    540
gagtgcgcag agcgagccga gcccggcgcc gcccgcccaa ccccagatct accccctggat    600
gcgcaagctg cacataagtc atgacaacat aggcggcccg gaaggcaaaa gggcccggac    660
ggcctacacg cgctaccaga ccctggagct ggagaaggag ttccacttca accgttacct    720
gacccgcaga aggaggattg aaatagcaca tgctctttgc ctctccgaga gacaaattaa    780
aatctggttc caaaaccgga gaatgaagtg gaaaaaagat aataagctga aaagcatgag    840
catggccgcg gcaggagggg ccttccgtcc ctgagtatct gagcgtttaa agtactgagc    900
agtattagcg gatcccgcgt agtgtcagta ctaaggtgac tttctgaaac tcccttgtgt    960
tccttctgtg aagaagccct gttctcgttg ccctaattca tcttttaatc atgagcctgt   1020
ttattgccat tatagcgcct gtataagtag atctgctttc tgttcatctc tttgtcctga   1080
atggctttgt cttgaaaaaa aatagatgtt ttaacttatt tatatgaagc aagctgtgtt   1140
acttgaagta actataacaa aaaaagaaaa gagaaaaaaa aacacacaaa aagtccccct   1200
tcaatctcgt ttagtgccaa tgttgtgtgt tgcactcaag ttgtttaact gtgcatgtgc   1260
gtggaagtgt tcctgtctca atagctccaa gctgttaaag atatttttat tcaaactacc   1320
tatattcctt gtgtaattaa tgctgttgta gaggtgactt gatgagacac aacttgttcg   1380
acgtgtagtg actagtgact ctgtgatgaa aactgtgact ccaagcggtg tgtccctgcg   1440
tgcctttata ggaccctttg cacgaactct ggaagtggct cttataagcg cagcttcagt   1500
gatgtatgtt tttgtgaaca aagttacaaa tattgtccaa gtctggctgt tttaagcaaa   1560
ctgtgatcag cttttttttt tttttttttt tttttgtatt tgtttttaag gaaaaaatac   1620
tgactggaac aaaaaataaa ctttctattg taagttc                            1657
```

<210> SEQ ID NO 6
<211> LENGTH: 802
<212> TYPE: DNA
<213> ORGANISM: Homo sapiens

<400> SEQUENCE: 6

```
cacagtcctg cagaggggcg cgcaaatgag ttcctatttt gtgaatccca ctttccccgg     60
gagccttccc agcggccagg actccttctt gggccagctg cccctctacc aggctggcta    120
tgacgcgctg aggcccttcc cggcctcgta cggggcgtcg agtctcccgg acaagacgta    180
cacctcacct tgtttctacc aacagtccaa ctcggtcctg gcctgcaacc gggcgtccta    240
cgagtacggg gcctcgtgtt tctattctga taaggacctc agtggcgcct cgccctcggg    300
cagtggcaag cagaggggcc ccggggacta cctgcacttt tctcccgagc agcagtacaa    360
acccgacagc agcagcgggc agggcaaagc actccatgac gaaggcgccg accggaagta    420
cacgagcccg gtttaccctt ggatgcagcg gatgaactcc tgcgcgggtg ctgtgtatgg    480
gagccatggg cgccgaggcc gccagaccta cacgcgctac cagacactgg agctggagaa    540
ggagttccac ttcaaccgct acctgacacg gcgccgccgc atcgagatcg ccaacgcgct    600
ctgcctcacc gagcgccaga tcaagatctg gttccagaac cgccgcatga agtggaaaaa    660
```

-continued

```
ggaaaacaag ctcatcaatt ccacgcagcc cagcggggag gactcagagg caaaggcggg    720

cgagtagatg cctgggcagg gaccaggcca gcgctgcaac ctccttcggc tttgccccct    780

tgccctcgcc tgttccccaa ct                                             802
```

<210> SEQ ID NO 7
<211> LENGTH: 2018
<212> TYPE: DNA
<213> ORGANISM: Homo sapiens

<400> SEQUENCE: 7

```
gtgctgcggc gagctccgtc caaaagaaaa tggggtttgg tgtaaatctg gggtgtaat      60

gttatcatat atcactctac ctcgtaaaac cgacactgaa agctgccgga caacaaatca    120

caggtcaaaa ttatgagttc ttcgtattat gtgaacgcgc tttttagcaa atatacggcg    180

ggggcttctc tgttccaaaa tgccgagccg acttcttgct cctttgctcc caactcacag    240

agaagcggct acggggcggg cgccggcgcc ttcgcctcga ccgttccggg cttatacaat    300

gtcaacagcc ccctttatca gagccccttt gcgtccggct acggcctggg cgccgacgcc    360

tacggcaacc tgccctgcgc ctcctacgac caaaacatcc ccgggctctg cagtgacctc    420

gccaaaggcg cctgcgacaa gacggacgag ggcgcgctgc atggcgcggc tgaggccaat    480

ttccgcatct acccctggat gcggtcttca ggacctgaca ggaagcgggg ccgccagacc    540

tacacgcgct accagacgct ggagctggag aaggagttcc acttcaaccg ctacctgacg    600

cggcgccgcc gcattgaaat cgcccacgcg ctctgcctca ccgagcgcca gattaagatc    660

tggttccaga accgccgcat gaagtggaag aaagagcata aggacgaagg tccgactgcc    720

gccgcagctc ccgagggcgc cgtgccctct gccgccgcca ctgctgccgc ggacaaggcc    780

gacgaggagg acgatgatga agaagaggaa gacgaggagg aatgaggggc cgatccgggg    840

ccctctctgc accggacagt cggaaaagcg tctttaagag actcactggt tttacttaca    900

aaaatgggaa aaataaaaga aaatgtaaaa aacaaaaaca aaaacaaaaa agcaacccag    960

tccccaacct gcactctacc cacccccatc acctactcca gctcccaact tttgtggact   1020

gagcggccgc agagactggg tcgccttgga ttccctctgc ctccgaggac cccaaaagac   1080

acccccaacc ccaggccagc cggccctgct ctggcgcgtc caaaatacta cctagcacag   1140

gcctctgctc gaggcacccc caaactacct atgtatccag ccccagaggg cctccattcc   1200

caggaagtcc ctatgtatcc caacactggc agacacccag caccaccctc ccagacccgc   1260

aagaaagtga atctcactac tacctactcc cctaaaacta cctattttgt gctggctggc   1320

ttgcctgcta cctagtgccg actgctccca ggcaagtccc ctgctgctta cagcccgcag   1380

cttttggggt ccctgaggct gccctgagaa tgtgctgagg tccaggatca gggtattggc   1440

atctatttaa atcgaaaaat aatatattta ttccaaaaag catcctaagt gcttgcaccc   1500

tagaatcaat ccctccttct ctggcttggc acccacagct caggcccatc aacccccact   1560

tctggagggg aatgttcctg agctggctgc agatctgtgg gttagcttct gcttagcagg   1620

actgtggaga tgcttccagc ttcgctgtcc tttcctctgg ctcctgtatc ttactgttca   1680

gctgtgttaa atatgtacgc cctgatgttt cctataatag cagatactgt atatttgaac   1740

aagatttttt tttatcattt ctatagtctt ggagttcatt tgtaaggcag tgtcttgact   1800

tggaaaggat gtgttaatgg ggtgactttg tagcatggta tgttgtcttg agttaactgt   1860

agtgggtggg gaggtccaat gccctccgca atgcccttca tctcctgtgt tgtcctgtac   1920

cctgctcagc tccatcctgg ggttcaggga aggcacactt cccagcccag ctgtgtttta   1980
```

tgtaaccgaa aataaagatg cgtggtgaca aagaaaaa 2018

<210> SEQ ID NO 8
<211> LENGTH: 2076
<212> TYPE: DNA
<213> ORGANISM: Homo sapiens

<400> SEQUENCE: 8
agttgttaca tgaaatctgc agtttcataa tttccgtggg tcgggccggg cgggccaggc 60
gctgggcacg gtgatggcca ccactggggc cctgggcaac tactacgtgg actcgttcct 120
gctgggcgcc gacgccgcgg atgagctgag cgttggccgc tatgcgccgg ggaccctggg 180
ccagcctccc cggcaggcgg cgacgctggc cgagcacccc gacttcagcc cgtgcagctt 240
ccagtccaag gcgacggtgt ttggcgcctc gtggaaccca gtgcacgcgg cgggcgccaa 300
cgctgtaccc gctgcggtgt accaccacca tcaccaccac ccctacgtgc acccccaggc 360
gcccgtggcg gcggcggcgc cggacggcag gtacatgcgc tcctggctgg agcccacgcc 420
cggtgcgctc tccttcgcgg gcttgccctc cagccggcct tatggcatta aacctgaacc 480
gctgtcggcc agaaggggtg actgtcccac gcttgacact cacactttgt ccctgactga 540
ctatgcttgt ggttctcctc cagttgatag agaaaaacaa cccagcgaag gcgccttctc 600
tgaaaacaat gctgagaatg agagcggcgg agacaagccc cccatcgatc ccaataaccc 660
agcagccaac tggcttcatg cgcgctccac tcggaaaaag cggtgcccct atacaaaaca 720
ccagaccctg gaactggaga aagagtttct gttcaacatg tacctcacca gggaccgcag 780
gtacgaggtg gctcgactgc tcaacctcac cgagaggcag gtcaagatct ggttccagaa 840
ccgcaggatg aaaatgaaga aaatcaacaa agaccgagca aaagacgagt gatgccattt 900
gggcttattt agaaaaaagg gtaagctaga gagaaaaaga aagaactgtc cgtcccccttt 960 ccgccttctc ccttctctca cccccaccct agcctccacc atccccgcac aaagcggctc 1020
taaacctcag gccacatctt ttccaaggca aaccctgttc aggctggctc gtaggcctgc 1080
cgctttgatg gaggaggtat tgtaagcttt ccattttcta taagaaaaag gaaaagttga 1140 gggggggca ttagtgctga tagctgtgtg tgttagcttg tatatatatt tttaaaaatc 1200
tacctgttcc tgacttaaaa caaaaggaaa gaaactacct ttttataatg cacaactgtt 1260
gatggtaggc tgtatagttt ttagtctgtg tagttaattt aatttgcagt ttgtgcggca 1320
gattgctctg ccaagatact tgaacactgt gttttattgt ggtaattatg ttttgtgatt 1380
caaacttctg tgtactgggt gatgcaccca ttgtgattgt ggaagataga attcaatttg 1440
aactcaggtt gtttatgagg ggaaaaaaac agttgcatag agtatagctc tgtagtggaa 1500
tatgtcttct gtataactag gctgttaacc tatgattgta aagtagctgt aagaatttcc 1560
cagtgaaata aaaaaaaatt ttaagtgttc tcggggatgc atagattcat cattttctcc 1620
accttaaaaa tgcgggcatt taagtctgtc cattatctat atagtcctgt cttgtctatt 1680
gtatatataa tctatatgat taaagaaaat atgcataatc agacaagctt gaatattgtt 1740
tttgcaccag acgaacagtg aggaaattcg gagctataca tatgtgcaga aggttactac 1800
ctagggttta tgcttaattt taattggagg aaatgaatgc tgattgtaac ggagttaatt 1860
ttattgataa taaattatac actatgaaac cgccattggg ctactgtaga tttgtatcct 1920
tgatgaatct ggggtttcca tcagactgaa cttacactgt atattttgca atagttacct 1980
caaggcctac tgaccaaatt gttgtgttga gatgatattt aactttttgc caaataaaat 2040
atattgattc ttttctaaaa aaaaaaaaaa aaaaaa 2076

<210> SEQ ID NO 9
<211> LENGTH: 2691
<212> TYPE: DNA
<213> ORGANISM: Homo sapiens

<400> SEQUENCE: 9
atgccaggcc ccccaccagc cacgttgggg cagcccccac agctcccggc cttcgggcca 60
aggtgtcggg gtgcgtctcc tggcccatca atacagatta catatttata tcaatcgcgg 120
gctctgaggg cgccctcgga gagcggcccc gcgcctacga aaccaaactg ggagtggtcg 180
cgcggaaact ctggctcggg attggctgcg ggcgcccgcc gcggtgcggg gggattgcta 240
atcgtattca gcatgttttg cacaagaaat gtcagccaga aagggctatc tgctcccttc 300
gccaaattat cccacaacaa tgtcatgctc ggagagcccc gccgcgaact ctttttttggt 360 cgactcgctc atcagctcgg gcagaggcga ggcaggcggc ggtggtggtg gcgcgggggg 420
cggcggcggt ggcggttact acgcccacgg cggggtctac ctgccgcccg ccgccgacct 480
gccatacggg ctgcagagct gcgggctctt ccccacgctg ggcggcaagc gcaatgaggc 540
agcgtcgccg ggcagcggtg gcggtggcgg gggtctaggt cccggggcgc acggctacgg 600
gccctcgccc atagacctgt ggctagacgc gccccggtct tgccggatgg agccgcctga 660
cgggccgccg ccgccgcccc agcagcagcc gccgcccccg ccgcaaccac cccagccagc 720
gccgcaggcc acctcgtgct ctttcgcgca gaacatcaaa gaagagagct cctactgcct 780
ctacgactcg gcggacaaat gccccaaagt ctcggccacc gccgccgaac tggctccctt 840
cccgcggggc ccgccgcccg acggctgcgc cctgggcacc tccagcgggg tgccagtgcc 900
tggctacttc cgcctttctc aggcctacgg caccgccaag ggctatggca gcggcggcgg 960
cggcgcgcag caactcgggg ctggcccgtt ccccgcgcag cccccggggc gcggtttcga 1020
tctcccgccc gcgctagcct ccggctcggc cgatgcggcc cggaaggagc gagccctcga 1080
ttcgccgccg ccccccacgc tggcttgcgg cagcggcggg ggctcgcagg gcgacgagga 1140
ggcgcacgcg tcgtcctcgg ccgcggagga gctctccccg gccccttccg agagcagcaa 1200
agcctcgccg gagaaggatt ccctgggtaa gcagggctgc agagggctgc agtcaggcgg 1260
gcagacaggc agacacaagg aggagaagga tcagaaaact aggagcccgc gcagcagccg 1320
gccggccttg gcccaagctg caggcaggct gaccttgtga acttgctttt taatatttgg 1380
gcgtgggggc gcagtaaaat tcatgtccgg cttagcgccc cacagcaaga cgtcctcggc 1440
gctggcctca gctcccctg actagggacg aggacaccag cgagcaggcc ccctcctgtg 1500
cgctctttcc tgtggccggg aggacccaga gccctggtcc ctgcccagcc tgcgcggcgc 1560
ggcccacgcg gggggagggg gagggaggga aagtagctcg cccgcagata gcgcggatgt 1620
ttgtaaggca tccaaaataa gcagccgcca gcgccaataa ataagcccat taaccggcga 1680
agttcgagtg tacgatcccc catgcttttt tcaaagttgc tgaggggcgg gaatcttcgt 1740
ggcgggaaga agaaaaggca aatccggcct ggaagcgggg ggccctgagc tgagagccag 1800
agaagggcca tttcccttcc cctggacctc ggaatcgccc agctatgtat cctggctcct 1860
ggagaaactt gagggagggc ccttgacccc cgaatcggtt tttcctgcct tccccattgg 1920
accaatgatg cccttctttc tccccttatc gagtcttggg caatcagggc cctggggtga 1980
gacagccaag ctgcctggcc catcttccaa gtaagcaccc cgcgctccta gcctgggggc 2040
tacaggaaat gcttgtctgc catatggcaa gaggcaaaga aaagcgttaa gttcaagatg 2100

```
tacagcctgc cctcccaggc ctttccttct gcaagcatct acggcttagc gctaaaacag   2160
gtgtttggaa aagtggggga aatgtaaatt ggaagggtca tgtagattga aggcccactc   2220
aatttttgtc atgacttatg gaggaactgc ttgctctcag caagccaaaa acgggggcac   2280
gactctcttc tctgtgactt gggacatctc tcttatggga gaaacggagg caattcaccc   2340
ccgcgggcag cccgtgtggc ctcgacttaa tcatcccctc tttattctct tacatgccag   2400
gcaattccaa aggtgaaaac gcagccaact ggctcacggc aaagagtggt cggaagaagc   2460
gctgccccta cacgaagcac cagacactgg agctggagaa ggagtttctg ttcaatatgt   2520
accttactcg agagcggcgc ctagagatta gccgcagcgt ccacctcacg gacagacaag   2580
tgaaaatctg gtttcagaac cgcaggatga aactgaagaa aatgaatcga gaaaaccgga   2640
tccgggagct cacagccaac tttaattttt cctgatgaat ctccaggcga c            2691
```

<210> SEQ ID NO 10
<211> LENGTH: 2653
<212> TYPE: DNA
<213> ORGANISM: Homo sapiens

<400> SEQUENCE: 10

```
cttcaaagag gcagctgcag tggagaatca tgttaagctc ggctactgcg gagagcccaa     60
ggtagcccaa taatggattt tgatgagcgt ggtccctgct cctctaacat gtatttgcca    120
agttgtactt actacgtctc gggtccagat ttctccagcc tcccttcttt tctgccccag    180
accccgtctt cgcgcccaat gacatactcc tactcctcca acctgcccca ggtccaaccc    240
gtgcgcgaag tgaccttcag agagtacgcc attgagcccg ccactaaatg gcaccccccgc    300
ggcaatctgg cccactgcta ctccgcggag gagctcgtgc acagagactg cctgcaggcg    360
cccagcgcgg ccggcgtgcc tggcgacgtg ctggccaaga gctcggccaa cgtctaccac    420
caccccaccc ccgcagtctc gtccaatttc tatagcaccg tgggcaggaa cggcgtcctg    480
ccacaggctt tcgaccagtt tttcgagaca gcctacggca ccccggaaaa cctcgcctcc    540
tccgactacc ccggggacaa gagcgccgag aaggggcccc cggcggccac ggcgacctcc    600
gcggcggcgg cggcggctgc aacgggcgcg ccggcaactt caagttcgga cagcggcggc    660
ggcggcggct gccgggagac ggcggcggca gcagaggaga aagagcggcg gcggcgcccc    720
gagagcagca gcagccccga gtcgtcttcc ggccacactg aggacaaggc cggcggctcc    780
agtggccaac gcacccgcaa aaagcgctgc ccctatacca agtaccagat ccgagagctg    840
gaacgggagt tcttcttcag cgtctacatt aacaaagaga agcgcctgca actgtcccgc    900
atgctcaacc tcactgatcg tcaagtcaaa atctggtttc agaacaggag aatgaaggaa    960
aaaaaaatta acagagaccg tttacagtac tactcagcaa atccactcct ctaagactcc   1020
agcggctgga attgggtggg gggcttcata cacatgagat aatatgcaga ttttgccctt   1080
gacaaagtca agccacatgg tgacttttga aaagaggtgt gcaagagagg gatgcatgga   1140
gatagcccca caggaggtgg tctgggactc tcttgattaa gatctcagtg gttaagattc   1200
ctaataatca ttggattctg agagctgtgc atcagctaga atgacaggtt tgggacccct   1260
ggtggttcac tcttggagcc tgcagagctg cgggctgggt gtggtctcca ctggggattg   1320
ggcccctgcc agaccccctg gagactaacc ccaccacacc ctccctctac tgggagccta   1380
cccaccccca ggacccctga gtaaaaaagc tgtgtgctct ccaagcccag ttcagcttgg   1440
ggacaggggc aggaggaagg ggtaggatta ctaggtgccc agaatgaggc tgctttccaa   1500
```

agccaatgtg aacagcggct ggacttggag gtagctttga ggtggaagag ggctgcaaat 1560
ccttgtggga aaagaaatct atgattccag gtggcatcag tgtctttcca ctcctcctag 1620
ccacccacca cactgatcca gccctgagtt cctagccacc gcctcctaca gcccacctgg 1680
cttttctttc taccaaatga gggtcttggt tccagcctgc cactcaggcc caaagcctcg 1740
acacagagtg gactgttccc tgaggtggga gatgtggaaa agccaagagg ctgcagccag 1800
gccactggcc cctgagatct ctgcaggaaa tggctgtgga gtgtggcagt ttggcaaact 1860
ctccaccaca cgtaatgaaa cttggatttg ctcagtgtct ggctgcagag cagtgggcct 1920
ggccagcagg tccccagctt tggctatgag ggccttgagt cccccaaaac accgggttcc 1980
agcaccacac tcagccctca ttggctcttg aactgagctt ggaagcttct ggtgaccttc 2040
caagagcctg agagtgaggt ggaattattt taaaagataa atattatatt atatatatat 2100
atatttccct gaaggaacca aagcgaattt taaaagatgc aatgtagagg ggaaaagaga 2160
tgatgaaaat atttaaaggc cctatctgtt tacagtgttc cgtggttaaa ctcgctcact 2220
gctaagaata tttgaatgta tgcttcatac agggatggtg ttcaaaaaac ttgtaaataa 2280
aggaaccata atcaattttc ttttctttct ttctcttttt ctttttctt ttgccattag 2340 ttgatttcct ttagggtgtt ggagggggtg gaaaaggtat tgagaatggt ctttttaatc 2400
tcttgcaaca tttggaaaga gttagggaaa tgctcagagg cagtcggcct ggccggcctg 2460
gggatctcat ctgggaaagc caggcaccct cccattgaat ctcctttgcc tccctgtgtt 2520
aagaaatgtc tgttggctcc atttgtactg ggagtgttgg cctgtcctca attctggttc 2580
ttacccaccg tgtgtgttgc agcacttata caggcaactg ggcacaagga aaataaagac 2640
ggtggaaatt tga 2653

<210> SEQ ID NO 11
<211> LENGTH: 2514
<212> TYPE: DNA
<213> ORGANISM: Homo sapiens

<400> SEQUENCE: 11
actggggtct tctccatgcg gctcgggcta tgacagcctc cgtgctcctc cacccccgct 60
ggatcgagcc caccgtcatg tttctctacg acaacggcgg cggcctggtg gccgacgagc 120
tcaacaagaa catggaaggg gcggcggcgg ctgcagcagc ggctgcagcg gcggcggctg 180
ccggggccgg gggcgggggc ttcccccacc cggcggctgc ggcggcaggg ggcaacttct 240
cggtggcggc ggcggccgcg gctgcggcgg cggccgcggc caaccagtgc cgcaacctga 300
tggcgcaccc ggcgcccttg gcgccaggag ccgcgtccgc ctacagcagc gcccccgggg 360
aggcgccccc gtcggctgcc gccgctgctg ccgcggctgc cgctgcagcc gccgccgccg 420
ccgccgcgtc gtcctcggga ggtcccggcc cggcgggccc ggcgggcgca gaggccgcca 480
agcaatgcag cccctgctcg gcagcggcgc agagctcgtc ggggcccgcg gcgctgccct 540
atggctactt cggcagcggc tactacccgt gcgcccgcat gggcccgcac cccaacgcca 600
tcaagtcgtg cgcgcagccc gcctcggccg ccgccgccgc cgccttcgcg gacaagtaca 660
tggataccgc cggcccagct gccgaggagt tcagctcccg cgctaaggag ttcgccttct 720
accaccaggg ctacgcagcc gggccttacc accaccatca gcccatgcct ggctacctgg 780
atatgccagt ggtgccgggc ctcgggggcc ccggcgagtc gcgccacgaa cccttgggtc 840
ttcccatgga aagctaccag ccctgggcgc tgcccaacgg ctggaacggc caaatgtact 900
gccccaaaga gcaggcgcag cctccccacc tctggaagtc cactctgccc gacgtggtct 960

-continued

```
cccatccctc ggatgccagc tcctatagga gggggagaaa gaagcgcgtg ccttatacca   1020

aggtgcaatt aaaagaactt gaacgggaat acgccacgaa taaattcatt actaaggaca   1080

aacggaggcg gatatcagcc acgacgaatc tctctgagcg gcaggtcaca atctggttcc   1140

agaacaggag ggttaaagag aaaaaagtca tcaacaaact gaaaaccact agttaatgga   1200

ttaaaaatag agcaagaagg caacttgaag aaacgcttca gaactcgttg ctttgcccag   1260

ataatgataa taatgcttaa taataattga agaatgggaa agagaaagag acagagactg   1320

gcattttcct ctcccgaagg agatctcttt ctctttaatg gaatctacaa ctgttttaaa   1380

actttaagaa aggtaaagac tgccagttct tccgccaacc ccatcagccc agcccgttaa   1440

atgtcaaacg tcaaccccca aaatacgcaa tttcagataa gttacgcagt tactgaaatc   1500

ttgtaagtat ttaagtgatc gttacatttt aggacactgc gttagatggt aataatctgg   1560

aagttggtta caaacgcaag aggccattgt aaacatctgc ttgtccttct taggtcgcca   1620

ttccctttgc atgttaagcg tctgctcagg taaatcttag tgaaattcct accgttgttg   1680

tacgttctgc aaaacatttt atgtatagat ttagagggga aacgagaagg tactgaaata   1740

atgatcttgg aatatttgct gtgaagggag aaagggagag aaaactcttc tgaggatcat   1800

ttgtcttggt agtatagtaa aaccaaccag ctgaaccttt caggctacaa gagaacccgg   1860

gtcggtaatg tctttttaag aataattttt aattgcttat aacaagcata ttttgtggca   1920

tttgaactat atttactgct ccaatatccg ttattttcca aaggattttg tatctttttg   1980

aaaatgttta catcatcaga tgatccacag aattcacttt atgtgagatc tcccgagagt   2040

ttccatccca acatgatgga ctttggtttg aacacaattc gtttttttcat ttgaattggc   2100

atttcccaat atttgctaaa catttgctgg agaaatcatt tttcttttttt cttttttaga   2160

aaactcagaa tgaaaattca ttcccctgaa atatttaggt gtctatattc tatattttga   2220

tctattaagg gattagtatt tttccatgtt tattgtgtta tcagagtgca ttagaaagat   2280

tagtgattca tcttcacagc acatttttaa tcaagcagtt atttcaacca gcacattcgt   2340

tttgttcata ttcactatag aatgatatct tgtaaataaa gacattcagc acactgtgaa   2400

aatgtatttg tgcacctgct ttttaaatat ttctactaaa aatgaaaaaa aaaaaccctt   2460

agacctgtag atagtgatat cgtaatatta attgttaata aaatagtcac tgcc         2514
```

<210> SEQ ID NO 12
<211> LENGTH: 1014
<212> TYPE: DNA
<213> ORGANISM: Homo sapiens

<400> SEQUENCE: 12

```
tgacgcatgg actataatag gatgaactcc ttcttagagt acccactctg taaccgggga     60

cccagcgcct acagcgccca cagcgcccca acctcctttc ccccaagctc ggctcaggcg    120

gttgacagct atgcaagcga gggccgctac ggtggggggc tgtccagccc tgcgtttcag    180

cagaactccg gctatcccgc ccagcagccg ccttcgaccc tgggggtgcc cttccccagc    240

tccgcgccct cggggtatgc tcctgccgcc tgcagcccca gctacgggcc ttctcagtac    300

taccctctgg gtcaatcaga aggagacgga ggctattttc atccctcgag ctacggggcc    360

cagctagggg gcttgtccga tggctacgga gcaggtggag ccggtccggg gccatatcct    420

ccgcagcatc ccccttatgg gaacgagcag accgcgagct ttgcaccggc ctatgctgat    480

ctcctctccg aggacaagga aacaccctgc ccttcagaac ctaacacccc cacggcccgg    540
```

```
accttcgact ggatgaaggt taagagaaac ccacccaaga cagcgaaggt gtcagagcca    600

ggcctgggct cgcccagtgg cctccgcacc aacttcacca caaggcagct gacagaactg    660

gaaaaggagt tccatttcaa caagtacctg agccgggccc ggagggtgga gattgccgcc    720

accctggagc tcaatgaaac acaggtcaag atttggttcc agaaccgacg aatgaagcag    780

aagaagcgcg agcgagagga aggtcgggtc cccccagccc caccaggctg ccccaaggag    840

gcagctggag atgcctcaga ccagtcgaca tgcacctccc cggaagcctc acccagctct    900

gtcacctcct gaactgaacc tagccaccaa tggggcttcc aggcactgga gcgccccagt    960

ccagccctat cccaggctct ccccaacccc aggcctgggc ttcactggcc tggg         1014


<210> SEQ ID NO 13
<211> LENGTH: 1614
<212> TYPE: DNA
<213> ORGANISM: Homo sapiens

<400> SEQUENCE: 13

aatctccccc tcccaaaatc gctccattac ataaatcggg gggggtgcag gagggggggtc     60

ccttccgatc ctccctcctg acgccccccc cagcagcccc ctcccccacc attgaaagcc    120

atgaattttg aatttgagag ggagattggg tttataaaca gccagccgtc gctcgccgag    180

tgtctgactt ccttccccgc tgtcttggag acatttcaaa cttcatcaat caaggagtcg    240

acattaattc ctcctcctcc tcctttcgag caaaccttcc ccagcctcca gcccggcgcc    300

tccacccttc agagacccag gagccaaaag cgagccgaag atgggcctgc tctgccgccg    360

ccaccgccgc cgccactccc cgctgccccc ccggcccccg agttcccttg gatgaaagag    420

aagaaatccg ccaagaaacc cagccaatcc gccacgtctc cttctccggc cgcctccgcc    480

gttccggcct ccggggtcgg atcgcctgca gatggcctgg gactgccgga ggctggtggc    540

ggcggggcgc gcaggctgcg cacggcttac accaacacgc agctgctgga actggagaag    600

gaattccact ttaataagta cctgtgccgg ccacgccgcg tcgagatcgc ggccttgctg    660

gacctcaccg aaaggcaggt caaagtctgg tttcagaacc ggcgcatgaa gcacaagcgg    720

cagacgcagc accgagagcc gccggatggg gagcctgcct gcccgggagc cctggaggac    780

atctgcgacc ctgccgagga acccgcggcc agcccgggcg gcccctccgc ctcgcgggcg    840

gcgtgggaag cctgctgtca cccgccggag gtggtgccgg gggccttaag cgcggacccc    900

cggcctttag ccgttcgctt agagggcgca ggcgcgtcga gtcccggctg cgcgctgcgc    960

ggggccggcg ggctggagcc cgggccattg ccagaagacg tcttctcggg gcgccaggat   1020

tcacctttcc ttcccgacct caacttcttc gcggccgact cctgtctcca gctatccgga   1080

ggcctctccc ctagcctaca gggttctctc gacagcccgg tccctttttc cgaggaagag   1140

ctggattttt tcaccagtac gctctgtgcc atcgacctgc agtttcccta acctgtttcc   1200

tcctcccggt cctttcgacc cccgcgctcc ttggccgtct actggaaaaa tcgagcctct   1260

cccaccctca gtcgcataga cttatgtgtt ttgctaaaat tcaggtatta ctgaattagc   1320

gtttaatcca ctccctttct tcttcttcta aaatattggg cactcggtta tcttttaaaa   1380

ttcacacaga aaaattccgt ttggtagact ccttccaatg aaatctcagg aataattaaa   1440

ctctaggggg actttcttaa aaataactag agggacctat tttcctcttt tttatgtttt   1500

agactgtaga ttatttatta aaattcttta ataataggaa aaggggaaag tatttattgt   1560

acattatttt catagattaa ataaatgtct ttataatacc aaaaaaaaaa aaaa         1614
```

<210> SEQ ID NO 14
<211> LENGTH: 3627
<212> TYPE: DNA
<213> ORGANISM: Homo sapiens

<400> SEQUENCE: 14
ctgggtaggg cagggggaac cgacaggccg gtgtccccag ccgcaaaaga gctgctgaac 60
tgtccgttta aatgctgctg ggagactcgt aaaaaaatca tcgtggacct ggaggatgag 120
aggggcgagc tttatttcgg tcggattgcg gtgtggtggt ttagctgcaa ggggatgccg 180
cagccccagt tgagggggaa aatagttctt aaaaagcata tgccccccta aggaatgtct 240
ctaaagaacc aaatcaaagc tgctctttgg aaggtatgaa tagaatttaa aaaaaaaaga 300
tttctatgga gcttaaagtt cacagccatt ctgtgtagac aagagctaag aaaaatgtga 360
gaattataca gaaaaccatt aatcacttct tttctttaaa tacgtatcct ctctcctttg 420
ttattattca acagcaaatc tccttggacc ggctgttggg ggaaaaaagt gttagccgtc 480
tctcccggat ctgcaagggg gaaaaaattt ggaaccataa agttgaaaac ttttttctct 540
cagtttggaa gaagcccttc gtcatgaatg ggatctgcag agttcgggcg agaggaggcg 600
agaggcgcaa aggaggggag atttgtcgcc tgccgctcgc tctggggctc gatgtgaata 660
tatattatgt ctgcctgttc tcccctcgtc ggtggctaag gtcagccgct tggaacagac 720
cccggaggag gggggcagag aggggaggtg gggggggggg gtccggcgtg tcacgtgacc 780
cccagggttg ccaatgtccg gtcctgaggg tatcaggcct ttccaagttg ccacccactg 840
cccaggcctc acccagcgat gcagaaagcc acctactacg acaacgccgc ggctgctctc 900
ttcggaggct attcctcgta ccctggcagc aatggcttcg gcttcgatgt cccccccaa 960 cccccatttc aggccgccac gcacctggag ggcgactacc agcgctcagc ttgctcgctg 1020
cagtccctgg gcaacgctgc cccacatgcc aagagcaagg agctcaacgg cagctgcatg 1080
aggccgggtc tggcccccga gcccctgtcg gccccgcctg gctcaccccc gcccagtgcc 1140
gcacctacca gtgccactag caacagcagt aatgggggcg ggcccagcaa aagtggtccc 1200
ccaaagtgcg gtcccggcac caactccacc ctcaccaaac agatattccc ctggatgaaa 1260
gagtcgaggc aaacgtccaa gctgaaaaac aactcccccg gcacagcaga gggctgtggt 1320
ggcggcggcg gtggcggcgg cggcggaggc agtggtggca gcgggggcgg tggcggcggc 1380
ggcgggggag gggacaagag ccccccgggg tcggcggcgt ccaagcgggc gcggacggcg 1440
tacacgagcg cgcagctggt ggagctggag aaggagttcc attttaaccg ctacctgtgc 1500
cggcctcgcc gtgtagagat ggccaacctg ctgaacctca gcgagcggca gatcaagatc 1560
tggttccaga accggcgcat gaagtacaag aaggaccaga aggccaaggg attggcctcg 1620
tcgtcggggg gcccatctcc agccggcagc cccccgcagc ccatgcagtc cacggccggc 1680
ttcatgaacg ccttacactc catgaccccc agctacgaga gcccgtcccc acccgccttc 1740
ggtaaagccc accagaatgc ctacgcgctg ccctccaact accagccccc tctcaaaggc 1800
tgcggcgccc cgcagaagta ccctccgacc ccggcgcccg agtatgagcc gcacgtcctc 1860
caagccaacg gggcgcccta cgggacgccc accatgcagg gcagtccggt gtacgtgggc 1920
gggggcggct acgcggatcc gctgccgccc cctgccggcc cctccctcta tggcctcaac 1980
cacctttccc atcacccttc cgggaacctg gactacaacg gggcgccccc tatggcgccc 2040
agccagcacc acggaccctg cgaaccccac cccacctaca cagacctctc ctctcaccac 2100
gcgcctcctc ctcagggtag aatccaagaa gcgcccaaat taacacacct gtgatgggaa 2160

-continued

```
agggcgaacg aggattaggg gatggggagg aagagagaga ctgtggagct ctggggggca   2220

acctggaggt ctgaaaagag gagccagaga aggtggtacc caggcttcct ggtcagaacc   2280

ggcctggagc tccttccctt ccccctggcc tgagaggttg cttttaagtc ttccacccct   2340

tgttccatct gcctgccaac ccatcggaaa ggaatccaca tcatattgga gatgacccca   2400

tcaaccccag ggctccagca ctaccaagtt ggaattccac gcccgggagt ggggtagagg   2460

aagacgagac aggacgaggc agaaaagcac attttaaaaa ccagacaaga tggctaggcc   2520

atcaccaacc aacggactta ccttacatct ttgtaggtaa ttccccccaa atcttgattt   2580

ttttttttcc tcaattatcc tttaaaaaat aagaaaacac atttcaaacc caaaaggcac   2640

aaaacacgtt cccttccaac tttcccaaaa cctcaaattt gttcccattt gaggtttatt   2700

gaggtacact tctagccccc ggtttttctg ctctagaaca ttcatatcta tacatcccac   2760

ccccatcaat tacagttttt agagggctca gggatggtga gagatcctga aagagctgcc   2820

tatattataa attatataca ttttttttta aggaaaagtg tggaggctag ggcaggcagg   2880

ttgttaggac tgaaggtttg cccattctgc tgcctccatc tcagctccag ctccatcccc   2940

ctctccacag aaagcagttg gtgacacgag gttctatact tttcttctgt tgctctcttg   3000

acttaacgtg aaaacagggt atatttgaac aaactgtccc aggcaggggc tgggcagggc   3060

ctgtgtgcct tgctcagcct cctgacagga cacttttgtt gcacttagaa tttacatttt   3120

aatggatgta aaaacaactg tgagagatgt ctgggcctgc agaagtccag cattgctcaa   3180

aaaagcgtgt gttctagtga acattttcat atatatttat tggttatagc ctgttaaaat   3240

atttctttt ttgtattatt tatcccccta cattatgtat ttatatgagg gaaaaaaagg   3300

aaaaaattgt actttttag tatttacctg ttacaaagga cattgtgttt cctgtcatgt   3360

aaaaccagct attttagtta ctattgtact ctagaaaaga gctgtagatt tatgttaaac   3420

tcgtacttac gaacaattgt aattagttct aaaaggcatg aactcagctc ctaatcgtca   3480

ctgtatagtc ctgaatttgt agaactagag ttaattccct cttggaactt tctttgttct   3540

tcagtagtta cttttttcct tacctaaaag ggttgtctgt caaacaattc ttgaataaac   3600

tttctgttat caattttaaa aaaaaaa                                       3627
```

<210> SEQ ID NO 15
<211> LENGTH: 2042
<212> TYPE: DNA
<213> ORGANISM: Homo sapiens

<400> SEQUENCE: 15

```
ggaaaacgag tcaggggtcg gaataaattt tagtatattt tgtgggcaat tcccagaaat     60

taatggctat gagttctttt ttgatcaact caaactatgt cgaccccaag ttccctccat    120

gcgaggaata ttcacagagc gattacctac ccagcgacca ctcgcccggg tactacgccg    180

gcggccagag gcgagagagc agcttccagc cggaggcggg cttcgggcgg cgcgcggcgt    240

gcaccgtgca gcgctacgcg gcctgccggg accctgggcc cccgccgcct ccgccaccac    300

ccccgccgcc cccgccaccg cccggtctgt cccctcgggc tcctgcgccg ccacccgccg    360

gggccctcct cccggagccc ggccagcgct gcgaggcggt cagcagcagc cccccgccgc    420

ctccctgcgc ccagaacccc ctgcacccca gcccgtccca ctccgcgtgc aaagagcccg    480

tcgtctaccc ctggatgcgc aaagttcacg tgagcacggt aaaccccaat tacgccggcg    540

gggagcccaa gcgctctcgg accgcctaca cgcgccagca ggtcttggag ctggagaagg    600

aatttcacta caaccgctac ctgacacggc gccggagggt ggagatcgcc cacgcgctct    660
```

gcctctccga gcgccagatc aagatctggt tccagaaccg gcgcatgaag tggaaaaaag 720
accacaagtt gcccaacacc aagatccgct cgggtggtgc ggcaggctca gccggagggc 780
cccctggccg gcccaatgga ggcccccgcg cgctctagtg cccccgcacg cgggagccac 840
gaacctcggg gtgggggtgg gcagtgagtg caggggatgg ggtgggggga caggaggggg 900
ccctggggcc tgggccccgg aaaaatctat ctgccctccc ccacacttta tatacgaata 960
aacgcagaag agggggaggg gaagctttat ttatagaaat gacaatagag ggccacgggg 1020
aggccccccc agaagcaaga ttcaaatctc ttgctttctt tcttaaaaaa aagaaaaaga 1080
aaaagcaaga agaaggaaga aagaaaaaga cagaaagaga aataggagga ggctgcagct 1140
cctcgttttc agctttggcg aagatggatc cacgtttcat ctttaatcac gccaggtcca 1200
ggcccatctg tcttgtttcc tctgccgagg agaagacggg cctcggtggc gaccattacc 1260
tcgacacccg ctaacaaatg aggcccggct cggccgcctc cgcctctgct actgccgctg 1320
ctggaagaca gcctggattt cctttctttg tcccccactc ccgataccca gcgaaagcac 1380
cctctgactg ccagatagtg cagtgttttg gtcacggtaa cacacacaca ctctccctca 1440
tctttcgtgc ccattcactg agggccagaa tgactgctca cccacttcca ccgtggggtt 1500
gggggtgggc aacagaggag gggagcaagt agggaagggg gtggccttga caactcagga 1560
gtgagcagga aaattgagtc caaggaaaaa gagagactca gagacccggg agggccttcc 1620
tctgaaaggc caagccaagc catgcttggc agggtgaggg gccagttgag ttctgggagc 1680
tgggcactac tctgccagtc cagagttgta cagcagaagc ctctctccta gactgaaaat 1740
gaatgtgaaa ctaggaaata aaatgtgccc ctcccagtct gggaggagga tgttgcagag 1800
ccctctccca tagtttatta tgttgcatcg tttattatta ttattgataa tattattatt 1860
actatttttt tgtgtcatgt gagtcctctc tccttttctc tttctgacat tccaaaacca 1920
ggccccttcc tacctctggg gctgcttgag tctagaaccc ttcgtatgtg tgaatatctg 1980
tgtgctgtac agagtgacaa tagaaataaa tgtttggttt cttgtgacca gcaaaaaaaa 2040
aa 2042

<210> SEQ ID NO 16
<211> LENGTH: 1830
<212> TYPE: DNA
<213> ORGANISM: Homo sapiens

<400> SEQUENCE: 16
gtgaagcaca gggttataac gaccacgatc cacaaatcaa gccctccaaa atcacccaaa 60
tgagctcgta ctttgtaaac tccttctcgg ggcgttatcc aaatggcccg gactatcagt 120
tgctaaatta tggcagtggc agctctctga gcggctctta cagggatccc gctgccatgc 180
acaccggctc ttacggctac aattacaatg ggatggacct cagcgtcaac cgctcctcgg 240
cctcctccag ccactttggg gcggtgggcg agagctcgcg cgccttcccc gcgcccgccc 300
aggagccccg cttcaggcaa gcggcttcga gctgctccct gtcctcgccc gagtccctgc 360
cctgcaccaa cggcgacagc cacggcgcca agccctctgc ttcgtccccc tccgaccagg 420
cgacctcagc cagctccagc gccaatttca ccgaaataga cgaggccagc gcgtcctcgg 480
agcctgagga agcggcaagc cagctaagca gccccagcct agctcgggcg cagccagagc 540
ccatggccac ctccacagcc gcgcccgagg ggcagactcc gcaaatattc ccctggatga 600
ggaagcttca catcagccat gatatgaccg ggccggacgg gaaaagggcc cggaccgcgt 660

-continued

```
atacccgcta ccagaccctg gagctggaaa aggagttcca cttcaaccgc tacctgaccc    720

ggcgacggcg catcgagatc gcccacgcac tctgcctgtc cgagcgccag atcaagatct    780

ggttccagaa ccggcgcatg aagtggaaga aggacaacaa attgaaaagt atgagcctgg    840

ctacagctgg cagcgccttc cagccctgag cccgcccaga ggagcccagc ggcccaagag    900

cccgtgccac ccccagccct ggcccctcca atcctccccg ctctgccgcc gcccgctggg    960

gaccggttcc cacaagcctg cctcgccttg tgttacgata tttcgtttgg tcttaggtct   1020

tcctgtggct ccctctctcc tggactggtt atcttgttat tattgttaat aataattatt   1080

attattattt tccttccatg ctcccaactc ccttctgctt gtcccaaatc cgccagtgtt   1140

tctgaatgtt tgtgtctgtg gttgcagtct ttcccccagg aaaaaaaaaa aaagaaattc   1200

gcatgtttaa tgtgaactct cccctcccca tctgtgttct aacttattta taaaaagatg   1260

atcgctgtat tttgagtttc agctggaaac ttctgtaagg ggcagcagtt gaggtggggt   1320

agtgccgcag tggggtcaag ctgagctggc ttcggagatg gagtcccttt tcattctcct   1380

cctcctccct cctcactccc taggcccaag tctcctaggg gcttggtcct agggtgggaa   1440

ggggctaggg aggaccaaag ggatggtatt gagaagagag aaagaagata gtgagattta   1500

agttcctgct gcctgggtag gccccacaag gcctggtctg ggagtatacg gaaacaaaaa   1560

tgatcctcag tgcaaaatgt cttgtgtatt tctctgtgaa tccatgggtc tggctagagg   1620

gcccaaagct tgtaaatatg ggatagtctt gggtcagacc catctctccc ttacccatct   1680

tgcttccaag accatttgta gtgagcgagt ggatgctgtg ctacgtgtga aatctgtctt   1740

tgcggggcct gtctcagtga ttcgcttttg gtatttgttt gtagctttcc tggaagtcaa   1800

ataaatgttt cccccactcc aaaaaaaaaa                                     1830


<210> SEQ ID NO 17
<211> LENGTH: 1686
<212> TYPE: DNA
<213> ORGANISM: Homo sapiens

<400> SEQUENCE: 17

caccacacct aggtcggagc actgtcgtcc ttcagggctc cagcctcttg atatttttgt     60

acttcagtat cagctcgata gagcaaaaga gagagaggac gagagagggg gtcagagaag    120

gggaagcaac ggctctcacg ttgggacaat attatctgga agctgaagaa gaaactgaat    180

actccttcct tcctccccac ccattccttt aaatccggag ggggaaaaaa tcccaaggtc    240

tgcaaaggcg cggcgctcgg actataaaac acaacaaatc ataaacccgg cggagcagca    300

gcggccgcgc gcgcctcccc tcccaatgag ttcctatttc gtgaactcca ccttccccgt    360

cactctggcc agcgggcagg agtccttcct gggccagcta ccgctctatt cgtcgggcta    420

tgcggacccg ctgagacatt accccgcgcc ctacgggcca gggccgggcc aggacaaggg    480

ctttgccact tcctcctatt acccgccggc gggcggtggc tacggccgag cggcgccctg    540

cgactacggg ccggcgccgg ccttctaccg cgagaaagag tcggcctgcg cactctccgg    600

cgccgacgag cagcccccgt tccaccccga gccgcggaag tcggactgcg cgcaggacaa    660

gagcgtgttc ggcgagacag aagagcagaa gtgctccact ccggtctacc cgtggatgca    720

gcggatgaat tcgtgcaaca gttcctcctt tgggcccagc ggccggcgag gccgccagac    780

atacacacgt taccagacgc tggagctgga gaaggagttt cactacaatc gctacctgac    840

gcggcggcgg cgcatcgaga tcgcgcacgc cctgtgcctg acggagaggc agatcaagat    900

atggttccag aaccgacgca tgaagtggaa aaaggagagc aaactgctca gcgcgtctca    960
```

gctcagtgcc gaggaggagg aagaaaaaca ggccgagtga aggtgctgga aagggaggga 1020
ggacgcgagg ggaaaggcct gtggggagcc gagggcgtca gagagacccg ggaaggaagg 1080
ctctcgggtg ggggagccag gagacctgct ctccggcgca gacaggcggg gcccagcgct 1140
ctcctggacg cccccgcccg cacagctccc ggcgggtgct ctgaggcctc actactcgag 1200
cccacccagc atcccgcgcg cccttccttc ccgaggaact cgcctcagcc tgatcaggct 1260
tcctggtgag aactgaggag cggactcact tgatgtttcc tggaagcaga gcaaaatgct 1320
cttgtccctg tcgcgtctca ttttgtccat gtcccccgtg cacggttcaa tggtagattc 1380
gctgtcccct cagcgggggc cttgaagact ccctgatccc agacctgtcg tctctcccac 1440
cccctcccca aagccactgg aaggagcaca tactacctag aagtaagaag aggagcctca 1500
gaagaaaaca aagttctatt ttattaattt tctatgtgtt gtgtttgtag tcttgtctta 1560
gctctggacg tgaaatactt cgatgatgat gatgatgatg atgatgataa taataataat 1620
aataacaaca acaacaacaa taataaagat gtgaaaactc gacgctcggt cacctcaaaa 1680
aaaaaa 1686

<210> SEQ ID NO 18
<211> LENGTH: 1377
<212> TYPE: DNA
<213> ORGANISM: Homo sapiens

<400> SEQUENCE: 18
ggtccttttt ggtgtaaatc tggactctaa ttctgtaata tatcaaggaa tctcgtaaaa 60
ccgacactaa aacgtccctg cctacaaatc atccggccaa attatgagtt cattgtatta 120
tgcgaatact ttattttcta aatatccagc ctcaagttcg gttttcgcta ccggagcctt 180
cccagaacaa acttcttgtg cgtttgcttc caaccccccag cgcccgggct atggagcggg 240
ttcgggcgct tccttcgccg cctcgatgca gggcttgtac cccggcgggg ggggcatggc 300
gggccagagc gcggccggcg tctacgcggc cggctatggg ctcgagccga gttccttcaa 360
catgcactgc gcgccctttg agcagaacct ctccggggtg tgtcccggcg actccgccaa 420
ggcggcgggc gccaaggagc agagggactc ggacttggcg gccgagagta acttccggat 480
ctacccctgg atgcgaagct caggaactga ccgcaaacga ggccgccaga cctacacccg 540
ctaccagacc ctggagctgg agaaagaatt tcactacaat cgctacctga cgcggcggcg 600
gcgcatcgag atcgcgcaca cgctctgcct cacggaaaga cagatcaaga tttggtttca 660
gaaccggcgc atgaagtgga aaaaggagaa caagaccgcg ggcccgggga ccaccggcca 720
agacagggct gaagcagagg aggaagagga agagtgaggg atggagaaag ggcagaggaa 780
gagacatgag aaagggagag gaagagaagc ccagctctgg gaactgaatc aggaaactca 840
aatcgaatag ggaagtaaaa aaacaaaaca aaaaacaaaa aaaacaaaaa aaaaacccta 900
tttaaatgaa aggagtttaa aaacattttt taaggaggga gaaaggagaa attttggttt 960
ttcaacactg aaaaaatact acctatagga aagtctgtca ggtttggttt ttttgtacaa 1020
tatgaaaagg atattatcta cctgttctgt agctttctgg aatttacctc cccttttcta 1080
tgttgctatt gtaaggtctt tgtaaaatct tgcagttttg taagccctct ttaatgctgt 1140
ctttgtggac tgtgggtctg gactaaccct gtggttgcct gccctcctga gcctccgcct 1200
tcccagcagc ggcaccaagg ggccttaggg agccccaaaa cctaccactc gcgtgttccc 1260
caagcgcctg gctgctgctt cttgcttccc gtcccccagc cccatgctcc cttttacatt 1320

-continued ctgtgtgtat ctaaaggatg gaaaaataaa acgcaattaa aaataaaaaa aaaaaaa 1377

<210> SEQ ID NO 19
<211> LENGTH: 1834
<212> TYPE: DNA
<213> ORGANISM: Homo sapiens

<400> SEQUENCE: 19
ccttttctat tcctggaaac cacaaaaagt gtgtcggctt cgagatcttc ttcgcctttt 60
ctttcttttc ttttttccc tcctctcttt ccctctcctt tcctggcgag ggtgactagg 120
agccggcgaa tccgcgtttt tttctctctc tccctccctt tccccctccc cacccccctcc 180 ccaacagccc ccaactatag cctccgccgc cgccgccgcc tcaaaattca ataaaatgag 240
ctcttatttc gtcaactcac tgttctccaa atacaaaacc ggggagtccc tgcgccccaa 300
ttattatgac tgcggcttcg cccaggacct gggcggccga cccaccgtgg tgtacggtcc 360
cagcagcggc ggcagcttcc agcacccgtc gcaaatccag gagttctacc acgggccgtc 420
gtcgctgtcc acggctccct accagcagaa cccgtgcgcc gtggcgtgcc acggggaccc 480
cggcaatttc tacggctacg acccgctgca acgccagagc ctattcggtg cgcaggatcc 540
agacctggtg cagtacgcag actgcaagct tgccgccgcc agcggcctgg gcgaggaggc 600
cgagggctcc gagcagagcc cgtcgcccac acagctcttc ccctggatgc gcccgcaagc 660
agccgccgga cgcaggcgag gccgacagac ctacagccgc taccagaccc tggagctgga 720
gaaggagttc ctatttaatc cctatctgac tcgtaagcgg cgaatcgagg tatcgcacgc 780
cctgggactg acagagagac aggtcaaaat ctggttccag aaccggagga tgaagtggaa 840
aaaagagaac aacaaagaca agttccccag cagcaaatgc gagcaggagg agctggagaa 900
acagaagctg gagcgggccc cagaggcggc ggacgagggc gacgcgcaga agggcgacaa 960
gaagtaggct tcagctggga ctgccagggc cgcggccgcc cgcacgtccg cgggtcccgg 1020
ccgcgccgcc gccgcgcgcc cctgcccgag agagctctgg ccccgctagc ggggccagga 1080
gccgggcctc ccaccgcagc gtcccccgcc gcgccagtcc ccgctagtgg tagtatctcg 1140
taatagcttc tgtgtgtgag ctaccgtgga tctccttccc ttctcttggg ggccgggggg 1200
aaagaaaagg atttaagcaa aggctccctc gccctgtgag ggcgagcggc aaaggcccgg 1260
ctgagccccc catgcccctc ccctccccgt gtaaaaagcc tccttgtgca attgtctttt 1320
ttttcctttg aacgtgcttc tttgtaatga ccaaggtacc gatttctgct aagttctccc 1380
aacaacatga aactgcctat tcacgccgta attctttctg tctcccttct ctctctctct 1440
ctcgctcgct cgctctcgct ctcgctctct ctcgctgcgt cctcatttcc cctcccaatc 1500
ctctctcccc tctgcaaccc cccagctcgc tggctttctc tctggcttct ctcttttcct 1560
cctccaccca cccccttttgg tttgacaatt ttgtcttaag tgtttctcaa aagaggttac 1620
tttagttagc atgcgcgctg tgggcaattg ttacaagtgt tcttaggttt actgtgaaga 1680
gaatgtattc tgtatccgtg aattgcttta tgggggggag ggagggctaa ttatatattt 1740
tgttgttcct ctatactttg ttctgttgtc tgcgcctgaa aagggcggaa gagttacaat 1800
aaagtttaca agcgagaacc cgaaaaaaaa aaaa 1834

<210> SEQ ID NO 20
<211> LENGTH: 2711
<212> TYPE: DNA
<213> ORGANISM: Homo sapiens

<400> SEQUENCE: 20

```
attttgcaag gagagctgag acgggctgct ccactgtact ttgttggctg agaagttgag     60
cagggggtgg gggtgggagg gtgggggct ggggggtcg cgtccgaaag ccctcacacc    120
ggtccgggtg ccacctctcc ctgcttgggc gccgccgcgc gagcgcttcc cttccccctg    180
caagcgcccg gataatgtct gagaatgtcc atttctggga cgcttagcag ctattatgtc    240
gactcgatca taagtcacga gagtgaggac gcgcctccag ccaagtttcc ttctggccag    300
tacgcgagct cgcggcagcc gggccacgcg gagcacctgg agttcccctc gtgcagcttc    360
cagcccaaag cgccggtgtt cggcgcctcc tgggcgccgc tgagcccgca cgcgtccggg    420
agcctgccgt ccgtctacca cccttacatc cagccccagg gcgtcccgcc ggccgagagc    480
aggtacctcc gcacctggct ggagccggcg ccgcgcggcg aagcggcccc ggggcagggc    540
caggcggcgg tgaaggcgga gccgctgctg ggcgcgcctg ggagctgct caaacagggc    600
acgcccgagt acagtttgga aacttcggcg ggcagggagg ccgtgctgtc taatcaaaga    660
cccggctacg gggacaataa aatttgcgaa ggaagcgagg acaaagagag gccggatcaa    720
accaacccct ccgccaactg gctgcacgct cgctcttccc ggaaaaagcg ctgtccctac    780
accaaatacc agacgctgga gctagagaag gagtttctgt tcaatatgta cctcaccagg    840
gaccgtaggc acgaagtggc cagactcctc aatctgagtg agagacaagt caaaatctgg    900
tttcagaacc ggcggatgaa aatgaagaaa atgaataagg agcagggcaa agagtaaaga    960
ttaaagatta cccccagtcc tccctagctc ttccccatct cactcttagt tatgtgacga   1020
ctgcaaagcc agtgctgtct gggatgtatt caagtgaatg gggaagggag tctctcttcc   1080
aagtccttta tctgcaccta gaacctccct cctttccttt gcccttacct gtctctctct   1140
tctctctagg tgtcaggaga aagttttgtt gatttagaag atagaaatag ttggttccta   1200
agaatgtgat gggccacaag gaaagagaga ccccagtcaa gctcctagta tgccctgtaa   1260
tttttctggg aagtcctagc ccctcacttc cagcttgcct gtttcttctc tacacccacc   1320
caaaagtcac ccagggacac tccaactcta cacagctcag cagacatcca cacacagtaa   1380
tggggtgagc tcacaaccac cattcagtca agtgaggtga cactccagtt gcagaccatc   1440
gcacaccaaa tttggcaaaa cagccctcag actgtcaggc aagcccgggt tctacccta    1500
atgcaaatac ccaccaggga gatgtctaga ggcagactcc tgagtgaggt gttgcagccc   1560
aaaggctgca gcattgccat accattccca tggagttgcc aactattctc aggccaaggg   1620
ccatggggaa gatggagcaa acctagcccc caagccggtg ggctagaaag tacaagaaaa   1680
ggcagcacgt ggttttatga agctatctta ggtggagcta ctccccacct cccaccaaca   1740
tatacatttt gttgcaggaa atgtttaatt ccgcatgatg tttccctctc cttccaacaa   1800
aagaaggtca aactgtgggt cgtagagcct tgacaatgtt gtcctcctgt tcatctgtgc   1860
accacttgac agactgtagc ttctcttgct ctcgaccggc cctgcattct tccgcaccct   1920
ccctagctct gaaatcaact ctcttcggtc gtatccacct tgcacccgca agtcaagccg   1980
ccccttgtag aaaaatccct ccaccttccg ttccccgcta ggtcaacccc actgtagaca   2040
ggaaagccag gccaggagag tccgaatgag aatttattgt gaatcgattc ccaagctccc   2100
ttccgggaca agtggtctgg gacagggagg agcaacggcc ccagcgcgca acgctctgcg   2160
cgttcctccg aatcccgtcg gcttctcgac ccacgcagag aagccccggg cttggcggct   2220
ctagccccag cgccaaagga gacccgcccc agggccgggc ttggcctcct gcttcatggg   2280
cctggatgca gatctgcgtg gctggtgcgt gcgcgcgctt ctgggaaaca gtcccgcgtg   2340
```

caaaggaaag gggcaaaatg gcacctaagc atcagatgga agcttactct ctgcttccgt 2400
tcctccccct gctcccctac ttctcagtcc ccttcaattt gtagactctt gctcctgctt 2460
ctcctgatcc tgcaagggga cattccagta gaagtttttt gctttgtcgg tggctgtcgt 2520
gaaattgtgc ttgtgtttcg tgatttcttt gggggtgatt gtctcgcttg ttttcagttg 2580
tcgattatat gggagggttc tgggtgggag tggggagggc gaggggccta gagctctaat 2640
tgtttgtttt ggaagaaaaa aagaaaaaga acaaaaaata tatatcactc tagaaaataa 2700
aaaaaaaaaa a 2711

<210> SEQ ID NO 21
<211> LENGTH: 3047
<212> TYPE: DNA
<213> ORGANISM: Homo sapiens

<400> SEQUENCE: 21
tcttgcgtca agacggccgt gctgagcgaa tgcaggcgac ttgcgagctg ggagcgattt 60
aaaacgcttt ggattccccc ggcctgggtg gggagagcga gctgggtgcc ccctagattc 120
cccgcccccg cacctcatga gccgaccctc ggctccatgg agcccggcaa ttatgccacc 180
ttggatggag ccaaggatat cgaaggcttg ctgggagcgg gagggggcg gaatctggtc 240 gcccactccc ctctgaccag ccacccagcg gcgcctacgc tgatgcctgc tgtcaactat 300 gccccttgg atctgccagg ctcggcggag ccgccaaagc aatgccaccc atgccctggg 360
gtgccccagg ggacgtcccc agctcccgtg ccttatggtt actttggagg cgggtactac 420
tcctgccgag tgtcccggag ctcgctgaaa ccctgtgccc aggcagccac cctggccgcg 480
taccccgcgg agactcccac ggccggggaa gagtacccca gccgccccac tgagtttgcc 540
ttctatccgg gatatccggg aacctaccag cctatggcca gttacctgga cgtgtctgtg 600
gtgcagactc tgggtgctcc tggagaaccg cgacatgact ccctgttgcc tgtggacagt 660
taccagtctt gggctctcgc tggtggctgg aacagccaga tgtgttgcca gggagaacag 720
aacccaccag gtcccttttg gaaggcagca tttgcagact ccagcgggca gcaccctcct 780
gacgcctgcg cctttcgtcg cggccgcaag aaacgcattc cgtacagcaa ggggcagttg 840
cgggagctgg agcgggagta tgcggctaac aagttcatca ccaaggacaa gaggcgcaag 900
atctcggcag ccaccagcct ctcggagcgc cagattacca tctggtttca gaaccgccgg 960
gtcaaagaga agaaggttct cgccaaggtg aagaacagcg ctacccctta agagatctcc 1020
ttgcctgggt gggaggagcg aaagtggggg tgtcctgggg agaccaggaa cctgccaagc 1080
ccaggctggg gccaaggact ctgctgagag gcccctagag acaacaccct tcccaggcca 1140
ctggctgctg gactgttcct caggagcggc ctgggtaccc agtatgtgca gggagacgga 1200
accccatgtg acagcccact ccaccagggt tcccaaagaa cctggcccag tcataatcat 1260
tcatcctgac agtggcaata atcacgataa ccagtactag ctgccatgat cgttagcctc 1320
atattttcta tctagagctc tgtagagcac tttagaaacc gctttcatga attgagctaa 1380
ttatgaataa atttggaagg cgatcccttt gcagggaagc tttctctcag acccccttcc 1440
attacacctc tcaccctggt aacagcagga agactgagga gaggggaacg ggcagattcg 1500
ttgtgtggct gtgatgtccg tttagcattt ttctcagctg acagctgggt aggtggacaa 1560
ttgtagaggc tgtctcttcc tccctccttg tccaccccat agggtgtacc cactggtctt 1620
ggaagcaccc atccttaata cgatgatttt tctgtcgtgt gaaaatgaag ccagcaggct 1680
gcccctagtc agtccttcct tccagagaaa aagagatttg agaaagtgcc tgggtaattc 1740
accattaatt tcctccccca aactctctga gtcttccctt aatatttctg gtggttctga 1800
ccaaagcagg tcatggtttg ttgagcattt gggatcccag tgaagtagat gtttgtagcc 1860
ttgcatactt agcccttccc aggcacaaac ggagtggcag agtggtgcca accctgtttt 1920
cccagtccac gtagacagat tcacagtgcg gaattctgga agctggagac agacgggctc 1980
tttgcagagc cgggactctg agagggacat gagggcctct gcctctgtgt tcattctctg 2040
atgtcctgta cctgggctca gtgcccggtg ggactcatct cctggccgcg cagcaaagcc 2100
agcgggttcg tgctggtcct tcctgcacct taggctgggg gtgggggcc tgccggcgca 2160 ttctccacga ttgagcgcac aggcctgaag tctggacaac ccgcagaacc gaagctccga 2220
gcagcgggtc ggtggcgagt agtggggtcg gtggcgagca gttggtggtg ggccgcggcc 2280
gccactacct cgaggacatt tccctcccgg agccagctct cctagaaacc ccgcggcggc 2340
cgccgcagcc aagtgtttat ggcccgcggt cgggtgggat cctagccctg tctcctctcc 2400
tgggaaggag tgagggtggg acgtgactta gacacctaca aatctattta ccaaagagga 2460
gcccgggact gagggaaaag gccaaagagt gtgagtgcat gcggactggg ggttcagggg 2520
aagaggacga ggaggaggaa gatgaggtcg atttcctgat ttaaaaaatc gtccaagccc 2580
cgtggtccag cttaaggtcc tcggttacat gcgccgctca gagcaggtca ctttctgcct 2640
tccacgtcct ccttcaagga agccccatgt gggtagcttt caatatcgca ggttcttact 2700
cctctgcctc tataagctca aacccaccaa cgatcgggca agtaaacccc ctccctcgcc 2760
gacttcggaa ctggcgagag ttcagcgcag atgggcctgt ggggaggggg caagatagat 2820
gagggggagc ggcatggtgc ggggtgaccc cttggagaga ggaaaaaggc cacaagaggg 2880
gctgccaccg ccactaacgg agatggccct ggtagagacc tttgggggtc tggaacctct 2940
ggactcccca tgctctaact cccacactct gctatcagaa acttaaactt gaggattttc 3000
tctgtttttc actcgcaata aattcagagc aaacaaaaaa aaaaaaa 3047

<210> SEQ ID NO 22
<211> LENGTH: 3198
<212> TYPE: DNA
<213> ORGANISM: Homo sapiens

<400> SEQUENCE: 22
atttgaggtg ttctgaccag aagaagacag agcggatgat cattcattca ccacgttgac 60
aacctcgcct gtgattgaca gctggagtgg cagaaagcca tgagatttgg tagttgggtc 120
tgaggggcgc tcttttttt cctttcttt ctttctttct ttttttttt ttaaactgat 180 ttttgggggga gagaagatct gcttttttt gcccccgctg ctgtcttgga aacggagcgc 240
ttttatgctc agtgactcgg gcgctttgct tcaggtcccg tagaccgaag atctgggacc 300
agtagctcac gttgctggag acgttaaggg atttttcgtc gtgctttttt tttttttttt 360
ttttttttcc gggggagttt gaatatttgt ttcttttcac actggcctta aagaggatat 420
attagaagtt gaagtaggaa gggagccaga gaggccgatg gcgcaaaggt acgacgatct 480
accccattac gggggcatgg atggagtagg catcccctcc acgatgtatg gggacccgca 540
tgcagccagg tccatgcagc cggtccacca cctgaaccac gggcctcctc tgcactcgca 600
tcagtacccg cacacagctc ataccaacgc catggccccc agcatgggct cctctgtcaa 660
tgacgcttta aagagagata aagatgccat ttatggacac cccctcttcc ctctcttagc 720
actgattttt gagaaatgtg aattagctac ttgtaccccc cgcgagccgg gggtggcggg 780

-continued

```
cggggacgtc tgctcgtcag agtcattcaa tgaagatata gccgtgttcg ccaaacagat    840
tcgcgcagaa aaacctctat tttcttctaa tccagaactg gataacttga tgattcaagc    900
catacaagta ttaaggtttc atctattgga attagagaag gtacacgaat tatgtgacaa    960
tttctgccac cggtatatta gctgtttgaa agggaaaatg cctatcgatt tggtgataga   1020
cgatagagaa ggaggatcaa aatcagacag tgaagatata acaagatcag caaatctaac   1080
tgaccagccc tcttggaaca gagatcatga tgacacggca tctactcgtt caggaggaac   1140
cccaggccct tccagcggtg gccacacgtc acacagtggg gacaacagca gtgagcaagg   1200
tgatggcttg gacaacagtg tagcttcccc cagcacaggt gacgatgatg accctgataa   1260
ggacaaaaag cgtcacaaaa agcgtggcat ctttcccaaa gtagccacaa atatcatgag   1320
ggcgtggctg ttccagcatc taacacaccc ttacccttct gaagaacaga aaaagcagtt   1380
ggcacaagac acgggactca ccatccttca agtgaacaat tggtttatta atgcccggag   1440
aagaatagtg cagcccatga tagaccagtc caaccgagca gtaagtcaag gaacacctta   1500
taatcctgat ggacagccca tgggaggttt cgtaatggac ggtcagcaac atatgggaat   1560
tagagcacca ggacctatga gtggaatggg catgaatatg ggcatggagg ggcagtggca   1620
ctacatgtaa ccttcatcta gttaaccaat cgcaaagcaa gggggaaggc tgcaaagtat   1680
gccaggggag tatgtagccc ggggtggtcc aatgggtgtg agtatgggac agccaagtta   1740
tacccaaccc cagatgcccc cccatcctgc tcagctgcgt catgggcccc ccatgcatac   1800
gtacattcct ggacaccctc accacccaac agtgatgatg catggaggac cgccccaccc   1860
tggaatgcca atgtcagcat caagccccac agttcttaat acaggagacc caacaatgag   1920
tggacaagtc atggacattc atgctcagta gcttaaggga atatgcattg tctgcaatgg   1980
tgactgattt caaatcatgt tttttctgca atgactgtgg agttccattc ttggcatcta   2040
ctctggacca aggagcatcc ctaattcttc atagggacct ttaaaaagca ggaaatacca   2100
actgaagtca atttggggga catgctaaat aactatataa gacattaaga gaacaaagag   2160
tgaaatattg taaatgctat tatactgtta tccatattac gttgtttctt atagattttt   2220
taaaaaaaat gtgaaatttt tccacactat gtgtgttgtt tccatagctc ttcacttcct   2280
ccagaagcct ccttacatta aaaagcctta cagttatcct gcaagggaca ggaaggtctg   2340
atttgcagga tttttagagc attaaaataa ctatcaggca gaagaatctt tcttctcgcc   2400
taggatttca gccatgcgcg cgctctctct ctttctctct cttttcctct ctctccctct   2460
ttctagcctg gggcttgaat ttgcatgtct aattcattta ctcaccatat ttgaattggc   2520
ctgaacagat gtaaatcggg aaggatggga aaaactgcag tcatcaacaa tgattaatca   2580
gctgttgcag gcagtgtctt aaggagactg gtaggaggag gcatggaaac caaaaggccg   2640
tgtgtttaga agcctaattg tcacatcaag catcattgtc cccatgcaac aaccaccacc   2700
ttatacatca cttcctgttt taagcagctc taaaacatag actgaagatt tatttttaat   2760
atgttgactt tatttctgag caaagcatcg gtcatgtgtg tatttttttca tagtcccacc   2820
ttggagcatt tatgtagaca ttgtaaataa attttgtgca aaaaggactg gaaaaatgaa   2880
ctgtattatt gcaatttttt tttgtaaaag tagcagtttg gtatgagttg gcatgcatac   2940
aagatttact aagtgggata agctaattat actttttgtt gtggataaac aaatgcttgt   3000
tgatagcctt tttctatcaa gaaaccaagg agctaattat taataacaat cattgcacac   3060
tgagtcttag cgtttctgat ggaaacagtt tggattgtat aataacgcca agcccagttg   3120
tagtcgtttg agtgcagtaa tgaaatctga atctaaaata aaaacaagat tatttttgtc   3180
```

```
aaaaaaaaaa aaaaaaaa                                                 3198

<210> SEQ ID NO 23
<211> LENGTH: 2911
<212> TYPE: DNA
<213> ORGANISM: Homo sapiens

<400> SEQUENCE: 23

gcggccgcct cccccteccc ctccccctct ttcttctcct ccctcgtcgc cgccgccgcc      60

gccgccgcct cagccttcgc ctcagccgcc gcccgctccc gcccgcgcgc ggcgggatgg     120

acgatcaatc caggatgctg cagactctgg ccggggtgaa cctggctggc cactcggtgc     180

aggggggcat ggccctgccg cctcccccgc acggccacga aggggcggac ggcgacggca     240

ggaagcagga catcggcgac atcctccacc agatcatgac catcaccgac cagagcttgg     300

acgaggcgca agcaaagaaa catgccctga actgtcacag aatgaaacca gcgctcttca     360

gcgtcctgtg tgagatcaaa gagaaaacag gtctcagcat cagaggagcc caggaggagg     420

accctcccga tccccagcta atgagactgg acaatatgct tttggcagaa ggggtttcag     480

gtcctgagaa aggtggggga tcggcggcag cagctgcagc cgcggcagcc tctggaggtt     540

cttcagataa ctctattgaa cactcagatt acagagccaa attgacccag atcagacaaa     600

tctatcacac agaactggag aaatatgaac aggcatgtaa tgaatttact acacatgtga     660

tgaaccttct ccgagaacag agtagaacac gtcccatttc tccaaaagag attgaaagaa     720

tggtgggcat catccatcga aaatttagtt ccattcagat gcagctcaaa caaagcactt     780

gtgaagcagt tatgatttta agatcaaggt tccttgatgc cagacggaaa aggcgtaact     840

tcagtaaaca ggccacagaa atcttgaatg aatattttta ctcacacctc agcaacccct     900

accccagtga agaagccaaa gaggagctgg ccaagaaatg cagcatcaca gtgtcacagg     960

tatccaattg gtttggcaac aaacgaatca ggtacaagaa gaacattggc aagtttcagg    1020

aagaagccaa cctctatgct gcaaagacgg ccgtgacagc tgcacacgca gtagcagcag    1080

ctgtgcagaa caaccagacc aattcgccca ccacaccaaa ttccggttct tctggttctt    1140

ttaacctccc aaattctggg gacatgttca tgaacatgca gagtctgaat ggggattctt    1200

accaagggtc ccaagtcgga gccaatgtgc aatcacaggt ggataccctc cgtcatgtta    1260

tcaatcagac gggaggctac agtgatggcc ttggaggaaa ttcactgtac agtccacata    1320

atttaaatgc taatggaggc tggcaggacg caacaactcc atcttctgtg acttctccta    1380

cagaaggccc aggaagtgtg cactcggata cctctaacta atctctggcc acacttttcc    1440

ctgagctaca tgccttgata agtgcattca gagcaatagg aggaaaagga aagcgttttt    1500

gtagcccacc atctacagct ttactgtaaa accttgtctt attcgagaac ttggtaaatc    1560

tgttttttaa ggaatcataa tcatttgtat ttatacttaa aaacacacaa tgttaaaaaa    1620

aataaagcac tttatccaat taggccaaga tttaacattg ttgacagtcc tgtagctatt    1680

ttatcataat ttattatcaa tattttacat taatggtttc acagttgcca attacttggc    1740

cttaagggta aaaagtacaa tatacactaa acctcaaccg ttaaagcaga tgcaaaaatt    1800

cacctcacct aaattgaact tcttgcatat ttccattact gacttggatt gtctttcttt    1860

catatcacta atggagttgg aataaagagc tgtttgccta tccctgttaa tgatggttgt    1920

gtttaagaat cttcctcgtc acgtttgtgt tcagatctct tatgttataa ttagatcaga    1980

gactggtagc atcgtttctc tctctgaaag caccagtgcc cagagtctgc tcggtaataa    2040
```

```
aattatggat ccagattgtt ctgagagacg aagatacttg ctgctgatag aggtgaaaac   2100
gagattgatc cgtctggggt tttacggtgt gcactgggtg ctgcacagac ttgtcaaggt   2160
ttgctacgtc ctctgggcat ctgcaaaagg ccctgctctc tggagtgttg tatatagtgt   2220
agcaaaagag tatttataca tcccaccaat caaaacacag ctttattacc tcatgcgaac   2280
tcatacaaac caatagaatt tcaacatgtt ctgtagctta gagtgctcac ttactacctc   2340
tgaacaatac tcacgctgta gtttgtctct ttcttatctt tttgcatctt gtaattaact   2400
ctttgtttcc cttcataaaa tgtaatgtac attgtaatct tttaaaagaa aaatcagggt   2460
tgcacttgca acttttaaaa aaccgagtgt ggaaacattg ggtcttaatt caacacagga   2520
tcggtaaaac tgttgtaaat actgagaaac attttgaatg ttcttcatct tattactaat   2580
ccatgcaaaa aaaaaaaaaa aagcagcgac taattgtgat gcattcagat ttcagtattc   2640
agtactgtat atttcaccct gtgtaatggg gccccctctc ctttctctct ttttgtattg   2700
tatgcgattc tgaaactgat tgagtcatga aaataatttg tggcggtgat tctaatgtat   2760
taaaaacgtt tcgtgttcct ttctaactgg attacaccct ggattgaaaa agtcttcctc   2820
gtggtagtta tatgtagttt caaacatgaa taaacttttt gctttcatga ttaaaaaaaa   2880
aaaaaaaaaa aaaaaaaaaa aaaaaaaaaa a                                  2911
```

<210> SEQ ID NO 24
<211> LENGTH: 2872
<212> TYPE: DNA
<213> ORGANISM: Homo sapiens

<400> SEQUENCE: 24

```
aggaggagga ggaagatcag gaggaggagg aagaagagga aaaaagagaa aaagaagaaa     60
tatcacagaa aaaaaaattc ttcgttgtct agactgggct ttttttcccc cctaaaaaat    120
agcatattgg agaattggga gaagtctctt tggtttggaa aaaaaaaaaa ggaatcttca    180
gcctagatca ctttcttatc cggactggga tattaaatat acgacacatc caggagttta    240
ttggagcgca gactgatggc gcaaaggtac gatgagctgc cccattacgg cgggatggac    300
ggagtagggg ttcccgcttc catgtacgga gaccctcacg cgccgcggcc gatcccccg    360
gttcaccacc tgaaccacgg gccgccgctc cacgccacac agcactacgg cgcgcacgcc    420
ccgcacccca atgtcatgcc ggccagtatg ggatccgctg tcaacgacgc cttgaagcgg    480
gacaaggacg cgatctatgg gcacccgttg tttcctctgt tagctctggt ctttgagaag    540
tgcgagctgg cgacctgcac tccccgggaa cctggagtgg ctggcggaga cgtctgctcc    600
tccgactcct tcaacgagga catcgcggtc ttcgccaagc aggttcgcgc cgaaaagcca    660
ctttttttcct caaatccaga gctggacaat ttgatgatac aagcaataca agtactaagg    720
tttcatcttt tggagttaga aaaggtccac gaactgtgcg ataacttctg ccaccgatac    780
attagctgtt tgaaggggaa aatgcccatc gacctcgtca ttgatgaaag agacggcagc    840
tccaagtcag atcatgaaga actttcaggc tcctccacaa atctcgctga ccataaccct    900
tcttcttggc gagaccacga tgatgcaacc tcaacccact cagcaggcac cccagggccc    960
tccagtgggg gccatgcttc ccagagcgga gacaacagca gtgagcaagg ggatggttta   1020
gacaacagtg tagcttcacc tggtacaggt gacgatgatg atccggataa ggacaaaaaa   1080
cgccagaaga aaagaggcat tttccccaaa gtagcaacaa atatcatgag agcatggctc   1140
ttccagcatc tcacacatcc gtacccttcc gaagagcaga agaaacagtt agcgcaagac   1200
acaggactta caattctcca agtaaacaac tggtttatta atgccagaag aagaatagta   1260
```

-continued

```
cagcccatga ttgaccagtc aaatcgagca ggttttcttc ttgatccttc agtgagccaa   1320

ggagcagcat atagtccaga gggtcagccc atggggagct ttgtgttgga tggtcagcaa   1380

cacatgggga tccggcctgc aggacctatg agtggaatgg gcatgaatat gggcatggat   1440

gggcaatggc actacatgta accttcatca tgtaaagcaa tcgcaaagca agggggaagt   1500

ttgcagagca tgccagggga ctacgtttct cagggtggtc ctatgggaat gagtatggca   1560

cagccaagtt acactcctcc ccagatgacc ccacacccta ctcaattaag acatggaccc   1620

ccaatgcatt catatttgcc aagccatccc caccacccag ccatgatgat gcacggagga   1680

ccccctaccc accctggaat gactatgtca gcacagagcc ccacaatgtt aaattctgta   1740

gatcccaatg ttggcggaca ggttatggac attcatgccc aatagtataa gggaactcaa   1800

gggaaaagga aacacacgca aaaactattt taagactttc tgaactttga ccagatgttg   1860

acacttaata tgaaattcca gacagctgtg attatttttt acttttgtca tttttcatca   1920

agcaacagag gaccaatgca acaagaacac aaatgtgaaa tcatgggctg actgagacaa   1980

ttctgtccat gtaaagatcc tctggaaaaa gactccgaga gttataacta ctgtagtata   2040

aatataggaa ctaagttaaa cttgtacatt tctgttgatc acgccgttat gttgcctcaa   2100

atagttttag aagagaaaaa aaaatatatc cttgttttcc acactatgtg tgttgttccc   2160

aaaagaatga ctgttttggt tcatcagtga attcaccatc caggagagac tgtggtatat   2220

attttaaacc tgttgggcca atgagaaaag aaccacactg gagatcatga tgaacttttg   2280

gctgaacctc atcactcgaa ctccagcttc agaatgtgtt ttcatgcccg gcctttgttc   2340

ctccataaat gtgtccttta gtttcaaaca gatctttata gttcgtgctt cataagccaa   2400

ttcttattat tatttttggg ggactcttct tcaaagagct tgccaatgaa gatttaaaga   2460

cagagcagga gcttcttcca ggagttctga gccttggttg tggacaaaac aatcttaagt   2520

tgggcagctt tcctcaacac aaaaaaaagt tattaatggt cattgaacca taactaggac   2580

tttatcagaa actcaaagct tggggggataa aaaggagcaa gagaatactg taacaaactt   2640

cgtacagagt tcggtctatt aattgtttca tgttagatat tctatgtgtt tacctcaatt   2700

gaaaaaaaaa agaatgtttt tgctagtatc agatctgctg tggaattggt attgtatgtc   2760

catgaattct tcttttctca gcacgtgttc ctcactagaa gaaaatgctg ttacctttaa   2820

gctttgtcaa atttacatta aaatacttgt atgaggactg tgacgttatg tt           2872
```

```
<210> SEQ ID NO 25
<211> LENGTH: 500
<212> TYPE: DNA
<213> ORGANISM: Homo sapiens

<400> SEQUENCE: 25

tactaccaaa ggtgttgaaa gaggaaatca gcaccaactg ggggaatgaa taagaactcc     60

cattagcagg tgggtttagc gctgggagag ctttggtcag tgttgttagg tcactgtttg    120

tgaactgact gcagaacata cataatgaaa cattcctatc catcctgagc agtatcagag    180

gaagtaattc cttcacatgg aaagtatcaa accatgatga ttccttgagt cagcaaaact    240

gtaagagaaa ttcaatccca gtgtattttc gcaatatatt caatatgaat tgaacaacta    300

ggtgagcctt ttaatagtcc gtgtctgggc aggacctgga agacagaagg tggcccaggg    360

agaatcacag agtctgcagg gacaaggaca tagcctcctt tgcttgcaaa ttaagggagc    420

cctttcccgg tccagcccag tctctcgtct ccctgtgtag ccttgggcta gtcacttccc    480
```

-continued

```
ctctcttggc cccggttccc                                             500


<210> SEQ ID NO 26
<211> LENGTH: 3705
<212> TYPE: DNA
<213> ORGANISM: Homo sapiens

<400> SEQUENCE: 26

tgaagaccag ctgggagccc actgcctgct gccacctcca actccggccc cctcaccatg     60

cactccctgg acgagccgct cgacctgaag ctgagtatca ccaagctccg ggcggcaaga    120

gagaagcggg agaggacgct gggtgtggtc cggccccgtg ctctgcacag ggagctgggc    180

ctggtggatg acagccccac acctggctct ccaggctccc cgccctcagg cttcctgctg    240

aactccaagt tccccgagaa ggtggaggga cgcttttcag cagcccctct cgtggacctc    300

agcctgtcac caccatctgg gctggactcc cccaatggca gcagctcgct gtcccccgag    360

cgccagggca acggggacct gcctccagtg cccagtgcct cggacttcca gccactgcgc    420

tatttggatg gtgtccccag ctccttccag ttcttcctgc ccctcggctc cggggggggcc    480

ctgcacctgc ctgcctcctc cttccttacc cctcccaagg acaagtgcct ctcgccagac    540

ctgcccctgc ccaagcagct ggtgtgtcgc tgggccaagt gtaaccagct ctttgagctc    600

ctgcaagacc tggtggacca tgtcaacgat taccatgtca agcccgagaa ggatgcgggg    660

tactgctgcc actgggaggg ctgcgcccgc catggccgag gtttcaacgc caggtacaag    720

atgctcatcc acatccgcac acacaccaac gagaagccac accgctgtcc gacctgcagc    780

aagagcttct cccgcctgga gaacctgaag atccacaacc ggtcgcacac aggtgagaag    840

ccctacgtct gcccctacga gggctgcaac aagcgctatt ccaactccag tgaccgcttt    900

aagcacacgc gcacccacta tgtggacaag ccctactact gcaagatgcc cggctgccac    960

aagcgctaca cggaccccag ctcactgcgc aagcacatca aggcccatgg ccactttgtg   1020

tcccacgagc agcaagagct cctgcagctg cgcccacccc ccaagccgcc actgcccgcc   1080

cccgacggcg gcccctatgt cagtggggcc cagatcatca tccccaaccc agctgccctc   1140

tttggaggcc ctggcctgcc cggcttaccc ctacccctgg cccccggccc ccttgacctc   1200

agtgccctgg cctgtggcaa cggtgggggc agtgggggtg gggggggcat gggccctggg   1260

ctgccaggcc ccgtcctgcc tctcaatctg gccaagaacc cgctgctgcc ctcgcccttt   1320

ggggctggcg gactgggctt gcctgtggtc tccctccttg ctggcgcagc tggtggcaag   1380

gccgaggggg agaaggggcg tgggtcggtg cccaccaggg ccctgggcat ggagggccac   1440

aagacgcccc ttgaaaggac ggagagcagc tgctcccggc caagccccga tggactcccc   1500

ctgctgccag gcaccgtgct ggacctgtcc acgggcgtca actcagctgc cagcagccca   1560

gaggcgttgg cccctggctg ggtggtcatc ccgccgggct cggtgctgct caaaccggct   1620

gtggtgaact gagcccatcc tgcggacagt tgtggtgccc ccccggcagc tcccggcact   1680

gcccccgacg aacggaaact cttctgtgaa atagcaataa tgtcctactg cccgggcagc   1740

cccagcccag cccgccggga gcaaggatgg tgctaggtca ttcatggctg gcctcccagc   1800

ccccgggtgg ggacctggcc tgtcatgcag ggagagctgt gctcctgggt gctgaagcct   1860

cgctcctgtc tgtcccccac cacctggccc tcagcttctg agaggctttc ccctgcccga   1920

cctcctcccg tttccctctc ccaccctggc acctccctca cctagtgacc acccatggca   1980

agttgccctc tcccagcaga gggggtgggt ggggtggcat ctgccctccc tgctagcacc   2040

aggctccccc ttcctgagag gagcccccag ggaccagagg cctgcccttc cctcctaggc   2100
```

ttacccagcc cctgccctgg gggctccttg gacccctttc cctctgaccc tgcctccaga 2160
gggaaagcaa gacagatgca ggcccctgca aagccccagg tagaagcatg ccccccagga 2220
caaggcgcct cccactagtt aggaggaggc ccgctctgca gccgccgtcc tcaccccagg 2280
ccaggcctgc agtaccagac gggatagctg gccactccac ccctgcaccc cagggtctcc 2340
tccctctacc ttttggggca ccctgggagc gtgggaagca ggtccgaggg cccctgagct 2400
ggcaagggga ggtgccaggc cagctgtggt gccaagatac tgagtgacct gggccctggc 2460
tcagggagca tgtggggcca ggcccagcgc cccgtcttcc tccttctacc cccgctgggc 2520
ctggcctggg cagcgccccc tgcagaggcc tttgggtcct tggtcctgta acaggaaggg 2580
ggaggctggc tggggacgac cgaccacagg ctgggacaca gctcctggtc tgggggctcc 2640
aagtgacagc atgcagggga gggggctccc agtcagtgct gtgttgggag ctttctggag 2700
gctgtggact gaaggccttg agggaagcag tggctggagg agggtgctgg acccatgaca 2760
cgttgcttcc tctggctttt ccctgctggg ccgctttctc agaggcactt ccccacccct 2820
aacacccagt gggccccccc aggttctgtg ccactcagag ggaccctggc aggggccaga 2880
accacttaag ggtggtgctg gagggccttg tgccccagtc ccatcccagg acgccctgag 2940
ggatggacgc agccatgcac cccccatctg gggcctctcc ctgctccctc tcccacctgg 3000
cagctgggag ttctggcttc taggcctgcc ctgtcaccag gcctctgagt ggccaggccc 3060
ttccacctcc ccatctgtaa aacgaggcag ctgcccggac agccttgggg tccttagtgg 3120
ccctgcaggt cctctggcag ctctgctgac cccaccctct cccggactgc ccttctgtcc 3180
cagaggggtc accctgaccc ggcccacctt gccactgggc tttggactcc agccctgaca 3240
gggcccagcc acactggctc tgcccctcga aggggctatg agcaaggtag gagggagctg 3300
gtctcctttc ttcgggcccc acccaggccc tgagcacccc ccacccctgt gagggcccca 3360
ggccttaagt ccctggcggg gtcatgggtt tgcgacttga gcagagcgga ggaacagggc 3420
actggaaggc cgacgagctc agcatgcgac tcggtgacgg accaggctcg gcagggccgg 3480
tgtacttttt gtggttgtca ttggtgtgtt gttgcacatt ccaggacgtc agtattttaa 3540
caggttctaa gtgcctttct atcgtagctt atgttttcct cctcttggct ccattgctgt 3600
tagcatagag ttttaaaaaa agagataagc taatgactat aacaatatat tcctccatgg 3660
gagaggaagt ttataaagaa acaataaaag tgagttgcaa agatg 3705

<210> SEQ ID NO 27
<211> LENGTH: 3732
<212> TYPE: DNA
<213> ORGANISM: Homo sapiens

<400> SEQUENCE: 27
ggccctctgc gcgctgcgcc cgaagcggcg gtcggtggca ggggtggtag cggcggcggc 60
gacggtttcg tgggggccgc gcgctgctct gtgagcggcg ggtggcagca ggggactcct 120
gacacttccc cttccccacc gaaccgcgct ttctgaaaca aagactcatt ttgaagatgt 180
ttaacaaatc atttggaaca ccctttgggg gtggcacagg tggctttggc acaacttcaa 240
catttggaca gaatactggc tttggcacta ctagtggagg ggcatttgga acatctgcat 300
ttggttctag caacaatact ggaggcctct ttggaaattc acagactaaa ccaggaggat 360
tgtttggaac cagttcattt agccagccag ctacctccac aagcactggc tttgggtttg 420
gtacgtcaac aggaacagca aataccttgt ttggaactgc aagcacaggg accagtctct 480

-continued

```
tctcatccca aaacaatgcc tttgcacaaa ataaaccaac tggctttggc aattttggaa    540
ccagtactag cagtggagga ctctttggaa ccacaaatac cacctctaat ccttttggca    600
gcacatctgg ctccctcttt gggccaagta gttttacagc tgctcctact gggactacta    660
ttaaatttaa ccctccaact ggtacagata ctatggtcaa agctggagtt agcactaaca    720
taagtaccaa gcaccagtgt attactgcta tgaaagaata tgaaagcaag tcactagagg    780
aacttcgttt agaggattat caggctaaca ggaagggccc acagaaccag gtgggagcag    840
gtaccacaac tggcttgttt gggtcttctc cagccacttc cagcgcaaca ggactcttca    900
gctcctccac cactaattca ggctttgcat atggtcagaa caaaactgcc tttggaacta    960
gtacaactgg atttggaaca aatccaggtg gtctctttgg ccaacagaat cagcagacta   1020
ccagcctctt cagcaaacca tttggccagg ctacaaccac ccagaacact ggcttttcct   1080
ttggtaatac cagcaccata ggacagccaa gcaccaacac catgggatta tttggagtaa   1140
cccaagcctc acagcctgga ggtctttttg ggacagctac aaacaccagc actgggacag   1200
catttggaac aggaacaggt ctctttgggc agaccaatac tggatttggt gctgttggtt   1260
cgaccctgtt tggcaataac aagcttacta catttggaag cagcacaacc agtgcacctt   1320
catttggtac aaccagtggc gggctctttg gtaacaaacc aaccctgact ttaggaacca   1380
atacaaacac ttctaatttt ggttttggca caaataccag tgggaatagt atttttggaa   1440
gtaaaccagc acctgggact cttggaactg ggcttggtgc aggatttgga acagctcttg   1500
gtgctggaca ggcatctttg tttgggaaca accaacctaa gattggaggg cctcttggta   1560
caggagcctt tggggcccct ggatttaata ctacgacagc cactttgggc tttggagccc   1620
cccaggcccc agtagctttg acagatccaa atgcttctgc tgcccagcag gctgttctcc   1680
agcagcacat caatagtcta acatactcac cttttggaga ctctcctctc ttccggaatc   1740
cgatgtcaga ccctaagaag aaggaagaga gattgaaacc aacaaatcca gcagcccaga   1800
aggctcttac tacacctact cattataaac tgacaccccg ccctgccact agagtccggc   1860
caaaggcttt acaaacaaca ggcacagcca agtcacatct ctttgatggg ctggatgacg   1920
atgaaccatc cctagccaat ggagcattca tgcccaagaa gagcattaag aagttggttt   1980
tgaagaacct taataatagc aatctctttt ctcctgttaa tcgtgattca gaaaatctag   2040
cttcaccatc tgaatatcca gaaaatggag agagatttag tttcctaagc aaacctgttg   2100
atgagaatca ccagcaggat ggagatgaag attcccttgt ttcacatttt tatactaacc   2160
ctattgccaa acctattcct caaaccccag aaagtgctgg aaataaacac agcaacagca   2220
acagtgtgga tgataccatt gttgcattaa acatgcgtgc tgctttgcga aatgggctgg   2280
aaggaagcag tgaagaaacg tcttttcatg atgagtcact tcaggatgac cgagaagaaa   2340
tagaaaataa ttcttaccat atgcacccag caggtattat tctcactaag gttggttact   2400
atactattcc atctatggat gaccttgcta aaattaccaa tgaaaaagga gagtgcattg   2460
tctctgattt cactattggt cggaaaggtt atggttcaat ctattttgaa ggagatgtga   2520
atttgacaaa tctaaatttg gatgatattg tgcatatccg gaggaaagaa gtagttgtct   2580
acttagatga taaccaaaaa ccacctgtgg gtgaagggct aaataggaag gctgaagtta   2640
cattggatgg agtttggcca acagataaaa catctcgttg tttaataaag agcccagatc   2700
gccttgctga tatcaactat gaaggaagat tggaagcagt ttcaaggaaa cagggagctc   2760
aattcaaaga ataccggcct gaaactggtt cttgggtgtt taaggtctcc catttttcta   2820
agtatggcct tcaggattct gatgaagagg aggaggagca tccgtctaaa actagtacaa   2880
```

-continued agaagttgaa gactgctcct ttgcctcctg caagccagac tacgcccttg cagatggctc 2940
ttaatggcaa acctgcacct ccacctcagg tagagaaaaa aggacagtga atttgaatgg 3000
aatccgtgat accgaagttg aaagcaagtc attcagctaa tacaaagctg ttttatgacc 3060
cttggaactt tgaagagtac aaacattggc aatcacgttg aaacaagtgc aagggagggc 3120
gtgaggtctt gcaggcatct gtctttttac tggagagatt taaagaattc tcttgctgtt 3180
tggattattc ctctacagat tgtcattttt aaaccctttg ttctctctca tttggacttg 3240
ctgaattctc tgctcagtga ttaacttaag atttgctcat gtgggttcat gcacagtaaa 3300
ttctgccttt attgactacc tgatgtgcag tttaatcttt ttctttacct ccatggtttt 3360
ttaaaagtta aattagcttt ctgaaagggt ttttaatctc catttttta aagttgtttg 3420 cttatacttc gggtaacctt gatatttgta ttttaatagt acataatctt tatgaaaaat 3480
agtttgggaa tgtaaatgaa ttattatttg gcttggggag attagggcct acattgttta 3540
tcgcaattac ttgtatcatt gatacgggat ttctttgtaa agcatcctct acctctcagc 3600
tgctgaaagc tagacctttg gtattttcca tgctataatt cttatggctg ctgaaatgtg 3660
tggtttttat gatttattaa ataatctctt aggaggcaaa aaaaaaaaaa aaaaaaaaaa 3720
aaaaaaaaaa aa 3732

<210> SEQ ID NO 28
<211> LENGTH: 8115
<212> TYPE: DNA
<213> ORGANISM: Homo sapiens

<400> SEQUENCE: 28
ggttgatgcc ggcccaggat ggatcagacc tgtgaactac ccagaagaaa ttgtctgctg 60
cccttttcca atccagtgaa tttagatgcc cctgaagaca aggacagccc tttcggtaat 120
ggtcaatcca atttttctga gccacttaat gggtgtacta tgcagttatc gactgtcagt 180
ggaacatccc aaaatgctta tggacaagat tctccatctt gttacattcc actgcggaga 240
ctacaggatt tggcctccat gatcaatgta gagtatttaa atgggtctgc tgatggatca 300
gaatcctttc aagaccctga aaaaagtgat tcaagagctc agacgccaat tgtttgcact 360
tccttgagtc ctggtggtcc tacagcactt gctatgaaac aggaaccctc ttgtaataac 420
tcccctgaac tccaggtaaa agtaacaaag actatcaaga atggctttct gcactttgag 480
aattttactt gtgtggacga tgcagatgta gattctgaaa tggacccaga acagccagtc 540
acagaggatg agagtataga ggagatcttt gaggaaactc agaccaatgc cacctgcaat 600
tatgagacta aatcagagaa tggtgtaaaa gtggccatgg gaagtgaaca agacagcaca 660
ccagagagta gacacggtgc agtcaaatcg ccattcttgc cattagctcc tcagactgaa 720
acacagaaaa ataagcaaag aaatgaagtg gacggcagca atgaaaaagc agcccttctc 780
ccagccccct tttcactagg agacacaaac attacaatag aagagcaatt aaactcaata 840
aatttatctt ttcaggatga tccagattcc agtaccagta cattaggaaa catgctagaa 900
ttacctggaa cttcatcatc atctacttca caggaattgc catttgttcc tcagaaaatt 960
ttgagtaaat gggaagccag tgttggactt gcagaacagt atgatgttcc caaggggtca 1020
aagaaccgaa aatgtattcc tggttcaatc aagttggaca gtgaagaaga tatgccattt 1080
gaagactgca caaatgatcc tgagtcagaa catgacctgt tgcttaatgg ctgtttgaaa 1140
tcactggctt ttgattctga acattctgca gatgagaagg aaaagccttg cgctaaatct 1200

-continued

```
cgagccagaa agagctctga taatccaaaa aggactagtg tgaaaaaggg ccacatacaa   1260
tttgaagcac ataaagatga acggagggga aagattccag agaaccttgg cctaaacttt   1320
atctctgggg atatatctga tacgcaggcc tctaatgaac tttccaggat agcaaatagc   1380
ctcacagggt ccaacactgc cccaggaagt tttctgtttt cttcctgtgg aaaaaacact   1440
gcaaagaaag aatttgagac ttcaaatggt gactctttat tgggcttgcc tgagggtgct   1500
ttgatctcaa agtgttctcg agagaagaat aaaccccaac gaagcctggt gtgtggttca   1560
aaagtgaagc tctgctatat tggagcaggt gatgaggaaa agcgaagtga ttccattagt   1620
atctgtacca cttctgatga tggaagcagt gacctggatc ccatagaaca cagctcagag   1680
tctgataaca gtgtccttga aattccagat gctttcgata gaacagagaa catgttatct   1740
atgcagaaaa atgaaaagat aaagtattct aggtttgctg ccacaaacac tagggtaaaa   1800
gcaaaacaga agcctctcat tagtaactca catacagacc acttaatggg ttgtactaag   1860
agtgcagagc ctggaaccga gacgtctcag gttaatctct ctgatctgaa ggcatctact   1920
cttgttcaca aaccccagtc agattttaca aatgatgctc tctctccaaa attcaacctg   1980
tcatcaagca tatccagtga gaactcgtta ataaagggtg gggcagcaaa tcaagctcta   2040
ttacattcga aaagcaaaca gcccaagttc cgaagtataa agtgcaaaca caaagaaaat   2100
ccagttatgg cagaaccccc agttataaat gaggagtgca gtttgaaatg ctgctcttct   2160
gataccaaag gctctccttt ggccagcatt tctaaaagtg ggaaagtgga tggtctaaaa   2220
ctactgaaca atatgcatga gaaaaccagg gattcaagtg acatagaaac agcagtggtg   2280
aaacatgttt tatccgagtt gaaggaactc tcttacagat ccttaggtga ggatgtcagt   2340
gactctggaa catcaaagcc atcaaaacca ttacttttct cttctgcttc tagtcagaat   2400
cacataccta ttgaaccaga ctacaaattc agtacattgc taatgatgtt gaaagatatg   2460
catgatagta agacgaagga gcagcggttg atgactgctc aaaacctggt ctcttaccgg   2520
agtcctggtc gtggggactg ttctactaat agtcctgtag gagtctctaa ggttttggtt   2580
tcaggaggct ccacacacaa ttcagagaaa aagggagatg gcactcagaa ctccgccaat   2640
cctagcccta gtgggggtga ctctgcatta tctggcgagt tgtctgcttc cctacctggc   2700
ttactgtccg acaagagaga cctccctgct tctggtaaaa gtcgttcaga ctgtgttact   2760
aggcgcaact gtggacgatc aaagccttca tccaaattgc gagatgcttt ttcagcccaa   2820
atggtaaaga acacagtgaa ccgtaaagcc ttaaagaccg agcgcaaaag aaaactgaat   2880
cagcttccaa gtgtgactct tgatgctgta ctgcagggag accgagaacg tggaggttca   2940
ttgagaggtg gggcagaaga tcctagtaaa gaggatcccc ttcagataat gggccactta   3000
acaagtgaag atggtgacca tttttctgat gtgcatttcg atagcaaggt taagcaatct   3060
gatcctggta aaatttctga aaaaggactc tcttttgaaa acggaaaagg cccagagctg   3120
gactctgtaa tgaacagtga gaatgatgaa ctcaatggtg taaatcaagt ggtgcctaaa   3180
aagcggtggc agcgtttaaa ccaaaggcgc actaaacctc gtaagcgcat gaacagattt   3240
aaagagaaag aaaactctga gtgtgccttt agggtcttac ttcctagtga ccctgtgcag   3300
gaggggcggg atgagtttcc agagcataga actccttcag caagcatact tgaggaacca   3360
ctgacagagc aaaatcatgc tgactgctta gattcagctg ggccacggtt aaatgtttgt   3420
gataaatcca gtgccagcat tggtgacatg gaaaaggagc caggaattcc cagtttgaca   3480
ccacaggctg agctccctga accagctgtg cggtcagaga agaaacgcct taggaagcca   3540
agcaagtggc ttttggaata tacagaagaa tatgatcaga tatttgctcc taagaaaaaa   3600
```

-continued

```
caaaagaagg tacaggagca ggtggataag gtaagttccc gctgtgaaga ggaaagcctt   3660
ctagcccgag gtcgatctag tgctcagaac aagcaggtgg acgagaattc tttgatttca   3720
accaaagaag agcctccagt tcttgaaagg gaggctccgt tttggagggg ccccttggct   3780
cagtcagaac ttggaggtgg acatgctgag ttgccgcagc tgaccttgtc tgtgcctgtg   3840
gctccggaag tctctccacg gcctgccctt gagtctgagg aattgctagt taaaacacaa   3900
ggaaattatg aaagtaaacg tcaaagaaaa ccaactaaga aacttcttga atccaatgat   3960
ttagaccctg gatttatgcc caagaagggg gaccttggcc tttctaaaaa gtgctatgaa   4020
gctggtcacc tggagaatgg cataactgaa tcttgtgcca catcttattc aaaagatttt   4080
ggtggaggca ctaccaagat atttgacaag ccaaggaagc gaaaacgaca gaggcatgct   4140
gtagccaaga tgcagtgcaa aaaagtgaaa aatgatgact cgtcaaaaga gattccaggc   4200
tcagagggag aactaatgcc tcacaggacg gccacaagcc ccaaggagac tgttgaggaa   4260
ggtgtagaac acgatcccgg gatgcctgcc tctaaaaaaa tgcagggtga acgcggtgga   4320
ggagctgcac tcaaggagaa tgtctgtcag aattgtgaaa aattgggtga gctgctgtta   4380
tgtgaggctc agtgctgtgg ggctttccac ctggagtgcc ttggattgac tgagatgcca   4440
agaggaaaat ttatctgcaa tgaatgtcgc acaggaatcc atacctgttt tgtatgtaag   4500
cagagtgggg aagatgttaa aaggtgcctt ctacccttgt gtggaaagtt ttaccatgaa   4560
gagtgtgtcc agaagtaccc acccactgtt atgcagaaca agggcttccg gtgctccctc   4620
cacatctgta taacctgtca tgctgctaat ccagccaatg tttctgcatc taaaggtcgg   4680
ttgatgcgct gtgtccgctg tcctgtggca taccacgcca atgacttttg cctggctgct   4740
gggtcaaaga tccttgcatc taatagtatc atctgcccta atcactttac ccctaggcgg   4800
ggctgccgaa atcatgagca tgttaatgtt agctggtgct ttgtgtgctc agaaggaggc   4860
agccttctgt gctgtgattc ttgccctgct gcttttcatc gtgaatgcct gaacattgat   4920
atccctgaag gaaactggta ttgcaatgac tgtaaagcag gcaaaaagcc acactacagg   4980
gagattgtct gggtaaaagt tggacgatac aggtggtggc cagctgagat ctgccatcct   5040
cgagctgttc cttccaacat tgataagatg agacatgatg tgggagagtt cccagtcctc   5100
tttttggat ctaatgacta tttgtggact caccaggccc gagtcttccc ttacatggag   5160
ggtgacgtga gcagcaagga taagatgggc aaaggagtgg atgggacata taaaaaagct   5220
cttcaggaag ctgcagcaag gtttgaggaa ttaaaggccc aaaaagagct aagacagctg   5280
caggaagacc gaaagaatga caagaagcca ccccccttata aacatataaa ggtaaaccgt   5340
cctattggca gggtacagat cttcactgca gacttatctg aaataccccg ttgcaactgt   5400
aaagctactg atgagaaccc ctgtgggata gactctgaat gcatcaaccg catgctgctc   5460
tatgagtgcc accccacagt gtgtcctgcc ggagggcgct gtcaaaacca gtgcttttcc   5520
aagcgccaat atccagaggt tgaaattttc cgcacattac agcggggttg gggtctacgg   5580
acccaagagg acatcagaaa gggagaattt gttaacgagt acgttgggga gctgatcgac   5640
gaggaggagt gcatggcgag aatcaagcac gcacacgaga acgacatcac ccacttctac   5700
atgctcacta tagacaagga ccgtataata gacgctggcc ccaaaggaaa ctactctcga   5760
tttatgaatc acagctgcca gcccaactgt gagaccctca agtggacagt gaatggggac   5820
actcgtgtgg gcctgtttgc cgtctgtgac attcctgcag ggacggagct gacttttaac   5880
tacaacctcg attgtctggg caatgaaaaa acggtctgcc ggtgtggagc ctccaattgc   5940
```

-continued

```
agtggcttct tgggtgtaag gccaaagaat caacccattg ccacggaaga aaagtcaaag   6000
aaattcaaga agaagcaaca gggaaagcgc aggacccagg gtgaaatcac aaaggagcga   6060
gaagatgagt gttttagttg tggggatgct ggccagctcg tctcctgcaa gaaaccaggc   6120
tgcccaaaag tttaccacgc agactgtctc aatctgacca agcgaccagc agggaaatgg   6180
gaatgtccgt ggcatcagtg tgacatctgc gggaaggaag cagcctcctt ctgtgagatg   6240
tgccccagct ccttttgtaa gcagcatcga gaagggatgc ttttcatttc caaactggat   6300
gggcgtctgt cttgtactga gcatgacccc tgtgggccca atcctctgga acctggggag   6360
atccgtgagt atgtgcctcc cccagtaccg ctgcctccag ggccaagcac tcacctggca   6420
gagcaatcaa caggaatggc tgctcaggca cccaaaatgt cagataaacc tcctgctgac   6480
accaaccaga tgctgtcgct ctccaaaaaa gctctggcag ggacttgtca gaggccactg   6540
ctacctgaaa gacctcttga gagaactgac tccaggcccc agcctttaga taaggtcaga   6600
gacctcgctg ggtcaggggc ccaatcccaa tccttggttt ccagccagag gccactggac   6660
aggccaccag cagtggcagg accaagaccc cagctaagcg acaaaccctc tccagtgacc   6720
agcccaagct cctcaccctc agtcaggtcc caaccactgg aatcacctct ggggacggct   6780
gacccaaggc tggataaatc cataggtgct gccagcccaa ggccccagtc actggagaaa   6840
acctcagttc ccactggcct gagacttccg ccgccagaca gactgctcat tactagcagt   6900
cccaaacccc agacttcaga caggcctact gacaaacccc atgcctcttt gtcccagaga   6960
ctcccacctc ctgagaaagt actatcagct gtggtccaga cccttgtagc taaagaaaaa   7020
gcactgaggc ctgtggacca gaatactcag tcaaaaaata gagctgcttt ggtgatggat   7080
ctcatagacc taactcctcg ccagaaggag cgggcagctt cacctcatca ggtcacacca   7140
caggctgatg agaagatgcc agtgttggag tcaagttcat ggcctgccag caaaggtctg   7200
gggcatatgc cgagagctgt tgagaaaggc tgtgtgtcag atcctcttca gacatctggg   7260
aaagcagcag ccccttcaga ggacccctgg caagctgtta aatcactcac ccaagccaga   7320
ctttcttctc agccttctgc caaagccttt ttatatgagc caaccactca ggcctcagga   7380
agagcttctg caggggctga acagacccag gggtttttta ccaaatcccc ggccttggtg   7440
gaaaacaagg gcaaaaccaa atgggtaggg aggccaacaa attacttgca tttggccgcc   7500
aagagttggc aatcttttag gtctctcggg aaggccccac cctcctcccc caatgaagaa   7560
aagaagttgg taaccacaga gcaaagtccc tgggccctgg gaaaagcctc atcacgggca   7620
gggctctggc ccatagtggc tggacagaca ctggcacagt cttgctggtc tgctgggagc   7680
acacagacat tggcacagac ttgctggtct cttggaagag ggcaagaccc caaaccagag   7740
caaaatacac ttccagctct taaccaggct ccttccagtc acaagtgtgc agaatcagaa   7800
cagaagtagt accaatcaat gtcacatgaa caaacaagct gcccccaggg taccatttgg   7860
ggaggggaaa tcttttcttt ctttcccccct taaaaaaaaa cacatctgcc ccgaacactt   7920
tcccactgtt attctttcct catatcccaa cactcagaac tcttgtgaca ttagccagtg   7980
ggggcttatg gttgtgtgaa ccatgtatga aaatccagtg ggccccaacc aaggagacag   8040
acagacttgg gtctctttcc cccaactttt ccacatggtc atcgtgaaat aaaaagtcca   8100
ctctggaaaa aaaaa                                                    8115
```

<210> SEQ ID NO 29
<211> LENGTH: 1092
<212> TYPE: DNA
<213> ORGANISM: Homo sapiens

<400> SEQUENCE: 29

```
ggttgttctc tggagcagcg ttcttttatc tccgtccgcc ttctctccta cctaagtgcg     60
tgccgccacc cgatggaaga ttcgatggac atggacatga gccccctgag gccccagaac    120
tatcttttcg gttgtgaact aaaggccgac aaagattatc actttaaggt ggataatgat    180
gaaaatgagc accagttatc tttaagaacg gtcagtttag gggctggtgc aaaggatgag    240
ttgcacattg ttgaagcaga ggcaatgaat tacgaaggca gtccaattaa agtaacactg    300
gcaactttga aaatgtctgt acagccaacg gtttcccttg gggctttga aataacacca    360
ccagtggtct taaggttgaa gtgtggttca gggccagtgc atattagtgg acagcactta    420
gtagctgtgg aggaagatgc agagtcagaa gatgaagagg aggaggatgt gaaactctta    480
agtatatctg gaaagcggtc tgcccctgga ggtggtagca aggttccaca gaaaaaagta    540
aaacttgctg ctgatgaaga tgatgacgat gatgatgaag aggatgatga tgaagatgat    600
gatgatgatg attttgatga tgaggaagct gaagaaaaag cgccagtgaa gaaatctata    660
cgagatactc cagccaaaaa tgcacaaaag tcaaatcaga atggaaaaga ctcaaaacca    720
tcatcaacac caagatcaaa aggacaagaa tccttcaaga aacaggaaaa aactcctaaa    780
acaccaaaag gacctagttc tgtagaagac attaaagcaa aaatgcaagc aagtatagaa    840
aaaggtggtt ctcttcccaa agtggaagcc aaattcatca attatgtgaa gaattgcttc    900
cggatgactg accaagaggc tattcaagat ctctggcagt ccctggagaa agtctcttta    960
agaaaatagt ttaaacaatt tgttaaaaaa ttttccgtct tatttcattt ctgtaacagt   1020
tgatatctgg ctgtcctttt tataatgcag agtgagaact ttccctaccg tgtttgataa   1080
atgttgtcca gg                                                       1092
```

<210> SEQ ID NO 30
<211> LENGTH: 4258
<212> TYPE: DNA
<213> ORGANISM: Homo sapiens

<400> SEQUENCE: 30

```
cagtgctgga tgcggggacc cagcgcagaa gcagcgccag gtggagccat cgaagccccc     60
acccacaggc tgacagaggc accgttcacc agagggctca acaccgggat ctatgtttaa    120
gttttaactc tcgcctccaa agaccacgat aattccttcc ccaaagccca gcagcccccc    180
agccccgcgc agccccagcc tgcctcccgg cgcccagatg cccgccatgc cctccagcgg    240
ccccggggac accagcagct ctgctgcgga gcgggaggag gaccgaaagg acggagagga    300
gcaggaggag ccgcgtggca aggaggagcg ccaagagccc agcaccacgg cacggaaggt    360
ggggcggcct gggaggaagc gcaagcaccc cccggtggaa agcggtgaca cgccaaagga    420
ccctgcggtg atctccaagt ccccatccat ggcccaggac tcaggcgcct cagagctatt    480
acccaatggg gacttggaga agcggagtga gccccagcca gaggagggga gccctgctgg    540
ggggcagaag ggcggggccc cagcagaggg agagggtgca gctgagaccc tgcctgaagc    600
ctcaagagca gtggaaaatg gctgctgcac ccccaaggag ggccgaggag cccctgcaga    660
agcgggcaaa gaacagaagg agaccaacat cgaatccatg aaaatggagg gctcccgggg    720
ccggctgcgg ggtggcttgg gctgggagtc cagcctccgt cagcggccca tgccgaggct    780
caccttccag gcgggggacc cctactacat cagcaagcgc aagcgggacg agtggctggc    840
acgctggaaa agggaggctg agaagaaagc caaggtcatt gcaggaatga atgctgtgga    900
```

-continued

```
agaaaaccag gggcccgggg agtctcagaa ggtggaggag gccagccctc ctgctgtgca    960
gcagcccact gaccccgcat cccccactgt ggctaccacg cctgagcccg tggggtccga   1020
tgctggggac aagaatgcca ccaaagcagg cgatgacgag ccagagtacg aggacggccg   1080
gggctttggc attggggagc tggtgtgggg gaaactgcgg ggcttctcct ggtggccagg   1140
ccgcattgtg tcttggtgga tgacgggccg gagccgagca gctgaaggca cccgctgggt   1200
catgtggttc ggagacggca aattctcagt ggtgtgtgtt gagaagctga tgccgctgag   1260
ctcgttttgc agtgcgttcc accaggccac gtacaacaag cagcccatgt accgcaaagc   1320
catctacgag gtcctgcagg tggccagcag ccgcgcgggg aagctgttcc cggtgtgcca   1380
cgacagcgat gagagtgaca ctgccaaggc cgtggaggtg cagaacaagc ccatgattga   1440
atgggccctg gggggcttcc agccttctgg ccctaagggc ctggagccac cagaagaaga   1500
gaagaatccc tacaaagaag tgtacacgga catgtgggtg gaacctgagg cagctgccta   1560
cgcaccacct ccaccagcca aaaagccccg gaagagcaca gcggagaagc ccaaggtcaa   1620
ggagattatt gatgagcgca caagagagcg gctggtgtac gaggtgcggc agaagtgccg   1680
gaacattgag gacatctgca tctcctgtgg gagcctcaat gttaccctgg aacacccccct   1740
cttcgttgga ggaatgtgcc aaaactgcaa gaactgcttt ctggagtgtg cgtaccagta   1800
cgacgacgac ggctaccagt cctactgcac catctgctgt gggggccgtg aggtgctcat   1860
gtgcggaaac aacaactgct gcaggtgctt ttgcgtggag tgtgtggacc tcttggtggg   1920
gccgggggct gcccaggcag ccattaagga agacccctgg aactgctaca tgtgcgggca   1980
caagggtacc tacgggctgc tgcggcggcg agaggactgg ccctcccggc tccagatgtt   2040
cttcgctaat aaccacgacc aggaatttga ccctccaaag gtttacccac ctgtcccagc   2100
tgagaagagg aagcccatcc gggtgctgtc tctctttgat ggaatcgcta cagggctcct   2160
ggtgctgaag gacttgggca ttcaggtgga ccgctacatt gcctcggagg tgtgtgagga   2220
ctccatcacg gtgggcatgg tgcggcacca ggggaagatc atgtacgtcg gggacgtccg   2280
cagcgtcaca cagaagcata tccaggagtg gggcccattc gatctggtga ttgggggcag   2340
tccctgcaat gacctctcca tcgtcaaccc tgctcgcaag ggcctctacg agggcactgg   2400
ccggctcttc tttgagttct accgcctcct gcatgatgcg cggcccaagg agggagatga   2460
tcgccccttc ttctggctct ttgagaatgt ggtggccatg ggcgttagtg acaagaggga   2520
catctcgcga tttctcgagt ccaaccctgt gatgattgat gccaaagaag tgtcagctgc   2580
acacagggcc cgctacttct ggggtaacct tcccggtatg aacaggccgt tggcatccac   2640
tgtgaatgat aagctggagc tgcaggagtg tctggagcat ggcaggatag ccaagttcag   2700
caaagtgagg accattacta cgaggtcaaa ctccataaag cagggcaaag accagcattt   2760
tcctgtcttc atgaatgaga aagaggacat cttatggtgc actgaaatgg aaagggtatt   2820
tggtttccca gtccactata ctgacgtctc caacatgagc cgcttggcga ggcagagact   2880
gctgggccgg tcatggagcg tgccagtcat ccgccacctc ttcgctccgc tgaaggagta   2940
ttttgcgtgt gtgtaaggga catgggggca aactgaggta gcgacacaaa gttaaacaaa   3000
caaacaaaaa acacaaaaca taataaaaca ccaagaacat gaggatggag agaagtatca   3060
gcacccagaa gagaaaaagg aatttaaaac aaaaaccaca gaggcggaaa taccggaggg   3120
ctttgccttg cgaaaagggt tggacatcat ctcctgattt ttcaatgtta ttcttcagtc   3180
ctatttaaaa acaaaaccaa gctcccttcc cttcctcccc cttccctttt ttttcggtca   3240
gaccttttat tttctactct tttcagaggg gttttctgtt tgtttgggtt ttgtttcttg   3300
```

```
ctgtgactga aacaagaagg ttattgcagc aaaaatcagt aacaaaaaat agtaacaata   3360
ccttgcagag gaaaggtggg agagaggaaa aaaggaaatt ctatagaaat ctatatattg   3420
ggttgttttt ttttttgttt tttgtttttt ttttttgggt tttttttttt actatatatc   3480
ttttttttgt tgtctctagc ctgatcagat aggagcacaa gcaggggacg gaaagagaga   3540
gacactcagg cggcagcatt ccctcccagc cactgagctg tcgtgccagc accattcctg   3600
gtcacgcaaa acagaaccca gttagcagca gggagacgag aacaccacac aagacatttt   3660
tctacagtat ttcaggtgcc taccacacag gaaaccttga agaaaatcag tttctagaag   3720
ccgctgttac ctcttgttta cagtttatat atatatgata gatatgagat atatatataa   3780
aaggtactgt taactactgt acaacccgac ttcataatgg tgctttcaaa cagcgagatg   3840
agtaaaaaca tcagcttcca cgttgccttc tgcgcaaagg gtttcaccaa ggatggagaa   3900
agggagacag cttgcagatg gcgcgttctc acggtgggct cttccccttg gtttgtaacg   3960
aagtgaagga ggagaacttg ggagccaggt tctccctgcc aaaaaggggg ctagatgagg   4020
tggtcgggcc cgtggacagc tgagagtggg attcatccag actcatgcaa taaccctttg   4080
attgttttct aaaaggagac tccctcggca agatggcaga gggtacggag tcttcaggcc   4140
cagtttctca ctttagccaa ttcgagggct ccttgtggtg ggatcagaac taatccagag   4200
tgtgggaaag tgacagtcaa aaccccacct ggagcaaata aaaaaacata caaaacgt     4258
```

<210> SEQ ID NO 31
<211> LENGTH: 1442
<212> TYPE: DNA
<213> ORGANISM: Homo sapiens

<400> SEQUENCE: 31

```
atgtccaaaa aaatcagtgg cggttctgtg gtagagatgc aaggagatga aatgacacga     60
atcatttggg aattgattaa agagaaactc attattccct acgtggaatt ggatctacat    120
agctatgatt taggcataga gaatcgtgat gccaccaacg accaagtcac caaggatgct    180
gcagaagcta taaagaagca taatgttggc gtcaaatgtg ccactatcac tcctgatgag    240
aagagggttg aggagttcaa gttgaaacaa atgtggaaat caccaaatgg caccatacga    300
aatattctgg gtggcacggt cttcagagaa gccattatct gcaaaaatat cccccggctt    360
gtgagtggat gggtagagcc tatcatcata ggtcgtcatg cttatgggga tcaatacaga    420
gcaactgatt ttgttgttcc tggccctgga aaagtagaga taacctacac accaagtgac    480
ggaacccaaa aggtgacata cctggtacat aactttgaag aaggtggtgg tgttgccatg    540
ggggatgtata atcaagataa gtcaattgaa gattttgcac acagttcctt ccaaatggct    600
ctgtctaagg gttggccttt gtatctgagc accaaaaaca ctattctgaa gaaatatgat    660
gggcgtttta aagacatctt tcaggagata tatgacaagc agtacaagtc ccagtttgaa    720
gctcaaaaga tctggtatga gcataggctc atcgacgaca tggtggccca agctatgaaa    780
tcagagggag gcttcatctg ggcctgtaaa aactatgatg gtgacgtgca gtcggactct    840
gtggcccaag ggtatggctc tctcggcatg atgaccagcg tgctggtttg tccagatggc    900
aagacagtag aagcagaggc tgcccacggg actgtaaccc gtcactaccg catgtaccag    960
aaaggacagg agacgtccac caatcccatt gcttccattt ttgcctggac cagagggtta   1020
gcccacagag caaagcttga taacaataaa gagcttgcct tctttgcaaa tgctttggaa   1080
gaagtctcta ttgagacaat tgaggctggc ttcatgacca agggcttggc tgcttgcatt   1140
```

-continued

```
aaaggtttac ccaatgtgca acgttctgac tacttgaata catttgagtt catggataaa   1200

cttggagaaa acttgaagat caaactagct caggccaaac tttaagttca tacctgagct   1260

aagaaggata attgtctttt ggtaactagg tctacaggtt tgcatttttc tgtgttacac   1320

tcaaggataa aggcaaaatc aattttgtaa tttgtttaga agccagagtt tatctttttct  1380

ataagtttac agcctttttc ttatatatac agttattgcc acctttgtga acatggcaag   1440

gg                                                                  1442
```

<210> SEQ ID NO 32
<211> LENGTH: 1740
<212> TYPE: DNA
<213> ORGANISM: Homo sapiens

<400> SEQUENCE: 32

```
ccagcgttag cccgcggcca ggcagccggg aggagcggcg cgcgctcgga cctctcccgc     60

cctgctcgtt cgctctccag cttgggatgg ccggctacct gcgggtcgtg cgctcgctct    120

gcagagcctc aggctcgcgg ccggcctggg cgccggcggc cctgacagcc cccacctcgc    180

aagagcagcc gcggcgccac tatgccgaca aaaggatcaa ggtggcgaag cccgtggtgg    240

agatggatgg tgatgagatg acccgtatta tctggcagtt catcaaggag aagctcatcc    300

tgccccacgt ggacatccag ctaaagtatt ttgacctcgg gctcccaaac cgtgaccaga    360

ctgatgacca ggtcaccatt gactctgcac tggccaccca gaagtacagt gtggctgtca    420

agtgtgccac catcacccct gatgaggccc gtgtggaaga gttcaagctg aagaagatgt    480

ggaaaagtcc caatggaact atccggaaca tcctgggggg gactgtcttc cgggagccca    540

tcatctgcaa aaacatccca cgcctagtcc ctggctggac caagcccatc accattggca    600

ggcacgccca tggcgaccag tacaaggcca cagactttgt ggcagaccgg gccggcactt    660

tcaaaatggt cttcacccca aaagatggca gtggtgtcaa ggagtgggaa gtgtacaact    720

tccccgcagg cggcgtgggc atgggcatgt acaacaccga cgagtccatc tcaggttttg    780

cgcacagctg cttccagtat gccatccaga agaaatggcc gctgtacatg agcaccaaga    840

acaccatact gaaagcctac gatgggcgtt tcaaggacat cttccaggag atctttgaca    900

agcactataa gaccgacttc gacaagaata agatctggta tgagcaccgg ctcattgatg    960

acatggtggc tcaggtcctc aagtcttcgg gtggctttgt gtgggcctgc aagaactatg   1020

acggagatgt gcagtcagac atcctggccc agggctttgg ctcccttggc ctgatgacgt   1080

ccgtcctggt ctgccctgat gggaagacga ttgaggctga ggccgctcat gggaccgtca   1140

cccgccacta tcgggagcac cagaagggcc ggcccaccag caccaacccc atcgccagca   1200

tctttgcctg gacacgtggc ctggagcacc gggggaagct ggatgggaac caagacctca   1260

tcaggtttgc ccagatgctg gagaaggtgt gcgtggagac ggtggagagt ggagccatga   1320

ccaaggacct ggcgggctgc attcacggcc tcagcaatgt gaagctgaac gagcacttcc   1380

tgaacaccac ggacttcctc gacaccatca agagcaacct ggacagagcc ctgggcaggc   1440

agtaggggga ggcgccaccc atggctgcag tggaggggcc agggctgagc cggcgggtcc   1500

tcctgagcgc ggcagagggt gagcctcaca gcccctctct ggaggccttt ctaggggatg   1560

tttttttata agccagatgt ttttaaaagc atatgtgtgt ttcccctcat ggtgacgtga   1620

ggcaggagca gtgcgtttta cctcagccag tcagtatgtt ttgcatactg taatttatat   1680

tgcccttgga acacatggtg ccatatttag ctactaaaaa gctcttcaca aaaaaaaaaa   1740
```

<210> SEQ ID NO 33
<211> LENGTH: 981
<212> TYPE: DNA
<213> ORGANISM: Homo sapiens

<400> SEQUENCE: 33
agtcagctgg aggagttggc ccctagggtt cttggactat aaggtgctga tcttgggtga 60
tgaccaagtc aaaagactta tgtaataaat tccaaaggat agacccatag caggaacatt 120
tgaaggagaa caggcattat ttcaggtgaa gaccgtagcc ggtgtgcaga ggggtgccct 180
gagaacaatc agtaaaagct gacaagtgcc tttgttcttg agggataagc ttctagaaac 240
cacaagctaa acaagatgcc aagatacctg tgctactctc aatgccttgg agcagaatgt 300
accatgaaaa tattggcatt aatggccaaa agtaatgtga aaaccaagca cttaagttgg 360
ttttcctatt ttactgtacc acccaagaac actggaaggc agtggttctc acctggggac 420
agttttgccc cttgggaaat ttggcaatgt ctggaaacat tttttattgt cctaactggg 480
gtgaggggga tgctattggc atctagaggc caaggatgct gctaaatatt ctccgatgct 540
caggacagac cccccccaac aaagaattat ttggccccaa atgtcaatag tactgccgtt 600
gtgaagctct tagaaggcat tctgtgaagc tctgaacagc agctaaggca tctggtgaaa 660
cctgaagtaa tcacaactgt ttgagagtcg actggaaagt tctgcagaga gggttgtcat 720
gccgctggca cgtccaggtg aaatgggcgt tgctgggtgc acagaaggag aggcaatgga 780
tcccaggtat tggtaggact gatcgtagga ccacggtggg gatggttgga tctgccttgt 840
atcctgcatc tgactctgag gctgagggtt aaaggcagtg gagtggttca aggaggcacg 900
agggttgggc gtgagctgag gtcgtgccat tgcactccag cctgggcaac aagagcaaaa 960
ctccatctcc aaaaaaaaaa a 981

<210> SEQ ID NO 34
<211> LENGTH: 9795
<212> TYPE: DNA
<213> ORGANISM: Homo sapiens

<400> SEQUENCE: 34
ggcagtggca gcggcgagag cttgggcggc cgccgccgcc tcctcgcgag cgccgcgcgc 60
ccgggtcccg ctcgcatgca agtcacgtcc gccccctcgg cgcggccgcc ccgagacgcc 120
ggccccgctg agtgatgaga acagacgtca aactgcctta tgaatattga tgcggaggct 180
aggctgcttt cgtagagaag cagaaggaag caagatggct gccctttagg atttgttaga 240
aaggagaccc gactgcaact gctggattgc tgcaaggctg agggacgaga acgaggctgg 300
caaacattca gcagcacacc ctctcaagat tgtttacttg cctttgctcc tgttgagtta 360
caacgcttgg aagcaggaga tgggctcagc agcagccaat aggacatgat ccaggaagag 420
cagtaaggga ctgagctgct gaattcaact agagggcagc cttgtggatg gccccgaagc 480
aagcctgatg gaacaggata gaaccaacca tgttgagggc aacagactaa gtccattcct 540
gataccatca cctcccattt gccagacaga acctctggct acaaagctcc agaatggaag 600
cccactgcct gagagagctc atccagaagt aaatggagac accaagtggc actctttcaa 660
aagttattat ggaataccct gtatgaaggg aagccagaat agtcgtgtga gtcctgactt 720
tacacaagaa agtagagggt attccaagtg tttgcaaaat ggaggaataa aacgcacagt 780
tagtgaacct tctctctctg ggctccttca gatcaagaaa ttgaaacaag accaaaaggc 840
taatggagaa agacgtaact tcggggtaag ccaagaaaga aatccaggtg aaagcagtca 900

-continued

```
accaaatgtc tccgatttga gtgataagaa agaatctgtg agttctgtag cccaagaaaa    960
tgcagttaaa gatttcacca gtttttcaac acataactgc agtgggcctg aaaatccaga   1020
gcttcagatt ctgaatgagc aggaggggaa aagtgctaat taccatgaca agaacattgt   1080
attacttaaa aacaaggcag tgctaatgcc taatggtgct acagtttctg cctcttccgt   1140
ggaacacaca catggtgaac tcctggaaaa aacactgtct caatattatc cagattgtgt   1200
ttccattgcg gtgcagaaaa ccacatctca cataaatgcc attaacagtc aggctactaa   1260
tgagttgtcc tgtgagatca ctcacccatc gcatacctca gggcagatca attccgcaca   1320
gacctctaac tctgagctgc ctccaaagcc agctgcagtg gtgagtgagg cctgtgatgc   1380
tgatgatgct gataatgcca gtaaactagc tgcaatgcta aatacctgtt cctttcagaa   1440
accagaacaa ctacaacaac aaaaatcagt ttttgagata tgcccatctc ctgcagaaaa   1500
taacatccag ggaaccacaa agctagcgtc tggtgaagaa ttctgttcag gttccagcag   1560
caatttgcaa gctcctggtg gcagctctga acggtattta aaacaaaatg aaatgaatgg   1620
tgcttacttc aagcaaagct cagtgttcac taaggattcc ttttctgcca ctaccacacc   1680
accaccacca tcacaattgc ttctttctcc ccctcctcct cttccacagg ttcctcagct   1740
tccttcagaa ggaaaaagca ctctgaatgg tggagtttta gaagaacacc accactaccc   1800
caaccaaagt aacacaacac ttttaaggga agtgaaaata gagggtaaac ctgaggcacc   1860
accttcccag agtcctaatc catctacaca tgtatgcagc ccttctccga tgctttctga   1920
aaggcctcag aataattgtg tgaacaggaa tgacatacag actgcaggga caatgactgt   1980
tccattgtgt tctgagaaaa caagaccaat gtcagaacac ctcaagcata acccaccaat   2040
ttttggtagc agtggagagc tacaggacaa ctgccagcag ttgatgagaa acaaagagca   2100
agagattctg aagggtcgag acaaggagca aacacgagat cttgtgcccc caacacagca   2160
ctatctgaaa ccaggatgga ttgaattgaa ggcccctcgt tttcaccaag cggaatccca   2220
tctaaaacgt aatgaggcat cactgccatc aattcttcag tatcaaccca atctctccaa   2280
tcaaatgacc tccaaacaat acactggaaa ttccaacatg cctgggggc tcccaaggca    2340
agcttacacc cagaaaacaa cacagctgga gcacaagtca caaatgtacc aagttgaaat   2400
gaatcaaggg cagtcccaag gtacagtgga ccaacatctc cagttccaaa aaccctcaca   2460
ccaggtgcac ttctccaaaa cagaccattt accaaaagct catgtgcagt cactgtgtgg   2520
cactagattt cattttcaac aaagagcaga ttcccaaact gaaaaactta tgtccccagt   2580
gttgaaacag cacttgaatc aacaggcttc agagactgag ccattttcaa actcacacct   2640
tttgcaacat aagcctcata aacaggcagc acaaacacaa ccatcccaga gttcacatct   2700
ccctcaaaac cagcaacagc agcaaaaatt acaaataaag aataaagagg aaatactcca   2760
gacttttcct caccccccaaa gcaacaatga tcagcaaaga gaaggatcat tctttggcca   2820
gactaaagtg gaagaatgtt ttcatggtga aaatcagtat tcaaaatcaa gcgagttcga   2880
gactcataat gtccaaatgg gactggagga agtacagaat ataaatcgta gaaattcccc   2940
ttatagtcag accatgaaat caagtgcatg caaaatacag gtttcttgtt caaacaatac   3000
acacctagtt tcagagaata aagaacagac tacacatcct gaactttttg caggaaacaa   3060
gacccaaaac ttgcatcaca tgcaatattt tccaaataat gtgatcccaa agcaagatct   3120
tcttcacagg tgctttcaag aacaggagca gaagtcacaa caagcttcag ttctacaggg   3180
atataaaaat agaaaccaag atatgtctgg tcaacaagct gcgcaacttg ctcagcaaag   3240
gtacttgata cataaccatg caaatgtttt tcctgtgcct gaccagggag gaagtcacac   3300
```

```
tcagacccct ccccagaagg acactcaaaa gcatgctgct ctaaggtggc atctcttaca   3360
gaagcaagaa cagcagcaaa cacagcaacc ccaaactgag tcttgccata gtcagatgca   3420
caggccaatt aaggtggaac ctggatgcaa gccacatgcc tgtatgcaca cagcaccacc   3480
agaaaacaaa acatggaaaa aggtaactaa gcaagagaat ccacctgcaa gctgtgataa   3540
tgtgcagcaa aagagcatca ttgagaccat ggagcagcat ctgaagcagt ttcacgccaa   3600
gtcgttattt gaccataagg ctcttactct caaatcacag aagcaagtaa aagttgaaat   3660
gtcagggcca gtcacagttt tgactagaca aaccactgct gcagaacttg atagccacac   3720
cccagcttta gagcagcaaa caacttcttc agaaaagaca ccaaccaaaa gaacagctgc   3780
ttctgttctc aataatttta tagagtcacc ttccaaatta ctagatactc ctataaaaaa   3840
tttattggat acacctgtca agactcaata tgatttccca tcttgcagat gtgtagagca   3900
aattattgaa aaagatgaag gtcctttttta tacccatcta ggagcaggtc ctaatgtggc   3960
agctattaga gaaatcatgg aagaaaggtt tggacagaag ggtaaagcta ttaggattga   4020
aagagtcatc tatactggta aagaaggcaa aagttctcag ggatgtccta ttgctaagtg   4080
ggtggttcgc agaagcagca gtgaagagaa gctactgtgt ttggtgcggg agcgagctgg   4140
ccacacctgt gaggctgcag tgattgtgat tctcatcctg gtgtgggaag gaatcccgct   4200
gtctctggct gacaaactct actcggagct taccgagacg ctgaggaaat acggcacgct   4260
caccaatcgc cggtgtgcct tgaatgaaga gagaacttgc gcctgtcagg gctggatcca   4320
gaaacctgtg gtgcctcctt ctcttttggt tgttcatgga gcatgtacta caatggatgt   4380
aagtttgcca gaagcaagat cccaaggaag tttaagctgc ttggggatga cccaaaagag   4440
gaagagaaac tggagtctca tttgcaaaac ctgtccactc ttatggcacc aacatataag   4500
aaacttgcac ctgatgcata taataatcag attgaatatg aacacagagc accagagtgc   4560
cgtctgggtc tgaaggaagg ccgtccattc tcaggggtca ctgcatgttt ggacttctgt   4620
gctcatgccc acagagactt gcacaacatg cagaatggca gcacattggt atgcactctc   4680
actagagaag acaatcgaga atttggagga aaacctgagg atgagcagct tcacgttctg   4740
cctttataca aagtctctga cgtggatgag tttgggagtg tggaagctca ggaggagaaa   4800
aaacggagtg gtgccattca ggtactgagt tcttttcggc gaaaagtcag gatgttagca   4860
gagccagtca agacttgccg acaaaggaaa ctagaagcca agaaagctgc agctgaaaag   4920
ctttcctccc tggagaacag ctcaaataaa aatgaaaagg aaaagtcagc cccatcacgt   4980
acaaaacaaa ctgaaaacgc aagccaggct aaacagttgg cagaactttt gcgactttca   5040
ggaccagtca tgcagcagtc ccagcagccc cagcctctac agaagcagcc accacagccc   5100
cagcagcagc agagacccca gcagcagcag ccacatcacc ctcagacaga gtctgtcaac   5160
tcttattctg cttctggatc caccaatcca tacatgagac ggcccaatcc agttagtcct   5220
tatccaaact cttcacacac ttcagatatc tatggaagca ccagccctat gaacttctat   5280
tccacctcat ctcaagctgc aggttcatat ttgaattctt ctaatcccat gaacccttac   5340
cctgggcttt tgaatcagaa tacccaatat ccatcatatc aatgcaatgg aaacctatca   5400
gtggacaact gctccccata tctgggttcc tattctcccc agtctcagcc gatggatctg   5460
tataggtatc caagccaaga ccctctgtct aagctcagtc taccacccat ccatacactt   5520
taccagccaa ggtttggaaa tagccagagt tttacatcta aatacttagg ttatggaaac   5580
caaaatatgc agggagatgg tttcagcagt tgtaccatta gaccaaatgt acatcatgta   5640
```

-continued

```
gggaaattgc ctccttatcc cactcatgag atggatggcc acttcatggg agccacctct   5700
agattaccac ccaatctgag caatccaaac atggactata aaaatggtga acatcattca   5760
ccttctcaca taatccataa ctacagtgca gctccgggca tgttcaacag ctctcttcat   5820
gccctgcatc tccaaaacaa ggagaatgac atgctttccc acacagctaa tgggttatca   5880
aagatgcttc cagctcttaa ccatgataga actgcttgtg tccaaggagg cttacacaaa   5940
ttaagtgatg ctaatggtca ggaaaagcag ccattggcac tagtccaggg tgtggcttct   6000
ggtgcagagg acaacgatga ggtctggtca gacagcgagc agagctttct ggatcctgac   6060
attgggggag tggccgtggc tccaactcat gggtcaattc tcattgagtg tgcaaagcgt   6120
gagctgcatg ccacaacccc tttaaagaat cccaatagga atcaccccac caggatctcc   6180
ctcgtctttt accagcataa gagcatgaat gagccaaaac atggcttggc tctttgggaa   6240
gccaaaatgg ctgaaaaagc ccgtgagaaa gaggaagagt gtgaaaagta tggcccagac   6300
tatgtgcctc agaaatccca tggcaaaaaa gtgaaacggg agcctgctga gccacatgaa   6360
acttcagagc ccacttacct gcgtttcatc aagtctcttg ccgaaaggac catgtccgtg   6420
accacagact ccacagtaac tacatctcca tatgccttca ctcgggtcac agggccttac   6480
aacagatata tatgatatca ccccctttg ttggttacct cacttgaaaa gaccacaacc   6540
aacctgtcag tagtatagtt ctcatgacgt gggcagtggg gaaaggtcac agtattcatg   6600
acaaatgtgg tgggaaaaac ctcagctcac cagcaacaaa agaggttatc ttaccatagc   6660
acttaatttt cactggctcc caagtggtca cagatggcat ctaggaaaag accaaagcat   6720
tctatgcaaa aagaaggtgg ggaagaaagt gttccgcaat ttacattttt aaacactggt   6780
tctattattg gacgagatga tatgtaaatg tgatcccccc cccccgctta caactctaca   6840
catctgtgac cacttttaat aatatcaagt ttgcatagtc atggaacaca aatcaaacaa   6900
gtactgtagt attacagtga caggaatctt aaaataccat ctggtgctga atatatgatg   6960
tactgaaata ctggaattat ggctttttga aatgcagttt ttactgtaat cttaactttt   7020
atttatcaaa atagctacag gaaacatgaa tagcaggaaa acactgaatt tgtttggatg   7080
ttctaagaaa tggtgctaag aaaatggtgt ctttaatagc taaaaattta atgcctttat   7140
atcatcaaga tgctatcagt gtactccagt gcccttgaat aataggggta ccttttcatt   7200
caagttttta tcataattac ctattcttac acaagcttag tttttaaaat gtggacattt   7260
taaaggcctc tggattttgc tcatccagtg aagtccttgt aggacaataa acgtatatat   7320
gtacatatat acacaaacat gtatatgtgc acacacatgt atatgtataa atattttaaa   7380
tggtgtttta gaagcacttt gtctacctaa gctttgacaa cttgaacaat gctaaggtac   7440
tgagatgttt aaaaaacaag tttactttca ttttagaatg caaagttgat ttttttaagg   7500
aaacaaagaa agcttttaaa atatttttgc ttttagccat gcatctgctg atgagcaatt   7560
gtgtccattt ttaacacagc cagttaaatc caccatgggg cttactggat tcaagggaat   7620
acgttagtcc acaaaacatg ttttctggtg ctcatctcac atgctatact gtaaaacagt   7680
tttatacaaa attgtatgac aagttcattg ctcaaaaatg tacagtttta agaattttct   7740
attaactgca ggtaataatt agctgcatgc tgcagactca acaaagctag ttcactgaag   7800
cctatgctat tttatggatc ataggctctt cagagaactg aatggcagtc tgcctttgtg   7860
ttgataatta tgtacattgt gacgttgtca tttcttagct taagtgtcct ctttaacaag   7920
aggattgagc agactgatgc ctgcataaga tgaataaaca gggttagttc catgtgaatc   7980
tgtcagttaa aaagaaacaa aaacaggcag ctggtttgct gtggtggttt taaatcatta   8040
```

atttgtataa agaagtgaaa gagttgtata gtaaattaaa ttgtaaacaa aacttttttta 8100 atgcaatgct ttagtatttt agtactgtaa aaaaattaaa tatatacata tatatatata 8160
tatatatata tatatatatg agtttgaagc agaattcaca tcatgatggt gctactcagc 8220
ctgctacaaa tatatcataa tgtgagctaa gaattcatta aatgtttgag tgatgttcct 8280
acttgtcata tacctcaaca ctagtttggc aataggatat tgaactgaga gtgaaagcat 8340
tgtgtaccat catttttttc caagtccttt tttttattgt taaaaaaaaa agcatacctt 8400
ttttcaatac ttgatttctt agcaagtata acttgaactt caaccttttt gttctaaaaa 8460
ttcagggata tttcagctca tgctctccct atgccaacat gtcacctgtg tttatgtaaa 8520
attgttgtag gttaataaat atattctttg tcagggattt aaccctttta ttttgaatcc 8580
cttctatttt acttgtacat gtgctgatgt aactaaaact aattttgtaa atctgttggc 8640
tctttttatt gtaaagaaaa gcattttaaa agtttgagga atcttttgac tgtttcaagc 8700
aggaaaaaaa aattacatga aaatagaatg cactgagttg ataaagggaa aaattgtaag 8760
gcaggagttt ggcaagtggc tgttggccag agacttactt gtaactctct aaatgaagtt 8820
tttttgatcc tgtaatcact gaaggtacat actccatgtg gacttccctt aaacaggcaa 8880
acacctacag gtatggtgtg caacagattg tacaattaca ttttggccta aatacatttt 8940
tgcttactag tatttaaaat aaattcttaa tcagaggagg cctttgggtt ttattggtca 9000
aatctttgta agctggcttt tgtcttttta aaaaatttct tgaatttgtg gttgtgtcca 9060
atttgcaaac atttccaaaa atgtttgctt tgcttacaaa ccacatgatt ttaatgtttt 9120
ttgtatacca taatatctag ccccaaacat ttgattacta catgtgcatt ggtgattttg 9180
atcatccatt cttaatattt gatttctgtg tcacctactg tcatttgtta aactgctggc 9240
caacaagaac aggaagtata gtttgggggg ttggggagag tttacataag gaagagaaga 9300
aattgagtgg catattgtaa atatcagatc tataattgta aatataaaac ctgcctcagt 9360
tagaatgaat ggaaagcaga tctacaattt gctaatatag gaatatcagg ttgactatat 9420
agccatactt gaaaatgctt ctgagtggtg tcaactttac ttgaatgaat ttttcatctt 9480
gattgacgca cagtgatgta cagttcactt ctgaagctag tggttaactt gtgtaggaaa 9540
cttttgcagt ttgacactaa gataacttct gtgtgcattt ttctatgctt ttttaaaaac 9600
tagtttcatt tcattttcat gagatgtttg gtttataaga tctgaggatg gttataaata 9660
ctgtaagtat tgtaatgtta tgaatgcagg ttatttgaaa gctgtttatt attatatcat 9720
tcctgataat gctatgtgag tgtttttaat aaaatttata tttatttaat gcactctaaa 9780
aaaaaaaaaa aaaaa 9795

<210> SEQ ID NO 35
<211> LENGTH: 9236
<212> TYPE: DNA
<213> ORGANISM: Homo sapiens

<400> SEQUENCE: 35
aaacagaagg tgggccgggg cggggagaaa cagaactcgg tcaatttccc agtttgtcgg 60
gtctttaaaa atacaggccc ctaaagcact aagggcatgc cctcggtgaa acaggggagc 120
gcttctgctg aatgagatta aagcgacaga aaagggaaag gagagcgcgg gcaacgggat 180
ctaaagggag atagagacgc gggcctctga gggctggcaa acattcagca gcacaccctc 240
tcaagattgt ttacttgcct ttgctcctgt tgagttacaa cgcttggaag caggagatgg 300

-continued

```
gctcagcagc agccaatagg acatgatcca ggaagagcag taagggactg agctgctgaa    360
ttcaactaga gggcagcctt gtggatggcc ccgaagcaag cctgatggaa caggatagaa    420
ccaaccatgt tgagggcaac agactaagtc cattcctgat accatcacct cccatttgcc    480
agacagaacc tctggctaca aagctccaga atggaagccc actgcctgag agagctcatc    540
cagaagtaaa tggagacacc aagtggcact ctttcaaaag ttattatgga ataccctgta    600
tgaagggaag ccagaatagt cgtgtgagtc ctgactttac acaagaaagt agagggtatt    660
ccaagtgttt gcaaaatgga ggaataaaac gcacagttag tgaaccttct ctctctgggc    720
tccttcagat caagaaattg aaacaagacc aaaaggctaa tggagaaaga cgtaacttcg    780
gggtaagcca agaaagaaat ccaggtgaaa gcagtcaacc aaatgtctcc gatttgagtg    840
ataagaaaga atctgtgagt tctgtagccc aagaaaatgc agttaaagat ttcaccagtt    900
tttcaacaca taactgcagt gggcctgaaa atccagagct tcagattctg aatgagcagg    960
aggggaaaag tgctaattac catgacaaga acattgtatt acttaaaaac aaggcagtgc   1020
taatgcctaa tggtgctaca gtttctgcct cttccgtgga acacacacat ggtgaactcc   1080
tggaaaaaac actgtctcaa tattatccag attgtgtttc cattgcggtg cagaaaacca   1140
catctcacat aaatgccatt aacagtcagg ctactaatga gttgtcctgt gagatcactc   1200
acccatcgca tacctcaggg cagatcaatt ccgcacagac ctctaactct gagctgcctc   1260
caaagccagc tgcagtggtg agtgaggcct gtgatgctga tgatgctgat aatgccagta   1320
aactagctgc aatgctaaat acctgttcct ttcagaaacc agaacaacta caacaacaaa   1380
aatcagtttt tgagatatgc ccatctcctg cagaaaataa catccaggga accacaaagc   1440
tagcgtctgg tgaagaattc tgttcaggtt ccagcagcaa tttgcaagct cctggtggca   1500
gctctgaacg gtatttaaaa caaaatgaaa tgaatggtgc ttacttcaag caaagctcag   1560
tgttcactaa ggattccttt tctgccacta ccacaccacc accaccatca caattgcttc   1620
tttctccccc tcctcctctt ccacaggttc ctcagcttcc ttcagaagga aaaagcactc   1680
tgaatggtgg agttttagaa gaacaccacc actaccccaa ccaaagtaac acaacacttt   1740
taagggaagt gaaaatagag ggtaaacctg aggcaccacc ttcccagagt cctaatccat   1800
ctacacatgt atgcagccct tctccgatgc tttctgaaag gcctcagaat aattgtgtga   1860
acaggaatga catacagact gcagggacaa tgactgttcc attgtgttct gagaaaacaa   1920
gaccaatgtc agaacacctc aagcataacc caccaatttt tggtagcagt ggagagctac   1980
aggacaactg ccagcagttg atgagaaaca aagagcaaga gattctgaag ggtcgagaca   2040
aggagcaaac acgagatctt gtgcccccaa cacagcacta tctgaaacca ggatggattg   2100
aattgaaggc ccctcgtttt caccaagcgg aatcccatct aaaacgtaat gaggcatcac   2160
tgccatcaat tcttcagtat caacccaatc tctccaatca aatgacctcc aaacaataca   2220
ctggaaattc caacatgcct gggggctcc caaggcaagc ttacacccag aaaacaacac   2280
agctggagca caagtcacaa atgtaccaag ttgaaatgaa tcaagggcag tcccaaggta   2340
cagtggacca acatctccag ttccaaaaac cctcacacca ggtgcacttc tccaaaacag   2400
accatttacc aaaagctcat gtgcagtcac tgtgtggcac tagatttcat tttcaacaaa   2460
gagcagattc ccaaactgaa aaacttatgt ccccagtgtt gaaacagcac ttgaatcaac   2520
aggcttcaga gactgagcca ttttcaaact cacacctttt gcaacataag cctcataaac   2580
aggcagcaca aacacaacca tcccagagtt cacatctccc tcaaaaccag caacagcagc   2640
aaaaattaca aataaagaat aaagaggaaa tactccagac ttttcctcac ccccaaagca   2700
```

-continued

```
acaatgatca gcaaagagaa ggatcattct ttggccagac taaagtggaa gaatgttttc   2760
atggtgaaaa tcagtattca aaatcaagcg agttcgagac tcataatgtc caaatgggac   2820
tggaggaagt acagaatata aatcgtagaa attcccctta tagtcagacc atgaaatcaa   2880
gtgcatgcaa aatacaggtt tcttgttcaa acaatacaca cctagtttca gagaataaag   2940
aacagactac acatcctgaa ctttttgcag gaaacaagac ccaaaacttg catcacatgc   3000
aatattttcc aaataatgtg atcccaaagc aagatcttct tcacaggtgc tttcaagaac   3060
aggagcagaa gtcacaacaa gcttcagttc tacagggata taaaaataga aaccaagata   3120
tgtctggtca acaagctgcg caacttgctc agcaaaggta cttgatacat aaccatgcaa   3180
atgtttttcc tgtgcctgac cagggaggaa gtcacactca gacccctccc cagaaggaca   3240
ctcaaaagca tgctgctcta aggtggcatc tcttacagaa gcaagaacag cagcaaacac   3300
agcaacccca aactgagtct tgccatagtc agatgcacag gccaattaag gtggaacctg   3360
gatgcaagcc acatgcctgt atgcacacag caccaccaga aaacaaaaca tggaaaaagg   3420
taactaagca agagaatcca cctgcaagct gtgataatgt gcagcaaaag agcatcattg   3480
agaccatgga gcagcatctg aagcagtttc acgccaagtc gttatttgac cataaggctc   3540
ttactctcaa atcacagaag caagtaaaag ttgaaatgtc agggccagtc acagttttga   3600
ctagacaaac cactgctgca gaacttgata gccacacccc agctttagag cagcaaacaa   3660
cttcttcaga aaagacacca accaaaagaa cagctgcttc tgttctcaat aattttatag   3720
agtcaccttc caaattacta gatactccta taaaaaattt attggataca cctgtcaaga   3780
ctcaatatga tttcccatct tgcagatgtg taggtaagtg ccagaaatgt actgagacac   3840
atggcgttta tccagaatta gcaaatttat cttcagatat gggattttcc ttcttttttt   3900
aaatcttgag tctggcagca atttgtaaag gctcataaaa atctgaagct tacatttttt   3960
gtcaagttac cgatgcttgt gtcttgtgaa agagaacttc acttacatgc agtttttcca   4020
aaagaattaa ataatcgtgc atgtttattt ttccctctct tcagatcctg taaaatttga   4080
atgtatctgt tttagatcaa ttcgcctatt tagctctttg tatattatct cctggagaga   4140
cagctaggca gcaaaaaaac aatctattaa aatgagaaaa taacgaccat aggcagtcta   4200
atgtacgaac tttaaatatt ttttaattca aggtaaaata tattagtttc acaagatttc   4260
tggctaatag ggaaattatt atcttcagtc ttcatgagtt gggggaaatg ataatgctga   4320
cactcttagt gctcctaaag tttccttttc tccatttata catttggaat gttgtgattt   4380
atattcattt tgattccctt ttctctaaaa tttcatcttt ttgattaaaa aatatgatac   4440
aggcatacct cagagatatt gtgggtttgg ctccatacca caataaaatg aatattacaa   4500
taaagcaagt tgtaaggact ttttggtttc tcactgtatg taaaagttat ttatatacta   4560
tactgtaaca tactaagtgt gcaatagcat tgtgtctaaa aaatatatac tttaaaaata   4620
atttattgtt aaaaaaatgc caacaattat ctgggccttt agtgagtgct aatctttttg   4680
ctggtggagg gtcgtgcttc agtattgatc gctgtggact gatcatggtg gtagttgctg   4740
aaggttgctg ggatggctgt gtgtgtggca atttcttaaa ataagacaac agtgaagtgc   4800
tgtatcaatt gatttttcca ttcacaaaag atttctctgt agcatgcaat gctgtttgat   4860
agcatttaac ccacagcaga atttctttga aaattggact cagtcctctc aaactgtgct   4920
gctgctttat caactaagtt tttgtaattt tctgaatcct ttgttgtcat ttcagcagtt   4980
tacagcatct tcattggaag tatattccat ctcaaacatt ctttgttcat ccataagaag   5040
```

-continued

```
caacttctta tcaagttttt tcatgacatt gcagtaactc agccccatct tcaggctcta   5100
cttctaattc tggttctctt gctacatctc cctcatctgc agtgacctct ccacggaagt   5160
cttgaactcc tcaaagtaat ccatgagggt tggaatcaac ttctaaactc ctgttaatgt   5220
tgatatattg accccctccc atgaattatg aatgttctta ataacttcta aatggtgata   5280
cctttccaga aggctttcaa tgtactttgc ccggatccat cagaagacta tcttggcagc   5340
tgtagactaa caatatattt cttaaatgat aagacttgaa agtcaaaagt actccttaat   5400
ccataggctg cagaatcaat gttgtattaa caggcacgaa aacagcatta atcttgtgca   5460
tctccatcgg agctcttggg tgactaggtg ccttgagcag taatattttg aaaggaggtt   5520
ttggttttgt tttttgtttt tttttttgt tttttagcag taagtctcaa cactgggctt   5580
aaaatattca gtaaactatg ttgtaaaaag atgtgttatc atccagactt tgttgttcca   5640
ttactctaca caagcagggt acacttagca taattcttaa gggccttgga attttcagaa   5700
tggtaaatga gtatgggctt caacttaaaa tcatcaactg cattagcctg taacaagaga   5760
gtcagcctgt cctttgaagc aaggcattga cttctatcta tgaaagtctt agatggcacc   5820
ttgtttcaat agtaggctgt ttagtacagc caccttcatc agtgatctta gctagatctt   5880
ctgcataact tgctgcagct tctacatcag cacttgctgc ctcaccttgt ccttttatgt   5940
tatagagaca gctgcgcttc ttaaacttta taaaccaact tctgctagct tccaacttct   6000
cttctgcagc ttcctcattc tcttcataga actgaaggga gtcaaggcct tgctctggat   6060
taagctttgg cttaaggaat gttgtggctg acgtgatctt ctatccagac cactaaagcg   6120
ctctccatat cagcaataag gccgttttgc tttcttacct ttcatgtgtt cactggagta   6180
atttccttca agaatttttc ctttacattc acaacttggc taactggcat gcaaggccta   6240
gctttcagcc tgtcttggct tttgacatgc cttcctcact tagctcgtca tatctagctt   6300
ttgatttaaa gtggcaggca tacaactctt cctttcactt gaacacttag aggccactgt   6360
agggttatta attggcctaa tttcaatatt gttgtgtttt agggaataga gaggcccagg   6420
gagagggaga gagcccaaac ggctggttga tagagcaggc agaatgcaca caacatttat   6480
cagattatgt ttgcaccatt taccagatta tgggtacggt ttgtggcacc ccccaaaaat   6540
tagaatagta acatcaaaga tcactgatca cagatcgcca taacataaat aataataaac   6600
tttaaaatac tgtgagaatt accaaaatgt gatacagaga catgaagtga gcacatgctg   6660
ttgaaaaaaa tgacactgat agacatactt aacacgtggg attgccacaa accttcagtt   6720
tgtaaaagtc acagtaactg tgactcacaa aagaacaaag cacaataaaa cgaggtatgc   6780
ctgtattttt aaaaaaagct ttttgttaaa attcaggata tgtaataggt ctgtaggaat   6840
agtgaaatat ttttgctgat ggatgtagat atatacgtgg atagagatga agatcttaat   6900
tatagctatg cagcatagat ttagtcaaag acatttgaaa agacaaatgt taaattagtg   6960
tggctaatga cctacccgtg ccatgttttc cctcttgcaa tgagataccc cacactgtgt   7020
agaaggatgg agggaggact cctactgtcc ctctttgcgt gtggttatta agttgcctca   7080
ctgggctaaa acaccacaca tctcatagat aatatttggt aagttgtaat cgtcttcact   7140
cttctcttat cacccacccc tatcttccca cttttccatc tttgttggtt tgcaacagcc   7200
ccttcttttt gcctgactct ccaggatttt ctctcatcat aaattgttct aaagtacata   7260
ctaatatggg tctggattga ctattcttat ttgcaaaaca gcaattaaat gttataggga   7320
agtaggaaga aaaaggggta tccttgacaa taaaccaagc aatattctgg gggtgggata   7380
gagcaggaaa ttttattttt aatcttttaa aatccaagta ataggtaggc ttccagttag   7440
```

ctttaaatgt ttttttttc cagctcaaaa aattggattg tagttgatac tacatataat 7500
acattctaat tccctcactg tattctttgt ttagtttcat ttatttggtt taaaataatt 7560
ttttatccca tatctgaaat gtaatatatt tttatccaac aaccagcatg tacatatact 7620
taattatgtg gcacattttc taatagatca gtccatcaat ctactcattt taaagaaaaa 7680
aaaattttaa agtcactttt agagccctta atgtgtagtt gggggttaag ctttgtggat 7740
gtagccttta tatttagtat aattgaggtc taaaataata atcttctatt atctcaacag 7800
agcaaattat tgaaaaagat gaaggtcctt tttataccca tctaggagca ggtcctaatg 7860
tggcagctat tagagaaatc atggaagaaa ggtaattaac gcaaaggcac agggcagatt 7920
aacgtttatc cttttgtata tgtcagaatt tttccagcct tcacacacaa agcagtaaac 7980
aattgtaaat tgagtaatta ttagtaggct tagctattct agggttgcca acactacaca 8040
ctgtgctatt caccagagag tcacaatatt tgacaggact aatagtctgc tagctggcac 8100
aggctgccca ctttgcgatg gatgccagaa aacccaggca tgaacaggaa tcggccagcc 8160
aggctgccag ccacaaggta ctggcacagg ctccaacgag aggtcccact ctggctttcc 8220
cacctgataa taaagtgtca aagcagaaag actggtaaag tgtggtataa gaaaagaacc 8280
actgaattaa attcacctag tgttgcaaat gagtacttat ctctaagttt tcttttacca 8340
taaaaagaga gcaagtgtga tatgttgaat agaaagagaa acatactatt tacagctgcc 8400 ttttttttt tttttcgcta tcaatcacag gtatacaagt acttgccttt actcctgcat 8460
gtagaagact cttatgagcg agataatgca gagaaggcct ttcatataaa tttatacagc 8520
tctgagctgt tcttcttcta gggtgccttt tcattaagag gtaggcagta ttattattaa 8580
agtacttagg atacattggg gcagctagga catattcagt atcattcttg ctccatttcc 8640
aaattattca tttctaaatt agcatgtaga agttcactaa ataatcatct agtggcctgg 8700
cagaaatagt gaatttccct aagtgccttt tttttgttgt ttttttgttt tgttttttaa 8760
acaagcagta ggtggtgctt tggtcataag ggaagatata gtctatttct aggactattc 8820
catattttcc atgtggctgg atactaacta tttgccagcc tccttttcta aattgtgaga 8880
cattcttgga ggaacagttc taactaaaat ctattatgac tccccaagtt ttaaaatagc 8940
taaatttagt aagggaaaaa atagtttatg ttttagaaga ctgaacttag caaactaacc 9000
tgaattttgt gctttgtgaa attttatatc gaaatgagct ttcccatttt cacccacatg 9060
taatttacaa aatagttcat tacaattatc tgtacatttt gatattgagg aaaaacaagg 9120
cttaaaaacc attatccagt ttgcttggcg tagacctgtt taaaaaataa taaaccgttc 9180
atttctcagg atgtggtcat agaataaagt tatgctcaaa tgttcaaata tttaaa 9236

<210> SEQ ID NO 36
<211> LENGTH: 7056
<212> TYPE: DNA
<213> ORGANISM: Homo sapiens

<400> SEQUENCE: 36
cacacccacg gcagacacgc acgcacccgg gcgccgaagg gaaagccgcg tctcgccctc 60
ccgccccgcc gtcggtcctg tctcagtccc tcagcagagc gggaaagcgg aggccggagc 120
cgtgacctct gaccccgtgg ttatgcggag ccgccgcatt ccttagcgat cgcggggcag 180
ccgccgctgc cgccgtgggc gactgacgca gcgcgggcgc gtggagccgc cgccgcccct 240
cccccaccgc cgctctcgcg ccagccggtc cccgcgtgcc cgccccttct ccccggccgc 300

-continued

```
acccgagacc tcgcgcgccg ccgctgccac gcgccccccc caccgccgcc gccgccccag    360
ccccgcgcca ccgccccagc ccgcccagcc cggaggtccc gcgtggagct gccgccgccg    420
ccggggagaa ggatgaagga caaacagaag aagaagaagg agcgcacgtg ggccgaggcc    480
gcgcgcctgg tattagaaaa ctactcggat gctccaatga caccaaaaca gattctgcag    540
gtcatagagg cagaaggact aaaggaaatg agaagtggga cttcccctct cgcatgcctc    600
aatgctatgc tacattccaa ttcaagagga ggagaggggt tgttttataa actgcctggc    660
cgaatcagcc ttttcacgct caagaaggat gccctgcagt ggtctcgcca tccagctaca    720
gtggagggag aggagccaga ggacacggct gatgtggaga gctgtgggtc taatgaagcc    780
agcactgtga gtggtgaaaa cgatgtatct cttgatgaaa catcttcgaa cgcatcctgt    840
tctacagaat ctcagagtcg acctctttcc aatcccaggg acagctacag agcttcctca    900
caggcgaaca aacaaaagaa aaagactggg gtgatgctgc ctcgagttgt cctgactcct    960
ctgaaggtaa acggggccca cgtggaatct gcatcagggt tctcgggctg ccacgccgat   1020
ggcgagagcg gcagcccgtc cagcagcagc agcggctctc tggccctggg cagcgctgct   1080
attcgtggcc aggccgaggt cacccaggac cctgccccgc tcctgagagg cttccggaag   1140
ccagccacag gtcaaatgaa gcgcaacaga ggggaagaaa tagattttga gacacctggg   1200
tccattcttg tcaacaccaa cctccgtgcc ctgatcaact ctcggacctt ccatgcctta   1260
ccatcacact tccagcagca gctcctcttc ctcctgcctg aagtagacag acaggtgggg   1320
acggatggcc tgttgcgtct cagcagcagt gcactaaata acgagttttt tacccatgcg   1380
gctcagagct ggcgggagcg cctggctgat ggtgaattta ctcatgagat gcaagtcagg   1440
atacgacagg aaatggagaa ggaaaagaag gtggaacaat ggaaagaaaa gttctttgaa   1500
gactactatg gacagaagct gggtttgacc aaagaagagt cattgcagca gaacgtgggc   1560
caggaggagg ctgaaatcaa aagtggcttg tgtgtcccag gagaatcagt gcgtatacag   1620
cgtggtccag ccacccgaca gcgagatggg cattttaaga aacgctctcg gccagatctc   1680
cgaaccagag ccagaaggaa tctgtacaaa aaacaggagt cagaacaagc aggggttgct   1740
aaggatgcaa aatctgtggc ctcagatgtt cccctctaca aggatgggga ggctaagact   1800
gacccagcag ggctgagcag tccccatctg ccaggcacat cctctgcagc acccgacctg   1860
gagggtcccg aattcccagt tgagtctgtg gcttctcgga tccaggctga gccagacaac   1920
ttggcacgtg cctctgcatc tccagacaga attcctagcc tgcctcagga aactgtggat   1980
caggaaccca aggatcagaa gaggaaatcc tttgagcagg cggcctctgc atcctttccc   2040
gaaaagaagc ccggcttgga agatcgtcag tcctttcgta acacaattga aagtgttcac   2100
accgaaaagc cacagcccac taaagaggag cccaaagtcc cgcccatccg gattcaactt   2160
tcacgtatca aaccaccctg ggtggttaaa ggtcagccca cttaccagat atgcccccgg   2220
atcatcccca ccacggagtc ctcctgccgg ggttggactg gcgccaggac cctcgcagac   2280
attaaagccc gtgctctgca ggtccgaggg gcgagaggtc accactgcca tagagaggcg   2340
gccaccactg ccatcggagg ggggggtggc ccgggtggag gtggcggcgg ggccaccgat   2400
gagggaggtg gcagaggcag cagcagtggt gatggtggtg aggcctgtgg ccaccctgag   2460
cccaggggag gcccgagcac ccctggaaag tgtacgtcag atctacagcg aacacaacta   2520
ctgccgcctt atcctctaaa tggggagcat acccaggccg gaactgccat gtccagagct   2580
aggagagagg acctgccttc tctgagaaag gaggaaagct gcctactaca gagggctaca   2640
gttggactca cagatgggct aggagatgcc tcccaactcc ccgttgctcc cactggggac   2700
```

-continued

```
cagccatgcc aggccttgcc cctactgtcc tcccaaacct cagtagctga gagattagtg   2760
gagcagcctc agttgcatcc ggatgttaga actgaatgtg agtctggcac cacttcctgg   2820
gaaagtgatg atgaggagca aggacccacc gttcctgcag acaatggtcc cattccgtct   2880
ctagtgggag atgatacatt agagaaagga actggccaag ctcttgacag tcatcccact   2940
atgaaggatc ctgtaaatgt gacccccagt tccacacctg aatcctcacc gactgattgc   3000
ctgcagaaca gagcatttga tgacgaatta gggcttggtg gctcatgccc tcctatgagg   3060
gaaagtgata ctagacaaga aaacttgaaa accaaggctc tcgtttctaa cagttctttg   3120
cattggatac ccatcccatc gaatgatgag gtagtgaaac agcccaaacc agaatccaga   3180
gaacacatac catctgttga gccccaggtt ggagaggagt gggagaaagc tgctcccacc   3240
cctcctgcat tgcctgggga tttgacagct gaggagggtc tagatcctct tgacagcctt   3300
acttcactct ggactgtgcc atctcgagga ggcagtgaca gcaatggcag ttactgtcaa   3360
caggtggaca ttgaaaagct gaaaatcaac ggagactctg aagcactgag tcctcacggt   3420
gagtccacgg atacagcctc tgactttgaa ggtcacctca cggaggacag cagtgaggct   3480
gacactagag aagctgcagt gacaaaggga tcttcggtgg acaaggatga gaaacccaat   3540
tggaaccaat ctgccccact gtccaaggtg aatggtgaca tgcgtctggt tacaaggaca   3600
gatgggatgg ttgctcctca gagctgggtg tctcgagtat gtgcggtccg ccaaaagatc   3660
ccagattccc tactgctggc cagtactgag taccagccaa gagccgtgtg cctgtccatg   3720
cctgggtcct cagtggaggc cactaaccca cttgtgatgc agttgctgca gggtagcttg   3780
cccctagaga aggttcttcc accagcccac gatgacagca tgtcagaatc ccccacaagta   3840
ccacttacaa aagaccagag ccatggctcg ctacgcatgg gatctttaca tggtcttgga   3900
aaaaacagtg gcatggttga tggaagcagc cccagttctt taagggcttt gaaggagcct   3960
cttctgccag atagctgtga aacaggcact ggtcttgcca ggattgaggc cacccaggct   4020
cctggagcac cccaaaagaa ttgcaaggca gtcccaagtt ttgactccct ccatccagtg   4080
acaaatccca ttacatcctc taggaaactg gaagaaatgg attccaaaga gcagttctct   4140
tcctttagtt gtgaagatca gaaggaagtc cgtgctatgt cacaggacag taattcaaat   4200
gctgctccag gaaagagccc aggagatctt actacctcga gaacacctcg tttctcatct   4260
ccaaatgtga tctcctttgg tccagagcag acaggtcggg ccctgggtga tcagagcaat   4320
gttacaggcc aagggaagaa gctttttggc tctgggaatg tggctgcaac ccttcagcgc   4380
cccaggcctg cggacccgat gcctcttcct gctgagatcc ctccagtttt tcccagtggg   4440
aagttgggac caagcacaaa ctccatgtct ggtggggtac agactccaag ggaagactgg   4500
gctccaaagc cacatgcctt tgttggcagc gtcaagaatg agaagacttt tgtgggggt    4560
cctcttaagg caaatgccga gaacaggaaa gctactgggc atagtcccct ggaactggtg   4620
ggtcacttgg aagggatgcc ctttgtcatg gacttgccct tctggaaatt accccgagag   4680
ccagggaagg ggctcagtga gcctctggag ccttcttctc tcccctccca actcagcatc   4740
aagcaggcat tttatgggaa gctttctaaa ctccaactga gttccaccag ctttaattat   4800
tcctctagct ctcccacctt tcccaaaggc cttgctggaa gtgtggtgca gctgagccac   4860
aaagcaaact ttggtgcgag ccacagtgca tcactttcct tgcaaatgtt cactgacagc   4920
agcacggtgg aaagcatctc gctccagtgt gcgtgcagcc tgaaagccat gatcatgtgc   4980
caaggctgcg gtgcgttctg tcacgatgac tgtattggac cctcaaagct ctgtgtattg   5040
```

tgccttgtgg tgagataata aattatggcc atgggaaaca ttgtatattt agtgtgtgta 5100
ttttgataat gattgatctt aaatctgtat acagaatatc attgatataa tactctttag 5160
gcaggagcac tcttgccttc ccccaaaatt tacactgcta aagccctctg tcacttggcg 5220
acccttctgg tcttgctgga ggggtttcct gggtataacc cattgggctg cccaaggcca 5280
gccagcctga gctctcctgc aagacagagc ctgatgtggc acggagtggg gttgcggggg 5340
gtggggggac tgcctgactc ccagagggac ttgaaactga agcaagaagg ttgcattctc 5400
caccaaggga gttaacctac ctgaactaag tagaaatgcc agtcttccac tacccccctcc 5460 ctgccatctt ttcttctgct actttgggga gttgatggcc aggaaagaag ccagcacagg 5520
gttaaagtaa ctcctggcat tgcccaccag gggctggtg cacctgctga cctcagggtc 5580
acagttgagt catttgccag ttgacggagc aagtttgacc ttggttctgt tgctgaagca 5640
aatttggaac ttttctgtct cagtgtgatc cactaaccca caggatcatt tggaaccttg 5700
aatagctctg cttggacaat ggggttgggg aatagggttg tctttcctat gaaaatgcca 5760
tctgtagacc ttgtgagtca gccgtccaga tgtttgcagg tgaattcctc tgcttgacat 5820
cctccctgtc actttggacc ctatgggagt gggcatctcc acgcacctgt gtatgtgaaa 5880
gtcattttac atttcaaagc agtgtgtgtt tcttattttt atatttttaa ctctttattc 5940
ttggatgtat aaagtgaact ttttggcttc tgtaagtatg ctctatgcac ctctaatgtt 6000
ttatcatgta tttatatgtt gtacacagta ctggctgatt ctgtaaatgg atgtattgta 6060
cagagaacat gaacgtctct tcctaatttt acatcttcag catcattgca ttaaagtggt 6120
gtaatctcct tctctacatc tgttgtcaga gccactgagt gctgtgctgc tcgacgtgag 6180
ggtgaaatga ttgacttgtg acctgccagg ttgcccgatg ccctgttggg tcaccggctg 6240
gacctgctgc agcctgcaga gccacagtca gcctgcccac atgccaccga gcaaacgcat 6300
cttgcttttc acatctctcc tcctacagcc ttaatggctg cttgctgcca tatgtgacaa 6360
atcaccacca ccagtgttaa gtgcttctgg attcatgggt gagttccctg ggcagccccc 6420
aggaaggcct tccagatctg gctccagggt caccacctgt cacagcaata cctgggacca 6480
tgctctcctg ggactgtgag gctccttttg acgtactttt gacatcaggc aggtttggga 6540
agaaacaaag ccatgcctgc tcctgcctct ctcccaacat gtttccagca agtagatgcc 6600
cctgtgtgtg ttttcccttg ccttgtttcc tgccttatat cttgtatttc gacttattac 6660
agagttgagg gttcttgctt aatttagatc aagtataaaa tttgtatgac ttcaagtctc 6720
attttatctg aaaggttttt ttctcattta atctgatgtg gcattttcgt catctgaagc 6780
atgagtgaca agttgggaat gatgtggtga tttagaatgc agtattggcc aagtccaagt 6840
tgtcaactta agcgtctgtt taccaaagac cgggaacagg ggcccaaaca tgtccagtcc 6900
tcttcttccc tctgctggaa cctttgggga cactcaaggg tacagtttga cactgatctg 6960
gtccatgagg ctgcccagag aaagcactgc ttctgtatgt ctcttgtggt attggaacaa 7020
taaacccgta caacctgcaa aaaaaaaaaa aaaaaa 7056

<210> SEQ ID NO 37
<211> LENGTH: 1084
<212> TYPE: DNA
<213> ORGANISM: Homo sapiens

<400> SEQUENCE: 37
cacacccacg gcagacacgc acgcacccgg gcgccgaagg gaaagccgcg tctcgccctc 60
ccgccccgcc gtcggtcctg tctcagtccc tcagcagagc gggaaagcgg aggccggagc 120
cgtgacctct gaccccgtgg ttatgcggag ccgccgcatt ccttagcgat cgcggggcag 180
ccgccgctgc cgccgtgggc gactgacgca gcgcgggcgc gtggagccgc cgccgcccct 240
cccccaccgc cgctctcgcg ccagccggtc cccgcgtgcc cgccccttct ccccggccgc 300
acccgagacc tcgcgcgccg ccgctgccac gcgccccccc caccgccgcc gccgccccag 360
ccccgcgcca ccgccccagc ccgcccagcc cggaggtccc gcgtggagct gccgccgccg 420
ccggggagaa ggatgaagga caaacagaag aagaagaagg agcgcacgtg ggccgaggcc 480
gcgcgcctgg tattagaaaa ctactcggat gctccaatga caccaaaaca gattctgcag 540
gtcatagagg cagaaggact aaaggaaatg agaagtggga cttcccctct cgcatgcctc 600
aatgctatgc tacattccaa ttcaagagga ggagaggggt tgttttataa actgcctggc 660
cgaatcagcc ttttcacgct caaggtgtga gccactgcac caggcccctt catcttaatt 720
ttaatatatc tttgaataaa caccattgta tgaacctgct gtaagcttgg gagtggtctg 780
ttagtctaca gcttgtgtct gagatgtgct aattgaatat ttgctcagta cctcatctta 840
actgcctttg gctttatgtt gcttatcctt catagtatct tgttcattgg ccttttacat 900
ccataggcat cacttctctg atattcgttg tgctctttta atggattaat ggtttgcttg 960
gttggttcct ctagttagac tgtaaactcc ttgagagcag agtctgtatt ttattaatta 1020
cccacagtac taggtacata gttgccttca ataaatatat atttaatgaa aaaaaaaaaa 1080
aaaa 1084

<210> SEQ ID NO 38
<211> LENGTH: 2723
<212> TYPE: DNA
<213> ORGANISM: Homo sapiens

<400> SEQUENCE: 38
ggcggcgctt gattgggctg ggggggccaa ataaaagcga tggcgattgg gctgccgcgt 60
ttggcgctcg gtccggtcgc gtccgacacc cggtgggact cagaaggcag tggagccccg 120
gcggcggcgg cggcggcgcg cgggggcgac gcgcgggaac aacgcgagtc ggcgcgcggg 180
acgaagaata atcatgggcc agactgggaa gaaatctgag aagggaccag tttgttggcg 240
gaagcgtgta aaatcagagt acatgcgact gagacagctc aagaggttca gacgagctga 300
tgaagtaaag agtatgttta gttccaatcg tcagaaaatt ttggaaagaa cggaaatctt 360
aaaccaagaa tggaaacagc gaaggataca gcctgtgcac atcctgactt ctgtgagctc 420
attgcgcggg actagggagt gttcggtgac cagtgacttg gattttccaa cacaagtcat 480
cccattaaag actctgaatg cagttgcttc agtacccata atgtattctt ggtctcccct 540
acagcagaat tttatggtgg aagatgaaac tgttttacat aacattcctt atatgggaga 600
tgaagtttta gatcaggatg gtactttcat tgaagaacta ataaaaaatt atgatgggaa 660
agtacacggg gatagagaat gtgggtttat aaatgatgaa atttttgtgg agttggtgaa 720
tgcccttggt caatataatg atgatgacga tgatgatgat ggagacgatc ctgaagaaag 780
agaagaaaag cagaaagatc tggaggatca ccgagatgat aaagaaagcc gcccacctcg 840
gaaatttcct tctgataaaa tttttgaagc catttcctca atgtttccag ataagggcac 900
agcagaagaa ctaaaggaaa aatataaaga actcaccgaa cagcagctcc caggcgcact 960
tcctcctgaa tgtaccccca acatagatgg accaaatgct aaatctgttc agagagagca 1020
aagcttacac tcctttcata cgcttttctg taggcgatgt tttaaatatg actgcttcct 1080

```
acatcgtaag tgcaattatt cttttcatgc aacacccaac acttataagc ggaagaacac   1140
agaaacagct ctagacaaca aaccttgtgg accacagtgt taccagcatt tggagggagc   1200
aaaggagttt gctgctgctc tcaccgctga gcggataaag accccaccaa aacgtccagg   1260
aggccgcaga agaggacggc ttcccaataa cagtagcagg cccagcaccc ccaccattaa   1320
tgtgctggaa tcaaaggata cagacagtga tagggaagca gggactgaaa cggggggaga   1380
gaacaatgat aaagaagaag aagagaagaa agatgaaact tcgagctcct ctgaagcaaa   1440
ttctcggtgt caaacaccaa taaagatgaa gccaaatatt gaacctcctg agaatgtgga   1500
gtggagtggt gctgaagcct caatgtttag agtcctcatt ggcacttact atgacaattt   1560
ctgtgccatt gctaggttaa ttgggaccaa aacatgtaga caggtgtatg agtttagagt   1620
caaagaatct agcatcatag ctccagctcc cgctgaggat gtggatactc ctccaaggaa   1680
aaagaagagg aaacaccggt tgtgggctgc acactgcaga aagatacagc tgaaaaagga   1740
cggctcctct aaccatgttt acaactatca accctgtgat catccacggc agccttgtga   1800
cagttcgtgc ccttgtgtga tagcacaaaa tttttgtgaa aagttttgtc aatgtagttc   1860
agagtgtcaa aaccgctttc cgggatgccg ctgcaaagca cagtgcaaca ccaagcagtg   1920
cccgtgctac ctggctgtcc gagagtgtga ccctgacctc tgtcttactt gtggagccgc   1980
tgaccattgg gacagtaaaa atgtgtcctg caagaactgc agtattcagc ggggctccaa   2040
aaagcatcta ttgctggcac catctgacgt ggcaggctgg gggattttta tcaaagatcc   2100
tgtgcagaaa aatgaattca tctcagaata ctgtggagag attatttctc aagatgaagc   2160
tgacagaaga gggaaagtgt atgataaata catgtgcagc tttctgttca acttgaacaa   2220
tgattttgtg gtggatgcaa cccgcaaggg taacaaaatt cgttttgcaa atcattcggt   2280
aaatccaaac tgctatgcaa aagttatgat ggttaacggt gatcacagga taggtatttt   2340
tgccaagaga gccatccaga ctggcgaaga gctgtttttt gattacagat acagccaggc   2400
tgatgccctg aagtatgtcg gcatcgaaag agaaatggaa atcccttgac atctgctacc   2460
tcctcccccc tcctctgaaa cagctgcctt agcttcagga acctcgagta ctgtgggcaa   2520
tttagaaaaa gaacatgcag tttgaaattc tgaatttgca aagtactgta agaataattt   2580
atagtaatga gtttaaaaat caacttttta ttgccttctc accagctgca aagtgttttg   2640
taccagtgaa tttttgcaat aatgcagtat ggtacatttt tcaactttga ataaagaata   2700
cttgaacttg tccttgttga atc                                           2723
```

<210> SEQ ID NO 39
<211> LENGTH: 2591
<212> TYPE: DNA
<213> ORGANISM: Homo sapiens

<400> SEQUENCE: 39

```
cggaggtgcg cgggcgcggg cgagcagggt ctccgggtgg gcggcggcga cgccccgcgc     60
aggctggagg ccgccgaggc tcgccatgcc gggagaactc taactccccc atggagtcgg    120
ccgacttcta cgaggcggag ccgcggcccc cgatgagcag ccacctgcag agccccccgc    180
acgcgcccag cagcgccgcc ttcggctttc cccggggcgc gggccccgcg cagcctcccg    240
ccccacctgc cgccccggag ccgctgggcg gcatctgcga gcacgagacg tccatcgaca    300
tcagcgccta catcgacccg gccgccttca acgacgagtt cctggccgac ctgttccagc    360
acagccggca gcaggagaag gccaaggcgg ccgtgggccc cacgggcggc ggcggcggcg    420
gcgactttga ctacccgggc gcgcccgcgg gccccggcgg cgccgtcatg cccgggggag    480
```

-continued

```
cgcacgggcc cccgcccggc tacggctgcg cggccgccgg ctacctggac ggcaggctgg    540
agcccctgta cgagcgcgtc ggggcgccgg cgctgcggcc gctggtgatc aagcaggagc    600
cccgcgagga ggatgaagcc aagcagctgg cgctggccgg cctcttccct taccagccgc    660
cgccgccgcc gccgccctcg cacccgcacc cgcacccgcc gcccgcgcac ctggccgccc    720
cgcacctgca gttccagatc gcgcactgcg gccagaccac catgcacctg cagcccggtc    780
accccacgcc gccgcccacg cccgtgccca gcccgcaccc cgcgcccgcg ctcggtgccg    840
ccggcctgcc gggccctggc agcgcgctca aggggctggg cgccgcgcac cccgacctcc    900
gcgcgagtgg cggcagcggc gcgggcaagg ccaagaagtc ggtggacaag aacagcaacg    960
agtaccgggt gcggcgcgag cgcaacaaca tcgcggtgcg caagagccgc gacaaggcca   1020
agcagcgcaa cgtggagacg cagcagaagg tgctggagct gaccagtgac aatgaccgcc   1080
tgcgcaagcg ggtggaacag ctgagccgcg aactggacac gctgcggggc atcttccgcc   1140
agctgccaga gagctccttg gtcaaggcca tgggcaactg cgcgtgaggc gcgcggctgt   1200
gggaccgccc tgggccagcc tccggcgggg acccagggag tggtttgggg tcgccggatc   1260
tcgaggcttg cccgagccgt gcgagccagg actaggagat tccggtgcct cctgaaagcc   1320
tggcctgctc cgcgtgtccc ctcccttcct ctgcgccgga cttggtgcgt ctaagatgag   1380
ggggccaggc ggtggcttct ccctgcgagg aggggagaat tcttggggct gagctgggag   1440
cccggcaact ctagtattta ggataacctt gtgccttgga aatgcaaact caccgctcca   1500
atgcctactg agtaggggga gcaaatcgtg ccttgtcatt ttatttggag gtttcctgcc   1560
tccttcccga ggctacagca gacccccatg agagaaggag gggagcaggc ccgtggcagg   1620
aggagggctc agggagctga gatcccgaca agcccgccag ccccagccgc tcctccacgc   1680
ctgtccttag aaaggggtgg aaacataggg acttggggct tggaacctaa ggttgttccc   1740
ctagttctac atgaaggtgg agggtctcta gttccacgcc tctcccacct ccctccgcac   1800
acaccccacc ccagcctgct ataggctggg cttccccttg ggcggaact cactgcgatg    1860
ggggtcacca ggtgaccagt gggagccccc accccgagtc acaccagaaa gctaggtcgt   1920
gggtcagctc tgaggatgta tacccctggt gggagaggga gacctagaga tctggctgtg   1980
gggcgggcat ggggggtgaa gggccactgg gaccctcagc cttgtttgta ctgtatgcct   2040
tcagcattgc ctaggaacac gaagcacgat cagtccatcc cagagggacc ggagttatga   2100
caagctttcc aaatatttg ctttatcagc cgatatcaac acttgtatct ggcctctgtg    2160
ccccagcagt gccttgtgca atgtgaatgt gcgcgtctct gctaaaccac cattttattt   2220
ggtttttgtt ttgttttggt tttgctcgga tacttgccaa aatgagactc tccgtcggca   2280
gctgggggaa gggtctgaga ctccctttcc ttttggtttt gggattactt ttgatcctgg   2340
gggaccaatg aggtgagggg ggttctcctt tgccctcagc tttccccagc ccctccggcc   2400
tgggctgccc acaaggcttg tcccccagag gccctggctc ctggtcggga agggaggtgg   2460
cctcccgcca acgcatcact ggggctggga gcagggaagg acggcttggt tctcttcttt   2520
tggggagaac gtagagtctc actctagatg ttttatgtat tatatctata atataaacat   2580
atcaaagtca a                                                        2591
```

<210> SEQ ID NO 40
<211> LENGTH: 4454
<212> TYPE: DNA
<213> ORGANISM: Homo sapiens

<400> SEQUENCE: 40
gaaacgtccc gtgtgggagg ggcgggtctg ggtgcggcct gccgcatgac tcgtggttcg 60
gaggcccacg tggccggggc ggggactcag gcgcctgggg cgccgactga ttacgtagcg 120
ggcggggccg gaagtgccgc tccttggtgg gggctgttca tggcggttcc ggggtctcca 180
acatttttcc cggctgtggt cctaaatctg tccaaagcag aggcagtgga gcttgaggtt 240
cttgctggtg tgaaatgact gagtacaaac tggtggtggt tggagcaggt ggtgttggga 300
aaagcgcact gacaatccag ctaatccaga accactttgt agatgaatat gatcccacca 360
tagaggattc ttacagaaaa caagtggtta tagatggtga aacctgtttg ttggacatac 420
tggatacagc tggacaagaa gagtacagtg ccatgagaga ccaatacatg aggacaggcg 480
aaggcttcct ctgtgtattt gccatcaata atagcaagtc atttgcggat attaacctct 540
acagggagca gattaagcga gtaaaagact cggatgatgt acctatggtg ctagtgggaa 600
acaagtgtga tttgccaaca aggacagttg atacaaaaca agcccacgaa ctggccaaga 660
gttacgggat tccattcatt gaaacctcag ccaagaccag acagggtgtt gaagatgctt 720
tttacacact ggtaagagaa atacgccagt accgaatgaa aaaactcaac agcagtgatg 780
atgggactca gggttgtatg ggattgccat gtgtggtgat gtaacaagat acttttaaag 840
ttttgtcaga aaagagccac tttcaagctg cactgacacc ctggtcctga cttccctgga 900
ggagaagtat tcctgttgct gtcttcagtc tcacagagaa gctcctgcta cttccccagc 960
tctcagtagt ttagtacaat aatctctatt tgagaagttc tcagaataac tacctcctca 1020
cttggctgtc tgaccagaga atgcacctct tgttactccc tgttattttt ctgccctggg 1080
ttcttccaca gcacaaacac acctctgcca ccccaggttt ttcatctgaa aagcagttca 1140
tgtctgaaac agagaaccaa accgcaaacg tgaaattcta ttgaaaacag tgtcttgagc 1200
tctaaagtag caactgctgg tgattttttt tttcttttta ctgttgaact tagaactatg 1260
ctaatttttg gagaaatgtc ataaattact gttttgccaa gaatatagtt attattgctg 1320
tttggtttgt ttataatgtt atcggctcta ttctctaaac tggcatctgc tctagattca 1380
taaatacaaa aatgaatact gaattttgag tctatcctag tcttcacaac tttgacgtaa 1440
ttaaatccaa ctttcacagt gaagtgcctt tttcctagaa gtggtttgta gacttccttt 1500
ataatatttc agtggaatag atgtctcaaa aatccttatg catgaaatga atgtctgaga 1560
tacgtctgtg acttatctac cattgaagga aagctatatc tatttgagag cagatgccat 1620
tttgtacatg tatgaaattg gttttccaga ggcctgtttt ggggctttcc caggagaaag 1680
atgaaactga aagcacatga ataatttcac ttaataattt ttacctaatc tccacttttt 1740
tcataggtta ctacctatac aatgtatgta atttgtttcc cctagcttac tgataaacct 1800
aatattcaat gaacttccat ttgtattcaa atttgtgtca taccagaaag ctctacattt 1860
gcagatgttc aaatattgta aaactttggt gcattgttat ttaatagctg tgatcagtga 1920
ttttcaaacc tcaaatatag tatattaaca aattacattt tcactgtata tcatggtatc 1980
ttaatgatgt atataattgc cttcaatccc cttctcaccc caccctctac agcttccccc 2040
acagcaatag gggcttgatt atttcagttg agtaaagcat ggtgctaatg gaccagggtc 2100
acagtttcaa aacttgaaca atccagttag catcacagag aaagaaattc ttctgcattt 2160
gctcattgca ccagtaactc cagctagtaa ttttgctagg tagctgcagt tagccctgca 2220
aggaaagaag aggtcagtta gcacaaaccc tttaccatga ctggaaaact cagtatcacg 2280
tatttaaaca tttttttttc ttttagccat gtagaaactc taaattaagc caatattctc 2340

-continued

```
atttgagaat gaggatgtct cagctgagaa acgttttaaa ttctctttat tcataatgtt   2400
ctttgaaggg tttaaaacaa gatgttgata aatctaagct gatgagtttg ctcaaaacag   2460
gaagttgaaa ttgttgagac aggaatggaa aatataatta attgatacct atgaggattt   2520
ggaggcttgg cattttaatt tgcagataat accctggtaa ttctcatgaa aaatagactt   2580
ggataacttt tgataaaaga ctaattccaa aatggccact ttgttcctgt ctttaatatc   2640
taaatactta ctgaggtcct ccatcttcta tattatgaat tttcatttat taagcaaatg   2700
tcatattacc ttgaaattca gaagagaaga aacatatact gtgtccagag tataatgaac   2760
ctgcagagtt gtgcttctta ctgctaattc tgggagcttt cacagtactg tcatcatttg   2820
taaatggaaa ttctgctttt ctgtttctgc tccttctgga gcagtgctac tctgtaattt   2880
tcctgaggct tatcacctca gtcatttctt ttttaaatgt ctgtgactgg cagtgattct   2940
ttttcttaaa aatctattaa atttgatgtc aaattaggga gaaagatagt tactcatctt   3000
gggctcttgt gccaatagcc cttgtatgta tgtacttaga gttttccaag tatgttctaa   3060
gcacagaagt ttctaaatgg ggccaaaatt cagacttgag tatgttcttt gaatacctta   3120
agaagttaca attagccggg catggtggcc cgtgcctgta gtcccagcta cttgagaggc   3180
tgaggcagga gaatcacttc aacccaggag gtggaggtta cagtgagcag agatcgtgcc   3240
actgcactcc agcctgggtg acaagagaga cttgtctcca aaaaaaaagt tacacctagg   3300
tgtgaatttt ggcacaaagg agtgacaaac ttatagttaa aagctgaata acttcagtgt   3360
ggtataaaac gtggttttta ggctatgttt gtgattgctg aaaagaattc tagtttacct   3420
caaaatcctt ctctttcccc aaattaagtg cctggccagc tgtcataaat tacatattcc   3480
ttttggtttt tttaaaggtt acatgttcaa gagtgaaaat aagatgttct gtctgaaggc   3540
taccatgccg gatctgtaaa tgaacctgtt aaatgctgta tttgctccaa cggcttacta   3600
tagaatgtta cttaatacaa tatcatactt attacaattt ttactatagg agtgtaatag   3660
gtaaaattaa tctctatttt agtgggccca tgtttagtct ttcaccatcc tttaaactgc   3720
tgtgaatttt tttgtcatga cttgaaagca aggatagaga aacactttag agatatgtgg   3780
ggttttttta ccattccaga gcttgtgagc ataatcatat ttgctttata tttatagtca   3840
tgaactccta agttggcagc tacaaccaag aaccaaaaaa tggtgcgttc tgcttcttgt   3900
aattcatctc tgctaataaa ttataagaag caaggaaaat tagggaaaat attttatttg   3960
gatggtttct ataaacaagg gactataatt cttgtacatt atttttcatc tttgctgttt   4020
ctttgagcag tctaatgtgc cacacaatta tctaaggtat ttgttttcta taagaattgt   4080
tttaaaagta ttcttgttac cagagtagtt gtattatatt tcaaaacgta agatgatttt   4140
taaaagcctg agtactgacc taagatggaa ttgtatgaac tctgctctgg agggaggga    4200
ggatgtccgt ggaagttgta agacttttat ttttttgtgc catcaaatat aggtaaaaat   4260
aattgtgcaa ttctgctgtt taaacaggaa ctattggcct ccttggccct aaatggaagg   4320
gccgatattt taagttgatt attttattgt aaattaatcc aacctagttc tttttaattt   4380
ggttgaatgt tttttcttgt taaatgatgt ttaaaaaata aaaactggaa gttcttggct   4440
tagtcataat tctt                                                     4454
```

<210> SEQ ID NO 41
<211> LENGTH: 5436
<212> TYPE: DNA
<213> ORGANISM: Homo sapiens

<400> SEQUENCE: 41

```
ggccgcggcg gcggaggcag cagcggcggc ggcagtggcg gcggcgaagg tggcggcggc      60
tcggccagta ctcccggccc ccgccatttc ggactgggag cgagcgcggc gcaggcactg     120
aaggcggcgg cggggccaga ggctcagcgg ctcccaggtg cgggagagag gcctgctgaa     180
aatgactgaa tataaacttg tggtagttgg agctggtggc gtaggcaaga gtgccttgac     240
gatacagcta attcagaatc attttgtgga cgaatatgat ccaacaatag aggattccta     300
caggaagcaa gtagtaattg atggagaaac ctgtctcttg gatattctcg acacagcagg     360
tcaagaggag tacagtgcaa tgagggacca gtacatgagg actggggagg gctttctttg     420
tgtatttgcc ataaataata ctaaatcatt tgaagatatt caccattata gagaacaaat     480
taaaagagtt aaggactctg aagatgtacc tatggtccta gtaggaaata aatgtgattt     540
gccttctaga acagtagaca caaaacaggc tcaggactta gcaagaagtt atggaattcc     600
ttttattgaa acatcagcaa agacaagaca gagagtggag gatgcttttt atacattggt     660
gagggagatc cgacaataca gattgaaaaa aatcagcaaa gaagaaaaga ctcctggctg     720
tgtgaaaatt aaaaaatgca ttataatgta atctgggtgt tgatgatgcc ttctatacat     780
tagttcgaga aattcgaaaa cataaagaaa agatgagcaa agatggtaaa aagaagaaaa     840
agaagtcaaa gacaaagtgt gtaattatgt aaatacaatt tgtacttttt tcttaaggca     900
tactagtaca agtggtaatt tttgtacatt acactaaatt attagcattt gttttagcat     960
tacctaattt ttttcctgct ccatgcagac tgttagcttt taccttaaat gcttatttta    1020
aaatgacagt ggaagttttt ttttcctcta agtgccagta ttcccagagt tttggttttt    1080
gaactagcaa tgcctgtgaa aaagaaactg aatacctaag atttctgtct tggggttttt    1140
ggtgcatgca gttgattact tcttattttt cttaccaatt gtgaatgttg gtgtgaaaca    1200
aattaatgaa gcttttgaat catccctatt ctgtgtttta tctagtcaca taaatggatt    1260
aattactaat ttcagttgag accttctaat tggtttttac tgaaacattg agggaacaca    1320
aatttatggg cttcctgatg atgattcttc taggcatcat gtcctatagt ttgtcatccc    1380
tgatgaatgt aaagttacac tgttcacaaa ggttttgtct cctttccact gctattagtc    1440
atggtcactc tccccaaaat attatatttt ttctataaaa agaaaaaaat ggaaaaaaat    1500
tacaaggcaa tggaaactat tataaggcca tttccttttc acattagata aattactata    1560
aagactccta atagcttttc ctgttaaggc agacccagta tgaaatgggg attattatag    1620
caaccatttt ggggctatat ttacatgcta ctaaattttt ataataattg aaaagatttt    1680
aacaagtata aaaaattctc ataggaatta aatgtagtct ccctgtgtca gactgctctt    1740
tcatagtata actttaaatc ttttcttcaa cttgagtctt tgaagatagt tttaattctg    1800
cttgtgacat taaaagatta tttgggccag ttatagctta ttaggtgttg aagagaccaa    1860
ggttgcaagg ccaggccctg tgtgaacctt tgagctttca tagagagttt cacagcatgg    1920
actgtgtccc cacggtcatc cagtgttgtc atgcattggt tagtcaaaat ggggagggac    1980
tagggcagtt tggatagctc aacaagatac aatctcactc tgtggtggtc ctgctgacaa    2040
atcaagagca ttgcttttgt ttcttaagaa aacaaactct tttttaaaaa ttacttttaa    2100
atattaactc aaaagttgag atttggggt ggtggtgtgc caagacatta atttttttt    2160
taaacaatga agtgaaaaag ttttacaatc tctaggtttg gctagttctc ttaacactgg    2220
ttaaattaac attgcataaa cacttttcaa gtctgatcca tatttaataa tgctttaaaa    2280
taaaaataaa aacaatcctt ttgataaatt taaaatgtta cttattttaa aataaatgaa    2340
```

-continued

```
gtgagatggc atggtgaggt gaaagtatca ctggactagg aagaaggtga cttaggttct   2400
agataggtgt cttttaggac tctgattttg aggacatcac ttactatcca tttcttcatg   2460
ttaaaagaag tcatctcaaa ctcttagttt ttttttttta caactatgta atttatattc   2520
catttacata aggatacact tatttgtcaa gctcagcaca atctgtaaat ttttaaccta   2580
tgttacacca tcttcagtgc cagtcttggg caaaattgtg caagaggtga agtttatatt   2640
tgaatatcca ttctcgtttt aggactcttc ttccatatta gtgtcatctt gcctccctac   2700
cttccacatg ccccatgact tgatgcagtt ttaatacttg taattcccct aaccataaga   2760
tttactgctg ctgtggatat ctccatgaag ttttcccact gagtcacatc agaaatgccc   2820
tacatcttat ttcctcaggg ctcaagagaa tctgacagat accataaagg gatttgacct   2880
aatcactaat tttcaggtgg tggctgatgc tttgaacatc tctttgctgc ccaatccatt   2940
agcgacagta ggatttttca aacctggtat gaatagacag aaccctatcc agtggaagga   3000
gaatttaata aagatagtgc tgaaagaatt ccttaggtaa tctataacta ggactactcc   3060
tggtaacagt aatacattcc attgttttag taaccagaaa tcttcatgca atgaaaaata   3120
ctttaattca tgaagcttac tttttttttt tggtgtcaga gtctcgctct tgtcacccag   3180
gctggaatgc agtggcgcca tctcagctca ctgcaacctc catctcccag gttcaagcga   3240
ttctcgtgcc tcggcctcct gagtagctgg gattacaggc gtgtgccact acactcaact   3300
aatttttgta tttttaggag agacggggtt tcaccctgtt ggccaggctg gtctcgaact   3360
cctgacctca agtgattcac ccaccttggc ctcataaacc tgttttgcag aactcattta   3420
ttcagcaaat atttattgag tgcctaccag atgccagtca ccgcacaagg cactgggtat   3480
atggtatccc caaacaagag acataatccc ggtccttagg tagtgctagt gtggtctgta   3540
atatcttact aaggcctttg gtatacgacc cagagataac acgatgcgta ttttagtttt   3600
gcaaagaagg ggtttggtct ctgtgccagc tctataattg ttttgctacg attccactga   3660
aactcttcga tcaagctact ttatgtaaat cacttcattg ttttaaagga ataaacttga   3720
ttatattgtt tttttatttg gcataactgt gattctttta ggacaattac tgtacacatt   3780
aaggtgtatg tcagatattc atattgaccc aaatgtgtaa tattccagtt ttctctgcat   3840
aagtaattaa aatatactta aaaattaata gttttatctg ggtacaaata aacaggtgcc   3900
tgaactagtt cacagacaag gaaacttcta tgtaaaaatc actatgattt ctgaattgct   3960
atgtgaaact acagatcttt ggaacactgt ttaggtaggg tgttaagact tacacagtac   4020
ctcgtttcta cacagagaaa gaaatggcca tacttcagga actgcagtgc ttatgagggg   4080
atatttaggc ctcttgaatt tttgatgtag atgggcattt ttttaaggta gtggttaatt   4140
acctttatgt gaactttgaa tggtttaaca aaagatttgt ttttgtagag attttaaagg   4200
gggagaattc tagaaataaa tgttacctaa ttattacagc cttaaagaca aaaatccttg   4260
ttgaagtttt tttaaaaaaa gctaaattac atagacttag gcattaacat gtttgtggaa   4320
gaatatagca gacgtatatt gtatcatttg agtgaatgtt cccaagtagg cattctaggc   4380
tctatttaac tgagtcacac tgcataggaa tttagaacct aacttttata ggttatcaaa   4440
actgttgtca ccattgcaca attttgtcct aatatataca tagaaacttt gtggggcatg   4500
ttaagttaca gtttgcacaa gttcatctca tttgtattcc attgattttt tttttcttct   4560
aaacattttt tcttcaaaca gtatataact ttttttaggg gatttttttt tagacagcaa   4620
aaactatctg aagatttcca tttgtcaaaa agtaatgatt tcttgataat tgtgtagtaa   4680
```

-continued

```
tgttttttag aacccagcag ttaccttaaa gctgaattta tatttagtaa cttctgtgtt   4740
aatactggat agcatgaatt ctgcattgag aaactgaata gctgtcataa aatgaaactt   4800
tctttctaaa gaaagatact cacatgagtt cttgaagaat agtcataact agattaagat   4860
ctgtgtttta gtttaatagt ttgaagtgcc tgtttgggat aatgataggt aatttagatg   4920
aatttagggg aaaaaaaagt tatctgcaga tatgttgagg gcccatctct ccccccacac   4980
ccccacagag ctaactgggt tacagtgttt tatccgaaag tttccaattc cactgtcttg   5040
tgttttcatg ttgaaaatac ttttgcattt ttcctttgag tgccaatttc ttactagtac   5100
tatttcttaa tgtaacatgt ttacctggaa tgtattttaa ctatttttgt atagtgtaaa   5160
ctgaaacatg cacattttgt acattgtgct ttcttttgtg ggacatatgc agtgtgatcc   5220
agttgttttc catcatttgg ttgcgctgac ctaggaatgt tggtcatatc aaacattaaa   5280
aatgaccact cttttaattg aaattaactt ttaaatgttt ataggagtat gtgctgtgaa   5340
gtgatctaaa atttgtaata tttttgtcat gaactgtact actcctaatt attgtaatgt   5400
aataaaaata gttacagtga caaaaaaaaa aaaaaa                              5436
```

<210> SEQ ID NO 42
<211> LENGTH: 9784
<212> TYPE: DNA
<213> ORGANISM: Homo sapiens

<400> SEQUENCE: 42

```
aggcctggac gtattctcgc gacatttgcc ggtcgcccgg cttgcactgc ggcgtttccc     60
gcgcgggcta cctcagttct cgggcgtacg gcgcggcctg tcctactgcc gccggcgccg    120
cggccgtcat ggggttcctg aaactgattg agattgagaa ctttaagtcg tacaagggtc    180
gacagattat cggaccattt cagaggttca ccgccatcat tggacccaat ggctctggta    240
agtcaaatct catggatgcc atcagctttg tgctaggtga aaaaaccagc aacctgcggg    300
taaagaccct gcgggacctg atccatggag ctcctgtggg caagccagct gccaaccggg    360
cctttgtcag catggtctac tctgaggagg gtgctgagga ccgtaccttt gcccgtgtca    420
ttgtaggagg ttcttctgag tacaagatca acaacaaagt ggtccaacta catgagtaca    480
gtgaggaatt agagaagttg ggcattctca tcaaagctcg taacttcctc gttttccagg    540
gtgctgtgga atctattgcc atgaagaacc ccaaagagag gacagctcta tttgaagaga    600
ttagtcgttc tggggagctg gcgcaggagt atgacaagcg aaagaaggaa atggtgaagg    660
ctgaagagga cacacagttt aattaccatc gcaagaaaaa tattgcggct gaacgcaagg    720
aagcaaagca ggagaaagaa gaggctgacc ggtaccagcg cctgaaggat gaggtagtac    780
gggctcaggt acagctgcag ctctttaagc tttaccataa tgaagtggaa attgagaagc    840
tcaacaagga actggcctca aagaacaagg agatcgagaa ggacaagaag cgtatggaca    900
aggtggagga tgaactgaag gagaagaaga aggagctggg caaaatgatg cgggagcagc    960
agcagattga gaaggagatc aaggagaagg actcagaatt gaaccagaag cggcctcagt   1020
acatcaaagc caaggagaac acctcccaca aaatcaagaa gctggaagca gccaagaagt   1080
ctctgcagaa tgctcagaag cactacaaga agcgtaaagg tgacatggat gagctggaga   1140
aggagatgct gtcagtggag aaggctcggc aggagtttga agaacggatg gaagaagaga   1200
gtcagagtca gggcagagat ttgacgttgg aggagaatca ggtgaagaaa taccaccggt   1260
tgaaagaaga agccagcaag agagcagcta ccctggccca ggagctggag aaattcaatc   1320
gagaccagaa agctgaccag gaccgtctgg atctggaaga acggaagaaa gtagagacag   1380
```

-continued

```
aggccaagat caagcaaaag ctgcgggaaa ttgaagagaa tcagaagcgg attgagaaac   1440
tggaggaata catcaccact agcaagcagt ccctagaaga gcagaagaag ctagaggggg   1500
agctgacaga ggaggtggag atggccaagc ggcgtattga tgaaatcaat aaggagctga   1560
accaggtgat ggagcagcta ggggatgccc gcatcgaccg ccaggagagc agccgccagc   1620
agcgaaaggc agagataatg gaaagcatca agcgccttta ccctggctct gtgtacggcc   1680
gcctcattga cctatgccag cccacacaaa agaagtatca gattgctgta accaaggttt   1740
tgggcaagaa catggatgcc attattgtgg actcggagaa gacaggccgg gactgtattc   1800
agtatatcaa ggagcagcgt ggggagcctg agaccttctt gcctcttgac tacctggagg   1860
tgaagcctac agatgagaaa ctccgggagc tgaagggggc caagctagtg attgatgtga   1920
ttcgctatga gccacctcat atcaaaaagg ccctgcagta tgcttgtggc aatgcccttg   1980
tctgtgacaa cgtggaagat gcccgccgca ttgcctttgg aggccaccag cgccacaaga   2040
cagtggcact ggatggaacc ctattccaga agtcaggagt gatctctggt ggggccagtg   2100
acctgaaggc caaggcacgg cgctgggatg agaaagcagt agacaagttg aaagagaaga   2160
aggagcgctt gacagaggag ctgaaagagc agatgaaggc aaaacggaaa gaggcagagc   2220
tgcgtcaggt gcagtctcag gcccatggac tgcagatgcg gctcaagtac tcccagagtg   2280
acctagaaca gaccaagaca cgacatctag ccctgaatct gcaggaaaaa tccaagctgg   2340
agagtgagct agccaacttt gggcctcgca ttaatgatat caagaggatc attcagagcc   2400
gagagaggga aatgaaagac ttgaaggaga agatgaacca ggtagaggat gaggtgtttg   2460
aagagttttg tcgggagatt ggtgtgcgca acatccggga gtttgaggaa gaaaaggtga   2520
aacggcagaa tgaaatcgcc aagaagcgtt tggagtttga gaatcagaag actcgcttgg   2580
gcattcagtt ggattttgaa aagaaccaac tgaaggagga ccaagataaa gtacacatgt   2640
gggagcagac agtgaaaaaa gatgaaaatg agatagaaaa gctcaaaaag gaggaacaaa   2700
gacacatgaa gatcatagat gagaccatgg ctcagctaca agacctgaag aatcagcatc   2760
tggccaagaa gtcggaagtg aatgacaaga atcatgagat ggaggagatt cgtaagaaac   2820
tcgggggcgc caacaaggaa atgacccatt tacagaagga ggtgacagcc attgagacca   2880
agcttgaaca gaagcgcagt gaccgtcaca acttgctaca ggcctgtaag atgcaggaca   2940
ttaagttgcc actgtcaaaa ggcaccatgg atgatattag tcaggaagag ggtagctccc   3000
agggggagga ctcagtgagt ggttcacaga gaatttccag tatctatgca cgagaggccc   3060
tcattgagat tgactacggt gatctgtgtg aggatctgaa ggatgcccag gctgaggaag   3120
agatcaagca agagatgaac acactgcagc agaagctgaa tgagcagcag agtgtgcttc   3180
agcgtattgc cgcccccaac atgaaggcca tggaaaagct ggaaagtgtc cgagacaagt   3240
tccaggagac ctcagatgag tttgaagcag cccgaaagcg agcaaagaag gccaagcagg   3300
cattcgaaca gatcaagaag gagcgctttg accgcttcaa tgcttgtttt gaatctgtgg   3360
ctaccaacat tgatgagatc tataaggccc tgtcccgcaa tagcagtgcc caggcattcc   3420
tgggccctga gaaccctgaa gagccctact tggatggcat caactacaac tgtgtggctc   3480
ctgggaaacg cttccggcct atggacaact tgtcaggcgg ggagaagaca gtggcagctc   3540
tggccctgct ctttgccatc cacagctaca agccagcccc cttcttcgtc ctggatgaga   3600
ttgatgctgc cttggataac accaacattg gcaaggtggc aaattacatc aaggagcagt   3660
cgacttgcaa cttccaggcc atcgtcatct ctctcaagga ggagttctac accaaggccg   3720
```

-continued

```
agagcctcat tggagtctat cctgagcaag gggactgtgt gatcagcaaa gtcctgacct   3780
tcgacctcac caagtaccca gatgccaacc ccaaccccaa tgagcagtag cagtattttt   3840
gccctcccgc cctgtctgga tccctaagct gtccctctcc caatctctgg atatttgact   3900
cccaaccttc cccctacctc ctggcccttt ttggtgtagt catgggattt aggcactgct   3960
aatcaagcat gaagaggaac agaggtgatg ttaggtctgg agcaaaaatt cctgaacgac   4020
agggagtatt ctggcctctg aaaggaggtg ctgagctgaa cagggccatc tgttcatcac   4080
acacaccccc ttcctccccc tcatcaccca taatcgtggg cccettgggc ctcttgccca   4140
ctgtgtgtgt gggtatgtat gtgtgtatgt atgtatccgc atgtgtgcat gtgagtatgt   4200
ttgcaaaata ataaaggata ttggagacct gttttagaag gagcctaggc tgaatttgat   4260
tccaagagag cttaggatga cagcacccct gagctgggca aaggtactca ggacctcata   4320
ggagtcttag gcagttacct gaaactgcct tcattcactc atttgtgtat tcattcattt   4380
atgtattcat cagacacata ccgaacaccc tctatttgtc aggctctgtg cttggaatac   4440
agagttgaat cagacatgat ctctaccctc ctagtaagga gatacagtgg gttcatgaat   4500
gactatagtt agctgaatgt catatgtact ttgaatttga gaagtgggtg atcccctcta   4560
ggcttcctgg aggtcacatt taagctagac cttgacaaat tggtaggatt tggtcaggca   4620
ctaggagtgg agcatgagct ctggggacag acagttatgg gttctggtcc cactttttat   4680
cacttactag ttgtttgacc ttgggcaagt catttgacct tctgtgcctc agtttcctca   4740
tctgtaaaat ggggctaaca atattaccta cctcatagga tttaatgatg tcaagctcct   4800
cactggaggc cttatccctt cgtggagccc actaggtgcc gacccctcag aatataaccc   4860
tcatgcctgg accccctgaga gcttctgatc ccagctatta gggacagaag aagcctccaa   4920
atctggaagg tgctgaatgc cctgctgact gggaaagttt cagggcactg atggggtcta   4980
cctggtaagc ggagggcctg aggaaacctg tagcttcaat catgtctggt aaccgggtgc   5040
ctgagcccca atctgggttg tgaggaaata ggggagaggt atcctgggcc acatcccagc   5100
ctaacacctg tgaggttcat tttaggaact aacctcatta gctataagga tcatgcagag   5160
gcagcaaagc cgggtgcgat gagctcagcc tttactcatt cacatacacc atcacacttt   5220
aattccaatc tgtatattgc tttttaaaag ttaagtccat tctaattacc caaatatgca   5280
tgaattcatt ctccttttga gaagttagat tgttaaagat agtctcattc agctaccaac   5340
cactccttga tccttccctt cttagtggct gttgtttgtt gtacttccgt ttagactttg   5400
ttttaatgct tgtacgtaca tatgtgaact cattggaaat attgtgtgtt taatgcaaat   5460
gatatattga attgtttagc aatttgtttt ctttgcttaa cgatgttttt gagatctgtg   5520
catgttactt aatgtagctc aatccatctt ctgtaattgc tgtatagatt gtcatcatat   5580
gattaccaca ttttacttac gcatttcttt tgtgatggac attaagactg tttttaggtt   5640
ttgctattac aaaatactac acaggagcat cactatgcct gtgtgaaagt atatgtatga   5700
aagtttacct agggttgatt cctagaagtg gaattgcaaa gtcataggat atttatatat   5760
tggtttttaa taatacttcc aaattgccct cctgtactat ttactcagta tttttcttga   5820
ggttgatctg aggtctaaca ttgttatcct atatcatttt catcccaagt agtgatatct   5880
gtgaaatcac aggtttgatg tgtgctaatt atgtattctt ctaatacata ttaaaagaca   5940
taactatcaa aacaaaataa atttgtctgt tttcaaccaa agaagtcacg taccactggt   6000
ggtactgtgt gccataattt ggcaaatgct ggcctttatg gacgagcaca attcgggggt   6060
cagacctggt tcaaattcta gctgtagaaa cttgtgcaag ttacttcacc tctgagccta   6120
```

agtttccaca tctgtaaaag gagataataa acacctacct tgcagtagtg aagcaaagag 6180
aaaattaaat atatatgaag caatttggct ggcatctaga tcattcacag ccctttaaag 6240
gtcacctttg ctgttctccc cactttacag ataaggaaac tgaggcccaa aaaggtttga 6300
acccaggtct tccaagtcat tcaagtgctt tctccactgt acaggtggtt atcaaccttg 6360
gctgcgcatc agaatcgttt gtaaagcttt ttctttttcc tttttaaaaa gtaaagcaat 6420
atatacacag gtaaaaaaat aaaatagtac agaagggctt ataatgagaa gcagcagttc 6480
cctgcttgca cccccacatc caaaggatgt ggagctcttt aaaaataaat tgctctggtc 6540
ccacctctgg aaatctgatt cagccagcat ggataataac ccagataact aacccctacc 6600
tcacaggata aaaaggatta catgagatgc cttaggctaa ggccctggca cacaggaaca 6660
catgtgctac aaaggagctt tggggactta agtcctgagg atccaggagg tgaggtgact 6720
tgtccaagat tccactggtt tagtggcaga gcctagactt ccactcggat ctatttagtg 6780
cttgccccct gctctctcct gtcgtgcccc accacctcct ggcatcacag ggcaaccgtt 6840
gtcaaggcta tgctcacggg aggctgggca ccacagtgtt tccaagagca agctggatcc 6900
gagtagattc cctagggctt gttggaggaa ctagtttgac tcccttatac tgtggacgca 6960
gtagccttgc tgtagggagt tgaagagtac tccacaacag tatcttaagt ttaactgggc 7020
acttccctct ggaaatcaca gtgttgtgca ccaggaacac aaagatgagt caaatcttta 7080
tcctgccttt gaggagctca ctgtttagtt ggggaaacca tttgtaaaac agccattaac 7140
catacagtgt gatcaacact gacaggagca caggaaaaac atctagctta tgtgaagatt 7200
cagagaaggc atcctgtagt ctaggtggtg atacctgaac tgagtcttga gggacgggta 7260
ggaattagcc agttgaggaa gtagaaggaa tttccagata ttggaaacag tatgcatgaa 7320
gacatgaagg caagaaacag caaaacaaat actgaagcat gaagattcct ggggtggggg 7380
gaaagcagca agaaaaggta gagaggaacc agattggaag agggtcgtaa atgcatggct 7440
acagaattca gatttgtttt gtaggacagt gtggttccca aactggctgt ataccacaaa 7500
caggtacggc attctgggcc ccggccccta aaacattcat taagtctggg gtgaagattt 7560
ggaatcttga atgcttataa aggttaccac atgactaggg tacagccaga tttggaaacc 7620
atagcttgaa ggcagtgagg gagccatgaa atggttttta atagggggac tccagatcag 7680
atgtgaactt aacctgtttc tggctggcta gccaaccagc atggaaaaca gattaggtta 7740
gatgttcatg ctgtatgtgc ccgtgcctgt agcttccctg ttaatcagct tcttacacta 7800
ctatatttgc ttattttgtc tctgaataag ctttaggcac cacaagggtg ggcctgggga 7860
tattttgctt accagtatag cccctgcaaa aaagcacagt gcctgacaca aaacaggcac 7920
ccagtaaagt ttttgaatga atgaatgcat gagtgaatcc atttgtgaga gagcgaatgg 7980
agatgacaag attagctagg agactggaaa aagaccagga ggcctgcact agggcaaagg 8040
ccagtaggaa tagattggag gtgttaaggt gtgaactgtt aaggtaagat gataacttaa 8100
tgactgatta ttggatgtgg agggtgactg agaggataga atgagtaccc atgaatagcc 8160
atgattccta ccctgtccca gtcatctctt tccttatcca tctctgaaac aatctgctta 8220
catcctcctc agcaactgga attcctcaag ttagttagac attctgtgtg ctgtgtggtc 8280
tctcactgcc cccccactcc ccacccctcc acaagccatt gattcattca tccagttcaa 8340
taaatcttgg ctaagcacct ccagtgtgca gtaaggctct tccaagccag gactctgact 8400
ccctctttcc tacctcaaga gatgtttttg agggctttcc caggtaagag tcacatctct 8460
tatacaataa cttatagtga gatacccaga atgtcagact tgtaagggaa gactgcccaa 8520
accccttctg aggtcctcag aggggaatta acttcctaag gtccgactgc taggaagtgt 8580
tggagccaga aatggaagct aggtttcctt tctatgtcat ctctggagtc ttgatcttga 8640
tctatcccat tgtagatcag gacaggcaga ggtggtcagg gagaaggtgg gacttaggtt 8700
gaaccttgaa ggtcaatgta ttggacaggt caaacaagat ggttgccaat tacactgccc 8760
ccttctggaa acccttagca aacctgccat gcttgcagtc ccttctaagg ggtttcctta 8820
gcataagttg ccatgctctg taccatgtga cctcacaatc ctggccacag atagctagat 8880
gtggatagtg tctggttcaa gggcaaccaa tctctaggct ggccagtggc ctgttagctg 8940
gactggcata aggacttcac cttacagggg tggcatgtat caaatggcaa atgtatgaaa 9000
caaccagatc tttcagggag gcagaatgtg agctattcag aagaagtgaa cgttaattag 9060
aatttaatga ggcattagtg gtggtggatg aggggtggcc agaaactaaa cagcaaaagc 9120
aaagagaaag ctgcagaaac cataagtaag cagaggtcat gagacatttg tataatgaga 9180
tcacggagcc acagggtggc agaagccatg aagcagcaag gcaacaatgg gctagaagcc 9240
atgaagcaat aggagccacg aggaacagaa accgtgagac aaaactgact atgagatcca 9300
caaagcagca gaaggcttga atagataaga tcatgagaca gtagaagcga tgagactgca 9360
agaaccacaa ggtagccaga accatgtggc aacatggcaa caggaatgga agaggcagca 9420
ggagctacaa tgcagaaaag ccatggatta ataggaactg aagcgccggg agccatgaag 9480
ctgcaggacc catgaggcag aaaaagccat gggctagcat cgaggggggc agaaagaagt 9540
tagtcagtag cagtaggagg agtataaata cagccagaaa ggagttgagt caccaatttg 9600
ggaagcacta gagaagggag caacagatgc ctgcagctga gggggtgaca agataagcca 9660
ggctctagag ctgctttgga tcatgaacca ttttcaagtt tctgttcttc catgaggctg 9720
cctgtgtagc tgttcttgtc ttccttattt ccctgtgaat gctttaataa atccccatca 9780
ctaa 9784

<210> SEQ ID NO 43
<211> LENGTH: 4131
<212> TYPE: DNA
<213> ORGANISM: Homo sapiens

<400> SEQUENCE: 43
ttttgtttgg ctgaggggag cgagcggcgc tttgggggag gggtcgcgta ggcgcctcac 60
ctgaccctgc ggccgtgcgg ttgctgctcc ggggcaggtc tccttccagg ccaggggccc 120
ggaatcatgt acataaagca ggtgattatc cagggttttc gaagttacag agatcaaaca 180
attgtagatc ccttcagttc aaaacataat gtgattgtgg gcagaaatgg atctggaaaa 240
agtaactttt tttatgcaat tcagtttgtt ctcagtgatg agtttagtca tcttcgtcca 300
gaacagcggt tggctttatt gcatgaaggt actggtcctc gtgttatttc tgcttttgtg 360
gagattattt ttgataattc agacaaccgg ttaccaatcg ataaagagga agtttcactt 420
cgaagagtta ttggtgccaa aaaggatcag tatttcttag acaagaagat ggtcacgaaa 480
aatgatgtga tgaacctcct tgaaagcgct ggtttttctc gaagcaatcc ttattatatt 540
gttaaacaag gaaagatcaa ccagatggca acagcaccag attctcagag attaaagcta 600
ttaagagaag tagctggtac tagagtgtat gacgaacgaa aggaagaaag catctcctta 660
atgaaagaaa cagagggcaa acgggaaaaa atcaatgagt tgttaaaata cattgaagag 720
agattacata ctctagagga agaaaaggaa gaactagctc agtatcagaa gtgggataaa 780
atgagacgag ccctggaata taccatttac aatcaggaac ttaacgagac tcgtgccaaa 840
cttgatgagc tttctgctaa gcgagagact agtggagaaa aatccagaca attaagagat 900
gctcagcagg atgcaagaga taaaatggag gatatcgaac gccaagttag agaattgaaa 960
acaaaaattt cagctatgaa agaagaaaaa gaacagctta gtgctgaaag acaagagcag 1020
attaagcaga ggactaagtt ggagcttaaa gccaaggatt tacaagatga actagcaggc 1080
aatagtgaac aaaggaaacg tttattaaaa gagaggcaga agctgcttga aaaaatagaa 1140
gaaaagcaga aagaactggc agaaacagaa cccaaattca acagtgtgaa agagaaagaa 1200
gaacgaggaa ttgctagatt ggctcaagct acccaggaaa gaacggatct ttatgcaaag 1260
cagggtcgag gaagccagtt tacatcaaaa gaagaaaggg ataagtggat taaaaaggaa 1320
ctcaagtctt tagatcaggc tattaatgac aagaaaagac agattgctgc tatacataag 1380
gatttggaag acactgaagc aaataaagag aaaaatctgg agcagtataa taaactggac 1440
caggatctta atgaagtcaa agctcgagta gaagaactgg acagaaaata ttacgaagta 1500
aaaaataaga aagatgaact acaaagtgaa agaaactact tgtggagaga agagaatgca 1560
gaacagcaag cacttgctgc taaaagagaa gatcttgaaa agaagcaaca acttcttaga 1620
gcagcaacag gaaaggccat tttaaatgga atagacagca taaacaaagt gctagaccac 1680
ttccgtcgaa aaggaataaa ccagcatgtt caaaatggct atcatggtat tgtaatgaat 1740
aactttgaat gtgaaccagc tttctacaca tgcgtggaag tcactgctgg aaacaggtta 1800
ttttatcaca ttgttgattc agatgaagtc agcacgaaga ttttaatgga gtttaataaa 1860
atgaatcttc ctggagaggt tacttttctg cctcttaaca agttagatgt cagggataca 1920
gcctatcctg aaaccaatga tgctattcct atgatcagca aactgaggta caatcccaga 1980
tttgacaaag ctttcaaaca tgtgtttgga aagactctta tttgtcgtag catggaagtt 2040
tcaacccagc tggcccgtgc tttcactatg gactgtatta ctttggaagg tgaccaagtc 2100
agccatcggg gtgctctaac tggggggttat tatgacacaa ggaagtctcg acttgaattg 2160
caaaaagatg ttagaaaagc agaagaagaa ctaggtgaac ttgaagcaaa gctcaatgaa 2220
aacctgcgca gaaatattga aaggattaat aatgaaattg atcagttgat gaaccaaatg 2280
caacagatcg agacccagca aaggaaattt aaagcatcta gagatagcat attatcagaa 2340
atgaagatgc taaaagagaa gaggcagcag tcagagaaaa ccttcatgcc taagcaacgt 2400
agcttacaga gtttggaggc aagcttgcat gctatggagt ctaccagaga gtcattgaaa 2460
gcagaactgg gaactgattt gctttctcaa ctgagtttgg aagatcagaa gagagtagat 2520
gcactgaatg atgagattcg tcaacttcag caggaaaaca gacagttgct aaatgaaaga 2580
attaaattag aaggtattat tactcgagta gagacttatc tcaatgagaa tctgagaaaa 2640
cgcttggacc aagtagaaca ggaacttaat gagctgagag agacagaagg gggtactgtt 2700
ctcacagcca caacatcaga acttgaagcc atcaataaaa gagtaaaaga cactatggca 2760
cgatcagaag atttggacaa ttccattgat aaaacagaag ctggaattaa ggagcttcag 2820
aagagtatgg agcgctggaa aaatatggaa aaagaacata tggatgctat aaatcatgat 2880
actaaagaac tggaaaagat gacaaatcgg caaggcatgc tattgaagaa gaaagaagag 2940
tgtatgaaga aaattcgaga acttggatca cttccccagg aagcatttga aaagtaccag 3000
acactgagcc tcaaacagtt gtttcgaaaa cttgagcagt gcaacacaga attaaagaag 3060
tacagccatg ttaacaaaaa ggctttggat cagtttgtaa atttctccga gcagaaagaa 3120

-continued

```
aagttaataa agcgtcaaga agagttagat aggggttaca aatcaatcat ggaactgatg   3180

aatgtacttg aacttcggaa atatgaagct attcagttaa ctttcaaaca ggtatctaag   3240

aacttcagtg aagtattcca gaagttagta cctggtggca aagctacttt ggtgatgaag   3300

aaaggagatg tggagggcag tcagtctcaa gatgaaggag aagggagtgg tgagagtgag   3360

aggggttctg gctcacaaag cagtgtccca tcagttgacc agtttactgg agttggaatt   3420

agggtgtcat ttacaggaaa acaaggtgaa atgagagaaa tgcaacagct ttcaggtgga   3480

cagaaatcct tggtagccct tgctctgatt tttgccattc agaaatgtga cccggctcca   3540

ttttacttgt ttgatgaaat tgaccaggct ctggatgctc agcacagaaa ggctgtgtca   3600

gatatgatta tggaacttgc tgtacatgct cagtttatta caactacttt taggcctgaa   3660

ctgcttgagt cagctgacaa attctatggt gtaaagttca gaaataaggt tagtcatatt   3720

gatgtgatca cagcagagat ggccaaagac tttgtagaag atgataccac acatggttaa   3780

ttggaaaata ctacctactg gtttgggaga tgtatatagt aatatgattc tcatacccag   3840

gaactgtaaa tttaaaccta aatatttggc caatagtttt cagacttaaa gcatcatagt   3900

ccttttatat ttgtctttgt attttataag atactctgta atgtcatgtt tgtactgata   3960

gtttaagaat ttaatttcct gtacaacttt ttgtaaaatg ttctgctcct attttaaatg   4020

ttttgaaaca tgctaaatat tctttcctaa ttattttatc acttatacta cctttttat   4080

agcttcaatt aaataatcgg ttttatgact aaaaaaaaaa aaaaaaaaaa a            4131
```

<210> SEQ ID NO 44
<211> LENGTH: 6277
<212> TYPE: DNA
<213> ORGANISM: Homo sapiens

<400> SEQUENCE: 44

```
aaaaaaaaaa aaaaaaaaag aaaaaaaacc ccgccggatc cgaccgccac tttcaaaacc     60

ccccaccgct ctagaaccgc gggagcttcc gtccctgagt agaattcgag ggtgtaaaga    120

agaggaaggg gaaaaatatc ttgtaccagc ccaggggtga agaagccccc ggcctgagaa    180

agaaggagga gtgggggagg cgaacagtct cgttgctgcc tctgtgtacg ctgagggggg    240

aggtggccac cgagtactaa attcacttgg gaataaaaga aaaacataag aaaattataa    300

gagaaaggaa ttgtcttaga agaaagaagg caagccacca ttttacccac gtaaatatat    360

gaatatattt ctgacattga ggtgttccag aagatgataa agaaatgata gcagctccag    420

aaataccaac tgattttaat ctactacagg agtcagaaac acatttttct tctgacacag    480

attttgaaga tatcgaagga aaaaaccaaa agcaaggcaa aggcaaaact tgtaaaaaag    540

gcaaaaaggg cccagcagaa aagggcaaag gtggaaatgg aggaggaaaa cctccttctg    600

gtccaaaccg aatgaatggt catcaccaac agaatggagt ggaaaacatg atgttgtttg    660

aagttgttaa aatgggcaag agtgctatgc agtcggtggt agatgattgg atagaatcat    720

acaagcatga ccgagatata gcacttcttg accttatcaa cttttttatt cagtgttcag    780

gctgtaaagg agttgtcaca gcagaaatgt ttagacatat gcagaactct gagataattc    840

gaaaaatgac tgaagaattc gatgaggata gtggagatta tccacttacc atggctggtc    900

ctcagtggaa gaagttcaaa tccagttttt gtgaattcat tggcgtgtta gtacggcaat    960

gtcaatatag tatcatatat gatgagtata tgatggatac agtcatttca cttcttacag   1020

gattgtctga ctcacaagtc agagcatttc gacatacaag caccctggca gctatgaagt   1080

tgatgacagc tttggtgaat gtggcactaa atcttagcat taatatggat aatacacaaa   1140
```

-continued

```
gacaatatga agcagaacgg aataaaatga ttggaaaacg agccaatgag aggctagaac   1200
tcctgctaca aaagcggaaa gagcttcagg aaaatcaaga tgaaatagaa aatatgatga   1260
atgcaatatt taaaggagtg tttgtacata gataccgtga tgcgatagct gaaattcgag   1320
ctatttgcat tgaagagatt ggcatttgga tgaagatgta tagtgatgcc tttcttaatg   1380
acagttattt aaaatatgtt ggttggacta tgcatgataa gcaaggtgaa gtaagactca   1440
aatgtcttac tgctctacaa gggctttatt ataacaaaga gcttaattcc aaactggaac   1500
tttttaccag tcggttcaag gatagaattg tgtctatgac ccttgacaaa gaatatgatg   1560
ttgcagtaca agcaataaaa ttactcactc ttgttttaca gagtagtgaa gaagttctca   1620
ctgcagaaga ttgtgaaaat gtctatcatc tggtttattc agctcaccgg ccagtagcag   1680
tagcagctgg agaatttctc tacaaaaagc tcttcagtcg tagagatcca gaggaggatg   1740
gaatgatgaa aagaagagga agacaaggtc caaatgccaa ccttgttaag acattggttt   1800
ttttctttct agaaagtgag ttacatgagc atgcagcata ccttgtggat agcatgtggg   1860
actgtgctac tgagctgctg aaagactggg aatgtatgaa tagcttgtta ctggaagagc   1920
cacttagtgg agaggaagca ctaacagata ggcaagagag tgctctgatt gaaataatgc   1980
tttgtaccat tagacaagcg gctgaatgtc atcctcccgt gggaagaggg acaggaaaaa   2040
gggtgcttac agcaaaggag aagaagacac agttggatga taggacaaaa atcactgagc   2100
tttttgccgt ggcccttcct cagttattag caaaatactc tgtagatgca gaaaaggtga   2160
ctaacttgtt gcagttgcct cagtactttg atttggaaat atataccact ggacgattag   2220
aaaagcattt ggatgcctta ttgcgacaga tccggaatat tgtagagaag cacacagata   2280
cagatgtttt ggaagcatgt tctaaaactt accatgcact ctgtaatgaa gagttcacaa   2340
tcttcaacag agtagatatt tcaagaagtc aactgataga tgaattggca gataaattta   2400
accggcttct tgaagatttt ctgcaagagg gtgaagaacc tgatgaagat gatgcatatc   2460
aggtattgtc aacattgaag aggatcactg cttttcataa tgcccatgac ctttcaaagt   2520
gggatttatt tgcttgtaat tacaaactct tgaaaactgg aatcgaaaat ggagacatgc   2580
ctgagcagat tgttattcac gcactgcagt gtactcacta tgtaatcctt tggcaacttg   2640
ctaagataac tgaaagcagc tctacaaagg aggacttgct gcgtttaaag aaacaaatga   2700
gagtattttg tcagatatgt caacattacc tgaccaacgt gaatactact gttaaggaac   2760
aggccttcac tattctgtgt gatattttga tgatcttcag ccatcagatt atgtcaggag   2820
ggcgtgacat gttagagcca ttagtgtata cccctgattc ttcattgcag tctgagttgc   2880
tcagctttat tttggatcat gtcttcattg aacaggatga tgataataat agtgcagatg   2940
gtcagcaaga ggatgaagcc agtaaaattg aagctctgca caagagaaga aatttacttg   3000
cagcattttg taagctaatt gtatatactg tggtggagat gaatacagct gcagatatct   3060
tcaaacagta tatgaagtat tataatgact atggagatat catcaaagaa acaatgagta   3120
aaacaaggca gatagacaaa attcagtgtg ctaagaccct tattctcagt ctgcaacagc   3180
tttttaatga aatgatacaa gaaaatggct ataattttga tagatcatcc tctacattta   3240
gtggcataaa agaacttgct cgacgttttg ctttaacttt tggacttgat cagttgaaaa   3300
caagagaagc cattgccatg ctacacaaag atggcataga atttgctttt aaagagccta   3360
atccgcaagg ggagagccat ccacctttaa atttggcatt tcttgatatt ctgagtgaat   3420
tttcttctaa actacttcga caagacaaaa gaacagtgta tgtttacttg gaaaagttca   3480
```

-continued

```
tgacctttca gatgtcactc cgaagagagg atgtgtggct tccactgatg tcttaccgaa   3540
attctttgct agctggtggt gatgatgaca ccatgtcagt cattagtgga atcagcagcc   3600
gggggtcaac agtacggagt aaaaaatcaa aaccatctac aggaaaacgg aaagtggttg   3660
agggcatgca gctttcactc actgaagaaa gtagtagtag tgacagtatg tggttaagca   3720
gagaacaaac actgcacacc cctgttatga tgcagacacc acaactcacc tccactatta   3780
tgagagagcc caaaagatta cggcctgagg atagcttcat gagtgtttat ccaatgcaga   3840
ctgaacatca tcaaacacct cttgattata acacgcaggt aacatggatg ttagctcaaa   3900
gacaacaaga ggaagcaagg caacagcagg agagagcagc aatgagctat gttaaactgc   3960
gaactaatct tcagcatgcc attcggcgtg gcacaagcct aatggaagat gatgaagagc   4020
caattgtgga agatgttatg atgtcctcag aagggaggat tgaggatctt aatgagggaa   4080
tggattttga caccatggat atagatttgc caccatcaaa gaacagacga gagagaacag   4140
aactgaagcc tgatttcttt gatccagctt caattatgga tgaatcagtt cttggagtgt   4200
caatgtttta ataccagtac acaattaaat ctgtggtgaa gtcattttct aagtggaaga   4260
ggaaatttta aagtgtggta gatacagtga aattctgtac agatttttct ctaaggagaa   4320
tatgacatgc ttatgcttac caagatcaag tgcattgagg ggcagttttg tttgcctgaa   4380
taaacgtaaa ggacaagtaa acaatttgat gataagctac agtttttctt agaaagtaaa   4440
tattttattt atgcgctgtt agttggcttt tgaatcgatt atttcatgct tttttttaaa   4500
aaaaaaaaaa aacaaaataa caatctgaag aggcatttgg tacagatatg aattctctta   4560
catttattta ctggttgtac taaataatga tgacctctgc tggatttctg tttacatcca   4620
gaaaacaatg ttaaggatgt atttattccc ctaccctgaa gaaagtgtag gatagaattg   4680
tttttagcat tctaaattta aatgcttaaa acgtcaatca acaaaacttt gttttaaata   4740
ttgtaattgt ggagaaaagt aaacttataa gcagaacttt tacaattttt tcatctaaaa   4800
gtattttaag atatttttaa aatccaagag cttctctata cttttcagaa atatccagat   4860
gcagtgaact gccagaaggt aaccagtctc aaacatgctt atcccattat caaccctgaa   4920
agtttgcttg tcctttaaga taaaaatgta atgttgtgat attccttcca gtaatgccac   4980
tgtattttgt ctccaaataa aagaagctta ttgtagtatg tttgcagaaa aattctaaac   5040
aaaaattata cagcttatta gagtgtggga atagggatct aaattttaaa taaaattata   5100
tatatatata aattggtgct gattttataa ttgcgcagtt tgtttagttt tttcttactt   5160
ttaaattcca acttaaaatt atgaggtttc agaaatatat tgaaagttta acaatgttta   5220
aaaatagaaa agcatgagtg ttcatgcttt aaaatgattt ttaaatttgt attttatatt   5280
gttttatcta tctgtctttg caagcagtct tcaggttaaa gatacttcta acaggttaca   5340
gtacatttcc tctgtatgta aattagatgg gataatagaa ttcataaccc ataatattct   5400
ttgaaagcta agctttaaac ttcattttat gtcctttcac aaataaatta gtttaaaaca   5460
gaaagtggct acttgccatt ttgacatcaa ctcattttgc gaggcttagg cagctagaca   5520
tcgtttaaaa caaaatatta acttatatta catgtgtatc tatctattgt cagtcgtctc   5580
tcagttcttg aggtatatta ttttaatcat tccatgcctt aatatgcttg caatacaaga   5640
atatcttcag atgggtgaat accaaaaggc tttcagtttt tagtcagaaa tcaagcattg   5700
ggctgtggta gccaaaaacc ataggttagc taaaaagatc atgatacaat tattttatta   5760
agtcatggtt aataacaaat gaatccagac ttgtctaaca gattttccat caacaaatat   5820
tgttatgtgc aaaagtattg cctatgttgt tttacacacc actgcattaa ctagaactgc   5880
```

-continued tgagaggact gtatatatga ttttaaacct aagttgattt tttttctcac tcttgaaagg 5940
agtacttctt tgtgaaagca gttcttacag ctttgttttc aaccagctaa aaatgtttta 6000
tatattactc taacctgttg tcctccacat tctattgtcc taattgtact gttttctgat 6060
ttgtatttat gtcttgagac agtaactttt tgaataaaaa taaacctaca gtatgttgta 6120
tgttttctct tgtactcaaa gggggagggt ggctataaat ggtttgcaaa tttatatcta 6180
ttatcacatc ttttaatgtg tttggggaat aatttataga gaataccatc agtttatatt 6240
tttaataaat catatgtatt tacaatgaaa aaaaaaa 6277

<210> SEQ ID NO 45
<211> LENGTH: 3773
<212> TYPE: DNA
<213> ORGANISM: Homo sapiens

<400> SEQUENCE: 45
aggcgcacag gtaccatttt gaccgtaaac atcctgccga tttgaaccga ggatttgggc 60
ggcaggaaga gccgcggcgt aacggcagcc atcttgtttg tttgagtgaa tcggaaagga 120
ggcgccggct gtggcggcgg cgggagctgc tcggaagcta cacctcgcaa gggctccccc 180
ctttccccac cccctccccc gaccctttttc ccctccccgg gccacccagc ccgcccaact 240
cccagcggag agcaaggttt tcttctgttt tcatagccag ccagaacaat gttctacgca 300
cattttgttc tcagtaaaag agggcctctg gccaaaattt ggctagcggc ccattgggat 360
aagaagctaa ccaaagccca tgtgttcgag tgtaatttag agagcagcgt ggagagtatc 420
atctcaccaa aggtgaaaat ggcattacgg acatcaggac atctcttact gggagtagtt 480
cgaatctatc acaggaaagc caaatacctt cttgcagact gtaatgaagc attcattaag 540
ataaagatgg cttttcggcc aggtgtggtt gacctgcctg aggaaaatcg ggaagcagct 600
tataatgcca ttactttacc tgaagaattt catgactttg atcagccact gcctgactta 660
gatgacatcg atgtggccca gcagttcagc ttgaatcaga gtagagtgga agagataacc 720
atgagagaag aagttgggaa catcagtatt ttacaagaaa atgattttgg tgattttgga 780
atggatgatc gtgagataat gagagaaggc agtgcttttg aggatgacga catgttagta 840
agcactacta cttctaacct cctattagag tctgaacaga gcaccagcaa tctgaatgag 900
aaaattaacc atttagaata tgaagatcaa tataaggatg ataattttgg agaaggaaat 960
gatggtggaa tattagatga caaacttatt agtaataatg atggcggtat ctttgatgat 1020
ccccctgccc tctctgaggc aggggtgatg ttgccagagc agcctgcaca tgacgatatg 1080
gatgaggatg ataatgtatc aatgggtggg cctgatagtc ctgattcagt ggatcccgtt 1140
gaaccaatgc caaccatgac tgatcaaaca acacttgttc caaatgagga agaagcattt 1200
gcattggagc ctattgatat aactgttaaa gaaacaaaag ccaagaggaa gaggaagcta 1260
attgttgaca gtgtcaaaga gttggatagc aagacaatta gagcccaact tagtgattat 1320
tcagatattg ttactacttt ggatctggca ccgcccacca agaaattgat gatgtggaaa 1380
gagacaggag gagtagaaaa actgttttct ttacctgctc agcctttgtg gaataacaga 1440
ctactgaagc tctttacacg ctgtcttaca ccgcttgtac cagaagacct tagaaaaagg 1500
aggaaaggag gagaggcaga taatttggat gaattcctca aagaatttga aaatccagag 1560
gttcctagag aggaccagca acagcagcat cagcagcgtg atgttatcga tgagcccatt 1620
attgaagagc caagccgcct ccaggagtca gtgatggagg ccagcagaac aaacatagat 1680
gagtcagcta tgcctccacc accacctcag ggagttaagc gaaaagctgg acaaattgac 1740
ccagagcctg tgatgcctcc tcagcaggta gagcagatgg aaataccacc tgtagagctt 1800
cccccagaag aacctccaaa tatctgtcag ctaataccag agttagaact tctgccagaa 1860
aaagagaagg agaaagagaa ggaaaaagaa gatgatgaag aggaagagga tgaagatgca 1920
tcagggggcg atcaagatca ggaagaaaga agatggaaca aaggactca gcagatgctt 1980 catggtcttc agcgtgctct tgctaaaact ggagctgaat ctatcagttt gcttgagtta 2040
tgtcgaaata cgaacagaaa acaagctgcc gcaaagttct acagcttctt ggttcttaaa 2100
aagcagcaag ctattgagct gacacaggaa gaaccgtaca gtgacatcat cgcaacacct 2160
ggaccaaggt tccatattat ataaggagct agaagcatta tagctagtgt ttgattcact 2220
agtgcttaca aattgccccc atgtgtaggg gacacagaac cctttgagaa aacttagatt 2280
tttgtctgta caaagtcttt gcctttttcc ttcttcattt ttttccagta cattaaattt 2340
gtcaatttca tctttgaggg aaactgatta gatgggttgt gtttgtgttc tgatggagaa 2400
aacagcaccc caaggactca gaagatgatt ttaacagttc agaacagatg tgtgcaatat 2460
tggtgcatgt aataatgttg agtggcagtc aaaagtcatg atttttatct tagttcttca 2520
ttactgcatt gaaaaggaaa acctgtctga gaaaatgcct gacagtttaa tttaaaacta 2580
tggtgtaagt ctttgacaag aaaaaaaaac aaacaaacac ttctttccat cagtaacact 2640
ggcaatcttc ctgttaacca ctctccttag ggatggtatc tgaaacaaca atggtcaccc 2700
tcttgagatt cgttttaagt gtaattccat aatgagcaga ggtgtacgcg aaattgtgtt 2760
atgactgata gccttcagct acaaaaagat aggactgacc tggtttaaag tgttctattt 2820
tgtaaatcat tccatttgag tctttctgat gaacttggct atactgaaat ctgttatttt 2880
agtgaggctc caaaatgagc aaagctaggc ctgattagag tagagtgact attaaaaaac 2940
ataactttct aggagctata aatcaaagtt ttaaaaagat gtttggatat atttgagtat 3000
tccgatcatg aaaacagaaa ttgccctgcc tactacaagg acagactgat gggaaattat 3060
gcacctggtc aacttagctt ttaagcagac gatgctgtaa aaactaacgg cttctctgat 3120
atttattgta agttttagta ctgatctcct tttccagtgc tgcacactcc tggtttggaa 3180
ctttaatagc gttgcaacga aatcctatat ccagtttcct gtaatttaat tgaagaaaaa 3240
tacatccaaa taaagacttt attattaaca gaccagatag catcagaaat catgtgactg 3300
ttatgattat cagaatgtct taacttttta gggcaaagtt aacactgaaa gttctagctt 3360
aagtgttgaa actttgtgg gaaaaaaaaa tcacttttga aactcagact tcagtgtata 3420
cccaataatt taaaattatg tgaaatgttt taaatttgtg aactcgtaat tactgtttta 3480
atgattcagt ttcttcagag tggtaattgt ataaaattgc tattgcagct ttacattcaa 3540
tatgatgtgc ctgtaaacca aggagttttc cccgtttgta aaaagacatt gtagataatt 3600
gaatgtttga ttttagaaag gtcattagtt tcttgttaca cattttgtta gtctggtttt 3660
tgttgcttat cgggtttaat attgttcttg aaaatagttg atgctatgtt atgtataact 3720
tttctaataa aagttgtgtt ataagctgta aaaaaaaaaa aaaaaaaaaa aaa 3773

<210> SEQ ID NO 46
<211> LENGTH: 2235
<212> TYPE: DNA
<213> ORGANISM: Homo sapiens

<400> SEQUENCE: 46
gtggagcaga agccacagtc acttcctgaa ggcagcggcc ccagctcggg tcccactcat 60
cccatggccc atcacctgcc tgcagccatg gagagccatc aggacttccg gagcatcaaa 120
gcaaagttcc aggcctctca gccggagccc agcgacctgc ccaaaaaacc tccgaagcct 180
gagtttggta aactgaagaa gttctcccag cctgagctaa gcgagcaccc caagaaggcc 240
ccgctgcctg agtttggtgc agtgtccttg aagcccccgc cgcctgaggt cactgacctc 300
cccaagaagc ccccgccgcc tgaggtcact gacctcccca agaagccccc gccgcctgag 360
gtcactgacc tccccaagaa gcccccgccg cctgaggtca ctgacctccc caagaagccg 420
tccaaactgg agttgagtga cctctccaag aagttcccac agctgggggc cactccgttt 480
ccaaggaagc cctgcagcc tgaggtcggt gaggcccctt tgaaggcctc gctgccggag 540
cctggtgcgc cggcccggaa acccctgcag cccgacgaac tcagtcaccc cgccagaccc 600
ccctccgaac ccaaatccgg cgcattcccc aggaagctct ggcaacccga ggccggtgag 660
gctaccccga ggtccccgca gcctgagttg agtacctttc ccaagaagcc tgcgcagcct 720
gagttcaacg tgtaccccaa aaagcctccg cagcctcagg tcggtggcct ccctaagaag 780
tccgtgccgc agcctgagtt cagcgaggcc gctcagactc ccctctggaa gcctcagtcc 840
agcgagccga agcgcgactc cagcgccttt cccaaaaagg cctcccagcc tccgctgagt 900
gactttccca agaagcctcc gcagcctgag cttggggacc tcaccaggac ctcctcagag 960
cccgaagtca gcgtgcttcc caagaggccg cggccggccg aattcaaagc gctctccaag 1020
aagcccccgc agcccgagct gggcggcctc cccaggacct cctcagagcc cgagttcaac 1080
tcactcccca ggaagctgct gcagccggag cgccgggggc caccccgcaa gttctcacag 1140
cctgagccca gcgctgtcct caagagacac ccgcagcctg agttcttcgg tgatctccct 1200
cgaaagcctc cactccccag ctccgcttcc gagagctcac tgcctgcggc cgtggccggc 1260
ttcagctccc ggcacccgct cagccctggg tttggagcgg ctgggacacc ccgctggagg 1320
tcaggaggcc tggttcacag tggaggggcc aggccaggcc tcagacccag ccatccaccc 1380
cggcggaggc ctctgccccc tgccagcagc ctgggacacc ctccagccaa gcccccgctg 1440
cccccggggc ccgtggatat gcagagcttt cggagaccct ctgcagcatc catagatcta 1500
cggaggaccc gctcggccgc tgggctccac ttccaggacc gacagcctga agacatcccg 1560
caggtcccag atgagatcta cgagctgtat gacgatgtgg aacccagaga tgactccagc 1620
cccagcccca agggcagaga tgaagcgccc tcagttcagc aagccgccag gaggccacca 1680
caagacccag cgctcaggaa ggagaaggat ccccagccac agcagttgcc acccatggac 1740
ccaaagttgc tgaagcagct gaggaaggca gagaaggccg agagggagtt ccggaagaag 1800
ttcaagtttg aaggggagat cgtggttcac acgaagatga tgatcgaccc caacgctaag 1860
acacgtcgcg gggtggcaa gcacctcggg atccggcgcg gggagatcct ggaggtgatc 1920
gagttcacca gcaatgagga gatgctgtgc cgggacccca aaggcaaata tggctacgtg 1980
cccagaacag cgctcctgcc cctggagacg gaggtgtacg atgatgtcga cttctgcgat 2040
cccctggaaa accaaccact ccccctggga cggtaagacc ggtaggcgtg gggccaggac 2100
agccagccag cccagcgccc gctcacccag gagccctgga tcccggcgcg ggaaagtcac 2160
agagctgcct gggcttgtac ctggccacat aaagccccag tttaaagcaa aaaaaaaaaa 2220
aaaaaaaaaa aaaaa 2235

<210> SEQ ID NO 47
<211> LENGTH: 2217
<212> TYPE: DNA

<213> ORGANISM: Homo sapiens

<400> SEQUENCE: 47
gccatcaaaa tcacagtgga tgggccccga gaacctcgaa atcgtactga gaagcactcc 60
acaatgccag actcacctgt ggatgtgaag acgcaatcta ggctgactcc tccaacaatg 120
ccacctcccc caactactca aggagctcca agaaccagtt catttacacc gacaacgtta 180
actaatggca cgagccattc tcctacagcc ttgaatggcg ccccctcacc acccaatggc 240
ttcagcaatg ggccttcctc ttcttcctcc tcctctctgg ctaatcaaca gctgccccca 300
gcctgtggtg ccaggcaact cagcaagctg aaaaggttcc ttactaccct gcagcagttt 360
ggcaatgaca tttcacccga gataggagaa agagttcgca ccctcgttct gggactagtg 420
aactccactt tgacaattga agaatttcat tccaaactgc aagaagctac taacttccca 480
ctgagacctt ttgtcatccc atttttgaag gccaacttgc ccctgctgca gcgtgagctc 540
ctccactgcg caagactggc caaacagaac cctgcccagt acctcgccca gcatgaacag 600
ctgcttctgg atgccagcac cacctcacct gttgactcct cagagctgct tctcgatgtg 660
aacgaaaacg ggaagaggcg aactccagac agaaccaaag aaaatggctt tgacagagag 720
cctttgcact cagaacatcc aagcaagcga ccatgcacta ttagcccagg ccagcggtac 780
agtccaaata acggcttatc ctaccagccc aatggcctgc ctcaccctac ccccacctcca 840 cctcagcatt accgtttgga tgatatggcc attgcccacc actacaggga ctcctatcga 900
caccccagcc acagggacct cagggacaga aacagaccta tggggttgca tggcacacgt 960
caagaagaaa tgattgatca cagactaaca gacagagaat gggcagaaga gtggaaacat 1020
cttgaccatc tgttaaactg cataatggac atggtagaaa aaacaaggcg atctctcacc 1080
gtactaaggc ggtgtcaaga agcagaccgg gaagaattga attactggat ccggcggtac 1140
agtgacgccg aggacttaaa aaaaggtggc ggcagtagca gcagccactc taggcagcag 1200
agtcccgtca acccagaccc agttgcacta gacgcgcatc gggaattcct tcacaggcct 1260
gcgtctggat acgtgccaga ggagatctgg aagaaagctg aggaggccgt caatgaggtg 1320
aagcgccagg cgatgacgga gctgcagaag gccgtgtctg aggcggagcg gaaagcccac 1380
gacatgatca caacagagag ggccaagatg gagcgcacgg tcgccgaggc caaacggcag 1440
gcggcggagg acgcactggc agttatcaat cagcaggagg attcaagcga gagttgctgg 1500
aattgtggcc gtaaagcgag tgaaacctgc agtggctgta acacagcccg atactgtggc 1560
tcattttgcc agcacaaaga ctgggagaag caccatcaca tctgtggaca gaccctgcag 1620
gcccagcagc agggagacac acctgcagtc agctcctctg tcacgcccaa cagcggggct 1680
gggagcccga tggacacacc accagcagcc actccgaggt caaccacccc gggaacccct 1740
tccaccatag agacaacccc tcgctagacg tgaactcaga actgtcggag gaaagacaac 1800
acaaccaacg cgaaaccaat tcctcatcct cagatgctca aagttgtttt ttttgtttgt 1860
ttgtttatta gatgaattat cctatttcag tacttcagca agagagaacc taactgtatc 1920
ttgaggtggt agtaaaacac agagggccag taacgggtca taatgactta ttgtggataa 1980
caaagatatc ttttctttag agaactgaaa agagagcaga gaatataaca tgaaatgata 2040
gatttgacct cctccctgaa attttcaagt agctgggatt ttaaactaga tgacctcatt 2100
aaccgatgct ttaccaaaca ccaaaccaag agattgctaa ttgctgttga aagcaaaaat 2160
gctaatatta aaagtcacaa tgttctttat atacaataat ggaaaaaaaa aaaaaaa 2217

<210> SEQ ID NO 48
<211> LENGTH: 4372
<212> TYPE: DNA
<213> ORGANISM: Homo sapiens

<400> SEQUENCE: 48

```
acagctggct gcctcacccg caggctgcag ggagaccttc cccagcctgc agccccaggc     60
ccgccccgcg tcacatgagc cccagggctc ccaccccctc cccagggcag aggacaccca    120
gttggtggcc gggagggcct cggctttcca gggacagagg cccaactcca ggacgcccca    180
gctggcccag cccctcctct ttccctcaag gctgcaggag gtcgggaaag gcagtcctgg    240
tagaggcctg tcctgggctc caggttggcc cctgagggtg gccctcctca tgccggcttc    300
aagactgagg gacagggcag ccagttcagc ctcgggatcc acctgtggct ccatgtccca    360
gacgcaccct gtgctggaga gcggcctcct ggcatctgcc ggctgctccg caccccgggg    420
tcccaggaag ggcggcccag ccccagtgga caggaaagct aaggcctcag cgatgccgga    480
ctccccagcg gaggtgaaga cgcagccccg gtccacaccc cccagcatgc cgcccccacc    540
gcctgccgca tcccaggggg ccacacgccc cccctccttc acgccacaca cacatcgaga    600
ggacgggcct gcgacgctgc cccacggccg ttttcatggc tgcttaaaat ggtctatggt    660
ctgtctcttg atgaacggca gcagccactc accaacagcc atcaatggtg caccgtgcac    720
acccaacggc ttcagcaatg gcccggccac ctcgtccaca gcctccttgt ccacacagca    780
cctgccccca gcctgcgggg cccggcagct cagcaagctc aagcgcttcc tcaccacact    840
gcagcagttt ggcagcgaca tctccccaga gattggggag cgcgtgcgca cactggtgct    900
gggcctggtg aactcgacat tgacgatcga ggagtttcat tccaagcttc aggaggccac    960
caacttccct ctgcggccgt ttgtcattcc cttcctgaag gcaaacctgc ccttgctgca   1020
gcgggagctc ctgcactgtg cacgcctggc caagcagacg cccgcccagt acttggccca   1080
gcatgagcag ctcctgctgg acgccagcgc ctcctccccc atcgactcct cagagctgct   1140
actggaagtc aacgagaacg gcaagaggag gacgcccgac aggaccaaag agaacgggtc   1200
agaccgcgac ccgctgcacc ccgagcacct cagcaaacgg ccatgcaccc tgaaccctgc   1260
ccagcgctac agccccagca acgggccacc gcagcccaca ccgccgccgc actaccgcct   1320
ggaggacata gccatggccc accacttccg agatgcctac cgccacccag acccccggga   1380
gctacgagag cgccatcggc cgcttgtggt gcctgggtcc cggcaggaag aagtgatcga   1440
ccacaagctc acagagcgtg agtgggcaga agagtggaag cacctcaaca acctcctgaa   1500
ctgcatcatg gacatggtgg agaagacgcg gcgctcgctc acggtgctgc gcaggtgcca   1560
ggaggccgac cgcgaggagc tcaaccactg ggcgcggcgc tacagcgacg ccgaggacac   1620
aaagaagggc cccgctcccg ccgcggcccg gccccgcagc agctccgccg gtcccgaagg   1680
gcctcagcta gacgtgcctc gcgagttcct gccgaggacc ctcaccggct acgtgcctga   1740
ggacatctgg aggaaggctg aagaggccgt gaatgaggtg aagcggcagg ccatgtcgga   1800
gctgcagaaa gccgtgtcgg acgcggagcg caaagcgcac gagctcatca ccacggagcg   1860
tgccaagatg gagcgggccc tggccgaggc gaagcggcag gcctccgagg acgccctgac   1920
ggtcatcaac cagcaggagg actccagcga gagctgctgg aactgcgggc ggaaagccag   1980
tgagacgtgc agcggctgca acgcggcacg ctactgcggg tccttctgcc agcatcggga   2040
ctgggagaag catcaccacg tgtgtggcca gagcctgcag ggccccacag ccgtggtggc   2100
cgacccggtg cctggaccgc ccgaagccgc ccacagcctg ggccccctccc tgcctgtggg   2160
```

-continued

```
tgctgccagc cccagcgaag ccggctctgc ggggccttct cgccccggct cccccagccc   2220
acctggccca ctggacaccg tgccccgctg accccactgg cccctggcct gccggacaca   2280
gcaccgtgcc aaccccaccc agctccaggc ccaccggatg ctgtgcctgg cctccgatgc   2340
ctggcctgcc agacactgcg ccccgcctga cctgggggag ccgaccaatt agtcactgct   2400
gctactgccc ctctccgaaa gaagacacag aaccaacaaa accgcattca gtgcacctgc   2460
ctcagctacc taatgattcc gcgcggagac ctcctgacaa cgtctcttca agcatcctca   2520
gaagcctcga ctgagcttta gacagcagag cagatgccgc aggcgcggcg gctctgccca   2580
cctctctttt cctctctgtc tgtctctccc cctctgtctt ctctatcctc tctctctcta   2640
tgactatcac acactttctc ttcaatgaaa aaatcgaatt ggtggcttat attttcagca   2700
aagaattttg gggggttttg tgtgttggca aaagagctac tcagaaatgg acaaagaaaa   2760
cggggggggtt ctccccctcc tgattaaaaa gggagaaaga aaactgcgat tttatagctg   2820
gagatctgaa cccagctgtg cccctccccc aggggcgtga ggctgatcag cgaagacggg   2880
aggaaagatt tcgatttctg actcaagatg catttttggt ttcagatttt tttttcctgt   2940
aatgttaaac tctttggctt taagtaaaaa tccaaaaagt ttttttaaaa aagcaaagga   3000
agcatacttg tgaactacct tgctagctag ccagccaagg ataccggaca cacctctgct   3060
ccaaaggaaa tccaaaaaag caaacacaag aaatcaaaat ccaaaatttg tttgtcactg   3120
ccaaagtatt tttttcactg tttcacttgc tcttgggttt gtttggatgt gggtcttttt   3180
ctcttctgtt ctgattttgt ttgtgggtgt cgggatattt gggtgcagag ggtttgtgcc   3240
cagttagaag cgacttttgt tctcttctgc gtaggcgttg gtgcgtccgc cgcgtgtgcg   3300
tggtccgtgt gccgttgctc cggcctgcgt ctccatatgt gtaggaaagg acacgccgtc   3360
tgtcctcacg ccccctgtga cttttcatat ttccgttttc cacttgtgga aaaaaagtgc   3420
taaagtttc ttcccagaga gagcataatt ccgaaacaaa actgtgacaa tcttttgggt   3480
tgattctcga ctgcttttcg agcatgcgga gccagcaggc ctccctgaaa cactgcttct   3540
cggccagccc gtcctcctct acctctctcc tctccgcgcc ctccgacctc tctcggcccc   3600
ctcaccccag ctccgacctc tctcagcccc atcgccccaa ctccaacctc tcggccccat   3660
cgccccaccg cagctactcc cctttcttcc aaacttttgc agaaaaaaca aaaaaaactac   3720
aaacaaaagc agccctctgc ctcctcccca gggaagaccc tgaccgtgta catagccctg   3780
gtgctcctgc ccagccaccc ctcagatgcg ttcgcctctg gccctggggt gtgtctcggt   3840
gacgttttct atcagacgtg ctccctccca tcctccagcc ctgcccaccc tccctccact   3900
cctctcaact gcctcagcga tttcaagaag gaaataaagg gataaagaaa ttcatgcttg   3960
caccgagtac aaggacagac agcaggcacg gcccgcagcc tggcatctgt gcgtgtggcg   4020
tggcccgtgg cttggcatct gtgtgcgtgg tgtggcccgt ggcctggcat ctgtgtgcgt   4080
ggcgtggccc gtggcctggc atctgtgtgt gtggcgtggc ccgtggcctg gcatctgtgc   4140
gcgtggcgtg gcccgtggcc tggcatctgt gtgcgtggct atcaggagtt ctaggaactc   4200
agtgcaatac gggagtgacc cagctactga accagccacg aacagcccgc cagaggcctg   4260
aagctgagcg tgtacgttaa tgtgaatgta tatagtcttt gcagaggtcc aaatgatatt   4320
catgatggta ataaacgaga tgtttgccaa ataaaaaaca gaaaccgcag ga           4372
```

METHODS FOR THE DETECTION AND TREATMENT OF LEUKEMIAS THAT ARE RESPONSIVE TO DOT1L INHIBITION

CROSS REFERENCE TO RELATED APPLICATIONS

This application is a continuation of U.S. patent application Ser. No. 14/909,713, filed Feb. 2, 2016, now U.S. Pat. No. 10,407,732, which is a 371 U.S. national phase application of PCT/US2014/049641, filed Aug. 4, 2014, which claims the benefit of and priority to U.S. Provisional Patent Application No. 61/885,947, filed Oct. 2, 2013, and also to U.S. Provisional Patent Application No. 61/861,923, filed Aug. 2, 2013, the entire contents of each of which are incorporated by reference herein.

GOVERNMENT SPONSORED RESEARCH OR DEVELOPMENT

The work described in this disclosure was funded in part by grants from the National Cancer Institute (U01CA105423). The U.S. government may have certain rights in this disclosure.

REFERENCE TO SEQUENCE LISTING

The present application includes a Sequence Listing as a txt file in electronic ASCII format titled "8540231_1.txt," created on 1 Aug. 2014 and having a size of 206202 bytes. The contents of txt file "8540231_1.txt" are incorporated by reference herein.

BACKGROUND OF THE DISCLOSURE

Field of the Disclosure

The present disclosure relates, generally, to the detection and treatment of cancer. More specifically, this disclosure provides: (i) methods for identifying leukemia patients that are susceptible to treatment with a DOT1L inhibitor by detecting one or more mutation(s) in a tissue sample or cell that are associated with elevated HOX cluster and/or HOX cluster-associated gene expression or by detecting elevated HOX cluster gene expression or elevated HOX cluster-associated gene expression; (ii) methods for identifying mutations in a leukemia patient tissue sample or cell that are predictive of the therapeutic efficacy of a DOT1L inhibitor because of their association with elevated HOX cluster and/or HOX cluster-associated gene expression; and (iii) methods for treating a leukemia patient, including an acute lymphoblastic leukemia (ALL) patient and/or an acute myelogenous leukemia (AML) leukemia patient, who has been determined to exhibit elevated HOX cluster and/or HOX cluster associated gene expression or to possess a mutation that is associated with elevated gene expression of either or both gene types by administering a DOT1L inhibitor. Additionally, the disclosure provides methods for identifying patients at high risk for developing ALL or AML who are susceptible to treatment with a DOT1L inhibitor. This disclosure also provides treatment for ALL and AML with a DOT1L inhibition in combination with another therapeutic agent, such as an FLT3 inhibitor, ATR inhibitor or CDK4/CDK6 inhibitor, and IDH1/2 inhibitor.

Description of the Related Art

The treatment for patients with acute myelogenous leukemia (AML) has not changed in over 20 years, and AML survival rates remain significantly below 50% for adults and around 60-70% for children. Even if patients are cured of their disease, there is often significant morbidity from conventional chemotherapy regimens and from bone marrow transplantation. More effective, less toxic therapies are clearly needed.

Enhanced understanding of the genes and mechanisms that lead to leukemogenesis has led to the development of a number of new therapeutic approaches that target the underlying genetic abnormalities responsible for leukemia cell survival and proliferation. See, e.g., U.S. Patent Publication Nos. 2009/026951, 2005/048634, and 2009/061443. The most prominent examples of the success of such therapies are the development of all trans-retinoic acid (ATRA), which targets the genetic abnormality that drives acute pro-myelocytic leukemia, and Imatinib, which targets the genetic abnormality that drives chronic myclogenous leukemia and certain subtypes of acute lymphoblastic leukemias, such as Philadelphia chromosome positive ALL. Those therapies have significantly improved the outcome for patients with those diseases, and are significantly less toxic than standard chemotherapy and radiation. Continued development of novel targeted approaches is critical.

Recently identified classes of proteins that control gene expression via histone and DNA modification are driving the development of new therapeutics that modulate chromatin structure. Genetic mutations responsible for leukemogenesis frequently use those proteins to reprogram normal cells into cancer cells. Recent experiments show that inhibitors of this process relieve the block in differentiation that is a hallmark of cancer cells and reactivate gene expression programs that drive cellular differentiation. This inhibits the growth of cancer cells and ultimately causes them to die. Drugs that target histone modifications, such as the histone deacetylase (HDAC) inhibitors Vorinostat and Romidepsin, have recently been approved for the treatment of cutaneous T-cell lymphoma, which demonstrates the feasibility of such approaches.

Translocations involving the Mixed Lineage Leukemia (MLL) gene are found in >70% of infant leukemias, whether they are acute myelogenous leukemias (AMLs) or acute lymphoblastic leukemias (ALLs), and approximately 10% of AML cases in older children. Biondi et al., *Blood* 96(1):24-33 (2000). Translocations involving MLL are also found in many cases of adult and therapy-related leukemias (B-ALL, T-ALL, and AML) and, as with infant leukemias, are frequently associated with a poor prognosis as compared to MLL-germline leukemias. In contrast to the high overall success rate in treating childhood ALL, where 5-year survival rates have reached ~80-90%, the genetically-defined subset of MLL-translocated ALL continues to predict poor survival rates of around 50%.

At the molecular level, MLL-translocated leukemias display characteristic gene expression profiles that are characterized by high level expression of the posterior homeobox-A (HOXA) gene cluster. Armstrong et al., *Nat. Genet.* J. Qill:41-47 (2002) and Ferrando et al., *Blood* 102(1):262-268 (2003).

Several HOX cluster genes are known to be regulated by MLL (Yu et al., *Nature* 378:505-508 (1995)), which has prompted a detailed comparison of the patterns of HOX gene expression in ALL and AML. HOXA4, HOXA5, and HOXA9 genes are not expressed, or are rarely expressed, in conventional ALL but are expressed, often at high levels, in most samples from leukemia patients exhibiting an MLL-translocation, an MLL rearrangement, or an MLL-primary tandem duplication (PTD). HOXC6 shows mildly elevated levels of expression in MLL-associated leukemias. MEIS 1, a HOX cluster associated cofactor for HOX proteins, which can accelerate HOXA9-dependent leukemia (Nakamura et al., *Nat. Genet.* 19:149-153 (1996)), is also significantly overexpressed in MLL-associated leukemias. Rozovskaia et al., *Oncogene* 20:874-878 (2001).

Several groups have demonstrated that HOXA cluster gene expression is necessary for proliferation and survival of MLL fusion driven leukemia cells and thus therapeutic approaches that suppress HOXA cluster gene expression should be efficacious against MLL-translocated leukemias.

Significant effort has been directed toward defining a unified mechanism of oncogenesis for the expressed chimeric MLL fusion proteins, including MLL translocations, MLL-rearrangements, and MLL-partial tandem duplications, since it would facilitate pharmacologic targeting of those shared leukemogenic mechanisms. Some broad patterns have emerged that are based on mechanisms that control MLL-target gene expression. The most commonly occurring MLL-translocations generate chimeric fusion proteins that harbor the NH3-terminus of MLL fused to proteins that are normally part of nuclear complexes, the function of which is now emerging. MLL fusions with nuclear proteins such as AF4, AF9, ENL, ELL, AFI0, AFI7, and AFF4, which collectively account for the vast majority of MLL leukemias, are all found to directly or indirectly recruit components of the transcriptional elongation machinery. Bitoun et al., *Hum. Mol. Genet.* 16(I):92-106 (2007); Mueller et al., *Blood* 110(13):4445-4454 (2007); Mueller et al., *PLoS Bioi.,* 7(II): e1000249 (2009); Mohan et al., *Nat. Rev. Cancer* 10(10): 721-728 (2010); Yokoyama et al., *Cancer Cell* 17(2):198-212 (2010); and Lin et al., *Molecular Cell* 37(3):429-437 (2010).

A number of complexes linked to transcriptional elongation have been reported, often with overlapping protein components, such as the ENL-associated protein (EAP) complex (Mueller (2009)), the AF4/ENLIP-TEFb (AEP) complex (Yokoyama (2010)), the super elongation complex (SEC) (Lin (2010)), and the complex comprising the histone 3 lysine 79 (H3K79) methyltransferase DOT1L (DotCom) (Mohan (2010)). These data point to aberrant control of transcriptional elongation as being involved for MLL fusion-mediated oncogenesis.

The wild type MLL protein is a histone 3 lysine 4 (H3K4) methyltransferase that methylates H3K4 near gene promoters. This modification imparts the potential for the gene to be activated during hematopoietic development. DOT1L is a histone 3 lysine 79 (H3K79) methyltransferase that modifies H3K79 within the body and promoters of actively-transcribed genes, including genes that are highly expressed in hematopoietic cells. Thus, MLL-mediated H3K4 methylation prepares genes for expression, which gene expression is promoted by DOT1L-mediated H3K79 methylation.

Studies in yeast have shown that the two complexes are regulated similarly and simultaneously, which suggests that H3K4 and H3K79 methylation work in concert in a highly regulated fashion during gene transcription. Lee et al., *Cell* 131: 1084-1096 (2007). Genome wide studies have demonstrated elevated H3K79 methylation at MLL-target genes in MLL-translocated ALL and AML cells. Krivtsov et al., *Cancer Cell* 15(5):355-368 (2008); Guenther et al., *Genes Dev.* 22(24):3403-3408 (2008); Bernt et al., *Cancer Cell* 20(1):66-78 (2011); Copeland et al., *Oncogene* 32:939-946 (2013); Krivtsov et al., *Nat. Rev. Cancer* 1:823-833 (2007); and Monroe et al., *Exp Hematol* 39:77-86 e71-75 (2011).

Several studies using conditional loss-of-function mouse models and RNAi approaches have formally demonstrated a critical role for DOT1L in MLL fusion-driven leukemias. Bernt (2011); Jo et al., *Blood* 117(18):4759-4768 (2011); Nguyen et al., *Blood* 117(25):6912-6922 (2011); and Chang et al., *Cancer Res.* 70(24):10234-10242 (2010). These studies demonstrate that genetic inactivation of DOT1L, or small molecule-mediated inhibition of DOT1L, leads to a decrease in MLL fusion target gene expression, including a rapid decrease in HOX cluster gene expression, which is correlated with an anti-proliferative response.

It has been hypothesized that translocations of MLL express aberrant MLL-fusion proteins that mistarget DOT1L to MLL target genes thereby disrupting the normal interplay between H3K79 and H3K4 methylation, which results in elevated gene expression, including elevated HOX cluster gene expression. Based upon this hypothesis, it has been suggested that DOT1L inhibitors might block the mistargeting of DOT1L to MLL-target genes in those leukemias that exhibit an MLL gene abnormalities thereby reducing the level of deregulated H3K79 and H3K4 methylation and the resulting elevation in gene expression.

Remarkably, inactivation of DOT1L does not affect the transformation potential of HOXA9 when it is expressed from a retroviral promoter. Expression of HOXA9 and its heterodimerizing partner MEIS1a, an example of a HOX cluster-associated gene expression product, rescues the anti-proliferative effect of DOT1L inhibitors on MLL-translocated leukemias. Furthermore, microarray-based gene expression studies showed that MLL-fusion target gene expression is much more dependent on DOT1L than is gene expression more generally (Bernt 2011). These studies highlight the importance of aberrant H3K79 methylation for the transforming activity of MLL fusion proteins including MLL-AF4, MLL-AF9, MLL-AF10, and MLL-ENL and show that DOT1L is required for continued HOXA cluster gene expression. These results potentially have profound clinical implications since these fusions are present in the vast majority of MLL-translocated leukemias.

The genetic and small molecule inhibitor data described above point to DOT1L as a potential therapeutic target in MLL-translocated, MLL-rearranged, and MLL-partial tandem duplication associated leukemias. A critical next step in the validation of DOT1L as a therapeutic target is to demonstrate that small molecule inhibitors exhibit similar responses as found in genetic loss-of-function models.

The small molecule DOT1L inhibitor EPZ004777 is an s-adenosyl methionine mimetic that has remarkable specificity for DOT1L as compared to other methyl transferases (FIG. 1). Daigle et al., Cancer Cell 20(1):53-65 (2011). EPZ004777 inhibits H3K79 methylation in MLL-translocated leukemia cell lines in the mid-nM range. EPZ004777 shows a dose-dependent inhibition of MLL fusion driven gene expression, including suppression of HOXA9 and MEIS1 (Bernt 2011). The growth of MV4-11 leukemia cells and the MLL-AF9 cell line Molm-13 is exquisitely sensitive to DOT1L inhibition, whereas the growth of MLL-germline Jurkat cells is unaffected by EPZ004777 (Daigle, 2011). In contrast, EPZ004777 has no anti-proliferative effect on MLL germline leukemia cell lines despite the inhibition of H3K79 methylation.

In total, these data provide strong support for the continued development of DOT1L as a potential therapeutic target in MLL-translocated, MLL-rearranged, and MLL-partial tandem duplication associated leukemias and have prompted the initiation of a phase 1 clinical trial (U.S. NIH, Clinical Trial No. NCT01684150), which is designed to assess the effect of DOT1L inhibitors in patients with relapsed/refractory hematologic malignancies.

The above mentioned data, however, do not support DOT1L as a potential target in other types of leukemia, namely leukemias that do not exhibit an MLL-translocation, an MLL-rearrangement, or an MLL-partial tandem duplication. Moreover, increased levels of HOX cluster HOX cluster-associated gene expression in leukemias other than those that exhibit an MLL-translocation, -rearrangement, or -partial tandem duplication has not been associated with the activity of DOT1L.

BRIEF SUMMARY OF THE DISCLOSURE

The present disclosure provides uses/methods for the identification of treatment susceptible patients and for the treatment of certain leukemias, including acute lymphoblastic leukemia (ALL) and acute myelogenous leukemia (AML), which do not exhibit MLL-translocations, MLL-rearrangements, and/or MLL-partial tandem duplications (PTDs), but which are nevertheless characterized by elevated expression of one or more HOX cluster gene(s) and/or one or more HOX cluster-associated gene(s) despite the absence of the foregoing MLL aberrations. The patients may possess one or more mutations that have been determined to be associated with elevated expression of one or more HOX cluster genes or HOX cluster-associated genes and the presence of such mutations may serve as a surrogate for assessing HOX cluster gene or HOX cluster-associated gene expression levels. As is described in detail herein, such leukemias may be effectively treated with one or more DOT1L inhibitor(s). Accordingly, the present disclosure also identifies the leukemia subtypes susceptible to treatment with DOT1L inhibitors.

Thus, the present disclosure greatly expands the range of patients that can be efficaciously treated by the administration of a DOT1L inhibitor beyond those exhibiting the MLL aberrations described above. The present disclosure provides a treatment for those patients having a disease or condition, including a leukemia, which is characterized by the elevated expression of one or more HOX cluster gene(s) and/or one or more HOX cluster-associated gene(s) regardless of whether those patients exhibit an MLL-translocation, an MLL-rearrangement, and/or an MLL-partial tandem duplication (PTD).

Within one embodiment, the present disclosure provides methods/uses for determining whether a leukemia patient is susceptible to treatment with a DOT1L inhibitor independently of whether it is known that the patient has a mutation other than an MLL-translocation, an MLL-rearrangement, and/or an MLL-PTDs. In other words susceptibility is inferred if the patient has a mutation associated with elevated expression of a HOX cluster gene or a HOX cluster-associated gene. By these methods, the level of expression of one or more HOX cluster gene(s) and/or one or more HOX cluster-associated gene(s) is determined in a leukemia patient tissue sample or cell and in a non-leukemia donor control tissue sample or cell (e.g., a tissue sample or cell from a healthy donor that is known not to exhibit elevated HOX cluster and/or HOX cluster-associated gene expression). By comparing the level of expression of one or more HOX cluster and/or one or more HOX cluster-associated gene(s) in the patient sample or cell (or to a predetermined standard) to the corresponding level of gene expression in the control sample or cell, an elevated level of HOX cluster and/or HOX cluster-associated gene expression is detected, which elevated HOX cluster and/or HOX cluster-associated gene expression is predictive of the therapeutic efficacy of a DOT1L inhibitor.

Within another embodiment, the present disclosure provides additional methods/uses for identifying in a leukemia patient, the susceptibility of the leukemia patient to treatment with a DOT1L inhibitor. By these methods, a leukemia patient tissue sample or cell is tested or has already been tested for the presence of genetic mutation, alteration, and/or abnormality, other than an MLL-translocation, an MLL-rearrangement, and/or an MLL-PTDs, which is known to be associated with an elevated expression of one or more HOX cluster gene(s) and/or one or more HOX cluster-associated gene(s), wherein the detection of such a genetic mutation, alteration, and/or abnormality is predictive of the therapeutic efficacy of a DOT1L inhibitor. If such a genetic mutation, alteration, and/or abnormality is detected in the leukemia patient, treatment with a DOT1L inhibitor can be initiated.

Within a further embodiment, the present disclosure provides additional methods/uses for identifying in a leukemia tissue sample or cell one or more genetic mutation, alteration, and/or abnormality, other than an MLL-translocation, an MLL-rearrangement, and/or an MLL-PTD, and determining the levels of expression of one or more HOX cluster gene(s) and/or one or more HOX cluster-associated gene(s) in the leukemia tissue sample or cell and in a non-leukemia control tissue sample or cell that is known not to exhibit elevated HOX cluster and/or HOX cluster-associated gene expression, wherein an elevated level of one or more HOX cluster gene and/or one or more HOX cluster-associated gene in the leukemia tissue sample or cell relative to the control tissue sample or cell is predictive of the therapeutic efficacy of a DOT1L inhibitor in a leukemia patient that exhibits one or more of the genetic mutation(s), alteration(s), and/or abnormality(ies) identified in the leukemia tissue sample or cell.

Within another embodiment, the present disclosure provides methods/uses for inhibiting the proliferation and/or inducing apoptosis of a leukemia cell, the methods comprising contacting a leukemia cell that has been known or determined to (i) exhibit one or more genetic mutation, alteration, and/or abnormality, other than an MLL-translocation, an MLL-rearrangement, and/or an MLL-PTD, which is known or determined to be associated with elevated expression of one or more HOX cluster gene and/or one or more HOX cluster-associated gene. The method comprises exposing such a leukemia cell to a DOT1L inhibitor.

Within yet other embodiments, the present disclosure provides methods/uses for the treatment of a leukemia patient who does not possess an MLL-translocation, or an MLL-rearrangement or an MLL-PTD, and yet exhibits a genetic mutation, alteration and/or abnormality which is known or determined to be associated with elevated expression of one or more HOX cluster gene and/or one or more HOX cluster-associated gene. By these methods, such a leukemia patient is treated by the administration of one or more DOT1L inhibitors, a composition or formulation comprising one or more DOT1L inhibitors, and/or a composition or formulation comprising one or more DOT1L inhibitor in combination with one or more other agent that is effective in the treatment of leukemia.

Within still further embodiments, the present disclosure provides methods/uses for treating a leukemia patient, comprising identifying in a tissue sample or cell from the leukemia patient one or more genetic mutation, alteration, and/or abnormality, other than an MLL-translocation, an MLL-rearrangement, and/or an MLL-PTD, which is known or determined to be associated with elevated expression of one or more HOX cluster gene and/or one or more HOX cluster-associated gene and treating the leukemia patient by administering one or more DOT1L inhibitor, one or more composition or formulation comprising one or more DOT1L inhibitor, and/or one or more composition or formulation comprising one or more DOT1L inhibitor in combination with one or more other agent that is effective in the treatment of leukemia.

Within yet other embodiments, the present disclosure provides methods/uses for treating a leukemia patient exhibiting elevated expression of one or more HOX cluster and/or one or more HOX cluster-associated gene by administering to the leukemia patient one or more DOT1L inhibitor, one or more composition or formulation comprising one or more DOT1L inhibitor, and/or one or more composition or formulation comprising one or more DOT1L inhibitor in combination with one or more other agent that is effective in the treatment of leukemia In a further embodiment the present disclosure provides a method/use of reducing the risk of therapy-related leukemia in a patient at high risk therefor said patient not having been treated previously with a DOT1L inhibitor, the method comprising administering to said patient a therapeutically effective amount of a DOT1L inhibitor, wherein the patient exhibits an actual or inferred elevated expression of a HOX cluster gene or a HOX cluster-associated gene and wherein the patient does not possess an MLL-translocation or an MLL-rearrangement or an MLL-partial tandem duplication.

In another embodiment the present disclosure provides a method/use for treating a leukemia patient exhibiting elevated expression of a HOX cluster gene and/or a HOX cluster-associated gene, said method comprising administering to said leukemia patient one or more DOT1L inhibitor, one or more composition or formulation comprising one or more DOT1L inhibitor, and/or one or more composition or formulation comprising one or more DOT1L inhibitor in combination with one or more other agent that is effective in the treatment of leukemia, wherein said leukemia patient does not exhibit an MLL-translocation, an MLL-rearrangement, and/or an MLL-PTD.

BRIEF DESCRIPTION OF THE DRAWINGS

FIG. 1A). The inhibition is specific for H3K79me as compared to methylation by other histone methyltransferases (right panel; FIG. 1B).

FIG. 5A is a graph of relative proliferation over time (up to 17 days), showing a decrease in proliferation upon treatment of NUP98-NSD1 cells with various concentrations (0.1, 1, and 10 μM) of EPZ004777 compared to the DMSO treated controls. FIG. 5B is a histogram showing mRNA expression of HOXA7, HOXA9, HOXA10, and MEIS1 relative to GAPDH (ddCT). A strong inhibitory effect of EPZ004777 on mRNA levels of HOXA7, HOXA9, HOXA10, and MEIS1 in NUP98-NSD1 transformed cells is observed.

FIGS. 6A, 6B, and 6C are, respectively, a plot of cell count versus days of exposure to tamoxifen (4-hydroxytamoxifen; 4-OHT), a photo micrograph of cells at day 0 and day 12, and a photograph of an agarose gel. These data show, collectively, the development of an inducible DOT1L loss-of-function cell line. Tamoxifen (4-OHT) induction of the Cre recombinase leads to growth arrest (left panel; FIG. 6A) and differentiation (top right panel; FIG. 6B). The conditional DOT1L allele (flox) is translocated upon cre induction and does not reappear by 12-days (bottom right panel; FIG. 6C).

FIGS. 7A-7D are plots of cell counts vs. time for human cell lines exhibiting leukemia associated mutations that are in contact with DMSO (negative control) or a DOT1L inhibitor (EPZ004777). An MLL-AF9 translocated human cell line (positive control, FIGS. 7A and 7B); an NPM1 mutant human cell line (FIG. 7C), and an AML1-ETO translocated human cell line (negative control, FIG. 7D) were treated with 10 μM EPZ004777 or DMSO (control) and cells were counted on the indicated days (days 3, 7, and 10). These data demonstrate that the DOT1L inhibitor dramatically inhibited the proliferation of the human cell line exhibiting an NPM1 mutation.

FIG. 8A is an autoradiograph showing decrease in histone methylation of H3K79 after treatment of cells with the DOT1L inhibitor EPZ004777 (10 μM). MLL-AF9 and NUP98-NSD1 transformed cells were treated with EPZ004777 (10 μM) for 10 days, and the protein levels of H3K79me2 were determined by Western blotting. FIG. 8B is a bar graph showing that the DOT1L inhibitor EPZ004777 induces apoptosis in both MLL-AF9 and NUP98-NSD1 transformed cells. Annexin V staining was assessed 10 days after treatment of MLL-AF9 or NUP98-NSD1 transformed cells with either DMSO control or with 10 μM EPZ004777. The percentage of Annexin V positive cells is shown.

FIG. 9 is a bar graph showing HOXA9 gene expression assessed by quantitative PCR in various cell lines, including the AML cell lines OCI-AML2 and OCI-AML3, which exhibit DNTM3A and NPM1 mutations, respectively, as compared to the negative control cell line HL60 and the positive control cell line Molm-13, which exhibits an MLL-AF9 translocation.

FIG. 10 is a graph of cell number plotted against the number of treatment days demonstrating that cell lines with DNTM3A or NPM1 mutations are sensitive to DOT1L inhibition. Cell lines OCI-AML2, OCI-AML3, Molm-13, and HL-60 were treated with either DMSO (control) or 10 μM DOT1L inhibitor EPZ004777. The number of cells was assessed at indicated time points and the percentage of cells present in the EPZ004777 treated vs. DMSO (control) treated conditions was graphed at each time point. OCI-AML2, OCI-AML3, and Molm-13 cell lines express high levels of HOXA9 and MEIS1, whereas HL60 does not express high levels of either HOXA9 or MEIS.

FIG. 11A is a bar graph showing OCI-AML3 cells treated with 10 μM EPZ004777 or DMSO (control) for 4, 7, or 10 days. The percentage of apoptotic cells was assessed by Annexin V staining. FIG. 11B is a series of graphs showing flow cytometry analysis of surface marker Cb11 expression in OCI-AML3 cells treated with 10 μM EPZ04777 for indicated number of days (4, 7, and 10). Increase in Cb11 marker expression indicates differentiation.

FIGS. 13A-13C show the effects of DOT1L inhibition on leukemia initiating potential in vivo. FIG. 13A shows the Kaplan-Meier survival curves (% survival versus days elapsed) for the syngeneic C57/BL6 mice injected with $Npm1^{cA/+}Rosa^{SB/+}$ AML cells previously treated for 6 days with either DMSO or 10 μM of EPZ004777. FIG. 13A indicates prolonged survival of animals treated with the DOT1L inhibitor. FIG. 13B is an image of peripheral blood smears isolated from animals injected with $Npm1^{cA/+}Rosa^{SB/+}$ AML cells (previously treated for 6 days with either DMSO or 10 μM of EPZ004777) on day 19 and stained with Wright-Giemsa stain. FIG. 13B indicates differentiation in EPZ00477 treated cells (and not in cells exposed to only DMSO). FIG. 13C is a series of graphs showing complete blood counts of samples collected on day 19 from mice injected with $Npm1^{cA/+}Rosa^{SB/+}$ AML cells treated for 6 days with either control (DMSO) or 10 μM of EPZ004777. Numbers of white blood cells and platelets are expressed as number of cells per microliter (μL) of blood. Hemoglobin levels are expressed in grams per deciliter (g/dl).

FIGS. 14A and 14B show that HOXA9, HOXA10, MEIS, HOX3A, HOXA4, and HOXA5 expression is decreased after treatment of both cell lines with 10 μM of EPZ004777.

DETAILED DESCRIPTION

Figure 1B:
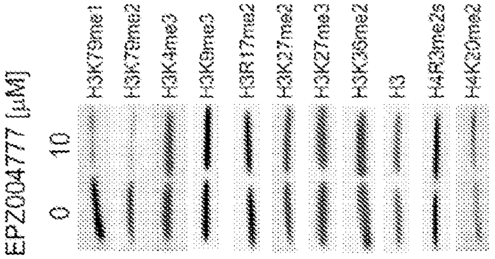
FIGS. 1A and 1B are autoradiographs showing histone methylation of H3K79me2 after treatment with the DOT1L inhibitor EPZ004777. H3K79me2 is inhibited by treatment with 0.048, 0.195, 0.781, 3.12, and 12.5 μm of the DOT1L inhibitor EPZ004777 in MLL-AF4 translocation cell line MV4-11 and MLL-AF9 translocated leukemia cells MOLM-13 (left panel.
Figure 1A:
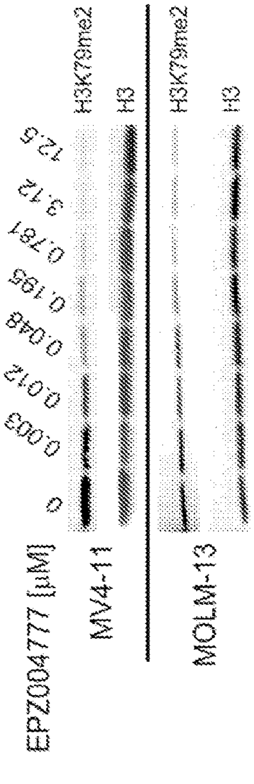

The present disclosure is based upon the discovery that leukemias that exhibit one or more genetic mutation(s), alteration(s), and/or abnormality(ies)—other than MLL-translocations, MLL-rearrangements, and MLL-partial tandem duplications (PTDs)—that are associated with elevated expression of one or more HOX cluster gene(s) and/or one or more HOX cluster-associated gene(s), are sensitive to DOT1L inhibitor-mediated growth inhibition and/or apoptosis. Moreover, leukemias exhibiting: (1) elevated expression of one or more HOX cluster gene(s) and/or one or more HOX cluster-associated gene(s) and/or (2) one or more leukemia-associated genetic mutation, alteration, and/or abnormality other than an MLL-translocation, MLL-rearrangement, or MLL-partial tandem duplication, which is associated with elevated expression of one or more HOX cluster gene(s) and/or one or more HOX cluster-associated gene(s) can be effectively treated by the administration of one or more DOT1L inhibitor(s). On other words, while a mutation causing elevated HOX cluster or HOX-cluster-associated gene expression most likely will be present, and if it is, it can serve as a surrogate for predicting that expression of HOX cluster or HOX cluster-associated genes will be elevated there is no requirement that such a mutation be present. Even if elevated expression is the result of some other factor, treatment with a DOT1L inhibitor is expected to be effective because it will reduce the elevated HOX cluster or HOX cluster-associated gene expression.

The wild type MLL protein is a histone 3 lysine 4 (H3K4) methyltransferase that methylates H3K4 near gene promoters. This modification imparts the potential to be activated during hematopoietic development. DOT1L is a histone 3 lysine 79 (H3K79) methyltransferase that modifies H3K79 on the promoters and bodies of genes that are actively transcribed. Thus, H3K4 methylation "prepares" the genes for expression and H3K79 methylation allows or promotes gene expression.

Studies in yeast have shown that the two complexes are regulated similarly and simultaneously leading to the hypothesis that these two modifications work together in a highly regulated fashion during gene transcription. It has been hypothesized that translocations of MLL lead to an aberrant protein that disrupts this intimate relationship between H3K79 and H3K4 methylation making it irreversible and leading to aberrant gene expression.

Prior to the discoveries that form the basis for the present disclosure, it was believed that this deregulated relationship accounted for the selectivity of DOT1L inhibitors in MLL-translocated, MLL-rearranged, and MLL-PTD leukemias. As disclosed herein, however, it was discovered that DOT1L is independently required for HOX gene expression during normal blood development and for HOX gene expression in leukemias that have high level HOX gene expression but no MLL abnormality. Thus, according to the present disclosure, DOT1L inhibition is broadly applicable to leukemias, beyond just leukemias exhibiting an MLL-translocation, an MLL-rearrangement, or an MLL-partial tandem duplication, which are associated with elevated HOX gene expression.

Based upon these and other discoveries, which are described in further detail herein, the present disclosure provides:

(1) Uses/methods for predicting or determining whether a leukemia tissue sample or cell is susceptible to growth and/or survival inhibition when contacted with a DOT1L inhibitor;

(2) Uses/methods for predicting or determining whether a newly-identified genetic mutation, alteration, and/or abnormality in a tissue or cell, in particular a leukemia tissue or cell, renders that tissue or cell susceptible to growth and/or survival inhibition when contacted with a DOT1L inhibitor;

(3) Uses/methods for inhibiting the growth and/or survival of a leukemia tissue or cell that either (i) exhibits one or more leukemia-associated genetic mutation, alteration, and/or abnormality other than an MLL-translocation, MLL-rearrangement, or MLL-partial tandem duplication, which is associated with elevated expression of a HOX cluster gene or HOX cluster-associated gene; or (ii) otherwise exhibits elevated expression of a HOX cluster or a HOX cluster-associated gene, by contacting that tissue or cell with one or more DOT1L inhibitor(s); and (4) Uses/methods for the treatment of a leukemia patient who either (i) exhibits one or more genetic mutation, alteration, and/or abnormality other than an MLL-translocation, MLL-rearrangement, or MLL-partial tandem duplication which is associated with elevated expression of a HOX cluster gene or HOX cluster-associated gene; or (ii) otherwise exhibits elevated expression of a HOX cluster or a HOX cluster-associated gene, by administering to the leukemia patient a composition comprising one or more DOT1L inhibitor(s).

(5) Uses/methods for inhibiting growth or survival of tissue or a cell or treatment of a leukemia patient fulfilling the characteristics outlined in paragraphs (3) and (4) above comprising contacting the tissue or cell with or administering to the patient one or more DOT1L inhibitors in combination with a FLT3 inhibitor.

As described in greater detail herein, these uses/methods for identifying, predicting, determining, inhibiting, and treatment are all based upon the newly discovered, and presently disclosed, relationships between: (1) the elevated expression of one or more HOX cluster gene(s) and/or one or more HOX cluster-associated gene(s) in a tissue and/or cell; (2) certain leukemia-associated genetic mutations, alterations, and/or abnormalities, which are not MLL-translocations, MLL-rearrangements, or MLL-partial tandem duplications; and (3) the therapeutic efficacy of a treatment regimen for leukemia that includes the administration of one or more DOT1L inhibitor(s).

These and other aspects of the present disclosure are described in further detail herein, including: (1) methodology for determining elevated HOX cluster and/or HOX cluster-associated gene expression; (2) methodology for detecting in a human tissue sample and/or cell genetic mutations, alterations, and/or abnormalities, other than MLL-translocations, MLL-rearrangements, or MLL-partial tandem duplications, which are associated with elevated HOX cluster and/or HOX cluster-associated gene expression with or without concomitantly assessing HOX cluster gene expression levels or HOX cluster-associated gene expression levels; (3) exemplary DOT1L inhibitors that may be advantageously employed to inhibit the proliferation and/or survival of a leukemia tissue or cell and to treat a leukemia patient exhibiting one or more genetic mutation, alteration, and/or abnormality, other than MLL-translocations, MLL-rearrangements, or MLL-partial tandem duplications, which is associated with elevated HOX cluster and/or HOX cluster-associated gene expression; (4) compositions, including pharmaceutical compositions, and formulations that include one or more DOT1L inhibitor; and (5) methodology for the treatment of a leukemia patient by the administration of a composition containing one or more DOT1L inhibitor, including methodology for administering one or more DOT1L inhibitors and suitable treatment regimen that employ the administration of one or more DOT1L inhibitors. The DOT1L inhibitors may be administered as monotherapy or in combination with an additional therapeutic agent such as an FLT3 inhibitor, and ATR inhibitor, an IDH1/2 inhibitor or a CDK4/CDK6 inhibitor. Nonlimiting examples of suitable ATR inhibitors include the following commercially available compounds AZ20, BEZ235; nonlimiting examples of CDK4/CDK6 inhibitors include LEE011; Nonlimiting examples of IDH1/2 inhibitors include AGI-6780 and AGI-5198. All are available from Selleckchem, Boston, Mass.

DEFINITIONS

"HOX cluster gene" and "HOX cluster-associated gene" are defined as is customary in the field. The term "HOX cluster" refers to a group of homeobox genes (class of regulatory genes that contain a 180 base pair long DNA sequence called homeobox) that are found in gene clusters on the chromosomes. HOX cluster genes code for proteins that are transcription factors and play a critical role in embryonic development and hematopoiesis. Humans contain 4 clusters (A-D) with 39 HOX genes identified to date: (1). cluster A on chromosome 7, which includes HOXA1, HOXA2, HOXA3, HOXA4, HOXA5, HOXA6, HOXA7, HOXA9, HOXA10, HOXA1, HOXA12, and HOXA13; (2) cluster B on chromosome 17, which includes HOXB1, HOXB2, HOXB3, HOXB4, HOXB5, HOXB6, HOXB7, HOXB8, HOXB9, and HOXB13; (3) cluster C on chromosome 12, which includes HOXC4, HOXC5, HOXC6, HOXC8, HOXC9, HOXC10, HOXC11, HOXC12, and HOXC13; and (4) cluster D on chromosome 2 which includes HOXD1, HOXD3, HOXD4, HOXD8, HOXD9, HOXD10, HOXD11, HOXD12, and HOXD13. The DNA-binding specificity of HOX genes is due in part to their interactions with other proteins which act as HOX cofactors and are referred to as HOX cluster-associated genes. Example of well-defined HOX cluster-associated genes are three-amino acid loop extension (TALE) genes, PBX3 and MEIS genes.

As used herein, the term "internal control" refers to a nucleotide sequence, typically but not exclusively a sequence of a housekeeping gene, or a portion thereof, which codes for a protein that is stably and constitutively expressed at high levels in most tissues and cells. Housekeeping genes are selected from those remaining generally unaffected by pathological and experimental conditions. Suitable genes that can serve as "internal controls" include, for example and without limitation, β-actin, β-tubulin, GAPDH, and cyclophyllin. The levels of HOX cluster and/or HOX cluster-associated gene expression and internal control gene expression (i.e. non-HOX cluster and non-HOX cluster-associated gene expression) can be determined (e.g., by quantifying the number of HOX and non-HOX transcripts), a ratio of HOX and non-HOX gene expression can be derived, and the level of HOX cluster and/or HOX cluster-associated gene expression within a given leukemia tissue sample or cell can be expressed in terms of the ratio of HOX and non-HOX gene expression.

In contrast, as used herein, the term "external control" refers to a HOX cluster or a HOX cluster-associated gene or genetic sequence from a non-leukemia tissue or cell, which HOX cluster or HOX cluster-associated gene or genetic sequence does not exhibit elevated expression in the non-leukemia tissue or cell but is being tested for elevated expression in a corresponding leukemia tissue or cell. Thus, for example, an "external control" can be used as a "negative control" for assessing whether a given HOX cluster gene or a given HOX cluster-associated gene exhibits elevated expression levels in a leukemia tissue sample or cell by comparing the level of expression (e.g., the number of mRNA transcripts) in a leukemia tissue sample or cell to a corresponding non-leukemia tissue sample, such as a tissue sample from a normal donor, or non-leukemia cell, such as a $CD34^+$ non-leukemia cell.

As used herein, the term “elevated gene expression,” in particular the terms “elevated HOX cluster gene expression” and “elevated HOX cluster-associated gene expression,” refers to increased expression of a specific gene product, including the increased amount of transcribed mRNA of HOX cluster gene(s) and HOX cluster-associated gene(s) which is elevated by at least about three-fold, at least about five-fold, at least about 10-fold, at least about 15-fold, at least about 20-fold, at least about 25-fold, or greater in a leukemia tissue sample or cell as compared to a control, including an internal control or an external control.

By “solid support” is meant a material that is essentially insoluble in the solvent and temperature conditions of a method such as the method comprising joining free chemical groups to an oligonucleotide or nucleic acid. The solid support can be covalently coupled to an oligonucleotide designed to bind, either directly or indirectly, a target nucleic acid. When the target nucleic acid is an mRNA, the oligonucleotide attached to the solid support is preferably a poly-T sequence. A preferred solid support is a particle, such as a micron- or submicron-sized bead or sphere. A variety of solid support materials are contemplated, such as, for example, silica, polyacrylate, polyacrylamide, metal, polystyrene, latex, nitrocellulose, polypropylene, nylon or combinations thereof. The solid support can be capable of being attracted to a location by means of a magnetic field, such as a solid support having a magnetite core. Exemplary supports include monodisperse magnetic spheres.

As used herein, “tissue sample” as it pertains to leukemia patients, includes without limitation, a blood sample, a bone marrow sample or a lymph node sample, or a collection of cells isolated from the patient such as, such as leukemic cells.

As used herein, the phrase “nucleic acid amplification conditions” refers to reaction conditions, including salt concentration, temperature, the presence or absence of temperature cycling, the presence of a nucleic acid polymerase, nucleoside triphosphates, and cofactors, that are sufficient to permit the production of multiple copies of a target nucleic acid or its complementary strand using a nucleic acid amplification method.

A “target-binding sequence” of an amplification primer is the portion that determines target specificity because that portion is capable of annealing to the target nucleic acid strand or its complementary strand but does not detectably anneal to non-target nucleic acid strands under the same conditions. The complementary target sequence to which the target-binding sequence hybridizes is referred to as a primer-binding sequence.

Methodologies for Detecting Elevated Expression of HOX Cluster and HOX Cluster-Associated Genes Elevated HOX cluster and HOX cluster-associated gene expression can be determined by one or more methodology(ies) that are well known in the art including, for example, microarray, quantitative PCR, including real-time-PCR (RT-PCR), and direct RNA sequencing. Each of the methodologies described herein for the detection of elevated HOX cluster gene or HOX cluster-associated gene expression has in common the detection of a leukemia-specific polynucleotide via the amplification, hybridization, and/or sequencing of one or more mRNA encoded by a HOX cluster gene and/or a HOX cluster-associated gene.

Elevated HOX cluster and/or HOX cluster-associated gene expression can also be assessed on the basis of the percentage or fraction of blasts (i.e., leukemia cells) relative to the total number of cells in a given tissue or blood sample from a leukemia patient. By this methodology, for example, the number of HOX cluster and/or HOX cluster-associated transcripts in a leukemia tissue sample can be quantified and multiplied by the inverse percentage or fraction of blasts in the leukemia tissue sample. The resulting HOX cluster and/or HOX cluster-associated transcript number can then be assessed relative to a threshold transcript number for HOX cluster and/or HOX cluster-associated gene expression and, based upon that assessment, the responsiveness of a leukemia patient from whom the leukemia tissue sample is derived to a therapeutic regimen comprising the administration of a DOT1L inhibitor can be predicted. More specifically, by this methodology, a transcript number for HOX cluster and/or HOX cluster-associated gene expression that is greater than a threshold transcript number would be predictive of the therapeutic efficacy of such a DOT1L inhibitor treatment regimen.

Elevated HOX cluster gene or HOX cluster-associated gene expression can, for example, be assessed by (1) quantifying a HOX cluster or HOX cluster-associated RNA (and/or protein) in a tissue sample from a leukemia patient; (2) quantifying the level of the HOX cluster or HOX cluster-associated RNA (and/or protein) in a tissue sample from a non-leukemia control donor; and (3) comparing the level of the HOX cluster or HOX associated cluster RNA (and/or protein) in the tissue sample from the leukemia patient with the level of the HOX cluster or HOX cluster-associated RNA (and/or protein) in the tissue sample from the control donor. It will be understood that an elevated level of HOX cluster or HOX cluster-associated RNA (and/or protein) in the leukemia patient tissue sample as compared to HOX cluster or HOX cluster-associated RNA and/or in the control donor tissue sample indicates the susceptibility of the leukemia patient to treatment with a DOT1L inhibitor.

Alternatively, elevated HOX cluster or HOX cluster-associated gene expression can be assessed by (1) quantifying a HOX cluster or HOX cluster-associated RNA in a tissue sample from a leukemia patient; (2) quantifying the level of a non-HOX cluster/non-HOX cluster-associated RNA in the leukemia patient tissue sample, such as, for example, GAPDH or actin; and (3) comparing the level of the HOX cluster or HOX cluster-associated RNA in the tissue sample from the leukemia patient with the level of the non-HOX cluster/non-HOX cluster-associated RNA in the leukemia patient tissue sample. It will be understood that an elevated level of the HOX cluster or HOX cluster-associated RNA in the leukemia patient tissue sample as compared to the non-HOX cluster/non-HOX cluster-associated RNA in the leukemia patient tissue sample indicates the susceptibility of the leukemia patient to treatment with a DOT1L inhibitor.

Within certain aspects of these methods a HOX cluster or HOX cluster-associated RNA can be quantified by amplifying RNA in a tissue sample, whether a leukemia tissue sample or cell, a non-leukemia tissue sample or cell from a leukemia patient, or a tissue sample or cell from a non-leukemia control donor, with a primer pair that is specific for a HOX cluster or HOX cluster-associated RNA (see Table 1). Likewise, a non-HOX cluster or non-HOX cluster-associated RNA can be quantified by amplifying RNA in a tissue sample, whether a leukemia tissue sample or cell, a non-leukemia tissue sample or cell from a leukemia patient, or a tissue sample or cell from a non-leukemia control donor, with a primer pair that is specific for a non-HOX cluster or non-HOX cluster-associated RNA, such as one of the housekeeping genes (GAPDH, β-actin, β-tubulin, etc). A primer pair comprises a forward primer and a reverse primer, wherein the forward primer hybridizes toward the 5' end of an RNA and wherein said reverse primer hybridizes toward the 3' end of the RNA, whether the RNA is a HOX cluster or HOX cluster-associated RNA or a non-HOX cluster or non-HOX cluster-associated RNA.

HOX cluster genes that are assessed for elevated expression in leukemia tissues and cells include, for example, one or more HOXA cluster gene(s) including, one or more of HOXA1, HOXA2, HOXA3, HOXA4, HOXA5, HOXA6, HOXA7, HOXA9, HOXA10, HOXA11, and HOXA13 such as, for example, one or more of HOXA5, HOXA6, HOXA7, HOXA9 and/or HOXA10. HOX cluster genes that are assessed for elevated expression in leukemia samples also include, for example, one or more HOXB cluster gene(s) including one or more of HOXB1, HOXB2, HOXB3, HOXB4, HOXB5, HOXB6, HOXB7, HOXB8, HOXB9, and HOXB13. HOX cluster-associated genes that are assessed for elevated expression in leukemia samples include, for example, one or more of MEIS1, PBX3, and MEIS2A.

Nucleotide sequences for mRNA encoded by each of those HOX cluster genes and HOX cluster-associated genes are presented in Table 1, as are the corresponding accession numbers, sequence identifiers, and citations to specific references within the scientific literature, each of which is incorporated by reference herein.

TABLE 1

Examples Homeobox (HOX) Cluster Genes and HOX Cluster-associated Genes

| *H. sapiens* HOX Cluster Gene (mRNA) | Accession Number | Sequence Identifier | References |
|---|---|---|---|
| HOXA1 (Var. 1) | NCBI: NM_005522.4 | SEQ ID NO: 1 | Zha, Tumour Biol. 33(6): 2125-2134 (2012) |
| HOXA2 | NCBI: NM_006735.3 | SEQ ID NO: 2 | Monks, Int. J. Pediatr. Otorhinolaryngol. 74(8): 878-882 (2010) |
| HOXA3 (Var. 2) | NCBI: NM_153631.2 | SEQ ID NO: 3 | Yerges, J. Bone Miner. Res. 24(12): 2039-2049 (2009) |
| HOXA4 | NCBI: NM_002141.4 | SEQ ID NO: 4 | Gray, JOP 12(3): 216-219 (2011) |
| HOXA5 | NCBI: NM_019102.3 | SEQ ID NO: 5 | Liang, J. Dermatol. Sci. 66(3): 197-206 (2012) |
| HOXA6 | NCBI: NM_024014.3 | SEQ ID NO: 6 | Yerges, J. Bone Miner. Res. 24(12): 2039-2049 (2009) |
| HOXA7 | NCBI: NM_006896.3 | SEQ ID NO: 7 | Li, Blood 119(10): 2314-2324 (2012) |
| HOXA9 | NCBI: NM_152739.3 | SEQ ID NO: 8 | Li, Blood 121(8): 1422-1431 (2013) |
| HOXA10 | GB: AF040714.1 | SEQ ID NO: 9 | Fleischman, Br. J. Haematol. 116(2): 367-375 (2002) |
| HOXA11 | NCBI: NM_005523.5 | SEQ ID NO: 10 | Li, Blood 119(10): 2314-2324 (2012) |
| HOXA13 | NCBI: NM_000522.4 | SEQ ID NO: 11 | Ekici, Gene 518(2): 267-272 (2013) |
| HOXB1 | NCBI: NM_002144.3 | SEQ ID NO: 12 | Webb, Am. J. Hum. Genet. 91(1): 171-179 (2012) |
| HOXB2 | NCBI: NM_002145.3 | SEQ ID NO: 13 | Boimel, Genomics 98(3): 164-172 (2011) |
| HOXB3 | NCBI: NM_002146.4 | SEQ ID NO: 14 | Chen, Cancer Lett. 330(2): 217-224 (2013) |
| HOXB4 | NCBI: NM_024015.4 | SEQ ID NO: 15 | Wen-jun, Cell Biochem. Biophys. 63(2): 133-141 (2012) |
| HOXB5 | NCBI: NM_002147.3 | SEQ ID NO: 16 | Stavnes, Gynecol. Oncol. 129(2): 358-363 (2013) |
| HOXB6 | NCBI: NM_018952.4 | SEQ ID NO: 17 | di Pietro, Proc. Natl. Acad. Sci. U.S.A. 109(23): 9077-9082 (2012) |
| HOXB7 | NCBI: NM_004502.3 | SEQ ID NO: 18 | Nguyen Kovochich, Cancer 119(3): 529-539 (2013) |
| HOXB8 | NCBI: NM_024016.3 | SEQ ID NO: 19 | Stavnes, Gynecol. Oncol. 129(2): 358-363 (2013) |
| HOXB9 | NCBI: NM_024017.4 | SEQ ID NO: 20 | Shrestha, FEBS J. 279(19): 3715-3726 (2012) |
| HOXB13 | NCBI: NM_006361.5 | SEQ ID NO: 21 | Stott-Miller, Prostate 73(6): 634-641 (2013) |
| *Homo sapiens* Hox Cluster-associated Gene (mRNA) | Accession Number | Sequence Identifier | References |
| MEIS1 | NCBI: NM_002398.2 | SEQ ID NO: 22 | Nurnberg, Blood 120(24): 4859-4868 (2012) |
| PBX3 (Var. 1) | NCBI: NM_006195.5 | SEQ ID NO: 23 | Li, Blood 121(8): 1422-1431 (2013) |
| MEIS2A | GB: AF178948.1 | SEQ ID NO: 24 | Yang, J. Biol. Chem. 275(27): 20734-20741 (2000) |

In order to identify a leukemia tissue sample or cell that has elevated HOX cluster gene or HOX cluster-associated gene expression, mRNA can be isolated from a leukemia tissue sample or cell and from a non-leukemia control tissue sample or cell, the level of expression of a given mRNA can be determined, and an assessment of elevated gene expression can be made by comparing the mRNA levels determined for a leukemia tissue sample or cell and a non-leukemia control tissue sample or cell.

Alternatively, a leukemia tissue sample or cell that has elevated HOX cluster gene or HOX cluster-associated gene expression can be identified by isolating for example, mRNA from a leukemia tissue sample or cell and then (i) determining the ratio of a HOX cluster gene or HOX cluster-associated gene mRNA level to the mRNA level of a housekeeping control gene in a leukemia tissue or cell; (ii) determining the ratio of HOX cluster gene or HOX cluster-associated gene mRNA level to the mRNA level of a housekeeping control gene in a healthy tissue or cell, and (iii) comparing the ratio of (i) to the ratio of (ii) and concluding that elevated expression exists if the ratio of (i) is at least 3× higher than the ratio of (ii). As used in this context, a housekeeping gene mRNA refers to a mRNA from a gene that has stable expression in both leukemic tissue or cell and a healthy tissue or cell. Suitable mRNA housekeeping genes include, for example, β-actin, β-tubulin, GAPDH, and cyclophyllin. Another way of assessing HOX cluster gene and HOX cluster-associated gene expression elevation in a leukemia tissue or cell is by comparison to a predetermined standard curve. The standard can be generated for example by qPCR of a reference HOX RNA/DNA expression (i.e. normal not elevated expression). Furthermore, in addition to mRNA levels, HOX cluster gene and HOX cluster-associated gene elevation can be determined by measuring DNA and/or protein levels.

Suitable leukemia tissue samples include, for example, blood, lymph node, bone marrow, and/or tumor biopsy samples from a leukemia patient. Suitable non-leukemia control tissue samples include, for example, blood, lymph node, and/or bone marrow samples from a non-leukemia donor, such as a healthy, disease-free donor. Such blood, lymph node, and/or bone marrow samples from a non-leukemia donor typically contain $CD34^+$ cells. It will be understood that, regardless of the precise nature or source of the donor tissue sample or cell, it is essential that the donor tissue or cell is known not to exhibit elevated expression of a HOX cluster gene or a HOX cluster-associated gene.

Suitable leukemia cells include, for example, lymphocytes or myclocytes from a leukemia patient. Suitable non-leukemia control cells, in particular non-leukemia $CD34^+$ control cells, include, for example, lymphocytes or myelocytes from a non-leukemia donor, such as a healthy, disease-free donor or one or more cell line, such as a $CD34^+$ cell line including, for example, the Kasumi-1 cell line. Regardless of its source or identity, it will be understood that a suitable non-leukemia control tissue sample or cell will not display elevated levels of the particular HOX cluster gene(s) or HOX cluster-associated gene(s) that are being tested for elevated expression in the leukemia patient tissue sample or cell.

Methodologies for detecting elevated expression of HOX cluster and HOX cluster-associated gene expression have been described. For example, Armstrong et al., *Nat. Genet.* 30(1):41-47 (2002) and U.S. Patent Publication No. 2009/0324618 describe the detection and quantification of HOXA5, HOXA6, HOXA7, HOXA9, and HOXA10 as well as the HOX cluster gene associated co-factor MEIS1 by amplifying a cDNA from total RNA using primer pairs that are specific for each HOX cluster gene or HOX cluster-associated gene. Ferrando et al., *Blood* 102(1):262-268 (2003) and Ferrando et al., *Cancer Cell* 1:75-87 (2002) describe quantitative real-time reverse transcriptase polymerase chain reaction (RT-PCR) methodology to quantify the expression of the oncogenic transcription factors HOX11 and HOX11L2.

These and other methodologies for quantifying expression levels that can be readily adapted to detecting elevated expression of HOX cluster and HOX cluster-associated genes are now described in further detail.

Microarray Analysis

Elevated HOX cluster and HOX cluster-associated gene expression can be detected and quantified by microarray analysis of RNA isolated from a leukemia patient and/or control donor tissue sample- or cell. Microarray is an effective method for simultaneously evaluating the expression level of multiple HOX cluster and HOX cluster-associated genes. But, due to limitations on its sensitivity, microarray methodology may not accurately determine the absolute tissue distribution of low abundance genes or may underestimate the degree of elevated HOX cluster and HOX cluster-associated gene expression due to signal saturation. For those genes showing elevated expression by microarray expression profiling, further analysis can be performed using one or more quantitative PCR methodology such as, for example, RT-PCR based on Taqman™ probe detection (Invitrogen Life Sciences, Carlsbad, Calif.), or the fluorescent dye SYBR Green, both of which provide a greater dynamic range of sensitivity.

Briefly, microarray analysis includes that PCR amplification of RNA extracted from a leukemia patient or control donor tissue sample or cell with primer pairs that hybridize to coding sequences within each HOX cluster and HOX cluster-associated gene and/or coding sequences within each non-HOX cluster and non-HOX cluster-associated gene the expression of which is to be detected and/or quantified. PCR products are dotted onto slides in an array format, with each PCR product occupying a unique location in the array. The RNA is then reverse transcribed and fluorescent-labeled cDNA probes are generated. Microarrays probed with the fluorescent-labeled cDNA probes are scanned, and fluorescence intensity is measured. The level of fluorescence intensity correlates with hybridization intensity, which correlates with relative level of gene expression.

HOX cluster and HOX cluster-associated gene expression analysis can be performed using a commercially available microarray (e.g., the U133A chip; Affymetrix, Santa Clara, Calif.) or using a custom microarray. Alternatively, elevated HOX cluster and HOX cluster-associated gene expression can be detected using a Synteni microarray (Palo Alto, Calif.) according to the manufacturer's instructions and as described by Schena et al., *Proc. Natl. Acad. Sci. U.S.A.* 93:10614-10619 (1996) and Heller et al., *Proc. Natl. Acad. Sci. U.S.A.* 94:2150-2155 (1997). Microarray hybridization can be performed according to methodology described in Abraham et al., *Blood* 105:794-803 (2005).

Probe level data can be normalized using a commercial algorithm (e.g., the Affymetrix Microarray Suite 5.0 algorithm) or a custom algorithm. HOX cluster and HOX cluster-associated gene expression intensity values as well as non-HOX cluster and non-HOX cluster-associated gene expression intensity values can be log transformed, median centered, and/or analyzed using commercially available programs (e.g., GeneSpring 7.3.1 GX; Agilent Technologies, Santa Clara, Calif.) or a custom algorithm.

A number of factors can be used to assess the quality of the HOX cluster and HOX cluster-associated gene expression analysis such as, for example, the GAPDH 3':5' ratio and the actin 3':5' ratio. While an ideal 3':5' ratio is 1, the ratio for the housekeeping genes should not exceed 3.

Elevated HOX cluster and HOX cluster-associated gene expression can be determined using Welch's ANOVA (analysis of variance) using variance computed by applying the cross-gene error model based on deviation from 1 available within GeneSpring. This can overcome a lack of replicates and variance associated with the individual samples and can be considered to be similar in principle to variance filtering. Unsupervised clustering can be done using a hierarchical agglomerative algorithm. Pearson's correlation coefficient and centroid linkage can be used as similarity and linkage methods, respectively.

To detect possible differences between samples, genes can be extracted from the dataset that had 1.5-fold difference in expression between individual samples and/or were statistically significant at a corrected P value of 0.05 by Student's t test with Benjamini-Hochberg multiple testing corrections. Differentially expressed genes can be assessed for Gene Ontology (GO) enrichment (e.g., using GeneSpring).

Quantitative PCR

Depending upon such factors as the relative number of leukemia cells present in a leukemia tissue sample and/or the level of HOX cluster and HOX cluster-associated gene expression within each leukemia cell within a tissue sample, it may be preferred to perform a quantitative PCR analysis to detect and/or quantify the level of HOX cluster and HOX cluster-associated gene expression.

For example, at least two oligonucleotide primers can be employed in a PCR-based assay to amplify at least a portion of a HOX cluster or HOX cluster-associated gene mRNA and/or a non-HOX cluster/non-HOX cluster-associated gene mRNA, or a corresponding cDNA, which is derived from a leukemia tissue sample or cell and/or a non-leukemia control donor tissue sample or cell. At least one of the oligonucleotide primers is specific for, and hybridizes to a nucleic acid portion fragment specific for HOX cluster and HOX cluster-associated gene. The amplified cDNA may, optionally, be subjected to a fractionation step such as, for example, gel electrophoresis prior to detection.

RT-PCR is a quantitative PCR methodology in which PCR amplification is performed in conjunction with reverse transcription. RNA is extracted from a tissue sample or cell, such as a blood, lymph node, bone marrow, and/or tumor biopsy sample, and is reverse transcribed to produce cDNA molecules. PCR amplification using at least one specific primer amplifies the cDNA molecule, which may be separated and visualized using, for example, gel electrophoresis. Amplification may be performed on tissue samples or cells taken from a patient and from a heathy individual who serves as a negative control. The amplification reaction may be performed on several dilutions of cDNA spanning two orders of magnitude. An increase in expression of at least about three-fold, at least about five-fold, at least about 10-fold, at least about 15-fold, at least about 20-fold, at least about 25-fold, or greater in several dilutions of the test leukemia patient sample as compared to the same dilutions of the non-leukemia healthy control donor sample is typically considered positive.

HOX cluster and HOX cluster-associated gene expression may be further characterized or, alternatively, originally detected and/or quantified by employing the quantitative real-time PCR methodology. Gibson et al., *Genome Research* 6:995-1001 (1996) and Heid et al., *Genome Research* 6:986-994 (1996). Real-time PCR is a technique that evaluates the level of PCR product accumulation during the course of amplification. This technique permits quantitative evaluation of mRNA levels in multiple samples. By this methodology, a leukemia tissue sample or cell may be tested along-side a corresponding non-leukemia control donor sample or cell and/or a panel of unrelated normal non-leukemia tissue samples or cells.

Real-time PCR may, for example, be performed either on the ABI 7700 Prism or on a GeneAmp® 5700 sequence detection system (Applied Biosystems, Foster City, Calif.). The 7700 system uses a forward and a reverse primer in combination with a specific probe with a 5' fluorescent reporter dye at one end and a 3' quencher dye at the other end (Taqman™). When real-time PCR is performed using Taq DNA polymerase with 5'-3' nuclease activity, the probe is cleaved and begins to fluoresce allowing the reaction to be monitored by the increase in fluorescence (real-time). The 5700 system uses SYBR®green, a fluorescent dye, which only binds to double stranded DNA, and the same forward and reverse primers as the 7700 instrument. Matching primers and fluorescent probes may be designed according to the primer express program (Applied Biosystems, Foster City, Calif.). Optimal concentrations of primers and probes are initially determined by those of ordinary skill in the art. Control (e.g., β-actin-specific) primers and probes may be obtained commercially from, for example, Perkin Elmer/Applied Biosystems (Foster City, Calif.).

To quantify the amount of HOX cluster and HOX cluster-associated gene expression in a sample, a standard curve is generated using a plasmid containing the gene of interest. Standard curves are generated using the Ct values determined in the real-time PCR, which are related to the initial cDNA concentration used in the assay. Standard dilutions ranging from 10-$10^6$ copies of the gene of interest are generally sufficient. In addition, a standard curve is generated for the control sample sequence. This permits standardization of initial RNA content of a leukemia tissue sample or cell to the amount of a control tissue sample or cell for comparison purposes.

Total RNA may be isolated and extracted from leukemia tissue samples or cells and non-leukemia control tissue samples or cells using Trizol reagent as described herein. First strand synthesis may be carried out using 1-2 μg of total RNA with SuperScript II reverse transcriptase (Life Technologies, Carlsbad, Calif.) at 42° C. for one hour to yield full length cDNA. cDNA may then be amplified by PCR using HOX cluster and HOX cluster-associated gene-specific primers that are designed based upon the HOX cluster and HOX cluster-associated mRNA sequences presented in Table 1, disclosed within the references cited in Table 1, or that are otherwise known and readily available to those skilled in the art.

To ensure the quantitative nature of the RT-PCR, a housekeeping gene, such as β-actin, can be used as an internal control for each of the leukemia patient and non-leukemia control donor tissue samples and/or cells examined. Serial dilutions of the first strand cDNAs are prepared and RT-PCR assays are performed using β-actin specific primers. A dilution is then chosen that enables the linear range amplification of the β-actin template and that is sensitive enough to reflect the differences in the initial copy numbers. Using these conditions, the β-actin levels are determined for each reverse transcription reaction from each tissue. DNA contamination is minimized by DNase treatment and by assuring a negative PCR result when using first strand cDNA that was prepared without adding reverse transcriptase.

In an exemplary RT-PCR reaction using the Dynabeads mRNA direct microkit (Invitrogen, Life Sciences Technologies, Carlsbad, Calif.), samples containing $10^5$ cells or less are tested in a total reaction volume of 30 μl with 14.25 μl $H_2O$; 1.5 μl BSA; 6 μl first strand buffer; 0.75 mL of 10 mM dNTP mix; 3 μl Rnasin; 3 μl 0.1 M dTT; and 1.5 μl Superscript II. The resulting solution is incubated for 1 hour at 42° C., diluted 1:5 in $H_2O$, heated at 80° C. for 2 min to detach cDNA from the beads, and immediately placed on MPS. The supernatant containing cDNA is transferred to a new tube and stored at −20° C.

RNA Sequencing

Elevated expression of one or more HOX cluster gene and/or one or more HOX cluster-associated gene can be determined by the direct sequencing of mRNA in a leukemia patient tissue sample or cell and/or a non-leukemia donor control tissue sample or cell. Alternatively, elevated expression of one or more HOX cluster gene and/or one or more HOX cluster-associated gene can be determined following conversion of mRNA into cDNA by reverse transcription.

True Single Molecule Sequencing (tSMS™) and/or Direct RNA Sequencing (DRS™) are useful techniques for quantifying gene expression that can be readily adapted for detecting and quantifying the expression one or more HOX cluster gene and/or one or more HOX cluster-associated gene. These sequencing-by-synthesis technologies can be performed on mRNAs derived from a tissue sample or cell without the need for prior reverse transcription or PCR amplification.

Direct RNA sequencing technology (Helicos BioSciences Corporation, Cambridge, Mass.) and transcriptome profiling using single-molecule direct RNA sequencing are described in Ozsoolak et al., *Nature* 461(7265):814-818 (2009) and Ozsolak and Milos, *Methods Mol Biol* 733:51-61 (2011). True Single Molecule and Direct RNA Sequencing technologies are further described in U.S. Patent Publication Nos. 2008/0081330, 2009/0163366, 2008/0213770, 2010/0184045, 2010/0173363, 2010/0227321, 2008/0213770, and 2008/0103058 as well as U.S. Pat. Nos. 7,666,593; 7,767,400; 7,501,245; and 7,593,109, each of which is hereby incorporated by reference in its entirety.

mRNAs encoded by HOX cluster and HOX cluster-associated genes as well as non-HOX cluster and non-HOX cluster-associated genes can be directly sequenced by True Single Molecule and Direct RNA Sequencing technologies by utilizing specific sequencing primers that are designed based upon the HOX cluster and HOX cluster-associated mRNA sequences and non-HOX cluster and non-HOX cluster-associated mRNA sequences (e.g., as presented in Table 1, disclosed within the references cited in Table 1, or which are otherwise known and readily available to those skilled in the art).

Methodologies for Detecting Leukemias Exhibiting Elevated HOX Cluster and/or HOX Cluster-Associated Gene Expression In general, a leukemia cell may be detected in a patient based on the presence of one or more genes that are known to be associated with leukemia, a subset of which are also known to be associated with elevated HOX cluster and HOX cluster-associated gene expression. According to the present disclosure, leukemia patients that exhibit one or more genetic mutation, alteration, and/or other abnormality, other than an MLL-translocation, MLL-rearrangement, or MLL-partial tandem duplication, which is known, or determined to be associated with elevated HOX cluster and HOX cluster-associated gene expression, are suitably treated by the administration of one or more DOT1L inhibitor as described herein.

This section describes representative methodologies that are well known and that can be easily adapted by those skilled in the art to the detection of one or more genetic mutation, alteration, and/or other abnormality in a tissue sample or cell. These methodologies include, for example, nucleic acid amplification and sequencing technologies; nucleic acid hybridization technologies, including fluorescent in situ hybridization (FISH).

Exemplary genes that, when mutated or otherwise altered, are known to be associated with leukemia in a patient are presented in Tables 2 and 3. Table 2 presents those leukemia-associated genes, including NPM1, DNMT3A, IDH1, IDH2, RUNX1, TET2, and ASXL1 mutations and NUP98-NSD1 and other NUP98 translocations, which, when exhibiting one or more mutation(s), rearrangement(s), and/or translocation(s) (other than MLL-translocation(s), an MLL-rearrangement(s), and/or an MLL-partial tandem duplication(s)), are known to be associated with elevated expression of one or more HOX cluster and/or HOX cluster-associated gene(s) in a cell, as compared to the level of expression of the respective HOX cluster and/or HOX cluster-associated gene(s) in a normal $CD34^+$ bone marrow cells.

The detection and/or presence of one or more mutation(s), rearrangement(s), translocation(s) and/or other genetic alteration(s) or abnormality(s) in one or more of the leukemia-associated genes from Table 2 in a leukemia patient tissue sample or cell is, according to the discoveries upon which the present disclosure is based, predictive of a leukemia tissue sample or cell the proliferation and/or survival of which can be inhibited, prevented, or terminated by contacting with one or more DOT1L inhibitor.

Thus, according to the present disclosure, a leukemia patient having a tissue or cell that exhibits (1) one or more of the mutation(s), rearrangement(s), translocation(s) and/or other genetic alteration(s) or abnormality(s) in one or more of the leukemia-associated genes presented in Table 2 and/or (2) one or more mutation(s), rearrangement(s), translocation(s) and/or other genetic alteration(s) or abnormality(s) in one or more leukemia-associated gene(s) that is determined (e.g., according to the methods provided herein) to be associated with elevated HOX cluster and/or HOX cluster-associated gene expression, may be advantageously treated by the administration of one or more DOT1L inhibitor, including a composition or formulation comprising one or more DOT1L inhibitor, either individually, as a combination of two or more DOT1L inhibitors, and/or in further combination with another suitable therapeutic agent. Suitable DOT1L inhibitors, compositions, formulations, and other suitable therapeutic agents for the treatment of leukemia are described in further detail herein, are well known to those of skill in the art, and are presented in the scientific and patent literature cited herein, each of which is incorporated by reference into the present disclosure.

TABLE 2

| Leukemia Genes Associated with Elevated HOX Cluster and/or HOX Cluster-associated Gene Expression | | | | |
|---|---|---|---|---|
| *H. sapiens* Leukemia Gene (mRNA) | Accession Number | Sequence Identifier | Level HOXA9 Gene Expression Relative to Normal CD34+ Bone Marrow Cells | References |
| NUP98 | GenBank: AB040538.1 | SEQ ID NO: 27 | 25** (NUP98-NSD1) | Hollink, NUP98/NSD1 Characterizes a Novel Poor Prognostic Group in Acute Myeloid Leukemia with a Distinct HOX Gene Expression Pattern, Blood 118(13): 3645-56 (2011)<br>Wang, NUP98-NSD1 Links H3K36 Methylation to Hox-A Gene Activation and Leukaemogenesis, Nat Cell Biol 9(7): 804-12 (2007)<br>Arai, Heterogenous Fusion Transcripts Involving the NUP98 Gene and HOXD13 Gene Activation in a Case of Acute Myeloid Leukemia with the t(2; 11)(q31; p15) Translocation, Leukemia 14(9): 1621-9 (2000) |
| NSD1 | GenBank: AF322907.1 | SEQ ID NO: 28 | | Jaju, A Novel Gene, NSD1, is Fused to NUP98 in the t5; 11)q35; p15.5) in De novo Childhood Acute Myeloid Leukemia, Blood 98(4): 1264-1267 (2001) |
| NPM1 | GenBank: AY740639.1 | SEQ ID NO: 29 | 18* | Zangenberg, The Combined Expression of HOXA4 and MEIS1 is an Independent Prognostic Factor in Patients with AML, Eur J Haematol 83(5): 439-48 (2009)<br>Haferlach, AML with Mutated NPM1 Carrying a Normal or Aberrant Karyotype Show Overlapping Biologic, Pathologic, Immunophenotypic, and Prognostic Features, Blood 114(14): 3024-32 (2009)<br>Mullighan, Pediatric Acute Myeloid Leukemia with NPM1 Mutations is Characterized by a Gene Expression Profile with Dysregulated HOX Gene Expression Distinct from MLL-rearranged Leukemias, Leukemia 21(9): 2000-9 (2007)<br>Falini, Cytoplasmic Nucleophosmin in Acute Myelogenous Leukemia with a Normal Karyotype, N. Engl. J. Med. 352(3): 254-266 (2005) |
| DNMT3A | GenBank: AF331856.1 | SEQ ID NO: 30 | 13* | Hajkova, Decreased DNA Methylation in Acute Myeloid Leukemia Patients with DNMT3A Mutations and Prognostic Implications of DNA Methylation, Leuk Res 36(9): 1128-33 (2012)<br>Kim, Co-operation and Communication between the Human Maintenance and De novo DNA (cytosine-5) Methyltransferases, EMBO J 21(15): 4183-95 (2002) |
| IDH1 | GenBank: CR533522.1 | SEQ ID NO: 31 | 13* | Schaap, Mutations in the Isocitrate Dehydrogenase Genes IDH1 and IDH2 in Tumors, Adv Anat Pathol 20(1): 32-8 (2013)<br>Feng, Prognostic Significance of IDH1 Mutations in Acute Myeloid Leukemia: A Meta-Analysis, Am J Blood Res 2(4): 254-64 (2012)<br>Westman, IDH1 and IDH2 Mutations in Therapy-related Myelodysplastic Syndrome and Acute Myeloid Leukemia are Associated with a Normal Karyotype and with Der(1; 7)(q10; p10), Leukemia 27(4): 957-9 (2013)<br>Ibáñez, Rapid screening of ASXL1, IDH1, IDH2, and c-CBL mutations in de novo acute myeloid leukemia by high-resolution melting, J Mol Diagn 14(6): 594-601 (2012)<br>Zhou, Potential Application of IDH1 and IDH2 Mutations as Prognostic Indicators in Non-promyelocytic Acute Myeloid Leukemia: A Meta-Analysis, Leuk Lymphoma 53(12): 2423-9 (2012)<br>Brecqueville, Mutation Analysis of ASXL1, CBL, DNMT3A, IDH1, IDH2, JAK2, MPL, NF1, SF3B1, SUZ12, and TET2 in Myeloproliferative Neoplasms, Genes Chromosomes Cancer 51(8): 743-55 (2012)<br>Chotirat, Molecular Alterations of Isocitrate Dehydrogenase 1 and 2 (IDH1 and IDH2) Metabolic Genes and Additional Genetic Mutations in Newly Diagnosed Acute Myeloid Leukemia Patients, J Hematol Oncol 5: 5 (2012)<br>Byers, Detection of IDH1 R132H Mutation in Acute Myeloid Leukemia by Mutation-specific Immunohistochemistry, Appl Immunohistochem Mol Morphol 20(1): 37-40 (2012) |
| IDH2 | NCBI: NM 002168.2 | SEQ ID NO: 32 | 8* | See, IDH1 |
| RUNX1 | GenBank: AY509915.1 | SEQ ID NO: 33 | 10* | Grossmann, The molecular profile of adult T-cell acute lymphoblastic leukemia: mutations in RUNX1 and DNMT3A are associated with poor prognosis in T-ALL, Genes Chromosomes Cancer 52(4): 410-22 (2013)<br>Mendler, RUNX1 Mutations are Associated with Poor Outcome in Younger and Older Patients with Cytogenetically Normal Acute Myeloid Leukemia and with Distinct Gene and MicroRNA Expression Signatures, J Clin Oncol 30(25): 3109-18 (2012)<br>Greif, RUNX1 Mutations in Cytogenetically Normal Acute Myeloid Leukemia are Associated with a Poor Prognosis and Up-regulation of Lymphoid Genes, Haematologica 97(12): 1909-15 (2012)<br>Camós, Gene Expression Profiling of Acute Myeloid Leukemia with Translocation t(8; 16)(p11; p13) and MYST3-CREBBP |

TABLE 2-continued

Leukemia Genes Associated with Elevated HOX Cluster and/or HOX Cluster-associated Gene Expression

| *H. sapiens* Leukemia Gene (mRNA) | Accession Number | Sequence Identifier | Level HOXA9 Gene Expression Relative to Normal CD34+ Bone Marrow Cells | References |
|---|---|---|---|---|
| | | | | Rearrangement Reveals a Distinctive Signature with a Specific Pattern of HOX Gene Expression, Cancer Res 66(14): 6947-54 (2006) |
| TET2 | NCBI: NM_001127208.2 NCBI: NM_017628.4 | SEQ ID NO: 34 SEQ ID NO: 35 | 7* | Liang, Cooperating Gene Mutations in Childhood Acute Myeloid Leukemia with Special Reference on Mutations of ASXL1, TET2, IDH1, IDH2, and DNMT3A, Blood 121(15): 2988-2995 (2013) Tefferi, Detection of Mutant TET2 in Myeloid Malignancies other than Myeloproliferative Neoplasms: CMML, MDS, MDS/MPN and AML, Leukemia 23(7): 1343-1345 (2009) Jankowska, Loss of Heterozygosity 4q24 and TET2 Mutations Associated with Myelodysplastic/Myeloproliferative Neoplasms, Blood 113 (25), 6403-6410 (2009) |
| ASXL1 | NCBI: NM_015338.5 NCBI: NM_001164603.1 | SEQ ID NO: 36 SEQ ID NO: 37 | 3* | Schnittger, ASXL1 Exon 12 Mutations are Frequent in AML with Intermediate Risk Karyotype and are Independently Associated with an Adverse Outcome, Leukemia 27(1): 82-91 (2013) Ibanez, Rapid screening of ASXL1, IDH1, IDH2, and c-CBL mutations in de novo acute myeloid leukemia by high-resolution melting, J Mol Diagn 14(6): 594-601 (2012) Abdel-Wahab, Role of TET2 and ASXL1 mutations in the pathogenesis of myeloproliferative neoplasms, Hematol. Oncol. Clin. North Am. 26(5): 1053-1064 (2012) |

*Compared to CD34+ Bone Marrow Cells
**Compared to NUP98-NSD1 Negative Patients

Table 3 presents those leukemia-associated genes that, when exhibiting one or more mutation(s), rearrangement(s), and/or translocation(s), are known not to be associated with elevated expression of a HOX cluster and/or HOX cluster-associated gene in a cell, as compared to the level of expression of the respective HOX cluster and/or HOX cluster-associated gene(s) in a normal CD34$^+$ bone marrow cells.

The detection and/or presence of one or more mutation(s), rearrangement(s), translocation(s) and/or other genetic alteration(s) or abnormality(s) in one or more of the leukemia-associated genes from Table 3 in a leukemia patient tissue sample or cell is, according to the discoveries upon which the present disclosure is based, predictive of a leukemia tissue sample or cell the proliferation and/or survival of which cannot be inhibited, prevented, or terminated by contacting with one or more DOT1L inhibitor.

Thus, according to the present disclosure, a leukemia patient having a tissue or cell that exhibits one or more of the mutation(s), rearrangement(s), translocation(s) and/or other genetic alteration(s) or abnormality(s) in one or more of the leukemia-associated genes in Table 3, but does not also exhibit (1) one or more of the mutation(s), rearrangement(s), translocation(s) and/or other genetic alteration(s) or abnormality(s) in one or more of the leukemia-associated genes in Table 2; (2) one or more MLL-translocation(s), MLL-rearrangement(s), and/or an MLL-partial tandem duplication(s); and/or (3) one or more mutation(s), rearrangement(s), translocation(s) and/or other genetic alteration(s) or abnormality(s) in one or more leukemia-associated gene(s) that is determined (e.g., according to the methods provided herein) to be associated with elevated HOX cluster and/or HOX cluster-associated gene expression, is likely not advantageously treated by the administration of one or more DOT1L inhibitor.

TABLE 3

Leukemia Genes that are Not Associated with Elevated HOX Cluster and/or HOX Cluster-associated Gene Expression

| *H. sapiens* Leukemia Gene (mRNA) | Accession Number | Sequence Identifier | References |
|---|---|---|---|
| EZH2 | NCBI: NM_004456.4 | SEQ ID NO: 38 | Larsson, The Changing Mutational Landscape of Acute Myeloid Leukemia and Myelodysplastic Syndrome, Mol Cancer Res. [Epub ahead of print] (2013) Wang, EZH2 Mutations are Related to Low Blast Percentage in bone Marrow, PLoS One 8(4): e61341 (2013) |
| CEBPA | NCBI: NM_004364.3 | SEQ ID NO: 39 | Zhang, Molecular Genetic Tests for FLT3, NPM1, and CEBPA in Acute Myeloid Leukemia, Methods Mol Biol. 999: 105-21 (2013) van Vliet, Detection of CEBPA Double Mutants in Acute Myeloid Leukemia using a Custom Gene Expression Array, Genet Test Mol Biomarkers 17(5): 395-400 (2013) Greif, GATA2 Zinc Finger 1 Mutations Associated with Biallelic CEBPA Mutations Define a Unique Genetic Entity of Acute Myeloid Leukemia, Blood 120(2): 395-403 (2012) Hendricks-Taylor, The CCAAT/enhancer binding protein (C/EBP alpha) gene (CEBPA) maps to human chromosome 19q13.1 and the related nuclear factor NF-IL6 (C/EBP beta) gene (CEBPB) maps to human chromosome 20q13.1, Genomics 14(1): 12-17 (1992) |

TABLE 3-continued

Leukemia Genes that are Not Associated with Elevated HOX Cluster and/or HOX Cluster-associated Gene Expression

| *H. sapiens* Leukemia Gene (mRNA) | Accession Number | Sequence Identifier | References |
|---|---|---|---|
| NRAS | NCBI: NM_002524.4 | SEQ ID NO: 40 | Aly, Prognostic Significance of NRAS Gene Mutations in Children with Acute Myelogenous Leukemia, Mediterr. J. Hematol. Infect. Dis. 3(1): e2011055 (2011)<br>Paulsson, Mutations of FLT3, NRAS, KRAS, and PTPN11 are Frequent and Possibly Mutually Exclusive in High Hyperdiploid Childhood Acute Lymphoblastic Leukemia, Genes Chromosomes Cancer 47(1): 26-33 (2008)<br>Hirai, Transforming Genes in Human Leukemia Cells, Blood 66(6): 1371-1378 (1985)<br>Hall, Human N-ras: cDNA Cloning and Gene Structure, Nucleic Acids Res. 13(14): 5255-5268 (1985) |
| KRAS | NCBI: NM_033360.2 | SEQ ID NO: 41 | Mansour, Oncogenic Kras and Notch-1 Cooperate in T-cell Acute Lymphoblastic Leukemia/Lymphoma, Expert Rev Hematol 2(2): 133-6 (2009)<br>Sabnis, Oncogenic Kras Initiates leukemia in Hematopoietic Stem Cells, PLoS Biol 7(3): e59 (2009)<br>Bollag, Biochemical Characterization of a Novel KRAS Insertion Mutation from a Human Leukemia, J Biol Chem 271(51): 32491-4 (1996) |
| SMC1A | NCBI: NM_006306.3 | SEQ ID NO: 42 | Homme, Low SMCIA Protein Expression Predicts Poor Survival in Acute Myeloid Leukemia, Oncol Rep 24(1): 47-56 (2010)<br>Laugsch, Imbalance of SMC1 and SMC3 Cohesins Causes Specific and Distinct Effects, PLoS One 8(6): e65149 (2013)<br>Sun, The SMC1-SMC3 Cohesion Heterodimer Structures DNA through Supercoiling-dependent Loop Formation, Nucleic Acids Res 41(12): 6149-60 (2013)<br>Stursberg, Cloning and Characterization of Mammalian SMC1 and SMC3 Genes and Proteins, Components of the DNA Recombinant Complexs RC-1, Gene 228(1-2): 1-12 (1999) |
| SMC3 | NCBI: NM_005445.3 | SEQ ID NO: 43 | See, SMC1 |
| STAG2 | NCBI: NM_001042749.1 | SEQ ID NO: 44 | Chung, Somatic Mutation of STAG2, an Aneuploidy-related Gene, is Rare in Acute Leukemias, Leuk Lymphoma 53(6): 1234-5 (2012)<br>Chen, Novel Non-TCR Chromosome Translocations t(3; 11)(q25; p13) and t(X; 11)(q25; p13) Activating LMO2 by Juxtaposition with MBNL1 and STAG2, Leukemia 25(10): 1632-5 (2011) |
| RAD21 | NCBI: NM_006265.2 | SEQ ID NO: 45 | Deardorff, RAD21 Mutations Cause a Human Cohesinopathy, Am J Hum Genet 90(6): 1014-27 (2012) |
| PRAM1 | NCBI: NM_032152.4 | SEQ ID NO: 46 | Choi, Spectra of Chromosomal Aberations in 325 Leukemia Patients and Implications for the Development of New Molecular Detection Systems, J Korean Med Sci 26(7): 886-92 (2011)<br>Moog-Lutz, PRAM-1 is a Novel Adaptor Protein Regulated by Retinoic Acid (RA) and Promyelocytic Leukemia (PML)-RA Receptor Alpha in Acute Promyelocytic Leukemia Cells, J Biol Chem 276(25): 22375-81 (2001) |
| AML1-ETO | GenBank: S78158.1 | SEQ ID NO: 47 | Licht, AML1 and the AML1-ETO Fusion Protein in the Pathogenesis of t(8; 21) AML, Oncogene 20(40): 5660-79 (2001) |
| CBFA2T3 | NCBI: NM_005187.5 | SEQ ID NO: 48 | Masetti, CBFA2T3-GLIS2 Fusion Transcript is a novel Common Feature in Pediatric, Cytogenetically Normal AML, not Restricted to FAB M7 Subtype, Blood 121(17): 3469-72 (2013)<br>Gruber, An Inv(16)(p13.3q24.3)-encoded CBFA2T3-GLIS2 Fusion Protein Defines an Aggressive Subtype of Pediatric Acue Megakaryoblastic Leukemia, Cancer Cell 22(5): 683-97 (2012)<br>Kawashima, Childhood Acute Myeloid Leukemia with Bone Marrow Eosinophilia Caused by t(16; 21)(q24; q22), Int J Hematol 95(5): 577-80 (2012) |
| GLIS2 | NCBI: NM_032575.2 | SEQ ID NO: 26 | See, GLIS2 |

Mutations in one or more of the NPM1, DNMT3A, IDH1, IDH2, RUNX1, TET2, and ASXL1 genes and NUP98-NSD1 and other NUP98 translocations presented in Table 2 can be detected by one or more of the gene-detection methodologies that are well known in the art and that can be readily adapted, as appropriate, by skilled artisan.

Nucleic Acid Amplification

Genomic DNA from a leukemia or control tissue sample or cell can be PCR amplified by utilizing specific primer pairs that are designed based upon the NUP98, NSD1, NPM1, DNMT3A, IDH1, IDH2, RUNX1, TET2, and ASXL1 sequences that are presented in Table 2, disclosed within the references cited in Table 2, or that are otherwise known and readily available to those skilled in the art. The resulting PCR amplicon can then be isolated and subjected to a sequencing and/or hybridization reaction to determine whether any of the known mutations in the NPM1, DNMT3A, IDH1, IDH2, RUNX1, TET2, and ASXL1 genes and NUP98-NSD1 and other NUP98 translocations, which are associated with leukemia, as well as elevated HOX cluster and/or HOX cluster-associated gene expression are present in the respective leukemia patient's genomic DNA.

As used herein, the term "amplification" refers to the production of multiple copies of a target nucleic acid that contains at least a portion of the intended specific target nucleic acid sequence. The multiple copies are referred to, interchangeably, as amplicons or amplification products. In certain aspects of the present disclosure, the amplified target contains less than the complete target mRNA sequence (i.e., spliced transcript of exons and flanking untranslated sequences) and/or target genomic sequence (including introns and/or exons). For example, specific amplicons may be produced by amplifying a portion of the target polynucleotide by using amplification primers that hybridize to, and initiate polymerization from, internal positions of the target polynucleotide. The amplified portion contains a detectable target sequence that may be detected using any of a variety of well-known methods.

Many well-known methods of nucleic acid amplification require thermocycling to alternately denature double-stranded nucleic acids and hybridize primers; however, other well-known methods of nucleic acid amplification are isothermal. The polymerase chain reaction (PCR; described in U.S. Pat. Nos. 4,683,195; 4,683,202; 4,800,159; 4,965,188) uses multiple cycles of denaturation, annealing of primer pairs to opposite strands, and primer extension to exponentially increase copy numbers of the target sequence. In a variation called RT-PCR, reverse transcriptase (RT) is used to make a complementary DNA (cDNA) from mRNA, and the cDNA is then amplified by PCR to produce multiple copies of DNA.

The ligase chain reaction (LCR; Weiss, *Science* 254:1292 (1991) uses two sets of complementary DNA oligonucleotides that hybridize to adjacent regions of a target nucleic acid. The DNA oligonucleotides are covalently linked by a DNA ligase in repeated cycles of thermal denaturation, hybridization, and ligation to produce a detectable double-stranded ligated oligonucleotide product.

Strand displacement amplification (SDA; Walker et al., *Proc. Natl. Acad. Sci. USA* 89:392-396 (1992); U.S. Pat. Nos. 5,270,184 and 5,455,166) uses cycles of annealing pairs of primer sequences to opposite strands of a target sequence, primer extension in the presence of a dNTPαS to produce a duplex hemi-phosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Patent No. 0 684 315).

Other amplification methods include: nucleic acid sequence based amplification (U.S. Pat. No. 5,130,238), commonly referred to as NASBA; one that uses an RNA Replicase to amplify the probe molecule itself (Lizardi et al., *BioTechnol* 6:1197-1202 (1988)), commonly referred to as Qβ Replicase; a transcription based amplification method (Kwoh et al., *Proc. Natl. Acad. Sci. U.S.A.* 86:1173-1177 (1989)); self-sustained sequence replication (Guatelli et al., *Proc. Natl. Acad. Sci. U.S.A.* 87:1874-1878 (1990)); and, transcription mediated amplification (U.S. Pat. Nos. 5,480,784 and 5,399,491), commonly referred to as TMA. For further discussion of known amplification methods see Persing, "In Vitro Nucleic Acid Amplification Techniques" in Diagnostic Medical Microbiology: Principles and Applications pp. 51-87 (Persing et al., Eds.; American Society for Microbiology, Washington, D.C., 1993).

TMA employs an RNA polymerase to produce multiple RNA transcripts of a target region and a "promoter-primer" that hybridizes to a target nucleic acid in the presence of a reverse transcriptase and an RNA polymerase to form a double-stranded promoter from which the RNA polymerase produces RNA transcripts. These transcripts can become templates for further rounds of TMA in the presence of a second primer capable of hybridizing to the RNA transcripts. Unlike PCR, LCR or other methods that require heat denaturation, TMA is an isothermal method that uses an RNase H activity to digest the RNA strand of an RNA:DNA hybrid, thereby making the DNA strand available for hybridization with a primer or promoter-primer. Generally, the RNase H activity associated with the reverse transcriptase provided for amplification is used.

In an illustrative TMA method, one amplification primer is an oligonucleotide promoter-primer that comprises a promoter sequence which becomes functional when double-stranded, located 5' of a target-binding sequence, which is capable of hybridizing to a binding site of a target RNA at a location 3' to the sequence to be amplified. A promoter-primer may be referred to as a "T7-primer" when it is specific for T7 RNA polymerase recognition. Under certain circumstances, the 3' end of a promoter-primer, or a sub-population of such promoter-primers, may be modified to block or reduce primer extension. From an unmodified promoter-primer, reverse transcriptase creates a cDNA copy of the target RNA, while RNase H activity degrades the target RNA. A second amplification primer then binds to the cDNA. This primer may be referred to as a "non-T7 primer" to distinguish it from a "T7-primer". From this second amplification primer, reverse transcriptase creates another DNA strand, resulting in a double-stranded DNA with a functional promoter at one end.

When double-stranded, the promoter sequence is capable of binding an RNA polymerase to begin transcription of the target sequence to which the promoter-primer is hybridized. An RNA polymerase uses this promoter sequence to produce multiple RNA transcripts (i.e., amplicons), generally about 100 to 1,000 copies. Each newly-synthesized amplicon can anneal with the second amplification primer. Reverse transcriptase can then create a DNA copy, while the RNase H activity degrades the RNA of this RNA:DNA duplex. The promoter-primer can then bind to the newly synthesized DNA, allowing the reverse transcriptase to create a double-stranded DNA, from which the RNA polymerase produces multiple amplicons. Thus, a billion-fold isothermic amplification can be achieved using two amplification primers.

For primers or amplification methods that do not require additional functional sequences in the primer (e.g., PCR amplification), the primer sequence includes a target-binding sequence, whereas other methods (e.g., TMA or SDA) include additional specialized sequences adjacent to the target-binding sequence (e.g., an RNA polymerase promoter sequence adjacent to a target-binding sequence in a promoter-primer or a restriction endonuclease recognition sequence for an SDA primer).

It will be appreciated by those skilled in the art that all of the primer and probe sequences of the present disclosure may be either commercially available or synthesized using standard in vitro synthetic methods. Also, it will be appreciated that those skilled in the art could modify primer sequences disclosed herein using routine methods to add additional specialized sequences (e.g., promoter or restriction endonuclease recognition sequences) to make primers susceptible to use in a variety of amplification methods. Similarly, promoter-primer sequences described herein can be modified by removing the promoter sequences to produce amplification primers that are essentially target-binding sequences susceptible to amplification procedures that do not use these additional functional sequences.

By "target sequence" is meant the nucleotide base sequence of a nucleic acid strand, at least a portion of which is capable of being detected using primers and/or probes in the methods as described herein, such as a labeled oligonucleotide probe. Primers and probes bind to a portion of a target sequence, which includes either complementary strand when the target sequence is a double-stranded nucleic acid.

By "equivalent RNA" is meant a ribonucleic acid (RNA) having the same nucleotide base sequence as a deoxyribonucleic acid (DNA) with the appropriate U for T substitution (s). Similarly, an "equivalent DNA" is a DNA having the same nucleotide base sequence as an RNA with the appropriate T for U substitution(s). It will be appreciated by those skilled in the art that the terms "nucleic acid" and "oligonucleotide" refer to molecular structures having either a DNA or RNA base sequence or a synthetic combination of DNA and RNA base sequences, including analogs thereof, which include "abasic" residues.

By "detecting" an amplification product or an amplicon is meant any of a variety of methods for determining the presence of an amplified nucleic acid, such as, for example, hybridizing a labeled probe to a portion of the amplified product. A labeled probe is an oligonucleotide that specifically binds to another sequence and contains a detectable group that may be, for example, a fluorescent moiety, chemiluminescent moiety, radioisotope, biotin, avidin, enzyme, enzyme substrate, or other reactive group. A labeled probe can include an acridinium ester (AE) moiety that can be detected chemiluminescently under appropriate conditions (as described, e.g., in U.S. Pat. No. 5,283,174).

Other well-known detection techniques include, for example, gel filtration, gel electrophoresis and visualization of the amplicons, and High Performance Liquid Chromatography (HPLC). The detecting step may either be qualitative or quantitative.

Assays for purifying and detecting a target polynucleotide often involve capturing a target polynucleotide on a solid support. The solid support retains the target polynucleotide during one or more washing steps of a target polynucleotide purification procedure. One technique involves capture of the target polynucleotide by a polynucleotide fixed to a solid support and hybridization of a detection probe to the captured target polynucleotide (e.g., U.S. Pat. No. 4,486,539). Detection probes not hybridized to the target polynucleotide are readily washed away from the solid support. Thus, remaining label is associated with the target polynucleotide initially present in the sample.

Another technique uses a mediator polynucleotide that hybridizes to both a target polynucleotide and a polynucleotide fixed to a solid support such that the mediator polynucleotide joins the target polynucleotide to the solid support to produce a bound target (e.g., U.S. Pat. No. 4,751,177). A labeled probe can be hybridized to the bound target and unbound labeled probe can be washed away from the solid support.

The primers and probes of the present disclosure may be used in amplification and detection methods that use nucleic acid substrates isolated by any of a variety of well-known and established methodologies (e.g., Sambrook et al., Molecular Cloning, A laboratory Manual, $2^{nd}$ ed., pp. 7.37-7.57 (Cold Spring Harbor Laboratory Press, Cold Spring Harbor, N.Y., 1989); Lin et al., "Simple and Rapid Sample Preparation Methods for Whole Blood and Blood Plasma" in Diagnostic Molecular Microbiology, Principles and Applications, pp. 605-616 (Persing et al., Eds., American Society for Microbiology, Washington, D.C., 1993).

In one illustrative example, the target mRNA may be prepared by the following procedure to yield mRNA susceptible to use in amplification. Briefly, a tissue sample or cell (e.g., peripheral blood or bone marrow cells) are lysed by contacting the cell suspension with a lysing solution containing at least about 150 mM of a soluble salt, such as lithium halide, a chelating agent and a non-ionic detergent in an effective amount to lyse the cellular cytoplasmic membrane without causing substantial release of nuclear DNA or RNA.

The cell suspension and lysing solution are mixed at a ratio of about 1:1 to 1:3. The detergent concentration in the lysing solution is between about 0.5-1.5% (v/v). Any of a variety of known non-ionic detergents are effective in the lysing solution (e.g., TRITON®-type, TWEEN®-type, and NP-type); typically, the lysing solution contains an octylphenoxy polyethoxyethanol detergent, preferably 1% TRITON® X-102.

This procedure may be used advantageously with leukemia tissue sample that contain cell suspensions (e.g., blood and bone marrow), but it works equally well on other tissues if the cells are separated using standard mincing, screening and/or proteolysis methods to separate cells individually or into small clumps.

After cell lysis, the released total RNA is stable and may be stored at room temperature for at least 2 hours without significant RNA degradation without additional RNase inhibitors. Total RNA may be used in amplification without further purification or mRNA may be isolated using standard methods generally dependent on affinity binding to the poly-A portion of mRNA.

In certain aspects of the present disclosure, mRNA isolation employs capture particles that include poly-dT oligonucleotides attached to insoluble particles. The capture particles are added to the above-described lysis mixture, the poly-dT moieties annealed to the poly-A mRNA, and the particles separated physically from the mixture. Generally, superparamagnetic particles may be used and separated by applying a magnetic field to the outside of the container. For example, a suspension of about 300 μg of particles (in a standard phosphate buffered saline (PBS), pH 7.4, of 140 mM NaCl) having either $dT_{14}$ or $dT_{30}$ linked at a density of about 1 to 100 pmoles/mg, or 10 to 100 pmols/mg, or from 10 to 50 pmols/mg are added to about 1 ml of lysis mixture.

Any superparamagnetic particles may be used, although typically the particles are a magnetite core coated with latex or silica (e.g., commercially available from Serodyn or Dynal) to which poly-dT oligonucleotides are attached using standard procedures (Lund et al., *Nuc. Acids Res.* 16:10861-10880 (1988)). The lysis mixture containing the particles is gently mixed and incubated at about 22-42° C. for about 30 minutes, when a magnetic field is applied to the outside of the tube to separate the particles with attached mRNA from the mixture and the supernatant is removed. The particles are washed one or more times, generally three, using standard resuspension methods and magnetic separation as described above. Then, the particles are suspended in a buffer solution and can be used immediately in amplification or stored frozen.

A number of parameters may be varied without substantially affecting the sample preparation. For example, the number of particle washing steps may be varied or the particles may be separated from the supernatant by other means (e.g., filtration, precipitation, centrifugation). The solid support may have nucleic acid capture probes affixed thereto that are complementary to the specific target sequence or any particle or solid support that non-specifically binds the target nucleic acid may be used (e.g., polycationic supports as described, for example, in U.S. Pat. No. 5,599,667).

For amplification, the isolated RNA is released from the capture particles using a standard low salt elution process or amplified while retained on the particles by using primers that bind to regions of the RNA not involved in base pairing with the poly-dT or in other interactions with the solid-phase matrix. The exact volumes and proportions described above are not critical and may be varied so long as significant release of nuclear material does not occur. Vortex mixing is preferred for small-scale preparations but other mixing procedures may be substituted. It is important, however, that samples derived from a leukemia patient tissue or a non-leukemia control donor tissue be treated to prevent coagulation and that the ionic strength of the lysing solution be at least about 150 mM, preferably 150 mM to 1 M, because lower ionic strengths lead to nuclear material contamination (e.g., DNA) that increases viscosity and may interfere with amplification and/or detection steps to produce false positives. Lithium salts are preferred in the lysing solution to prevent RNA degradation, although other soluble salts (e.g., NaCl) combined with one or more known RNase inhibitors would be equally effective.

Alternatively, amplification techniques, such as those described above, can be useful for obtaining at least a portion of one or more NPM1, DNMT3A, IDH1, IDH2, RUNX1, TET2, and/or ASXL1 gene and/or a NUP98-NSD1 or other NUP98 translocation. One such amplification technique is inverse PCR (see Triglia et al., *Nucl. Acids Res.* 16:8186 (1988)), which uses restriction enzymes to generate a fragment in the known region of the gene. The fragment is then circularized by intramolecular ligation and used as a template for PCR with divergent primers derived from the known region.

Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in PCT Patent Publication No. WO 1996/038591.

Another such technique is "rapid amplification of cDNA ends" or RACE, which uses an internal primer and an external primer, which hybridizes to a sequence that is 5' or 3' of a known sequence. Additional techniques include capture PCR (Lagerstrom et al., *PCR Methods Applic.* 1:111-119 (1991)) and walking PCR (Parker et al., *Nucl. Acids. Res.* 19:3055-3060 (1991)). Other methods employing amplification may also be employed to obtain a full length cDNA sequence.

A wide variety of labels and conjugation techniques are known by those skilled in the art and may be used in various nucleic acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used include radionuclides, enzymes, fluorescent, chemiluminescent, or chromogenic agents as well as substrates, cofactors, inhibitors, magnetic particles, and the like.

Nucleic Acid Sequencing

Chain termination methods were first developed by Frederick Sanger, and can be referred to as Sanger sequencing methods. In chain termination methods, four PCR reactions are performed wherein each reaction is spiked with a single dideoxynucleotide (ddNTP), which is a nucleotide lacking a 3' hydroxyl group (e.g., ddATP, ddTTP, ddCTP, ddGTP). When a ddNTP is incorporated into a nascent chain of DNA, synthesis of the nascent chain is halted; this generates a mixture of variable length oligonucleotides that can be resolved by size using, for example, DNA electrophoresis in a slab gel or capillary. Any number of detection methods can be used to read the DNA sequence as determined by the relative lengths of oligonucleotides in each of the four reactions, for example, autoradiography, UV light detection, or fluorescent dye detection. Dye termination methods are a variation of chain termination methods whereby each type of ddNTP (e.g., ddATP, ddTTP, ddCTP, ddGTP) is labeled with a different color fluorescent dye. This enables DNA to be sequenced in a single PCR reaction.

Massively Parallel Signature Sequencing (MPSS) is a high-throughput sequencing method that can be used in the methods disclosed herein. It is a bead-based method that utilized adapter ligation followed by adapter decoding to generated hundreds of thousands of short DNA sequences. Further information on this technology can be found in Brenner et al., *Nat Biotechnol.* 18(6):630-634 (2000); Reinartz et al., *Brief Funct Genomic Proteomic.* 1(1):95-104 (2002); and U.S. Pat. No. 6,013,445.

Polony sequencing is another high throughput sequencing technology that can be used according to the methods disclosed herein. Polony sequencing combines emulsion PCR, an automated microscope, and ligation-based sequencing chemistry. Further information on this technology can be found in U.S. Patent Publication Nos. 2009/0318298, 2011/0172127, 2010/0047876, and 2009/0099041 and U.S. Pat. No. 7,425,431.

454 pyrosequencing is a high-throughput sequencing method that can be used in the methods disclosed herein. In 454 pyrosequencing, DNA is amplified inside water droplets in an oil solution (emulsion PCR), with each droplet containing a single DNA template attached to a single primer-coated bead, forming a clonal colony. The sequencing machine contains many picolitre-volume wells, each containing a single bead and sequencing enzymes. Luciferase generated light is used to detect individual nucleotides added to the nascent DNA, and the combined data are used to generate sequence read-outs. Further information on this technology can be found in U.S. Pat. Nos. 6,210,891 and 7,648,824.

A high-throughput sequencing method that can be useful in the methods disclosed herein is the sequencing by synthesis (SBS) technology (Illumina®, San Diego, Calif.), which utilizes reversible dye-terminators. Single stranded polynucleotides are first attached to primers on a slide and amplified so that local clonal colonies are formed. Four differentially labeled ddNTPs are added, extending the nascent polynucleotides by one base-pair, after which the non-incorporated nucleotides are washed away. An image of the slide is recorded and the terminal nucleotide for each nascent DNA molecule is determined based upon the color of the fluorescent signal. Then, the dye and the terminal 3' blocker are chemically removed from the DNA, allowing the next cycle. More information on this technology can be found in U.S. Pat. Nos. 7,985,565; 7,115,400; 7,972,820; and 7,790,418 and U.S. Patent Publication Nos. 2008/0286795, 2002/0055100, and 2007/0015200.

SOLiD (Sequencing by Oligonucleotide Ligation and Detection) sequencing is another high-throughput sequencing method that can be used in the methods disclosed herein. (Applied Biosystems). This method involves multiple rounds of sequencing by ligation, wherein each ligation probe is eight-bases long and each base is effectively probed in two ligation reactions. Base calls are made based upon fluorescence data captured by a camera. More information on this technology can be found in U.S. Patent Publication No. 2009/0181860 and U.S. Pat. No. 7,851,158.

Ion semiconductor sequencing can be a useful high-throughput sequencing technology according to the methods disclosed herein. In ion semiconductor sequencing, the hydrogen ions that are released during polymerization of DNA are detected. A microwell containing a single template DNA strand is flooded with a single polynucleotide, which is incorporated into a nascent strand of DNA if it is complementary to the leading nucleotide of the template strand. The level of hydrogen detected can be used to detect insertion of more than one nucleotide, for example in regions of polynucleotide repeat. Further information on this technology can be found in U.S. Pat. Nos. 7,242,241; 7,888,015; 7,649,358; 7,686,929; and 8,114,591 and U.S. Patent Publication No. 2010/0159461.

DNA nanoball sequencing is another useful high-throughput sequencing technique that can be utilized in the methods disclosed herein. In this technology, rolling circle replication is used to generate DNA nanoballs from DNA fragments. Then, the DNA nanoballs can be anchored into a microarray flow cell, where a process termed unchained sequencing by ligation is used to generate reads about 10 by in length (Complete Genomics). Further information can be found in U.S. Patent Publication Nos. 2009/0011943, 2009/0270273, 2011/0268347, and 2009/0264299.

According to the methods disclosed herein, paired-end tag libraries can be constructed from polynucleotides (e.g., DNA, RNA, mRNA, cDNA, etc.) derived from a tissue sample and used in the high-throughput sequencing technology to increase the speed and/or accuracy sequence assembly. Nucleotides can be sequenced utilizing capture-based technology; alternatively, nucleotides can be sequenced after amplification by PCR. Nucleotides can be treated with bisulfites prior to sequencing in order to identify methylated sequences. Methylation specific PCR can be utilized prior to sequencing in order to determine whether specific loci are methylated. Polynucleotides derived from a leukemia sample can be sequence using paired-end whole exome sequencing (WES), shallow mate-pair whole genome sequencing (sMP-WGS), and/or paired-end RNA sequencing (RNAseq). Polynucleotides derived from a leukemia sample can be sequenced using Illumina® sequencing.

Fluorescent In Situ Hybridization

Mutations in one or more of a NPM1, DNMT3A, IDH1, IDH2, RUNX1, TET2, and/or ASXL1 genomic sequence and/or a NUP98-NSD1 or other NUP98 translocation within a leukemia tissue sample or cell can be detected by fluorescent in situ hybridization (FISH).

FISH is a cytogenetic technique that can be used to detect and localize the presence or absence of specific DNA sequences on chromosomes. FISH uses fluorescently-tagged nucleic acid probes that bind to only those parts of the chromosome with which they show a high degree of sequence complementarity. Thus, FISH can be employed to localize specific nucleotide sequences within a tissue or cell (e.g., on a particular chromosome or within a particular cell). Thus, FISH can be utilized to permit karyotype analysis and the detection of translocations, rearrangements, duplications, and copy number variations through the gain or loss of chromosomal material that include one or more of a NPM1, DNMT3A, IDH1, IDH2, RUNX1, TET2, and/or ASXL1 genomic sequence and/or a NUP98-NSD1 or other NUP98 translocation. FISH can also be used to detect and localize specific RNA targets, including mRNA, in leukemia tissues and cells and can be used to define spatial-temporal patterns of gene expression within leukemia tissues and cells.

FISH can also be utilized to localize mRNAs within a tissue or cell, thereby detecting expression of a gene, such as a gene carrying a mutation associated with leukemia including a mutation in one or more of a NPM1, DNMT3A, IDH1, IDH2, RUNX1, TET2, and/or ASXL1 genomic sequence and/or a NUP98-NSD1 or other NUP98 translocation.

Probes that are susceptible to use with FISH technology can be designed for detecting one or more mutations in one or more of a NPM1, DNMT3A, IDH1, IDH2, RUNX1, TET2, and/or ASXL1 genomic sequence and/or a NUP98-NSD1 or other NUP98 translocation and/or for visualization of an mRNA that is encoded by one or more of a NPM1, DNMT3A, IDH1, IDH2, RUNX1, TET2, and/or ASXL1 genomic sequence and/or a NUP98-NSD1 or other NUP98 translocation in a leukemia tissue or cell.

Suitable probes contain duplexes of at least about 20 consecutive nucleotides of one or more of a NPM1, DNMT3A, IDH1, IDH2, RUNX1, TET2, and/or ASXL1 genomic sequence and/or a NUP98-NSD1 or other NUP98 translocation and can be derived from PCR amplicons generated by amplification of a region within one or more of those genomic sequences. Probes must be large enough to hybridize specifically with its target sequences but not so large as to impede hybridization process or to bind non-specifically to non-target sequences. A mixture of probe sequences that hybridize along an entire chromosome can be used to detect gene translocations or to identify extra-chromosomal fragments of chromatin. Fluorescent tagging of probes can be achieved by nick translation of by PCR using tagged nucleotides.

Formalin-fixed paraffin-embedded (FFPE) or frozen tissue sections are fixed, then permeabilized to allow target accessibility. Interphase or metaphase chromosomes are prepared and attached to a solid substrate, such as a glass slide. A probe is then applied to the chromosome DNA and incubated for approximately 12 hours to permit hybridization of the target-specific probe to the target mRNA(s) and/or genomic DNA(s). Several wash steps remove unhybridized or partially hybridized probes. Target-specific hybridization is then visualized and/or quantified via fluorescent microscopy, which employs technologies to exciting the fluorescent dye and record images.

A mixture of smaller probes that are specific to a particular region (locus) of DNA can be used to detect deletion mutations. When combined with a specific color, a locus-specific probe mixture is used to detect very specific translocations.

QuantiGene ViewRNA FISH is a technique for detecting and quantifying RNA molecules in tissue samples and cells that are formalin-fixed paraffin-embedded (FFPE). ViewRNA FISH probes allow single molecule RNA sensitivity with virtually no background. Each oligonucleotide pair forms a platform for assembly of a signal amplification structure (tree) through a series of sequential hybridization steps using branched DNA (bDNA) signal amplification technology. Each fully-assembled structure, covers a space of 40-50 bit/s of the target nucleic acid, and has the capacity for 400-fold signal amplification.

Stellaris FISH, (a/k/a Single Molecule RNA FISH) is a method of detecting and quantifying mRNA and other long RNA molecules in a thin tissue sample. Targets can be reliably imaged through the application of multiple short singly labeled oligonucleotide probes. The binding of up to 48 fluorescently-labeled oligonucleotides to a single molecule of mRNA provides sufficient fluorescence to accurately detect and localize each target mRNA in a wide-field fluorescent microscopy image. Probes that do not bind to an intended nucleotide sequence do not achieve sufficient localized fluorescence to be distinguished from background. Single-molecule RNA FISH assays can be performed in simplex or multiplex and can be used as a follow-up experiment to quantitative PCR or imaged simultaneously with a fluorescent antibody assay.

Fiber FISH is a technique in which interphase chromosomes are attached to a slide in such a way that they are stretched out in a straight line, rather than being tightly coiled, as in conventional FISH, or adopting a random conformation, as in interphase FISH. This is accomplished by applying mechanical shear along the length of the slide (e.g., by chromosome combing), either to cells that have been fixed to the slide and then lysed, or to a solution of purified DNA. The extended conformation of the chromosomes allows dramatically higher resolution, even down to a few kilobases.

Following are exemplary applications of the techniques described herein as well as other techniques known and available in the art for the detection of mutations within genomic sequences. In particular, the following describes the detection of MLL-translocations and MLL-partial tandem duplications as well as a variety of mutations within one or more of the NPM1, DNMT3A, IDH1, IDH2, RUNX1, TET2, and/or ASXL1 genomic sequences and/or a NUP98-NSD1 or other NUP98 translocations disclosed herein. One skilled in the art will recognize that the various techniques described herein can be broadly applied to other genes and other mutations by adapting the techniques described and exemplified herein.

MLL-Translocations and MLL-Partial Tandem Duplications (PTDs)

Gene expression profiles of lymphoblastic leukemias that possess an MLL-translocation and MLL-partial tandem duplications (PTDs) are remarkably consistent, differ significantly from those of other leukemias, and are considered a distinct disease that is referred to as MLL for "Mixed Lineage Leukemia." Methodology for detecting MLL-translocations are described in U.S. Patent Publication No. 2006/0057630. Evaluation of expression profiles using principal component analysis distinguishes MLL from conventional ALL and also AML. A subset of human acute leukemias with a decidedly unfavorable prognosis possess a chromosomal translocation involving the Mixed Lineage Leukemia (MLL, HRX, AU-1) gene on chromosome segment 11q23. A DNA segment spanning the human MLL-gene translocation breaking point is provided as SEQ ID NO: 25.

Methodology for detecting MLL-primary tandem duplications (PTDs) is described in US Patent Publication No. 20070212687; Whitman et al., *Blood* 106:345-352 (2005); and Caligiuri et al., *Cancer Res.* 58:55-59 (1998). Such PTDs have been described, e.g., in Strout, M. P., et al. *PNAS* (USA) 95:2390-2395, (1998), incorporated by reference. Methodology for screening for MLL-PTD include nested RT-PCR and Southern blotting. Conventional nested reverse transcription-polymerase chain reaction (RT-PCR) can be performed as previously described by Caligiuri et al., *Cancer Res.* 56(6):1418-1425 (1996). Cloned PCR products can then be sequenced.

MLL-PDT can also be detected by quantitative real-time RT-PCR (QRT-PCR). Primer pairs and dual-labeled probe sets are designed to amplify sites that are unique to the MLL-PTD or common to both MLL PTD and MLL WT transcripts. Primer and probe sets can be designed to amplify the "unique amplicons" exon 11 to exon 5 or exon 12 to exon 5 fusions specific for the 2 most common forms of the MLL PTD, and to amplify the "common amplicons" exon 11 to exon 12, exon 13 to exon 14, and exon 26 to exon 27 junctions that can be found in both the MLL-PTD and the MLL WT transcripts. Standard curves can be constructed to allow for measurement of target amplicon copy numbers. QRT-PCR data can then be collected using the ABI Prism 7700 Sequence Detection System (PE Applied Biosystems, Foster City, Calif.).

Immunoblotting analysis for detection of the p300-kDa MLL WT and p420-kDa MLL PTD N-terminal fragments can be carried out as described by Nakamura et al., *Mol. Cell.* 10:1119-1128 (2002). Briefly, nuclear extracts are size fractionated in a 4.9% sodium dodecyl sulfate-polyacrylamide gel electrophoresis (SDS-PAGE). After transfer, membranes are probed with anti-MLL 170 antibody, an affinity-purified anti-MLL antibody directed against the N-terminal p300 MLL WT posttranslational cleavage product. Proteins can be visualized using enhanced chemiluminescence Plus (Amersham-Pharmacia, Piscataway, N.J.).

MLL 5'-CpG islands can be identified using the algorithm described in http://www.ebi.ac.uk/emboss/cpgplot/ and MLL genomic sequence (NCBI GenBank Accession No. NT033899.6). Methylation status can be assessed by bisulfite PCR sequencing (BS-PCR) of genomic DNA as previously described. Frommer et al., *Proc. Natl. Acad. Sci. USA*. (1992). PCRs can be optimized to minimize the potential for bias toward amplification of nonmethylated sequences. Single PCR products can then be purified from the agarose gel, cloned into the pCR2.1 cloning vector (Invitrogen, Carlsbad, Calif.), and sequenced. In the present example, a minimum of 10 clones per PCR would be evaluated.

An MLL-specific primer pair is designed to amplify a region upstream of the transcriptional initiation site in MLL (nucleotides −168 to −2). For normalization, ChIP analysis of the housekeeping gene such as GAPDH, can be performed using GAPDH promoter-specific primers previously described in Barlev et al., *Mol Cell.* 8:1243-1254 (2001). PCR conditions can be optimized such that products are detected during the exponential phase of amplification. Relative quantification can be carried out using SybrGreen dye and real-time PCR. The comparative real-time PCR ($2^{-\Delta\Delta CT}$) method can be used, normalizing first to input DNA followed by depsipeptide-treated levels relative to control levels.

NPM1 Mutations

Mutations in nucleophosmin NPM1 are the most frequent acquired molecular abnormalities in acute myeloid leukemia (AML). Mutations in exon 12 of the gene encoding NPM1 in approximately 35% of cases of de novo AML and typically include a four nucleotide insertion that results in a frame shift and consequent replacement of the 7 C-terminal amino acids of the NPM1 protein by 11 different residues. It has been suggested that the disruption of 1 of the 2 C-terminal tryptophan residues and the last 5 residues (i.e., VSLRK) the final 9 amino acids (i.e., AVEEVSLRK) are important for NPM1 mutant function. Falini et al., *N. Engl. J. Med.* 352:254-266 (2005) and Verhaak et al., *Blood* 106(12):3747-3754 (2005).

Mutations in NPM1 can be detected by a variety of methodologies that are well known in the art as exemplified by those methodologies described in Verhaak et al., *Blood* 106(12):3747-3754 (2005). RNA can be isolated from leukemia cells and cDNA synthesis performed as previously described. Valk et al., *N. Engl. J. Med.* 350:1617-1628 (2004) and Van der Reijden and van der Poel et al., *Hematol. J.* 2:206-209 (2001).

NPM1 mutations in exon 12 can, for example, be determined by polymerase chain reaction (PCR) amplification using the primers NPM1-FOR 5'-CTTCCG-GATGACTGACCAAGAG-3' and primer NPM1-REV 5'-CCTGGACAACATTTATCAAACACG-3' in a reaction containing 25 mM deoxyribonucleoside triphosphate [dNTP], 15 pmol primers, 2 mM $MgCl_2$, Taq polymerase, and 10× buffer [Invitrogen Life Technologies, Breda, The Netherlands]). Cycling conditions for NPM1 mutation detection can include 1 cycle, 5 minutes at 94° C.; 30 cycles, 1 minute at 94° C., 1 minute at 58° C., and 1 minute at 72° C.; and 1 cycle, 7 minutes at 72° C.

PCR products can be subjected to dHPLC using a Transgenomics (Omaha, Nebr.) WAVE dHPLC system (Choy et al., *Ann. Hum. Genet.* 63(pt 5):383-391 (1999)) and samples run at 56° C. and 58° C. The exact NPM1 mutant sequence can be confirmed for samples showing an abnormal high-performance liquid chromatography (dHPLC) profile and PCR products can be purified using the Multiscreen-PCR 96-well system (Millipore, Bedford, Mass.) followed by direct sequencing with NPM1-REV using an ABI-PRISM3100 genetic analyzer (Applied Biosystems. Foster City, Calif.). Each NPM1 mutation variant reveals a specific dHPLC WAVE profile. Thus, each type of NPM1 mutation could be predicted on the basis of a specific dHPLC WAVE profile.

Gene expression profiling is a powerful way to comprehensively classify individuals with AML and to further resolve the heterogeneous nature of AML. Valk et al., *Curr. Opin. Hematol.* 12:76-81 (2005). The effect of mutant NPM1 has been studied using gene expression profiling and revealed a distinctive signature for NPM1 mutations. Alcalay et al., *Blood* 106:899-902 (2005). AML cases with an NPM1 mutation cluster in specific subtypes of AML with previously established gene expression signatures, are highly associated with a homeobox gene-specific expression signature, and can be predicted with high accuracy. Among players in this signature were several homeodomain-containing family members of homeobox (HOX) transcription factors.

Leukemia cells can also be analyzed by gene expression profiling and unsupervised cluster analyses using Affymetrix HGU133A GeneChips (Affymetrix, Santa Clara. Calif.). Valk et al., *N Engl J Med.* 350:1617-1628 (2004). Unsupervised cluster analysis on the basis of the gene expression profiles can be performed using the correlation view tool (version 3.6) of OmniViz (Maynard, Mass.). The Pearson correlation values calculated in OmniViz can be imported into the MicroArray Data Explorer (MADEx) and used to visualize the relations between the OmniViz unsupervised clustering results and other parameters, such as clinical and molecular characteristics of the cells from leukemia patients. MADEx is a database system that stores, mines, and visualizes microarray data in a secure and scalable manner.

A dominant homeobox (HOX) gene-specific signature is strongly associated with AML carrying an NPM1 mutation. Moreover, the expression of members of the HOXA and HOXB gene families, but also the HOX gene-related three-amino acid loop extension (TALE) genes, PBX3 and MEIS1, is increased.

NPM1 mutation prediction analyses can be performed using a PAM algorithm. Tibshirani et al., *Proc Natl Acad Sci USA.* 99:6567-6572 (2002). AML samples are randomly assigned to a training set, consisting of samples without NPM1 mutations and samples with NPM1 mutations, and a validation series, consisting of samples lacking the NPM1 mutation and samples with mutations in NPM1. Cross-validation can be used to predict the mutation status of NPM1 on the training set NPM1 mutant AML cases have a distinct signature and are, therefore, predicted with high accuracy. AML cases with mutant NPM1 exhibit a strong HOX gene-specific SAM and PAM signatures. Previous studies have demonstrated for a number of HOX genes that sustained overexpression and coexpression with the protein binding partner MEIS1, results in leukemia. Daser and Rabbitts, *Semin. Cancer Biol.* 15:175-188 (2005).

NUP98-NSD1 Translocations

In AML, the recurring t(5; 11)(q35; p15.5) translocation fuses nuclear receptor-binding SET domain-containing protein 1 (NSD1) to nucleoporin 98 (NUP98). Cerveira et al., *Leukemia* 17:2244-2247 (2003). NUP98-NSD1 was shown to induce AML in vivo and sustain self-renewal of myeloid stem cells in vitro. Wang et al., *Nat Cell Biol* 9:804-812 (2007).

Mechanistically, the NUP98-NSD1 complex binds genomic elements adjacent to HOXA7 and HOXA9, and maintains EZH2-mediated transcriptional repression of the HOXA locus during differentiation through regulation of histone H3 Lys 36 (H3K36) methylation and histone acetylation. Wang et al., *Nat Cell Biol* 9:804-812 (2007). Either deletion of the NUP98 FG-repeat domain or mutations in NSD1 that lead to inactivation of the methyltransferase activity, preclude both HOXA gene activation and myeloid progenitor immortalization, indicating that the methyltransferase activity of NSD1 is likely to play a critical role in tumorigenesis.

In a NUP98-NSD1 translocation, the NUP98 and NSC1 mRNA are fused in-frame joining nucleotides 1552 of NUP98 to nucleotide 3506 of NSD1. The reciprocal transcript fuses NSD1 and NUP98 mRNA in-frame joining nucleotide 3505 of NSD1 to nucleotide 1553 of NUP98.

NUP98-NSD1 translocation can be detected by polymerase chain reaction (PCR) amplification using the sense NUP98-5 (5'-TCTTGGTACAGGAGCCTTTG-3'), and antisense NSD1-1 (5'TCCAAAAGCCACTTGCTTGGC-3') primers in a reaction containing 25 mM deoxyribonucleoside triphosphate [dNTP], 15 pmol primers, 2 mM $MgCl_2$, Taq polymerase, and 10× buffer [Invitrogen Life Technologies, Breda, The Netherlands]). Cycling conditions for NPM1 mutation detection can include 1 cycle, 5 minutes at 94° C.; 30 cycles, 1 minute at 94° C., 1 minute at 58° C., and 1 minute at 72° C.; and 1 cycle, 7 minutes at 72° C.

DOT1L Inhibitors

DOT1L inhibitors that may be suitably employed in the presently disclosed methods for treating leukemia patients with a DOT1L inhibitor are generally disclosed in US Patent Publication No. 2012/0142625 and PCT Patent Publication Nos. WO 2012/075381; WO 2012/075492; WO 2012/075500; and WO 2012/082436; Yu et al., *Nat. Commun.* 3:1288 (2013); Yu et al., *Nat. Commun.* 4:1893 (2013); Yu et al., *Bioorg. Med. Chem.* 21(7):1787-1794 (2013); Yao et al., *J. Am. Chem. Soc.* 133(42):16746-16749 (2011); Basavapathruni et al., *Chem. Biol. Drug Des.* 80(6):971-980 (2012); and Daigle et al., *Cancer Cell* 20(1):53-65 (2011). Each of these references, as well as all other references disclosed herein, is incorporated herein by reference in its entirety. Several DOT1L inhibitors are commercially available including EPZ005676; EPZ004777; SGC-0946; SYC-522; SYC-534; SYC-687 and others commercially available, e.g., from Selleckchem, Boston, Mass. or from Otava Chemicals, Inc. Vaughan, Ontario.

DOT1L inhibitors susceptible to use in the methods disclosed herein inhibit DOT1L with an IC50 of from about 100 nM to about 10 μM or from about 250 nM to about 5 μM or from about 500 nM to about 1 μM and include the purine, 7-deazapurine, and carbocycle-substituted purine compounds described herein, which are exemplified by EPZ004777 (1-(3-((((2R,3S,4R,5R)-5-(4-Amino-7H-pyrrolo[2,3-d]pyrimidin-7-yl)-3,4-dihydroxytetrahydrofuran-2-yl)methyl)(isopropyl)amino) propyl)-3-(4-(tert-butyl)phenyl)urea) and EPZ005676 (9H-Purin-6-amine, 9-[5-deoxy-5-[[cis-3-[2-[6-(1,1-dimethylethyl)-1H-benzimidazol-2-yl]ethyl]cyclobutyl](1-methylethyl)amino]-β-D-ribofuranosyl]-).

DOT1L inhibitors that may be suitably employed in the presently disclosed methods for inhibiting the proliferation and/or survival of cell and for treatment of leukemia patients include the 7-deazapurine compounds as described in WO 2012/075500 and WO/2012/082436 as represented by Formula I:

I

Formula I

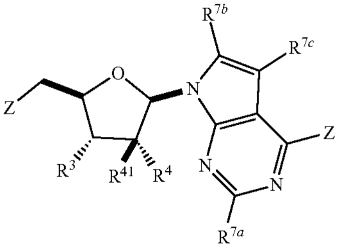

DOT1L inhibitors that may be suitably employed in the presently disclosed methods for inhibiting the proliferation and/or survival of cell and for treatment of leukemia patients include carbocycle-substituted purine and 7-deazapurine compounds as described in WO 2012/075492 as represented by Formula II:

Formula II

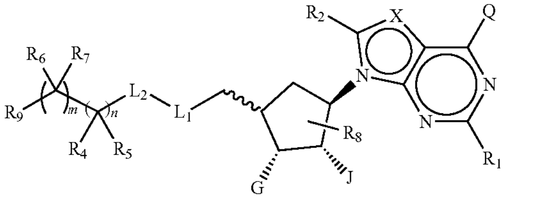

DOT1L inhibitors that may be suitably employed in the presently disclosed methods for inhibiting the proliferation and/or survival of cell and for treatment of leukemia patients include purine and 7-deazapurine compounds as described in US 2012/0142625 and WO 2012/075381 as represented by Formula III:

Formula III

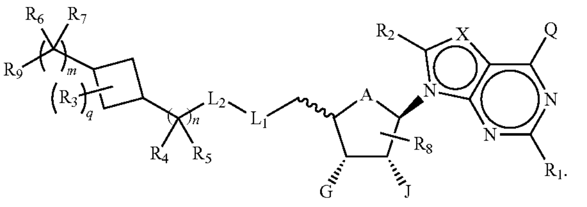

Compounds that are encompassed within the range of compounds defined by Formulas I, II, and III, and methodologies for the synthesis of those compounds, are presented in U.S. Patent Publication No. 2012/0142625 and PCT Patent Publication Nos. WO 2012/075381; WO 2012/075492; WO 2012/075500; and WO 2012/082436. Two exemplary such compounds are EPZ004777 and EPZ005676, which are presented in the following section along with a description of methodologies for synthesizing those compounds from readily available starting materials (e.g., Sigma-Aldrich, St. Louis, Mo.).

EPZ004777

The small molecule DOT1L inhibitor EPZ004777 is an s-adenosyl methionine mimetic is highly specific for DOT1L as compared to other methyl transferases. Daigle et al., *Cancer Cell* 20(1):53-65 (2011) and Yu et al., *Nat. Commun.* 3:1288 (2013). EPZ004777 binds within the S-(5'-adenosyl)-1-methionine (SAM) binding site in the catalytic domain of human DOT1L.

EPZ004777 binds to DOT1L with a $K_i$ value of 0.3 nM and exhibits >1,000-fold selectivity for DOT1L as compared to other methyltransferases tested, as measured biochemically in vitro and in cells. Daigle further confirmed highly selective antiproliferative, differentiating, and apoptotic activities of EPZ004777 toward leukemia cells harboring MLL fusions that correlate with transcriptional repression of the key leukemogenic MLL fusion target genes HOXA9 and MEIS1. Leukemic cells lacking MLL fusions are less sensitive to EPZ004777 by a factor of approximately 100. This in vitro selectivity translates to the targeting of leukemic cells in mouse models of mixed-lineage leukemia, which results in prolonged survival.

The chemical structure of EPZ004777 (1-(3-((((2R,3S,4R,5R)-5-(4-Amino-7H-pyrrolo[2,3-d]pyrimidin-7-yl)-3,4-dihydroxytetrahydrofuran-2-yl)methyl)(isopropyl)amino) propyl)-3-(4-(tert-butyl)phenyl)urea) is presented as Formula XIV:

Formula IV

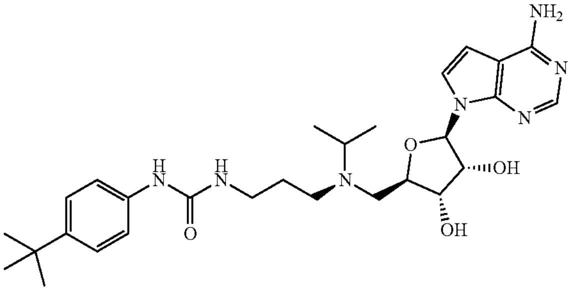

The synthesis of EPZ004777 (1-(3-((((2R,3S,4R,5R)-5-(4-Amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea) is described in PCT Patent Publication No. WO 2012/075500.

Step 1: Synthesis of (2R,3R,4S,SR)-2-(4-((2,4-dimethoxybenzyl)amino)-7H-py pyrrolo[2,3-d]pyrimidin-7-yl)-S-(hydroxymethyl)tetrahydrofuran-3,4-diol A suspension of 7-chloro tubercidin (1.67 g, 5.84 mmol) in 1-butanol (16.0 ml) is treated with N,N-diisopropylethylamine (1.22 ml, 7.01 mmol) and 1-(2,4-dimethoxyphenyl) methanamine (1.05 ml, 7.01 mmol) and heated at 100-110° C. overnight. After 20 h, LCMS indicated a new product forms and the starting material is consumed. The mixture is cooled to room temperature and the solvent removed under high vacuum. The material is purified by flash chromatography (200 g silica gel; 5-10% MeOH/$CH_2Cl_2$) to yield the title compound (2.19 g, 90%) as a foam: MS (ES1+) for C20H24N4O6 m/z 417.1 (M+H)+; (ES1−) for C20H24N4O6 m/z 415.2 $(M-H)^-$; HPLC purity 97% (ret. time, 2.41 min).

Step 2: ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl) methanol A solution of (2R,3R,4S,5R)-2-(4-((2,4-dimethoxybenzyl)amino)-7H-pyrrolo[2,3-d]pyrimidin-7-yl)-5-(hydroxymethyl)tetrahydrofuran-3,4-diol (3.30 g, 7.45 mmol) in acetone (76.5 ml) and 2,2-dimethoxypropane (16.5 ml, 134 mmol) is treated with 10-camphorsulfonic acid (1.73 g, 7.44 mmol) in one portion and the reaction is allowed to stir at room temperature. After 1 h, all SM is consumed by HPLC. The reaction is quenched by the addition of sodium bicarbonate (1.88 g, 22.3 mmol) and the reaction mixture is stirred for 30 minutes during which time a precipitate formed. The reaction mixture is partitioned between 200 ml CHCl3 and 75 ml H2O. The mixture is diluted with 15 ml brine, extracted and the phases separated. The aqueous phase is washed twice with 50 ml portions of CHCl3 and the combined organic phase is dried over Na2SO4. The solution is filtered and concentrated to yield a foam. The crude product is taken up in methanol (130 ml, 3200 mmol) and treated with p-toluenesulfonic acid monohydrate (1.27 g, 6.70 mmol) in one portion. The mixture is stirred at room temperature for 2 h upon which time the reaction mixture is quenched with sodium bicarbonate (1.88 g, 22.3 mmol) and the mixture is stirred for 30 minutes. The solvent is removed in vacuuo and the residue partitioned between 50 ml H2O and 150 ml CH2Cl2 and extracted. The organic phase is washed with 50 ml sat NaHCO3, dried over Na2SO4, filtered and concentrated to yield a foam. The product is isolated by flash chromatography (120 g silical gel, 60-80% EA/hept) to yield the title compound (2.83 g, 83%) as a light yellow stiff foam: MS (ES1+) for C23H28N4O6 m/z 457.4 (M+H)+; (ES1−) for C23H28N4O6 m/z 455.2 (M−H); HPLC purity 99% (ret. time, 3.08 min).

Step 3: 7-((3aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine A solution of ((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methanol (2.83 g, 6.20 mmol) and triphenylphosphine (2.28 g, 8.68 mmol) in dry tetrahydrofuran (32 ml) is cooled at 0° C. in an ice/water bath. Diisopropyl azodicarboxylate (1.71 ml, 8.68 mmol) is added dropwise, followed by a solution of diphenylphosphonic azide (1.87 ml, 8.68 mmol) in tetrahydrofuran (5.3 ml, 66 mmol). Upon addition of the DPPA solution, a white milky precipitate forms. After about 30 minutes, the reaction mixture is allowed to warm to room temperature and stir overnight. After 24 h, HPLC indicates that all the starting material has been consumed. The reaction mixture is concentrated to about ½ the original volume and purified by flash chromatography (175 g silica gel, 10-55% EA/hept) to yield the title compound (2.49 g, 83%) as a slightly yellow stiff foam: MS (ES1+) for C23H27N7O5 m/z 482.2 (M+H)+; (ESI−) for C23H27N7O5 m/z 480.1 (M+H)−, m/z 526.1 (M+CO2H)−; HPLC purity 97% (ret. time, 3.64 min).

Step 4: 7-((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine A solution of ((3 aR,4R,6R,6aR)-6-(azidomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (2.49 g, 5.17 mmol) in tetrahydrofuran (50 mL, 600 mmol) is treated dropwise with a solution of 1.0 M of trimethylphosphine in tetrahydrofuran (7.24 mL, 7.24 mmol) and the mixture is stirred at room temperature overnight. After 20 h all starting material is consumed by HPLC. The reaction mixture is treated with water (1.80 mL, 99.9 mmol) and stirred at rt for 2 h. The reaction mixture is concentrated, the crude product is taken up in 90 mL CH2Clz and washed with four 30 mL portions of H20 and 15 ml brine. The solution is dried over Na2SO4, filtered and concentrated to yield an oil that under the application of a high vacuum becomes a foam. The crude material is purified by flash chromatography (120 g silica gel, 3-10% 7N NH3 in CH30H/CH2Clz) to yield the title compound (1.76 g, 75%) as a foam: MS (ES1+) for C23H29NO5 m/z 456.2 (M+Ht; (ES1−) for C26H3SNsOs m/z 454.1 (M−HY; HPLC purity 92% ret. time, 2.65 min).

Step 5: N-(2,4-dimethoxybenzyl)-7-((3aR,4R,6R,6aR)-6-((isopropylamino)methyl)-2,2-dimethyltetrahydrofuro[3,4-d][1,3]dioxol-4-yl)-7H-pyrrolo[2,3-d]pyrimidin-4-amine A solution of ((3aR,4R,6R,6aR)-6-(aminomethyl)-2,2-dimethyltetrahydrofuro[3,4-d][1,3]dioxol-4-yl)-N-(2,4-dimethoxybenzyl)-7H-pyrrolo[2,3-d]pyrimidin-4-amine (1.76 g, 3.86 mmol) in 1,2-dichloroethane (34 ml) is treated with acetone (0.31 ml, 4.2 mmol) and acetic acid (0.22 ml, 3.9 mmol) dropwise followed by sodium triacetoxyborohydride (0.98 g, 4.6 mmol) and the mixture is stirred at room temperature until complete. After 1 h, HPLC indicated the starting material had been consumed and the reaction is complete. The reaction mixture is diluted with 60 mL $CH_2Cb$ and washed with 50 mL sat $NaHCO_3$. The aqueous phase is washed with 30 mL $CH_2Cb$ and the combined organic phase is washed with 40 mL brine and dried over $Na_2SO_4$. The solution is filtered and concentrated to yield the title compound (1.76 g, 92%) as a glass that is used directly in the next step: MS (ES1+) for C26H3SNsOs m/z 498.3 (M+Ht; HPLC purity 90% (ret. time, 2.74 min).

Step 6: 2-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)isoindoline-1,3-dione A mixture of y-bromopropylphthalimide (2.37 g, 8.85 mmol), tetra-n-butylammonium iodide (0.234 g, 0.632 mmol), N,N-diisopropylethylamine (1.40 ml, 8.04 mmol) and N-(2,4-dimethoxybenzyl)-7-((3aR,4R,6R,6aR)-6-((isopropylamino)methyl)-2,2-dimethyl tetrahydrofuro[3,4-d][1,3]dioxol-4-yl)-7H-pyrrolo[2,3-d]pyrimidin-4-amine (3.42 g, 6.32 mmol) is taken up in propanenitrile (25 ml) and is heated at 95° C. After 48 hours at 95° C., HPLC indicates that the reaction is nearly complete. The reaction mixture is cooled to room temperature, the mixture is diluted with 200 ml ethyl acetate and washed with two 100 ml portions of $H_2O$ and 100 ml brine. The organic phase is dried over $Na_2SO_4$, filtered and concentrated to yield a glass. The crude material is purified by flash chromatography (250 g silica gel, 2-4% 7N NH3 in CH30H/CH2Cb) to yield the title compound (3.12 g, 72%) as a foam: MS (ES1+) for C37H44N6O7 m/z 685.2 (M+Ht, (ESI−) for C37H44N607 m/z 729 (M+HC02Y; HPLC purity 99% (ret. time, 3.17 min).

Step 7: N1-(((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)-N1-isopropylpropane-1,3-diamine 2-(3-((((3 aR,4R,6R,6aR)-6-(4-((2,4-dimethoxybenzyl) amin0)-7H-pyrrolo[2,3-d]pyrimidin-7-yl)-2,2-dimethyltetrahydrofuro[3,4-d][1,3]dioxol-4-yl)methyl)(isopropyl) amino)propyl)isoindoline-I,3-dione (1.37 g, 2.00 mmol) is dissolved in 2M methylamine in methanol (30 mL, 60 mmol). The solution is stirred at room temperature for 5 minutes then heated at 55-60° C. After 1 h, the SM is consumed by HPLC. The reaction mixture is cooled to room temperature and concentrated in vacuo. The resultant tan oil is taken up in 20 mL MeOH and concentrated. The procedure is repeated to an oil. The material is placed on high vacuum to yield a solid which contained the title compound along with N-methylphthalimide and is used as is in the next step: MS (ES1+) for C29H42N60S m/z 555.4 (M+Ht; HPLC ret. time 2.57 min.

Step 8: 1-(4-(tert-butyl)phenyl)-3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino) propyl)urea A suspension of N1-(((3aR,4R,6R,6aR)-6-(4-((2,4-dimethoxybenzyl)amino)-7Hpyrrolo[2,3-d]pyrimidin-7-yl)-2,2-dimethyltetrahydrofuro[3,4-d][1,3]dioxol-4-yl)methyl)-N1_isopropylpropane-1,3-diamine (1.11 g, 2.00 mmol, crude from step 6) in methylene chloride (40 ml) is treated dropwise with a solution of I-tert-butyl-4-isocyanatobenzene (0.36 ml, 2.0 mmol) in methylene chloride (3.5 ml) and allowed to stir at room temperature. After 1 h, reaction is complete by HPLC. The reaction mixture is concentrated to yield a glass. The crude material is purified by flash chromatography (100 g silica gel, 2-4% 7N NH3 in CH30H/CH2Cb to yield the title compound (1.07 g, 73%) as a foam: MS (ES1+) for C4oHssN706 m/z 730.4 (M+Ht; (ESI−) for C4oHssN706 m/z 728.5 (M−HY; HPLC purity, 89% (ret. time, 3.78 min).

Step 9: 1-(3-((((2R,3S,4R,SR)—S-(4-amino-7H-pyrrolo[2,3-d]pyrimidin-7-yl)-3,4-dihydroxytetrahydrofuran-2-yl)methyl)(isopropyl)amino)propyl)-3-(4-(tertbutyl)phenyl)urea 1-(4-(tert-butyl)phenyl)-3-(3-((((3aR,4R,6R,6aR)-6-(4-((2,4-dimethoxybenzyl)amino)-7H-pyrrolo[2,3-d]pyrimidin-7-yl)-2,2-dimethyltetrahydrofuro[3,4-d][1,3]dioxol-4-yl)methyl)(isopropyl)amino)propyl)urea (1.07 g, 1.39 mmol) is dissolved in a mixture of trifluoroacetic acid (25 ml) and water (2.5 ml) which has been cooled at 0° C. and the resulting solution is stirred at 0° C. for 30 minutes, then warmed to room temperature. After 4 h, the reaction is confirmed to be complete by HPLC. The reaction mixture is concentrated in vacuuo and the residue is taken up in 25 mL MeOH (white slurry) and concentrated. This process is repeated three times and the resultant residue is placed under high vacuum. The material is taken up in 100 mL 10% MeOH/CH2Cb and washed with two 75 mL portions of sat NaHC03 and 50 mL 1% aq Na2C03. The organic phase is dried over Na2S04, filtered and concentrated to yield a glass/solid. The crude material is purified by flash chromatography (100 g silica gel, 5-10% 7N NH3 in CH30H/CH2Clz) to yield the title compound (0.35 g, 46%) as a colorless glass: MS (ES1+) for C28H41N704 m/z 540.3 (M+Ht; (ESI−) for C28H41N704 m/z 538.3 (M−Hr, m/z 584.4 (M+HC02Y; HPLC purity 98% (ret. time 2.86 min); 1H NMR (400 MHz, d4-MeOH) ppm 8.05 (s, 1H), 7.27 (d, 1=3.73 Hz, 1H), 7.24 (m, 2H), 7.18 (m, 2H), 6.63 (d, 1=3.73 Hz, 1H), 6.15 (d, 1=4.77 Hz, 1H), 4.46 (t, 1=5.08 Hz, 1H), 4.18 (t, 1=5.39 Hz, 1H), 4.11 (m, 1H), 3.22 (m, 2H), 3.07 (m, 1H), 2.85 (m, 1H), 2.72 (m, 1H), 2.60 (t, 1=6.43 Hz, 2H), 1.68 (m, 2H), 1.28 (s, 9H), 1.05 (d, 1=6.63 Hz, 3H), 1.01 (d, 1=6.43 Hz, 3H).

Step 10: 1-(3-((((2R,3S,4R,5R)-5-(4-Amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea Hydrochloride A solution of 1-(3-((((2R,3S,4R,5R)-5-(4-amino-7H-pyrrolo[2,3-d]pyrimidin-7-yl)-3,4-dihydroxytetrahydrofuran-2-yl)methyl)(isopropyl)amino)propyl)-3-(4-(tert-butyl)phenyl)urea (1.64 g, 3.04 mmol) in 50 ml 50% aq methanol is treated with 1.0N of hydrogen chloride in water (3.87 mL, 3.04 mmol). The solution is concentrated to remove most of the methanol and lyophilized overnight. The cloudy mixture is filtered through a fine frit and the filtrate is concentrated in vacuuo to remove the MeOH. The resultant solution is lyophilized overnight to yield the title compound (1.70 g, 97%) as a solid: MS (ES1+) for C28H41N704 m/z 540.4 (M+Ht; MS (ES1+) for C28H41N704 m/z 538.4 (M+Ht, m/z 574.4 (M+C1Y; HPLC purity 97% (ret. time, 2.88 min); 1H NMR (400 MHz, d4-MeOH) ppm 8.12 (s, 1H), 7.29 (m, 2H), 7.23 (m, 3), 6.68 (m, 1H), 6.09 (br. s., 1H), 4.57 (m, 1H), 4.35 (m, 2H), 3.79 (br. s., 1H), 3.55 (m, 2H), 3.26 (br. s., 4H), 1.94 (m, 2H), 1.35 (m, 6H), 1.29 (s, 9H). ICso<10 nM.

In vivo administration of EPZ004777 leads to extension of survival in a mouse MLL xenograft model and support the efficacy of EPZ004777 for the treatment of MLL-translocated leukemias.

EPZ005676

EPZ005676 is a small molecule S-adenosyl methionine (SAM) competitive inhibitor of DOT1L methyltransferase activity that displays a Ki value of 80 pM and a drug-target residence time of >24 hours. Daigle et al., *Blood Epub Ahead of Print* (2013). The compound is highly selective for DOT1L, demonstrating >37,000-fold selectivity against all other methyltransferases tested.

The chemical structure of EPZ005676 (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol is presented as Formula V:

Formula V

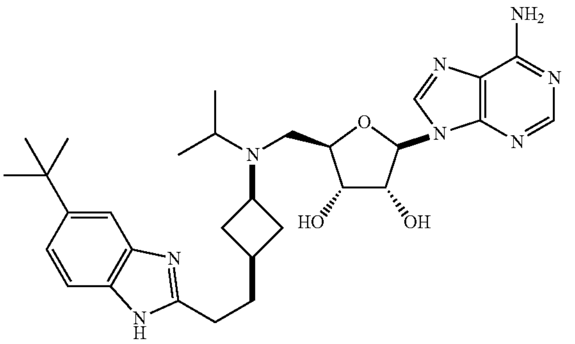

The synthesis of EPZ005676 (2R,3R,4S,5R)-2-(6-amino-9H-purin-9-yl)-5-((((1r,3 S)-3-(2-(5-(tert-butyl)-1H-benzo[d]imidazol-2-yl)ethyl)cyclobutyl)(isopropyl)amino)methyl)tetra-hydrofuran-3,4-diol is described in U.S. Patent Publication No. 2002/0142625.

Step 1: Synthesis of Cis And Trans Methyl 3-((((3aR,4R,6R,6aR)-6-(6-amino-9H-purin-9-yl)-2,2-dimethyltetrahydrofuro-[3,4-d][1,3]dioxol-4-yl)methyl)amino)cyclobutanecarboxylate A solution of methyl 3-oxocyclobutanecarboxylate (4.60 g, 35.94 mmol), 9-((3aR,4R,6R,6aR)-6-(aminomethyl)-2,2-dimethyltetrahydrofuro[3,4-d][1,3]dioxol-4-yl)-9H-purin-6-amine (11.0 g, 35.94 mmol) and $Ti(iPrO)_4$ (4.0 g, 14.08 mmol) in MeOH (80 ml) is stirred at 45° C. for 2 h, then $NaCNBH_3$ (4.5 g, 71.87 mmol) is added. The reaction is stirred at RT overnight. The reaction is quenched with aq. sat. $NaHCO_3$ (40 ml) and filtered, extracted with DCM (80 ml×3), dried over $Na_2SO_4$ and concentrated. The residue is purified by preparative-HPLC to obtain the title compound (6.2 g, Yield 41%). NMR (500 MHz, CDCl3): On 8.38-8.34 (m, 1H), 7.90 (s, 1H), 5.98 (d, J=3.0 Hz, 1H), 5.75 (br s, 2H), 5.48-5.46 (m, 1H), 5.03-5.01 (m, 1H), 4.35-4.33 (m, 1H), 3.69-3.66 (m, 3H), 3.50-3.17 (m, 1H), 3.05-2.73 (m, 3H), 2.48-2.44 (m, 2H), 1.95-1.91 (m, 2H), 1.62 (s, 3H), 1.39 (s, 3H) ppm; ESI-MS (m/z): 419.2 [M+1]+. The cis/trans mixture of methyl 3-((((3aR,4R,6R,6aR)-6-(6-amino-9H-purin-9-yl)-2,2-dimethyltetrahydrofuro-[3,4-d][1,3]dioxol-4-yl)methyl)amino)cyclobutanecarboxylate (6.2 g) is separated via chiral HPLC(CHIRALCEL AD-H 20*250 mm, 5 um (Daicel), Column temperature: 35° C., mobile phase: $CO_2$/Methanol (0.1% DEA)=70/30, Flow rate: 50 g/min) to give the pure cis product (3.5 g) and pure trans product (1.7 g).

Step 2. Synthesis of (1S,3s)-methyl 3-((((3aR,4R,6R,6aR)-6-(6-amino-9H-purin-9-yl)-2,2-dimethyltetrahydrofuro-[3,4-d][1,3]dioxol-4-yl)methyl)(isopropyl)amino)cyclobutanecarboxylate To a solution of cis methyl 3-((((3aR,4R,6R,6aR)-6-(6-amino-9H-purin-9-yl)-2,2-dimethyltetrahydrofuro-[3,4-d][1,3]dioxol-4-yl)methyl)amino)cyclobutanecarboxylate (2.0 g, 4.78 mmol) in $CH_3CN$ (15 ml) is added 2-iodopropane (4.0 g, 23.92 mmol) and $K_2CO_3$ (1.0 g, 7.18 mmol). The reaction is heated to 95° C. overnight in a sealed tube. The mixture is filtered, the filtrate is concentrated and purified by SGC (DCM:MeOH=12:1) to obtain the title compound (1.9 g, Yield 86%). 1H NMR (500 MHz, CDCl3): ΔH 8.37 (s, 1H), 7.89 (s, 1H), 6.03 (d, J=1.5 Hz, 1H), 5.53-5.48 (m, 3H), 5.00 (br s, 1H), 4.25 (brs, 1H), 3.66 (s, 3H), 3.19-3.18 (m, 1H), 2.96 (brs, 1H), 2.80-2.78 (m, 1H), 2.67-2.58 (m, 2H), 2.20-2.12 (m, 4H), 1.62 (s, 3H), 1.39 (s, 3H), 1.00 (d, J=6.0 Hz, 3H), 0.84 (d, J=6.0 Hz, 3H) ppm; ESI-MS (m/z): 461.4 [M+1]+.

Step 3: Synthesis of (1S,3s)-3-((((3aR,4R,6R,6aR)-6-(6-amino-9H-purin-9-yl)-2,2-dimethyltetrah-ydro-furo[3,4-d][1,3]dioxol-4-yl)methyl)(isopropyl)amino)cyclobutanecarbaldehyde To a solution of (1S,3s)-methyl 3-((((3aR,4R,6R,6aR)-6-(6-amino-9H-purin-9-yl)-2,2-dimethyltetrahydrofuro-[3,4-d][1,3]dioxol-4-yl)methyl)(isopropyl)amino)cyclobutane-carboxylate (1.2 g, 2.60 mmol) in DCM (50 ml) is added DIBAL-H dropwise at −78° C. until all the starting material is consumed as determined by TLC. MeOH (2 ml) is added and the mixture is stirred to RT for 30 min upon which water (50 ml) is added and the mixture is extracted with DCM (50 ml×2). The organic layer is dried over $Na_2SO_4$ and concentrated to obtain crude title compound (1.0 g which is used) directly in the next step. 1H NMR (500 MHz, CDCl3): ΔH 9.56 (d, J=2.5 Hz, 1H), 8.36 (s, 1H), 7.88 (s, 1H), 6.03 (d, J=2.5 Hz, 1H), 5.66 (br s, 2H), 5.50 (dd, J=2.0, 6.5 Hz, 1H), 5.01 (dd, J=3.5, 6.5 Hz, 1H), 3.331-3.337 (m, 1H), 2.96-2.97 (m, 1H), 2.77-2.59 (m, 3H), 2.14-2.05 (m, 4H), 1.60 (s, 3H), 1.39 (s, 3H), 1.01 (d, J=6.5 Hz, 3H), 0.85 (d, J=6.0 Hz, 3H) ppm.

Step 4. Synthesis of (E)-ethyl 3-((1S,3s)-3-((((3aR,4R,6R,6aR)-6-(6-amino-9H-purin-9-yl)-2,2-dimethyltet-rahydrofuro[3,4-d][1,3]dioxol-4-yl)methyl)(isopropyl)amino)cyclobutyl)acry-late To a solution of (1S,3s)-3-((((3aR,4R,6R,6aR)-6-(6-amino-9H-purin-9-yl)-2,2-dimethyltetrah-ydrofuro[3,4-d][1,3]dioxol-4-yl)methyl)(isopropyl)amino)cyclobutane carbaldehyde (930 mg, 2.16 mmol) in CH.sub.3CN:DCM=5:1 (50 ml) is added ethyl 2-(diethoxyphosphoryl)acetate (484 mg, 2.16 mmol), DBU (328 mg, 2.16 mmol) and LiCl (91 mg, 2.16=01). The mixture is stirred at RT for 1 h and then concentrated. Water (20 ml) is added and the mixture extracted with DCM (25 ml×3). The combined organic layers are dried over Na2SO4, concentrated and the residue is purified by SGC (DCM:MeOH=30:1) to obtain title compound (900 mg, Yield 83%). 1H NMR (500 MHz, CDCl3): ΔH 8.36 (s, 1H), 7.89 (s, 1H), 6.94-6.90 (m, 1H), 6.03 (s, 1H), 5.72-5.89 (m, 1H), 5.57 (s, 2H), 5.52 (d, J=4.5 Hz, 1H), 5.00 (dd, J=3.5, 6.0 Hz, 1H), 4.25 (d, J=3.0 Hz, 1H), 4.21-4.17 (m, 2H), 3.14 (brs, 1H), 2.961-2.936 (m, 1H), 2.74-2.52 (m, 3H), 2.22-2.14 (m, 2H), 1.79-1.76 (m, 2H), 1.60 (s, 3H), 1.40 (s, 3H), 1.30-1.27 (m, 3H), 1.00 (d, J=7.0 Hz, 3H), 0.82 (d, J=6.5 Hz, 3H) ppm; ESI-MS (m/z): 501.4 [M+1]+.

Step 5: Synthesis of ethyl 3-((1S,3r)-3-((((3aR,4R,6R,6aR)-6-(6-amino-9H-purin-9-yl)-2,2-dimethyltet-rahydrofuro[3,4-d][1,3]dioxol-4-yl)methyl)(isopropyl)amino)cyclobutyl)propanoate To a solution of (E)-ethyl 3-((1S,3s)-3-((((3aR,4R,6R,6aR)-6-(6-amino-9H-purin-9-yl)-2,2-dimethyltet-rahydro-furo[3,4-d][1,3]dioxol-4-yl)methyl)(isopropyl)amino)cy-clobutyl)acry-late (900 mg, 1.8 mmol) in MeOH (50 ml) is added Pd/C (20 mg). The mixture is stirred at RT overnight under an atmosphere of hydrogen. The mixture is filtered and the filtrate is concentrated to obtain title compound (700 mg, Yield 78%). 1H NMR (500 MHz, CDCl3): ΔH 8.36 (s, 1H), 7.89 (s, 1H), 6.03 (d, J=2.5 Hz, 1H), 5.69 (s, 2H), 5.51 (dd, J=2.5, 8.0 Hz, 1H), 4.99 (dd, J=4.0, 7.5 Hz, 1H), 4.26 (brs, 1H), 4.13-4.08 (m, 2H), 2.99-2.92 (m, 2H), 2.706-2.655 (m, 1H), 2.539-2.486 (m, 1H), 2.18-2.02 (m, 4H), 1.76 (brs, 1H), 1.65-1.60 (m, 5H), 1.43-1.37 (m, 5H), 1.26-1.23 (m, 2H), 0.97 (d, J=9.0 Hz, 3H), 0.79 (d, J=8.5 Hz, 3H) ppm; ESI-MS (m/z): 503.4 [M+1]+.

Step 6: Synthesis of 3-((1S,3r)-3-((((3aR,4R,6R,6aR)-6-(6-amino-9H-purin-9-yl)-2,2-dimethyltetra-hydro furo[3,4-d][1,3]dioxol-4-yl)methyl)(isopropyl)amino)cyclobutyl)propanoic acid To a solution of ethyl 3-((1S,3r)-3-((((3aR,4R,6R,6aR)-6-(6-amino-9H-purin-9-yl)-2,2-dimethyltet-rahydrofuro[3,4-d][1,3]dioxol-4-yl)methyl) (isopropyl)amino)cyclobutyl) propanoate (650 mg, 1.29 mmol) in THF:MeOH=5:1 (30 ml) is added LiOH.H2O (543 mg, 1.29 mmol). The mixture is stirred at RT overnight, concentrated and then taken up in MeOH (10 ml). 1M HCl solution is added dropwise at 0° C. until pH=7. The mixture is concentrated and purified with preparative-HPLC to give title compound (170 mg).

Step 7: Synthesis of N-(2-amino-4-(tert-butyl)phenyl)-3-((1S,3r)-3-((((3aR,4R,6R,6aR)-6-(6-ami-no-9H-purin-9-yl)-2,2-dimethyltetrahydrofuro[3,4-d][1,3]dioxol-4-yl)methyl-)(isopropyl)amino)cyclobutyl) propanamide To a solution of 3-((1S,3r)-3-((((3aR,4R,6R,6aR)-6-(6-amino-9H-purin-9-yl)-2,2-dimethyltet-rahydrofuro[3,4-d][1,3]dioxol-4-yl)methyl)(isopropyl)amino)cyclobutyl)prop-anoic acid (170 mg, 0.36 mmol) in DCM (15 ml) is added 4-tert-butylbenzene-1,2-diamine (117 mg, 0.72 mmol), EDCI (137 mg, 0.72 mmol), HOBT (97 mg, 0.72 mmol) and TEA (217 mg, 2.15 mmol). The mixture is stirred at RT overnight and concentrated. Saturated $NaHCO_3$ solution (20 ml) is added and the mixture extracted with DCM (20 ml×3). The organic layers are dried over Na2SO4 and concentrated. The crude is purified with preparative-TLC (DCM: MeOH=12:1) to afford the title compound (110 mg crude).

Step 8: Synthesis of 9-((3aR,4R,6R,6aR)-6-((((r,3S)-3-(2-(5-(tert-butyl)-1H-benzo[d]imidazol-2-yl)ethyl)cyclobutyl)(isopropyl)amino)methyl)-2,2-dim-ethyltetrahydrofuro[-3,4-d][1,3]dioxol-4-yl)-9H-purin-6-amine A solution of N-(2-amino-4-(tert-butyl)phenyl)-3-((1S,3r)-3-((((3 aR,4R,6R,6aR)-6-(6-ami-no-9H-purin-9-yl)-2,2-dimethyltetrahydrofuro[3,4-d][1,3]dioxol-4-yl)methyl-)(isopropyl)amino)cyclobutyl)propanamide (110 mg) in AcOH (10 ml) is heated to 65° C. Overnight. The mixture is concentrated, saturated $NaHCO_3$ solution (20 ml) is added and the mixture extracted with DCM (20 ml×3). The combined organic layers are dried over Na2SO4 and concentrated to give the title compound (105 mg crude). 1H NMR (500 MHz, CDCl3): ΔH 8.36 (s, 1H), 7.89 (s, 1H), 7.48-7.24 (m, 3H), 6.01 (d, f=1.5 Hz, 1H), 5.60-5.53 (m, 3H), 4.98 (dd, J=3.0, 6.5 Hz, 1H), 4.22 (brs, 1H), 2.97 (brs, 1H), 2.874-2.847 (m, 1H), 2.56-2.50 (m, 3H), 1.87-1.78 (m, 2H), 1.70-1.54 (m, 7H), 1.35-1.17 (m, 14H), 0.90 (d, J=6.5 Hz, 3H), 0.80 (d, J=6.5 Hz, 3H) ppm; ESI-MS (m/z): 603.5 [M+1]+.

Step 9. Synthesis of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl) amino)methyl)tetra-hydrofuran-3,4-diol A solution of 9-((3aR,4R,6R,6aR)-6-((((1r,3 S)-3-(2-(5-(tert-butyl)-1H-benzo[d]imidazol-2-yl)ethyl)cyclobutyl) (isopropyl)amino)methyl)-2,2-dimethyltetrahydrofuro[-3,4-d][1,3]dioxol-4-yl)-9H-purin-6-amine (105 mg) in HCl/MeOH (2.5 mol/L) (10 mL) is stirred at RT for 2 h, then concentrated to dryness. K2CO3 (96 mg) in water (0.5 mL) and MeOH (5 mL) are added and the resulting mixture is stirred for another 10 min at RT and then filtered. The filtrate is concentrated and the residue is purified by preparative-HPLC (xbridge 30 mm*150 mm, Mobile phase: A: water (10 mM NH4HCO3) B: CAN, Gradient: 35-45% B in 10 min, 45-45% B in 6 min, stop at 20 min, Flow rate: 50 ml/min) to give Compound 2 (50 mg, yield: 51%) as a white solid. 1H NMR (500 MHz, MeOD): ΔH 8.29 (s, 1H), 8.20 (s, 1H), 7.47-7.39 (m, 3H), 5.96 (d, J=4.0 Hz, 1H), 4.70-4.75 (m, 1H), 4.26-4.27 (m, 1H), 4.05-4.06 (m, 1H), 3.140-3.155 (m, 1H), 3.00-2.76 (m, 5H), 2.18-2.16 (m, 2H), 1.87-1.85 (m, 2H), 1.57-1.55 (m, 2H), 1.36 (s, 9H), 1.01 (d, J=6.5 Hz, 3H), 0.94 (d, J=6.5 Hz, 3H) ppm; ESI-MS (m/z): 563.4 [M+1]+.

EPZ005676 is soluble in aqueous solution and can be formulated for intravenous administration. The effective pharmacokinetic half-life of EPZ005676 in systemic circulation is 0.25 in rats and 1.5 h in dogs.

Continuous intravenous infusion of EPZ005676 for 21 days in a nude rat subcutaneous xenograft model of MLL-rearranged leukemia provides dose-dependent anti-tumor activity. At the highest dose, complete tumor regressions are achieved with no regrowth for up to 32 days after the cessation of treatment. No significant weight loss or obvious toxicity is observed in rats treated with EPZ005676. EPZ005676 is thus a potent, selective inhibitor of DOT1L that demonstrates strong efficacy in a rat xenograft model of MLL-rearranged leukemia.

EPZ005676 is currently being evaluated in a phase I study in human patients having relapsed/refractory leukemia involving translocations of the MLL gene at 11q23 or other advanced hematologic cancers. EPZ005676 is being administered via continuous intravenous infusion over 21 days.

Compositions and Formulations Comprising DOT1L Inhibitors

The present disclosure provides compositions, including therapeutic compositions comprising one or more DOT1L inhibitor(s) and/or one or more EZH2 inhibitor(s), for the treatment of a leukemia, such as ALL or AML. One or more DOT1L inhibitor(s) and/or one or more EZH2 inhibitor(s) can be administered to a human patient by themselves or in pharmaceutical compositions where they are mixed with suitable carriers or excipient(s) at doses to treat or ameliorate a disease or condition as described herein. Mixtures of these inhibitors can also be administered to the patient as a simple mixture or in suitably formulated pharmaceutical compositions.

Compositions within the scope of this disclosure include compositions wherein the therapeutic agent is a DOT1L inhibitor and/or an EZH2 inhibitor in an amount effective to inhibit the proliferation of a leukemia cell in a patient. Determination of optimal ranges of effective amounts of each component is within the skill of the art. The effective dose is a function of a number of factors, including the specific inhibitor, the presence of a prodrug, the patient and the clinical status of the latter.

Compositions comprising a DOT1L inhibitor and/or an EZH2 inhibitor may be administered parenterally. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion. Alternatively, or concurrently, administration may be orally.

The dosage administered will be dependent upon the age, health, and weight of the recipient, kind of concurrent treatment, if any, frequency of treatment, and the nature of the effect desired.

Compositions comprising a DOT1L inhibitor and/or an EZH2 inhibitor may, for example, be administered parenterally, such as intravenously via an intravenous push or bolus. Alternatively, compositions comprising a DOT1L inhibitor and/or an EZH2 inhibitor may be administered via an intravenous infusion. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

Suitable dosages for intravenous infusion of a composition comprising a DOT1L inhibitor and/or an EZH2 inhibitor include a dosage of at least about 2 mg inhibitor/m2/day or at least about 10 mg inhibitor/m2/day or at least about 20 mg inhibitor/m2/day or at least bout 50 mg inhibitor/m2/day or at least about 100 mg inhibitor/m2/day or at least about 200 mg inhibitor/m2/day or at least about 500 mg inhibitor/m2/day.

Compositions comprising a DOT1L inhibitor and/or a EZH2 inhibitor generally include a therapeutically effective amount of a compound, and a pharmaceutically acceptable carrier. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the inhibitor, preferably in purified form, together with a suitable amount of carrier so as to provide the form for proper administration to the patient. The formulation should suit the mode of administration.

Compositions can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The inhibitors disclosed herein can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

Many of the inhibitors of the present disclosure may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this invention. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present invention includes such salts.

Methods for Inhibiting the Growth and/or Survival of a Cell, and for Treating a Leukemia Patient Exhibiting a Genetic Mutation, Alteration, and/or Abnormality that is Associated with Elevated Expression of a HOX Cluster Gene and/or a HOX Cluster-Associated Gene The present disclosure further provides therapies that involve administering a composition comprising one or more DOT1L inhibitor and one or more EZH2 inhibitor to a human patient for treating a leukemia wherein the leukemia exhibits high level expression of one or more HOXA cluster genes but does not possess an MLL-translocation.

The amount of the DOT1L inhibitor and/or EZH2 inhibitor that will be effective in the treatment, inhibition, and/or prevention of a leukemia characterized by a high level expression of one or more HOX cluster genes, but not possessing an MLL-translocation can be determined by standard clinical techniques. In vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

The compounds or pharmaceutical compositions of the invention can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a compound on a cell line or a patient tissue sample. The effect of the compound or composition on the cell line and/or tissue sample can be determined utilizing techniques known to those of skill in the art including, but not limited to proliferation and apoptosis assays. In accordance with the present disclosure, in vitro assays that can be used to determine whether administration of a specific compound is indicated, include in vitro cell culture assays in which a patient tissue sample is grown in culture, and exposed to or otherwise administered a compound, and the effect of such compound upon the tissue sample is observed.

The present disclosure provides methods of treatment and inhibition by administration to a subject of an effective amount of a DOT1L and/or EZH2 inhibitor compound or pharmaceutical composition as described herein. In one aspect, the compound is substantially purified such that the compound is substantially free from substances that limit its effect or produce undesired side-effects.

Various delivery systems are known and can be used to administer a composition of the present disclosure, for example, encapsulation in liposomes, microparticles, microcapsules, receptor-mediated endocytosis (see, e.g., Wu and Wu, J. Biol. Chem. 262:4429-4432 (1987)), and the like as will be known by one of skill in the art.

Methods of administration include, but are not limited to, intradermal, intramuscular, intraperitoneal, intravenous, subcutaneous, intranasal, epidural, and oral routes. The inhibitors or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the inhibitors or compositions into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

It may be desirable to administer the inhibitors or compositions of locally to the area in need of treatment; this may be achieved by, for example, local infusion during surgery, topical application, by injection, by means of a catheter, by means of a suppository, or by means of an implant, said implant being of a porous, non-porous, or gelatinous material, including membranes, such as sialastic membranes, or fibers.

The inhibitor can be delivered in a vesicle, such as a liposome (Langer, *Science* 249:1527-1533 (1990)) or in a controlled release system. A controlled release system can be placed in proximity of the therapeutic target, thus requiring only a fraction of the systemic dose (see, e.g., Goodson, in Medical Applications of Controlled Release, Vol. 2, pp. 115-138 (1984)).

Intravenous infusion of a compositions comprising a DOT1L inhibitor and/or a EZH2 inhibitor may be continuous for a duration of at least about one day, or at least about three days, or at least about seven days, or at least about 14 days, or at least about 21 days, or at least about 28 days, or at least about 42 days, or at least about 56 days, or at least about 84 days, or at least about 112 days.

Continuous intravenous infusion of a composition comprising a DOT1L inhibitor and/or a EZH2 inhibitor may be for a specified duration, followed by a rest period of another duration. For example, a continuous infusion duration may be from about 1 day, to about 7 days, to about 14 days, to about 21 days, to about 28 days, to about 42 days, to about 56 days, to about 84 days, or to about 112 days. The continuous infusion may then be followed by a rest period of from about 1 day, to about 2 days to about 3 days, to about 7 days, to about 14 days, or to about 28 days. Continuous infusion may then be repeated, as above, and followed by another rest period.

Regardless of the precise continuous infusion protocol adopted, it will be understood that continuous infusion of a composition comprising a DOT1L inhibitor and/or a EZH2 inhibitor will continue until either desired efficacy is achieved or an unacceptable level of toxicity becomes evident.

KITS for Detecting HOXA Cluster Gene Expression

The present disclosure also provides kits for use in testing patient samples for the elevated expression of a HOX cluster gene or a HOX cluster-associated gene and/or the presence of genetic mutation, such as a mutation in one or more of the NPM1, DNMT3A, IDH1, IDH2, RUNX1, TET2, and ASXL1 genes and/or an NUP98-NSD1 or other NUP98 translocation and/or a mutation, alteration, and/or abnormality in any of the genes presented in Table 2, which is associated with elevated HOX cluster gene and/or a HOX cluster-associated gene expression.

The diagnostic kits include a primer pair for amplifying a HOX cluster gene and/or a HOX cluster-associated gene and/or any of the genes presented in Table 2 and a probe for detecting and/or sequencing the amplicon generated from an amplification reaction that employs the primer pair.

FLT3 Inhibitors

Within certain embodiments, the present disclosure provides methods that employ one or more DOT1L inhibitors in combination or in conjunction with one or more FLT3 inhibitors thereby providing a desired therapeutic benefit by further inhibiting the proliferation and/or survival of a cell exhibiting and for the treatment of leukemia patients whose leukemia is associated with elevated expression of a HOX cluster gene and/or a HOX cluster-associated gene.

The FMS-like tyrosine kinase 3 (FLT3) gene encodes a membrane bound receptor tyrosine kinase that affects hematopoiesis leading to hematological disorders and malignancies. See, e.g., Drexler et al., *Leukemia* 10:588-599 (1996);

Gilliland and Griffin, *Blood* 100:1532-1542 (2002); and Stirewalt and Radich, *Nat. Rev. Cancer* 3:650-665 (2003). Activation of FLT3 receptor tyrosine kinases is initiated through the binding of the FLT3 ligand (FLT3L) to the FLT3 receptor, which is expressed on hematopoietic progenitor and stem cells.

FLT3 is a frequently mutated gene in hematological malignancies, present in approximately 30% of adult acute myeloid leukemia (AML). Nakao et al., *Leukemia* 10:1911-1918 (1996); Kiyoi et al., *Leukemia* 12:1333-1337 (1998); Kottaridis et al., *Blood* 98:1742-1759 (2001); Yamamoto et al., *Blood* 97:2434-2439 (2001); and Thiede et al., *Blood* 99:4326-4335 (2002).

The most common FLT3 mutations are internal tandem duplications (ITDs) that lead to in-frame insertions within the juxtamembrane domain of the FLT3 receptor. FLT3-ITD mutations have been reported in 15-35% of adult AML patients. Nakao et al., *Leukemia* 10:1911-1918 (1996); Kiyoi et al., *Leukemia* 12:1333-1337 (1998); Kiyoi et al., *Leukemia* 11:1447-1452 (1997); and Schnittger et al., *Blood* 100:59-66 (2002). A FLT3-ITD mutation is an independent predictor of poor patient prognosis and is associated with increased relapse risk after standard chemotherapy, and decreased disease free and overall survival. AbuDuhier et al., *British J. Hematol.* 11:190-195 (2000); Kiyoi et al., *Blood* 93:3074-3080 (1999). Less frequent are FLT3 point mutations that arise in the activation loop of the FLT3 receptor. The most commonly affected codon is aspartate 835 (D835). Nucleotide substitutions of the D835 residue occur in approximately 5-10% of adult acute myeloid leukemia patients. Stirewalt and Radich, *Nature Rev. Cancer* 3:650-665 (2003); Yamamoto et al., *Blood* 97:2434-2439 (2001); Thiede et al., *Blood* 99:4326-4335 (2002); and Bacher et al., *Blood* 111:2527-2537 (2008).

The high frequency of constitutively activated mutant FLT3 in adult AML has made the FLT3 gene a highly attractive drug target in this leukemia. Several FLT3 inhibitors with varying degrees of potency and selectivity for the target have been or are currently being investigated and examined in AML patients. Kindler et al., *Blood* 116:5089-102 (2010).

FLT3 inhibitors are classified as Type I or Type II inhibitors. These two distinct classifications are based on relative affinities and mechanism of binding to phosphorylated and non-phosphorylated receptor sites. Type I inhibitors recognize the active conformation of kinases. This conformation is conducive to phosphotransfer. Type I inhibitors are generally composed of a heterocyclic ring system. Liu and Gray, *Nat. Chem. Biol.* 2:358-354 (2006). Examples of Type I FLT3 inhibitors include Crcnolanib besylate and Midostaurin. Muralidhara et al., *Cancer Res.* 72 8 Supp.:3683 (2012); and Cools et al., *Cancer Res.* 64:6385-6389 (2004). Mutations rendering the FLT3 receptor tyrosine kinase constitutively phosphorylated may also be sensitive to type I inhibitors.

Type II inhibitors bind to an inactive FLT3 conformation that is typically referred to as 'DFG-out,' which refers to the motif rearrangement. Zhang et al., *Nature Rev. Cancer* 9:28-39 (2009). Inhibitors such as Imatinib, Sorafenib, and Nilotinib (a/k/a/ AMN107 or Tasigna®) bind in the type II conformation. Manley et al., *Biochim. Biophys. Acta.* 1754: 3-13 (2005); Wan et al., *Cell* 116:855-867 (2004). Mutations that confer resistance to Type II inhibitors render the kinase domain of the FLT3 receptor tyrosine kinase constitutively phosphorylated. Type I inhibitors that target the phosphorylated kinase can overcome the resistance resulting from the treatment with Type II inhibitors, and therefore have potential use in treating diseases that harbor these resistance mutations.

FLT3 inhibitors that may be suitably employed in combination with one or more DOT1L inhibitors for use in the presently disclosed methods, including methods for treating leukemia patients, are reviewed, generally, in Leung et al., *Leukemia* 27:260-268 (2013); Grunwald and Levis, *Int. J. Hematol.* 97:683-694 (2013); Wiernik, *Clin. Adv. Hem. & Onc.* 8(6):429 (2010) and are disclosed in further detail in U.S. Pat. Nos. 8,557,847 and 7,977,338 (phenylacetamides); US Patent Publication No. 2003/0219827; PCT Patent Publication Nos. WO 2014/027199; WO 2013/142382; WO 2008/067280; WO 2006/020145; and within the scientific literature in Sato et al., *Blood* 117(12):3286-3293 (2011); Levis, *Hematology*, pp. 220-226 (Am. Soc. Hematol. Educ. Prog., Washington D.C., 2013); Fischer et al., *J. Clin. Oncol.* 28(28):4339-4345 (2010); Fischer, *Blood* 117(12):3247-3248 (2011); Kindler et al., *Blood* 116(24):5089-5102 (2010); and Fathi and Chabner, *Oncologist* 16:1162-1174 (2011).

Additional FLT3 inhibitors are disclosed in PCT Patent Publication Nos. WO 2002/032861, WO 2002/092599, WO 2003/035009, WO 2003/024931, WO 2003/037347, WO 2003/057690, WO 2003/099771, WO 2004/005281, WO 2004/016597, WO 2004/018419, WO 2004/039782, WO 2004/043389, WO 2004/046120, WO 2004/058749, WO 2004/058749, WO 2003/024969; U.S. Patent Publication No. 2004/0049032; and Levis et al., *Blood* 98(3):885-887 (2001); Tse et al., *Leukemia* 15(7):1001-1010 (2001); Smith et al., *Blood* 103:3669-3676 (2004); Griswold et al., *Blood* 104(9):2912-2918 (2004); Yee et al., *Blood* 100(8):2941-2949 (2002); O'Farrell et al., *Blood* 101(9):3597-3605 (2003); Stone et al., *Ann. Hematol.* 83 *Supp* 1:S89-90 (2004); Murata et al., *J. Biol. Chem.* 278(35):32892-32898 (2003); and Levis et al., *Curr. Pharm. Design* 10:1183-1193 (2004). The selection of candidate kinase inhibitors for pharmacological validation of drug targets is described in Uitdehaag et al., *Br. J. Pharmacol.* 166(3):858-76 (2012). Each of these references, as well as all other references disclosed herein, is incorporated herein by reference in its entirety.

FLT3 inhibitors that may be used in these methods include small-molecule tyrosine kinase inhibitor compounds including 2-phenyl amino pyrimidine compounds; imidazolothiazole compounds; 2,4,5-substituted pyrimidine and pyridopyrimidine compounds; pyrrole substituted 2-indolinone compounds; and substituted indolocarbazole compounds, which are well known in the art and are exemplified by specific compounds that have been shown to exhibit FLT3 inhibitory activity and which are being or have been investigated for the treatment of a variety of disease, in particular the hematological malignancies ALL and AML.

A number of small molecule FLT3 tyrosine kinase inhibitors (TKIs) are used routinely in the management of ALLs and are in development for the treatment of FLT3-mutated AML, including, for example, Tandutinib (a/k/a MLN-518 or CT53518, COR Therapeutics Inc. and Millennium Pharmaceuticals Inc.), CHIR-258 (Chiron Corp.); EBIO and IMC-EBIO (ImClone Systems Inc.); XL 999 (Exelixis USA and Symphony Evolution, Inc.); GTP 14564 (Merck Biosciences UK); AG1295 and AG1296; CEP-5214 and CEP-7055 (Cephalon); Nilotinib (a/k/a/ AMN107 or Tasigna®), Sorafenib, Sunitinib (a/k/a SUI 1248, Pfizer USA), Midostaurin (a/k/a PKC412, Novartis AG), Lestaurtinib (a/k/a CEP 701 or KT-555, Ccphalon), KW-2449, Quizartinib (a/k/a AC220, Ambit Biosciences), and Crenolanib. Of these FLT3 inhibitors, Lestaurtinib, Midostaurin, Sorafenib, KW-2449, and AC220 have been or are being evaluated in clinical trials. In addition, the small molecule compounds PLX3397 and AC220 have been developed for the specific purpose of treating patients with AML that is associated with FLT3 internal tandem duplications (ITDs).

FLT3 inhibitors that may be suitably employed in combination with one or more DOT1L inhibitors for use in the presently disclosed methods, including methods for treating leukemia patients, include the 2-phenyl amino pyrimidine compounds, which are described in U.S. Pat. No. 5,521,184; exemplified by the small molecule FLT3 tyrosine kinase inhibitor imatinib[N-(4-methyl-3-(4-(pyridin-3-yl)pyrimidin-2-ylamino)phenyl)-4-((4-methylpiperazin-1-yl)methyl) benzamide methanesulfonic acid]; and represented by Formula VI:

Formula VI

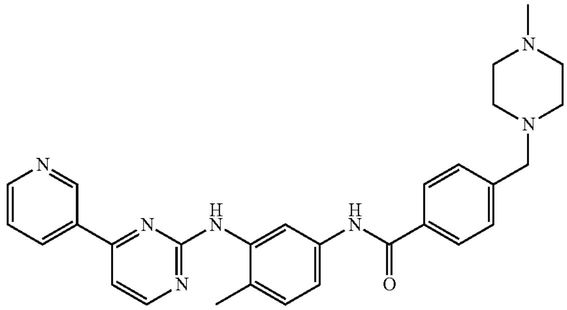

Imatinib (a/k/a STI-571) is available commercially from Novartis under the names Gleevec® in Canada, South Africa, and the United States or Glivec® in Australia, Europe and Latin America). The synthesis of a wide variety of 2-phenyl amino pyrimidine compounds, in addition to Imatinib, is disclosed in U.S. Pat. No. 5,521,184.

FLT3 inhibitors that may be suitably employed in combination with one or more DOT1L inhibitors for use in the presently disclosed methods, including methods for treating leukemia patients, include the imidazolothiazole compounds, which are described in U.S. 2007/0232604 and represented by Formula VII:

Formula VII

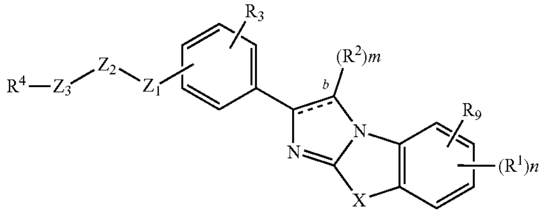

Imidazolothiazole compounds of Formula VII are exemplified herein by Quizartinib (a/k/a AC220), which is being developed by Ambit Biosciences (San Diego, Calif.) for the treatment of acute mycloid leukemia. Quizartinib has the chemical structure 1-(5-(tert-Butyl)isoxazol-3-yl)-3-(4-(7-(2-morpholinoethoxy)benzo[d]imidazo[2,1-b]thiazol-2-yl) phenyl)urea, which is presented as Formula VIIa:

Formula VIIa

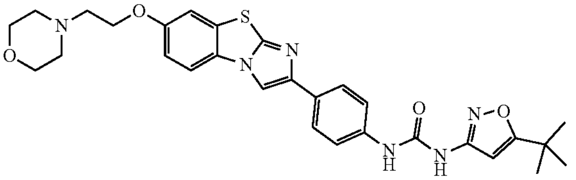

Quizartinib is a second-generation FLT3 inhibitor of Flt3(ITD/WT) having high affinity for FLT3, with a $K_d$ value of 1.6 nM, and an IC50 of 1.1 nM for Flt3-ITD and 4.2 nM for WT FLT3, which is about 10-fold greater than its IC50 for the related tyrosine kinase receptors KIT, PDGFRα, PDGFRβ, RET, and CSF-1R. The synthesis of Quizartinib is described in U.S. Pat. No. 7,820,657 and PCT Patent Publication Nos. WO 2007/109120, WO 2011/056939, and WO 2009/038757.

FLT3 inhibitors that may be suitably employed in combination with one or more DOT1L inhibitors for use in the presently disclosed methods, including methods for treating leukemia patients, include the 2,4,5-substituted pyrimidine compounds as disclosed in PCT Patent Publication No. WO 2014/027199 and represented by Formula Formula VIII:

Formual VIII

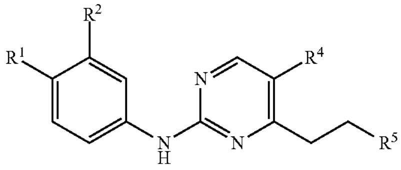

FLT3 inhibitors that may be suitably employed in combination with one or more DOT1L inhibitors for use in the presently disclosed methods, including methods for treating leukemia patients, include the pyridopyrimidine compounds as disclosed in PCT Patent Publication No. WO 2013/142382 and represented by Formula IX:

Formula IX

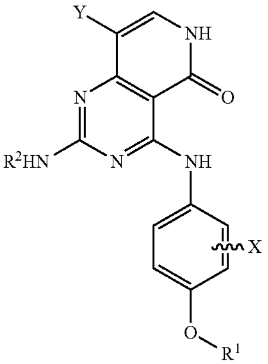

FLT3 inhibitors that may be suitably employed in the presently disclosed methods for inhibiting the proliferation and/or survival of cell and for treatment of leukemia patients include PLX3397 (Plexxikon Inc., Berkeley, Calif.). Synthesis of PLX3397 and related compounds is described in Zhang et al., *Proc. Natl. Acad. Sci. U.S.A.* 110(14):5689-94 (2013)

FLT3 inhibitors that may be suitably employed in the presently disclosed methods for inhibiting the proliferation and/or survival of cell and for treatment of leukemia patients include Tandutinib (MLN518; N-(4-isopropoxyphenyl)-4-(6-methoxy-7-(3-(piperidin-1-yl) propoxy) quinazolin-4-yl) piperazine-1-carboxamide) and is represented by Formula X:

Formula X

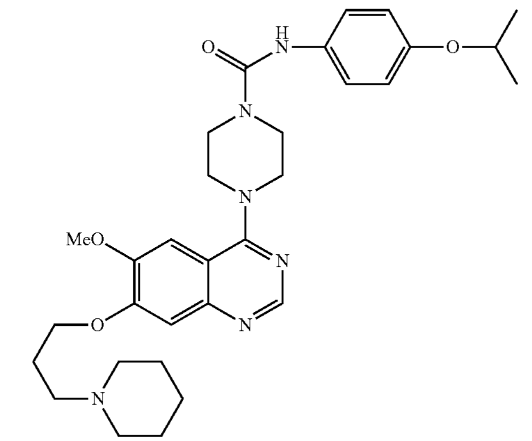

Tandutinib (MLN518, CT53518) is a potent FLT3 antagonist with IC50 of 0.22 μM, also inhibits PDGFR and c-Kit, 15 to 20-fold higher potency for FLT3 versus CSF-1R and >100-fold selectivity for the same target versus FGFR, EGFR and KDR. Tandutinib has been described for the treatment of AML. DeAngelo et al., *Blood* 108:3674-81 (2006).

Sorafenib (2-pyridinecarboxamide, 4-[4-[[[[4-chloro-3-trifluoromethyl)phenyl]amino]carbonyl]amino]phenoxy]-N-methyl-4-(4-(3-(4-chloro-3 trifluoro methylphenyl) ureido)phenoxy)pyridine-2-carboxyllic acid methyamide-4-methylbenzenesulfonate tosylate (a/k/a 4-(4-{3-[4-Chloro-3-(trifluoromethyl)phenyl]ureido}phenoxy) N2methylpyridine-2-carboxamide 4-methylbenzene-sulfonate) and is represented by the following Formula XI:

Formula Xi

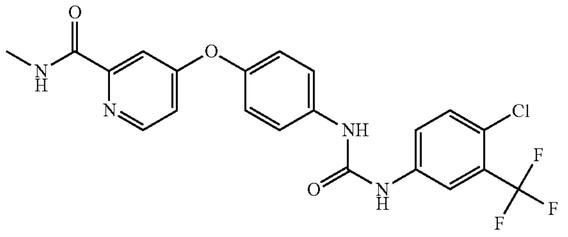

Sorafenib is co-developed and co-marketed by Bayer and Onyx Pharmaceuticals as Nexavar). The synthesis of sofafenib is disclosed in US Patent Publication No. 2008/0262236.

Pyrrole substituted 2-indolionone protein kinase inhibitors are disclosed in U.S. Pat. Nos. 7,119,090; 6,395,734; 6,575,293; and 7,125,905 and are represented by the following Formula XII:

Formula XII

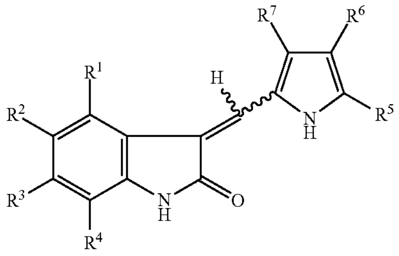

Sunitinib (N-(2-diethylaminoethyl)-5-[(Z)-(5-fluoro-2-oxo-1H-indol-3-ylidene)methyl]-2,4-dimethyl-1H-pyrrole-3-carboxamide); previously known as SU11248) is available commercially under the name Sutent® from Pfizer (New York, N.Y.). The synthesis of Sunitinib is disclosed in U.S. Pat. No. 6,573,293 (compound 80) and is represented by the following Formula XIII:

Formula XIII

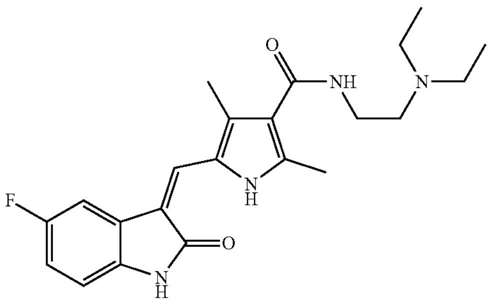

Substituted indolocarbazole compounds are exemplified by Midostaurin (PKC412; (9S,10R,11R,13R)-2,3,10,11,12,13-Hexahydro-10-methoxy-9-methyl-11-(methylamino)-9,13-epoxy-1H,9H-diindolo[1,2,3-gh:3',2',1'-lm]pyrrolo[3,4-j][1,7]benzodiamzonine-1-one), which is a multi-target protein kinase inhibitor being investigated for the treatment of AML (Levis, *Best Pract Res Clin Haematol* 23(4):489-494 (2010) and is represented by the following Formula XIV:

Formula XIV

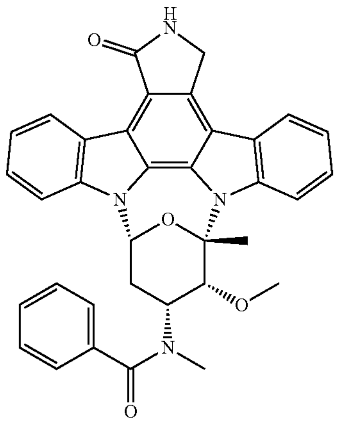

KW-2449 is a multiple-targeted inhibitor, mostly for Flt3 with IC50 of 6.6 nM (Shiotsu et al., *Blood* 114(8):(2009), which is represented by the following Formula XV:

Formula XV

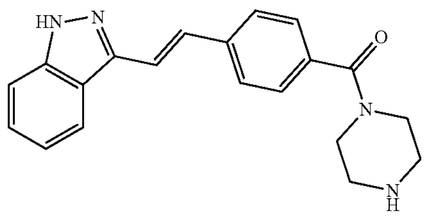

Combination Therapies Employing DOT1L Inhibitors and FLT3 Inhibitors

Within certain embodiments, the present disclosure provides methods, including therapeutic methods, which employ a combination of a DOT1L inhibitor that is administered prior to, coincident with, or after the administration of a FLT3 inhibitor as disclosed herein. These methods for inhibiting the growth and/or survival of a cell and for treating a patient, in particular a leukemia patient, exhibiting an elevated level of HOX cluster gene and/or HOX cluster-associated gene expression, employ a combination of compounds, including therapeutic compounds, including one or more DOT1L inhibitor(s) in combination with one or more Flt3 inhibitors, for the treatment of a leukemia, such as ALL or AML.

By these methods, one or more FLT3 inhibitors and one or more DOT1L inhibitor(s) can be administered to a human patient by themselves or in pharmaceutical compositions where they are mixed with suitable carriers or excipient(s) at doses to treat or ameliorate a disease or condition as described herein. Mixtures of these inhibitors can also be administered to the patient as a simple mixture or as pharmaceutical compositions.

Compositions within the scope of this disclosure include compositions wherein a first therapeutic agent is a DOT1L inhibitor and a second therapeutic agent is a FLT3 inhibitor, wherein the first therapeutic agent and the second therapeutic agent are administered at least substantially simultaneously or sequentially in an amount at a time that is effective to inhibit the proliferation of a leukemia cell in a patient. Determination of optimal ranges of effective amounts of each first and second therapeutic agent is within the skill of the art. The effective dose is a function of a number of factors, including the specific inhibitors and the patient's clinical status.

Compositions comprising a FLT3 inhibitor in combination with a DOT1L inhibitor may be administered parenterally. As used herein, the term "parenteral administration" refers to modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intra-articular, subcapsular, subarachnoid, intraspinal, and intrasternal injection and infusion.

Alternatively, a composition comprising a FLT3 inhibitor may be administered prior to, concurrently with, or following the administration of a DOT1L inhibitor. For example, the administration of a DOT1L inhibitor may occur following the completion of a first therapeutic regimen comprising the administration of a FLT3 inhibitor. Conversely the administration of a FLT3 inhibitor may occur following the completion of a first therapeutic regiment comprising the administration of a DOT1L inhibitor.

The dosage of each inhibitor that is administered will be dependent upon the age, health, and weight of the recipient, the nature of the concurrent treatment, the frequency of treatment, and the nature of the effect desired.

Suitable dosages for intravenous infusion of a composition comprising a FLT3 inhibitor and a DOT1L inhibitor will depend upon the therapeutic efficacy of each inhibitor administered and may, for example, include a dosage of at least about 2 mg of a first inhibitor/m2/day or at least about 10 mg of a first inhibitor/m2/day or at least about 20 mg of a first inhibitor/m2/day or at least about 50 mg of a first inhibitor/m2/day or at least about 100 mg first inhibitor/m2/day or at least about 200 mg of a first inhibitor/m2/day or at least about 500 mg of a first inhibitor/m2/day, where a first inhibitor may be a FLT3 inhibitor or a DOT1L inhibitor. Likewise, a second inhibitor may be administered at a dosage of at least about 2 mg of a second inhibitor/m2/day or at least about 10 mg of a second inhibitor/m2/day or at least about 20 mg of a second inhibitor/m2/day or at least about 50 mg of a second inhibitor/m2/day or at least about 100 mg of a second inhibitor/m2/day or at least about 200 mg of a second inhibitor/m2/day or at least about 500 mg of a second inhibitor/m2/day. It will be understood that if a first inhibitor is a FLT3 inhibitor then a second inhibitor is a DOT1L inhibitor. Conversely, if a first inhibitor is a DOT1L inhibitor then a second inhibitor is a FLT3 inhibitor.

Compositions comprising a FLT3 inhibitor, compositions comprising a DOT1L inhibitor, and compositions comprising a combination of a FLT3 inhibitor and a DOT1L inhibitor generally include a therapeutically effective amount of the compound(s), and a pharmaceutically acceptable carrier. Because the two inhibitors are used in combination, one or the other may be administered at a subthreshold level and that is still considered a therapeutically effective amount. As used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skimmed milk, glycerol, propylene, glycol, water, ethanol and the like. The composition, if desired, can also contain minor amounts of wetting or emulsifying agents, or pH buffering agents.

These FLT3 inhibitor and/or DOT1L inhibitor compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, and the like. Such compositions will contain a therapeutically effective amount of the inhibitor, preferably in purified form, together with a suitable amount of carrier so as to provide the form for proper administration to the patient. The formulation should suit the mode of administration.

Compositions can be formulated in accordance with routine procedures as a pharmaceutical composition adapted for intravenous administration to a human. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The inhibitors disclosed herein can be formulated as neutral or salt forms. Pharmaceutically acceptable salts include those formed with anions such as those derived from hydrochloric, phosphoric, acetic, oxalic, tartaric acids, and the like, and those formed with cations such as those derived from sodium, potassium, ammonium, calcium, ferric hydroxides, isopropylamine, triethylamine, 2-ethylamino ethanol, histidine, procaine, and the like.

Many of the inhibitors of the present disclosure may be provided as salts with pharmaceutically compatible counterions (i.e., pharmaceutically acceptable salts). A "pharmaceutically acceptable salt" means any non-toxic salt that, upon administration to a recipient, is capable of providing, either directly or indirectly, a compound or a prodrug of a compound of this disclosure. A "pharmaceutically acceptable counterion" is an ionic portion of a salt that is not toxic when released from the salt upon administration to a subject. Pharmaceutically compatible salts may be formed with many acids, including but not limited to hydrochloric, sulfuric, acetic, lactic, tartaric, malic, and succinic acids. Salts tend to be more soluble in water or other protic solvents than their corresponding free base forms. The present disclosure includes such salts.

The amount of the FLT3 inhibitor, DOT1L inhibitor and combination of the two that will be effective in the treatment, inhibition, and/or prevention of a leukemia characterized by a high level expression of one or more HOX cluster genes or HOX cluster associated genes, but not possessing an MLL-translocation can be determined by standard clinical techniques. In vitro assays may optionally be employed to help identify optimal dosage ranges. The precise dose to be employed in the formulation will also depend on the route of administration, and the seriousness of the disease or disorder. Effective doses may be extrapolated from dose-response curves derived from in vitro or animal model test systems.

The FLT3 and DOT1L inhibitor compounds or compositions comprising FLT3 and/or DOT1L compounds can be tested in vitro, and then in vivo for the desired therapeutic or prophylactic activity, prior to use in humans. For example, in vitro assays to demonstrate the therapeutic or prophylactic utility of a compound or pharmaceutical composition include the effect of a compound on a cell line or a patient tissue sample. The effect of the compound or composition on the cell line and/or tissue sample can be determined utilizing techniques known to those of skill in the art including, but not limited to proliferation and apoptosis assays. In accordance with the present disclosure, in vitro assays that can be used to determine whether administration of a specific compound is indicated, include in vitro cell culture assays in which a patient tissue sample is grown in culture, and exposed to or otherwise administered a compound, and the effect of such compound upon the tissue sample is observed.

The present disclosure provides methods of treatment and inhibition by administration to a subject of an effective amount of a first inhibitor or composition thereof prior to, concomitantly or in combination with, or following administration of a second inhibitor or composition thereof, wherein a first inhibitor or composition thereof may include a FLT3 inhibitor and a second inhibitor or composition thereof or may include a DOT1L inhibitor. Alternatively, a first inhibitor or composition thereof may include a DOT1L inhibitor and a second inhibitor or composition thereof may include a FLT3 inhibitor. In one aspect, the compound is substantially purified such that the compound is substantially free from substances that limit its effect or produce undesired side-effects.

Various delivery systems are known and can be used to administer a composition of the present disclosure, for example, encapsulation in liposomes, microparticles, microcapsules, receptor-mediated endocytosis (see, e.g., Wu and Wu, *J. Biol. Chem.* 262:4429-4432 (1987)), and the like as will be known by one of skill in the art.

Methods of administration include, but are not limited to, intradermal, intramuscular, intraperitoneal, intravenous, subcutaneous, intranasal, epidural, and oral routes. The inhibitors or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the inhibitors or compositions into the central nervous system by any suitable route, including intraventricular and intrathecal injection. Intraventricular injection may be facilitated by an intraventricular catheter, for example, attached to a reservoir, such as an Ommaya reservoir. Pulmonary administration can also be employed, for example, by use of an inhaler or nebulizer, and formulation with an aerosolizing agent.

The FLT3 and DOT1L inhibitors, individually or together, can be delivered in a vesicle, such as a liposome (Langer, *Science* 249:1527-1533 (1990)) or in a controlled release system. A controlled release system can be placed in proximity of the therapeutic target, thus requiring only a fraction of the systemic dose (see, e.g., Goodson, in Medical Applications of Controlled Release, Vol. 2, pp. 115-138 (1984)).

Intravenous infusion of a compositions comprising a FLT3 inhibitor, a DOT1L inhibitor or both may be continuous for a duration of at least about one day, or at least about three days, or at least about seven days, or at least about 14 days, or at least about 21 days, or at least about 28 days, or at least about 42 days, or at least about 56 days, or at least about 84 days, or at least about 112 days.

Continuous intravenous infusion of a composition comprising a FLT3 inhibitor, a DOT1L inhibitor may be for a specified duration, followed by a rest period of another duration. For example, a continuous infusion duration may be from about 1 day, to about 7 days, to about 14 days, to about 21 days, to about 28 days, to about 42 days, to about 56 days, to about 84 days, or to about 112 days. The continuous infusion may then be followed by a rest period of from about 1 day, to about 2 days to about 3 days, to about 7 days, to about 14 days, or to about 28 days. Continuous infusion may then be repeated, as above, and followed by another rest period.

Regardless of the precise continuous infusion protocol adopted, it will be understood that continuous infusion of a composition comprising a FLT3 inhibitor, a DOT1L inhibitor will continue until either desired efficacy is achieved or an unacceptable level of toxicity becomes evident.

Use of DOT1L Inhibitors in Patients at High Risk of Developing Therapy-Related Leukemia and Exhibiting Mutations Associated with HOX Gene Cluster Overexpression or HOX Cluster-Associated Gene Overexpression Therapy-related AML (t-AML) and therapy-related ALL (t-ALL) are well-recognized clinical syndromes believed to occur as a direct consequence of mutations induced by cytotoxic chemotherapy and/or radiation used to treat a pre-existing condition, such as hematopoietic and solid malignancies. Approximately, 8-10% of all patients treated for cancer will develop t-AML an average 5 years following the treatment. Development of t-AML has been reported after treatment of various primary cancers, including Hodgkin's lymphoma, non-Hodgin's lymphoma, ovarian, breast, and lung cancers. Larson R A, *Haematologica,* 2009 April; 94(4):454-9. Specifically, it has been shown that alkylating chemotherapy agents, which bind DNA and prevent its replication, increase the risk of therapy-related leukemia. Furthermore, use of topoisomerase II inhibitors to treat certain types of cancers, such as lung cancer, has too been linked to increased risk of developing therapy-related AML. Bhatia S. *Semin Oncol.* 2013; December; 40(6):666-75.

Cytogenetic abnormalities observed in t-AML and t-ALL resemble those found in de novo AML and ALL. For example, similar to de novo AML, MLL rearrangement is a common feature of therapy-related AML (Schoch, *Blood.* 2003 Oct. 1; 102 (7):2395-402.) Additionally, several of the known NUP90 translocations have been identified in patients with t-AML (Lam D H, *Leukemia,* 15(11):1689-95 (2001)). Similarly, it has been shown that IDH1 and IDH1 mutations are of the same type and occur at the same prevalence in t-AML and de novo AML (Westman, M K, Leukemia (2013) 27, 957-959). Overall, the cited evidence strongly suggests that de novo AML and t-AML share common biological characteristics including the presence of mutations associated with elevated HOX cluster gene expression. Accordingly, DOT1L inhibitors would be useful in treating the foregoing type of high-risk individuals when the individuals exhibit overexpression of one or more HOX cluster gene(s) and/or one or more HOX cluster-associated gene(s). Instead of measuring such overexpression, such individuals can be identified if they are shown to possess a genetic mutation, alteration, and/or abnormality, other than an MLL-translocation, an MLL-rearrangement, and/or an MLL-PTD, which is known or determined to be associated with elevated expression of one or more HOX cluster genes and/or one or more HOX cluster-associated genes. The aim of the therapy would be to decrease such overexpression and thus reduce the risk of these individuals developing t-ALL and t-AML.

It will be understood that, unless indicated to the contrary, terms intended to be "open" (e.g., the term "including" should be interpreted as "including but not limited to," the term "having" should be interpreted as "having at least," the term "includes" should be interpreted as "includes but is not limited to," etc.). Phrases such as "at least one," and "one or more," and terms such as "a" or "an" include both the singular and the plural.

It will be further understood that where features or aspects of the disclosure are described in terms of Markush groups, the disclosure is also intended to be described in terms of any individual member or subgroup of members of the Markush group. Similarly, all ranges disclosed herein also encompass all possible sub-ranges and combinations of sub-ranges and that language such as "between," "up to," "at least," "greater than," "less than," and the like include the number recited in the range and includes each individual member.

Moreover, all of the foregoing sections pertaining to methods, kits, compositions comprising DOT1L inhibitors are deemed to apply to DOT11 inhibitors and FLT3 inhibitors in combination or conjunction All references cited herein, whether supra or infra, including, but not limited to, patents, patent applications, and patent publications, whether U.S., PCT, or non-U.S. foreign, and all technical and/or scientific publications are hereby incorporated by reference in their entirety.

While various embodiments have been disclosed herein, other embodiments will be apparent to those skilled in the art. The various embodiments disclosed herein are for purposes of illustration and are not intended to be limiting, with the true scope and spirit being indicated by the claims.

The present disclosure will be further described with reference to the following non-limiting examples. The teaching of all patents, patent applications and all other publications cited herein are incorporated by reference in their entirety.

EXAMPLES

Example 1

Inhibition of DOT1L Inhibits Growth of Leukemia Cells that Exhibit an MLL-Translocation, MLL-Rearrangement, or MLL-Partial Tandem Duplication (Prior Art)

This Example confirms, as is generally understood in the art, that leukemias exhibiting an MLL-translocation, MLL-rearrangement, or MLL-partial tandem duplication and an elevated expression of one or more HOX cluster gene or one or more HOX cluster-associated gene are sensitive to DOT1L inhibition.

DOT1L is a histone methyltransferase that is central to the mechanism by which multiple leukemogenic fusion oncoproteins induce inappropriate gene expression in developing white blood cells, thus reprograming them and blocking their differentiation. Inhibition of DOT1L suppresses the leukemia-associated gene expression signature and induces differentiation of MLL-fusion driven leukemias.

It has been demonstrated that HOX cluster genes are important for continued proliferation and survival of leukemia cells (Faber et al., HOXA9 is required for Survival in Human MLL-rearranged Acute Leukemias, *Blood* 113(11):2375-85 (2009)) and it has been suggested that elevated HOX cluster gene expression in AML may be associated with adverse outcome. It has also been shown that, in MLL-translocated leukemias, inhibition of the DOT1L histone methyltransferase causes a decrease in HOX cluster gene expression and a corresponding decrease in cellular proliferation.

Based upon these findings, DOT1L was postulated as a potential therapeutic target for MLL-translocated leukemias, which depend upon DOT1L for continued proliferation and survival and exhibit elevated HOX cluster gene expression.

Figure 2:
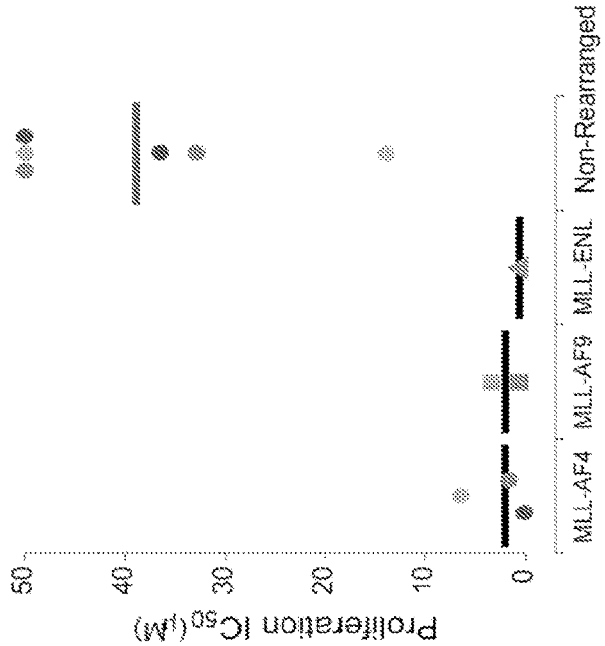
FIG. 2 is a graph presenting data that the DOT1L inhibitor EPZ004777 selectively inhibits the proliferation of MLL-translocated cell lines. The $IC_{50}$ for six MLL-translocated (MLL-AF4, MLL-AF9, MLL-ENL) and six non-rearranged MLL-germline leukemia cell lines is shown.
Figure 3A:
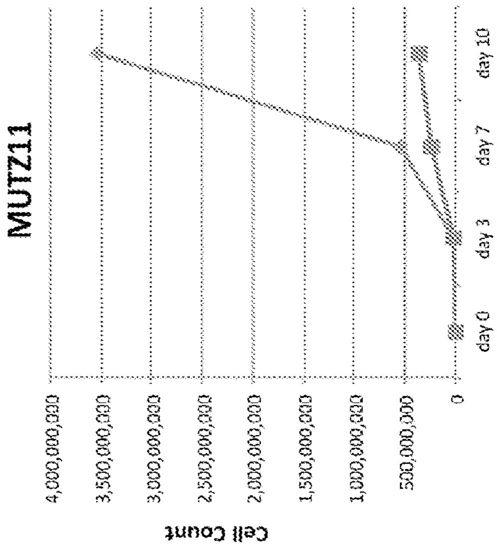
FIGS. 3A and 3B are growth curves showing number of cells (y axis) over 10 day period (x axis). The proliferation of the human MLL-PTD AML cell line (MUTZ11) is inhibited by DOT1L (FIG. 3A) whereas the proliferation of AML1-ETO (Kasumi) cells is insensitive to DOT1L (FIG. 3B). The indicated cell lines were treated with 10 μM EPZ004777 or DSMO (control) and cell counts were assessed on the days indicated.
Figure 3B:
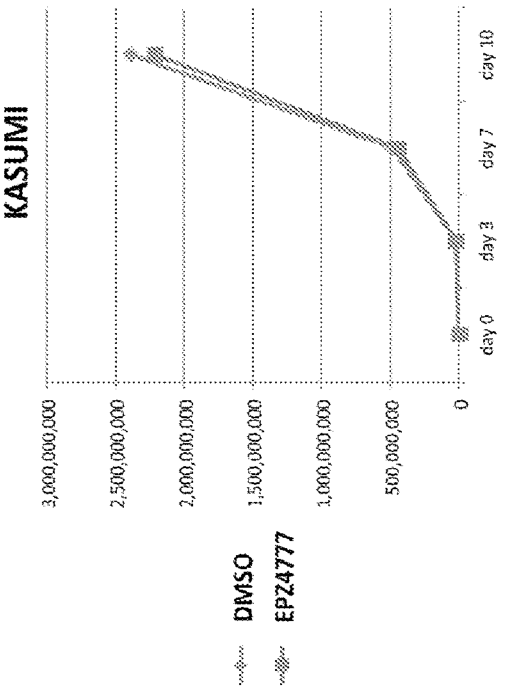

Studies were performed to determine the IC50 for cell proliferation in six leukemia cell lines with MLL-translocations and six cell lines without MLL-translocations. The IC50s for MLL-translocated lines are: MV4-11 (ATCC®, CRL-9591, Manassas, Va.), 170 nM; SEMK2 (S, Armstrong, MSKCC), 1.7 mM; KOPN-8 (Creative Bioarray, Shirley, N.Y.), 620 nM; Molm-13 (Creative Bioarray, Shirley, N.Y.), 720 nM; and THP-1 (ATCC® TIB-202), 3 mM. In contrast, the IC50s for non-MLL-translocated cell lines are: Jurkat (ATCC® CRL-2898), >50 mM; Kasumi-1 (ATCC® CRL-2724), 33 mM; 697 (Creative Bioarray, Shirley, N.Y.), 35 mM; REH (ATCC® CRL-8286), 14 mM; and HL-60 (ATCC® CCL-240), >50 mM (FIG. 2).

Dependencies on DOT1L and H3K79 methylation were identical in murine MLL-AF9 transformed cell lines whether DOT1L was genetically inactivated using a conditional knockout model or inhibited with the small molecule EPZ004777. Specifically, HOXA9/MEIS1 transformed cells were insensitive to DOT1L inhibition whereas MLL-AF9 transformed cells undergo cell cycle arrest and apoptosis as a result of DOT1L inhibition.

Two human leukemia cell lines, MUTZ-11 (H. Drexler, DSMZ, Braunschweig, Del.) and EOL-1 (Sigma-Aldrich, St. Louis, Mo.), which exhibit elevated HOX cluster gene expression and possess an MLL-partial tandem duplication (MLL-PTD) were tested for proliferation in the presence of the selective small molecule aminonucleoside DOT1L inhibitor EPZ004777 (Daigle et al., *Cancer Cell* 20(1):53-65, 2011). The MUTZ11 and EOL1 cell lines were treated with 10 μM EPZ004777, a concentration that does not influence the proliferation of cell lines that do not show elevated HOXA gene expression (FIG. 2). EPZ004777 significantly inhibited proliferation of both of the MLL-PTD cell lines tested over a 10-day period (FIG. 2).

Figure 4:
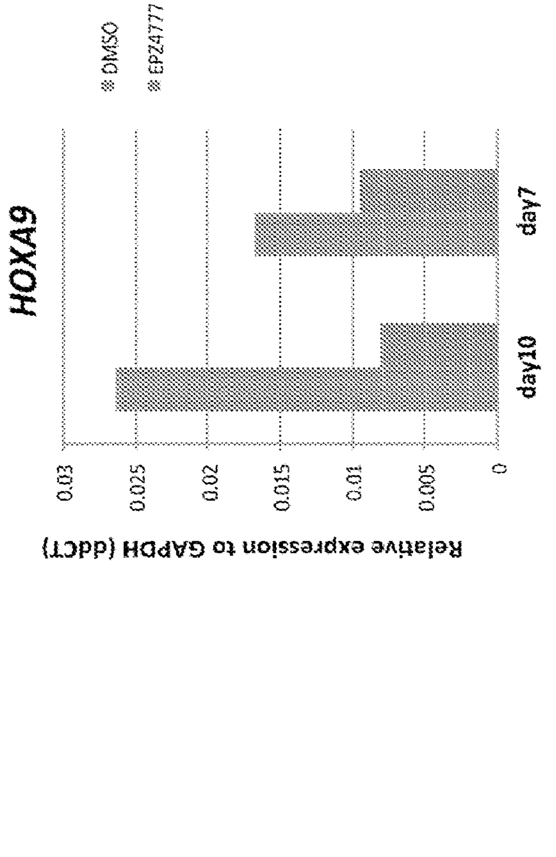
FIG. 4 is a bar graph showing relative expression of HOXA9 relative to GAPDH (ddCT) and showing that HOXA9 expression is decreased after treatment of MLL-PTD AML cell line MUTZ11 cells with the DOT1L inhibitor EPZ004777. MUTZ11 cells were treated with DMSO (control) or EPZ004777 and HOXA9 expression was assessed at days 7 and 10.

HOXA gene expression was assessed at seven and 10 days after treatment of the MLL-PTD cell line MUTZ11. HOXA cluster gene expression decreased significantly (FIG. 4), suggesting that DOT1L is required for continued proliferation and elevated HOXA cluster gene expression in MLL-PTD leukemia cells.

Example 2

Inhibition of DOT1L Inhibits Growth of Leukemia Cells that Exhibit a Genetic Mutation that is not an MLL-Translocation. MLL-Rearrangement, or MLL-Partial Tandem Duplication but is Associated with Elevated HOX Cluster Gene Expression This Example demonstrates that certain leukemia tissues and cells that exhibit: (1) one or more leukemia-associated mutation in a gene other than an MLL-translocation, MLL-rearrangement, or MLL-partial tandem duplication (MLL-PTD) and (2) elevated expression of one or more HOX cluster gene and/or one or more HOX cluster-associated gene, are sensitive to DOT1L inhibition and, therefore, may be advantageously treated by the administration of a DOT1L inhibitor.

In addition to leukemias associated with MLL-translocations, MLL-rearrangements, and MLL-PTDs, other leukemias, for example leukemias with one or more mutation(s) in any of the NPM1, DNMT3A, IDH1, IDH2, RUNX1, TET2, and/or ASXL1 genes and/or an NUP98-NSD1 and/or other NUP98 translocation also display elevated HOX cluster gene and/or HOX cluster-associated gene expression. (See Tables 2 and 3, which discloses leukemia associated genes that are associated with (Table 2) and that are not associated with (Table 3) elevated HOX cluster gene and/or HOX cluster-associated gene expression).

The role of DOT1L in regulating HOX cluster gene expression and HOX cluster-associated gene expression and maintenance of cell proliferation and survival was assessed as part of the present disclosure in representative leukemias exhibiting mutations in the NPM1, DNMT3A, IDH1, IDH2, RUNX1, TET2, and ASXL1 genes and NUP98-NSD1 and other NUP98 translocation, which leukemias do not also exhibit an MLL-translocation, an MLL-rearrangement, or an MLL-PTD.

Leukemia cells driven by the NUP98-NSD1 fusion protein also exhibit elevated HOX cluster gene expression, presumably as a result of aberrant H3K36 methylation as NSD1 is an H3K36 methyl-transferase. Wang et al., NUP98-NSD1 Links H3K36 Methylation to HOX-A Gene Activation and Leukaemogenesis, *Nature Cell Biology* 9(7):804-12 (2007).

As disclosed herein, proliferation of leukemia cells expressing a NUP98-NSD1 gene fusion is inhibited by EPZ004777 DOT1L. Because NSD1 drives aberrant H3K36 methylation, these data further implicate an important, and previously unrecognized, connection between histone K36 methylation by NSD1 and K79 methylation by DOT1L (FIG. 5).

An NPM1 mutant human AML cell line, OCI-AML3 (DSMZ, ACC-582; Braunschweig, Del.), was also treated with the DOT1L inhibitor EPZ004777 and proliferation of those EPZ004777-treated OCI-AML3 cells was compared to the proliferation of an EPZ004777-sensitive MLL-translocated line and an EPZ004777-insensitive AML1-ETO-translocated cell line in the presence of EPZ004777. The OCI-AML3 cells were as sensitive to growth inhibition by EPZ004777 as were the MLL-translocated lines while the AML1-ETO-translocated cell line was not sensitive to EPZ004777-mediated growth inhibition (FIG. 7A-D).

The data presented in this Example demonstrate that leukemias that exhibit elevated HOX cluster gene or HOX cluster-associated gene expression, but do not possess an MLL-translocation, an MLL-rearrangement, or an MLL-PTD, are responsive to DOT1L inhibition and that proliferation of such elevated HOX cluster gene expressing leukemia cells is reduced when such cells are contacted with a DOT1L inhibitor, such as EPZ004777.

Moreover, and without intending to be limited by theory, the data presented herein suggest that H3K79 methylation by DOT1L is important for the maintenance of HOX gene expression in normal hematopoietic cells and support the clinical efficacy of DOT1L inhibitors for the treatment of leukemias in patients exhibiting elevated HOX cluster gene expression, regardless of whether those leukemias possess an MLL-translocation, MLL-rearrangement, or MLL-PTD.

Example 3

A Mouse Model System for Defining Roles for Epigenetic Regulators in Leukemias In order to develop a mouse model system of NUP98-NSD1 driven leukemia, a cDNA that encodes the NUP98-NSD1 fusion protein was introduced it into Lin−, Sca1+, c-Kit+ (LSK) mouse bone marrow cells enriched for hematopoietic stem cells (HSCs). These cells proliferate indefinitely in culture and induce leukemia in mice. Therefore, NUP98-NSD1 transformed HSC-enriched LSK cells can be assessed for DOT1L inhibition.

Figure 5B:
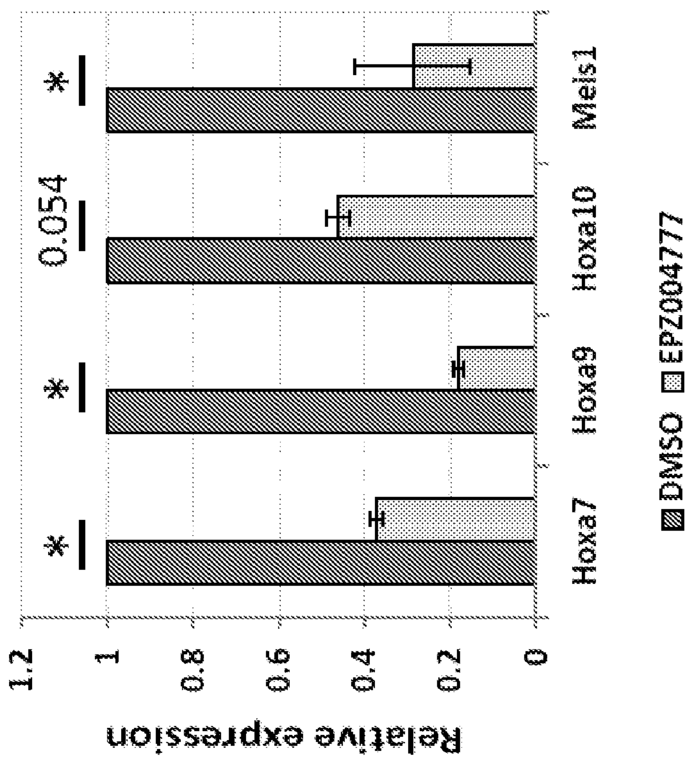
FIGS. 5A and 5B show effects of EPZ004777 in NUP98-NSD1 transformed mouse cells, where
Figure 5A:
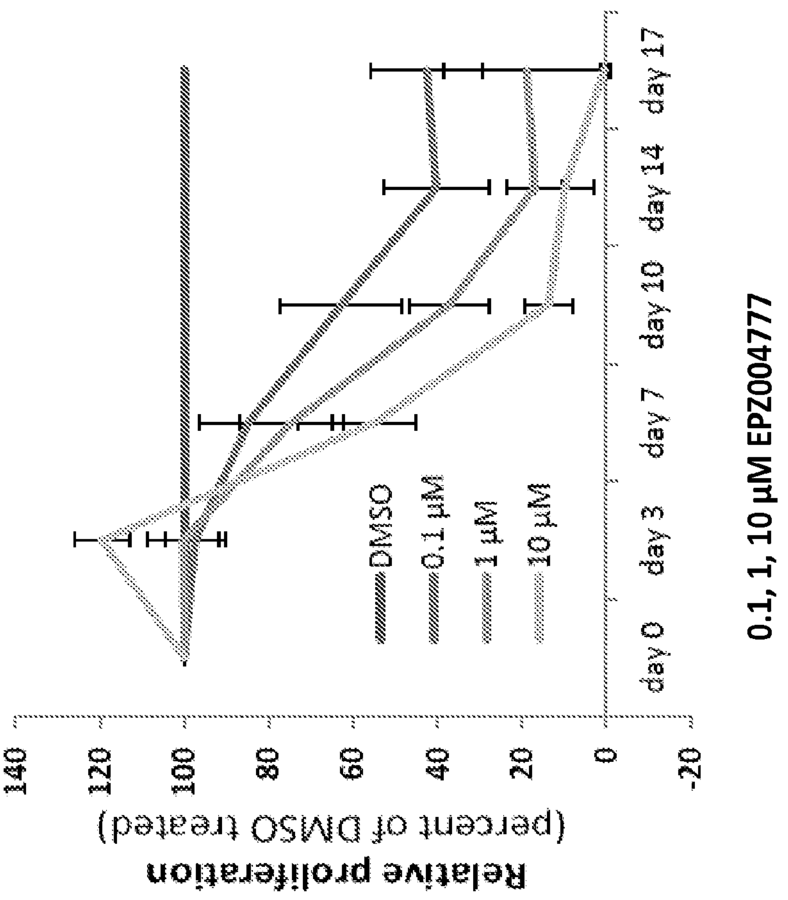
Figure 7A:
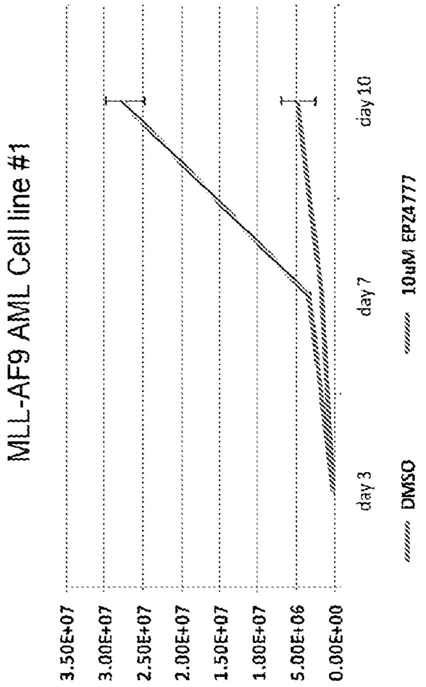
FIGS. 7A-7D show the effects of DOT1L inhibitor EPZ004777 versus vehicle control DMSO on proliferation of different leukemia cell lines.
Figure 7B:
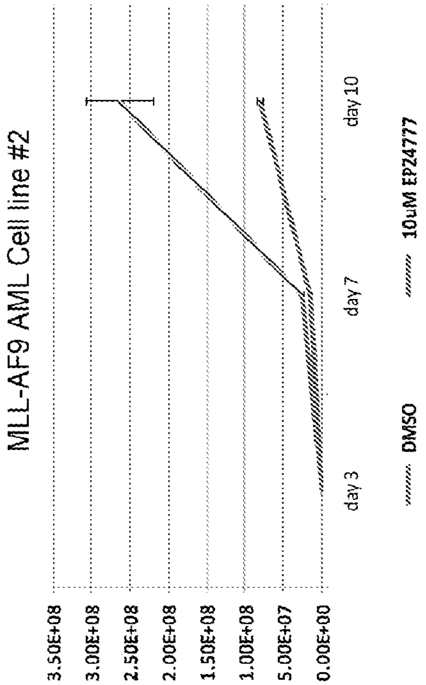
Figure 7C:
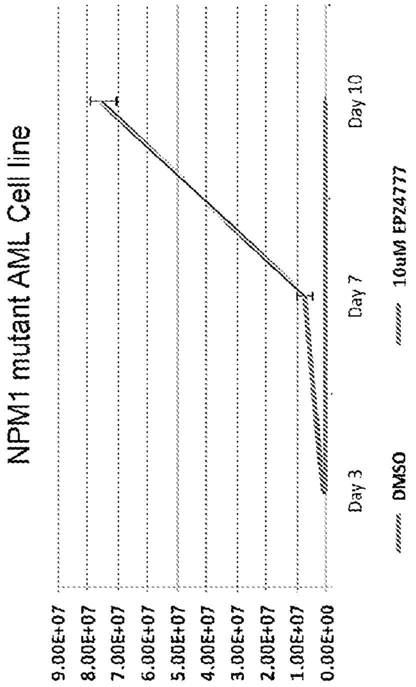
Figure 7D:
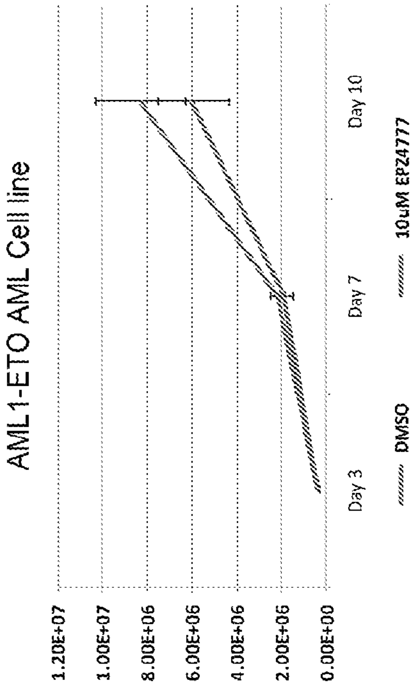

NUP98-NSD1 transformed HSC-enriched LSK cells were treated with the DOT1L inhibitor EPZ004777 and found to be remarkably sensitive to EPZ004777 as evident by proliferation defect upon the exposure of cells to various concentration of DOT1L inhibitor (FIG. 5A). Moreover, 7 day treatment of NUP98-NSD1 transformed mouse cells with 10 μM of DOT1L inhibitor significantly reduced HOX promoter associated H3K79 methylation, which was accompanied by a substantial decrease in HOXa7, HOXa9, HOXa10, and Meis1 cluster gene expression (FIG. 5B).

In order to begin to address the role of DOT1L in normal hematopoietic stem cells (HSC), a conditional DOT1L knockout mouse was crossed with a Mx1-CRE mouse to generate a mouse in which HSC DOT1L expression could be conditionally inactivated upon treatment with polyinosinic-polycytidylic acid (pIpC).

Inactivation of DOT1L led to a gradual decrease in the number and function HSCs. Prior to this decrease in number and function, global gene expression was assessed to determine which gene expression programs are DOT1L dependent in HSC. Inactivation of DOT1L led to a decrease in the expression of a number of genes important for HSC biology as well as in HOXA cluster and MEIS1 gene expression. Indeed, a number of the MLL-fusion target genes decreased in expression upon DOT1L inactivation in normal HSC. The fact that DOT1L and, thus, H3K79 methylation controls HOXA cluster gene expression in normal HSC further demonstrates that other leukemias (beyond those with MLL-translocations, MLL-rearrangements, or MLL-PTDs) that exhibit elevated HOXA cluster gene expression are also sensitive to DOT1L inhibition.

Example 4

Efficacy of DOT1L Inhibitors in Leukemias Associated with NPM1, DNMT3A, IDH1, IDH2, RUNX1, TET2, ASXL1, NUP98-NSD1 and Other NUP98 Translocations Experiments with DOT1L inhibitors are performed to further define the role for DOT1L in leukemias associated with mutations in the NPM1, DNMT3A, IDH1, IDH2, RUNX1, TET2, and ASXL1 genes and NUP98-NSD1 and other NUP98 translocations.

Figure 8B:
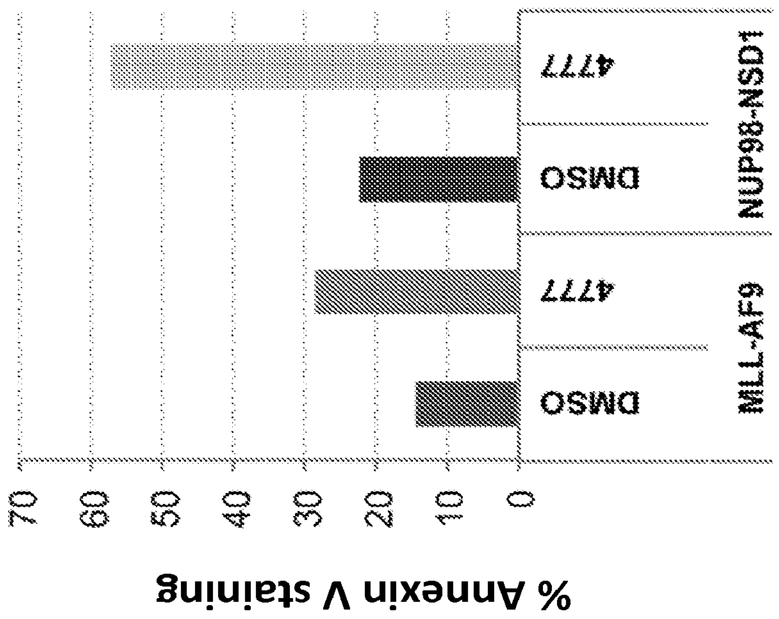
FIGS. 8A and 8B show the effects of EPZ004777 on H3K79me2 and apoptosis in MLL-AF9 and NUP98-NSD1 transformed cells, respectively.
Figure 8A:
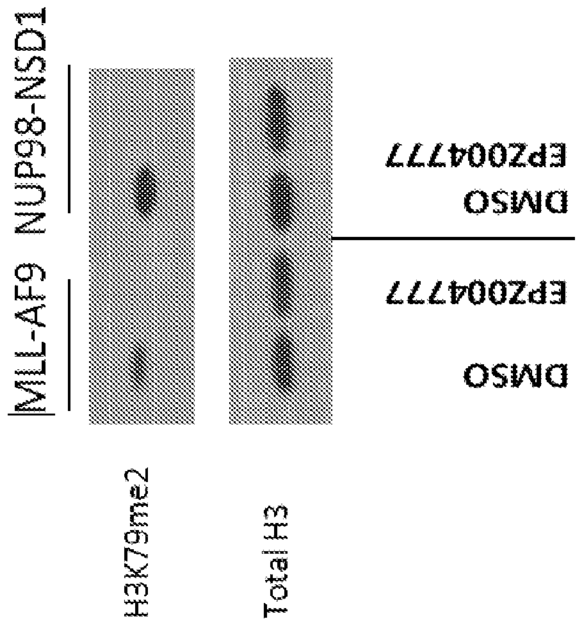

In order to determine if NUP98-NSD1 mouse transformed cells exhibit similar level of sensitivity to DOT1L inhibition as do previously described MLL-AF9 cells, the ability of DOT1L inhibitor EPZ004777 to reduce H3K79 methylation was monitored. Following 10-day treatment with 10 μM of EPZ004777, global H3K79 levels were determined in both NUP98-NSD1 and MLL-AF9 cells by Western blotting. While NUP98-NSD1 cells exhibit higher levels of endogenous H3K79me2, EPZ004777 treatment completely abrogated H3K79me2 in both cell types (FIG. 8A). Furthermore, in order to test if DOT1L inhibitor induced apoptosis in NUP98-NSD1 transformed cells, cells were treated with 10 μM of the DOT1L inhibitor EPZ004777 or vehicle control. Apoptosis was assessed by staining cells with Annexin V 10 days after treatment. The extent of apoptosis was compared to that found in MLL-AF9 transformed cells treated in a similar fashion. It was found that the DOT1L inhibitor induced more apoptosis in the NUP98-NSD1 transformed cells than in the MLL-AF9 transformed cells (FIG. 8B). To further test the hypothesis that cell lines expressing high levels of the HOXA9 and MEIS1 genes would be sensitive to treatment with DOT1L inhibitors independent of the presence of MLL mutations, two cell lines, OCI-AML2 and OCI-AML3, which exhibit DNTM3A and NPM1 mutations, respectively, and which exhibit high level of HOXA9 expression, but do not possess an MLL mutation, were treated with either 10 μM of the DOT1L inhibitor EPZ004777 or vehicle control. Simultaneously, HL60 cells (negative control), which do not express HOXA9, and Molm-13 cells (positive control), which exhibit high level expression of HOXA9 and possess an MLL-translocation, were also treated with either 10 μM of the DOT1L inhibitor EPZ004777 or vehicle control.

Figures 11A, 11B:
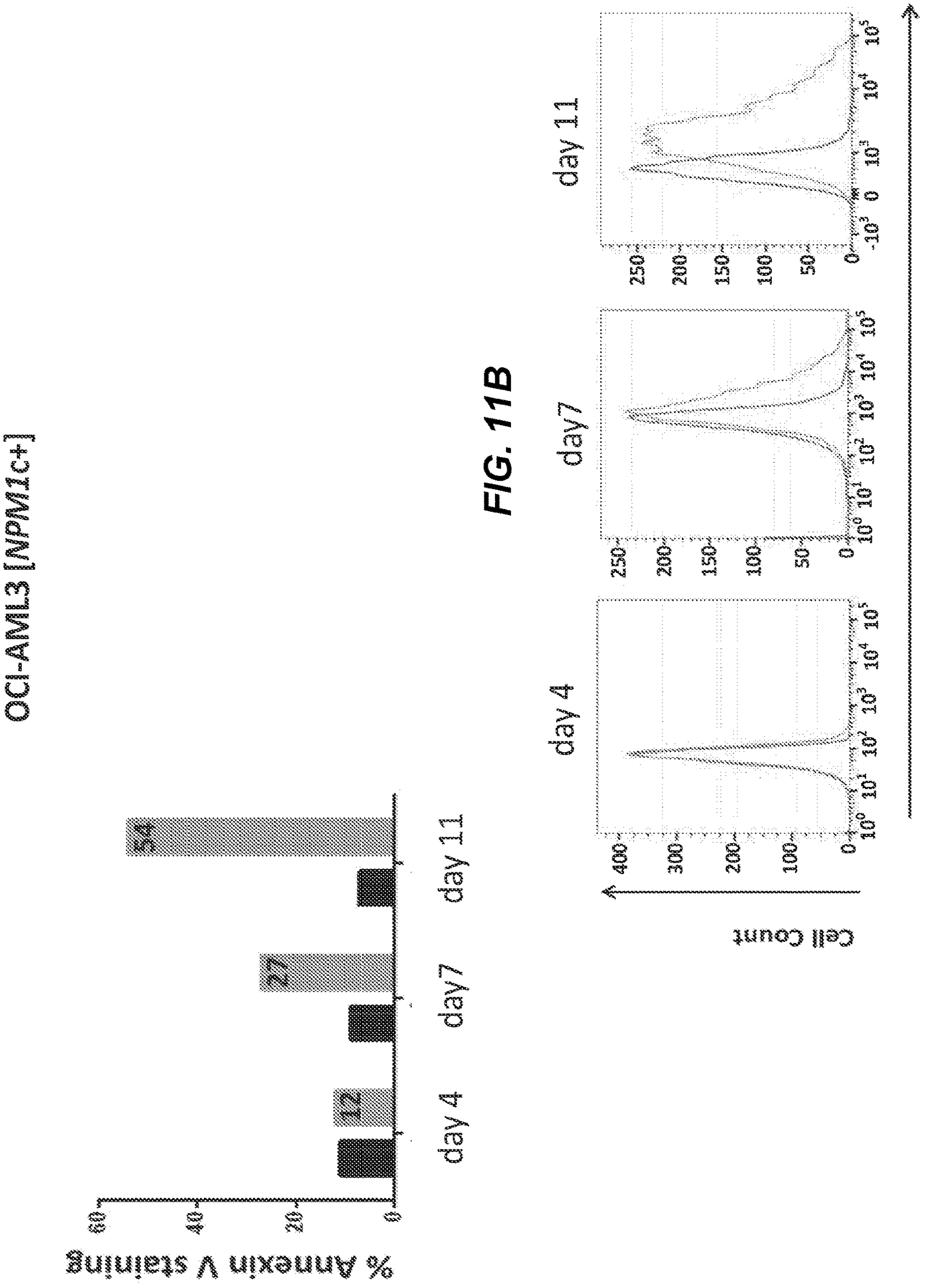
FIGS. 11A and 11B demonstrate that OCI-AML3 cells undergo apoptosis and differentiation in response to DOT1L inhibition.

Cell numbers were assessed at multiple time points after treatment was initiated. The OCI-AML2 and OCI-AML3 cells were equally, if not more sensitive, to the DOT1L inhibitor then were the MLL-rearranged cell line Molm-13 (FIGS. 9 and 10). Next, we assessed whether the DOT1L inhibitor induced apoptosis in the OCI-AML3 cells and found that it indeed induced a tremendous increase in apoptotic cells in the culture (FIG. 11A). Cell cycle status determined by flow cytometry showed that cells in contact with DOT1L inhibitor exhibited Sub G1 accumulation, which is suggestive of apoptosis. Evidence of differentiation was assessed after DOT1L inhibition via characterization of cell surface marker expression—such as CD11b and CD15 expression, both of which are induced upon differentiation of myelomonocytic leukemia cells. Treatment of OCI-AML3 cells with EPZ004777 was marked with increased differentiation as measured by the expression of cell surface differentiation marker CD11b (FIG. 11B).

OCI-AML2 and OCI-AML3 human cells, which exhibit DNTM3A and NPM1 mutations, respectively, were treated with increasing concentrations of DOT1L inhibitor EPZ00477 for up to 10 μM. MTT assays were performed on day 11. The IC50 was determined to be 0.15 μM for both OCI-AML2 and OCI-AML3 cell lines, which is lower than the historical IC50 values for MLL-fusion cell lines.

The influence of DOT1L inhibition is assessed on the colony growth from hematopoietic stem cells (Lin− c-kit+ Sca-1+ CD150+ CD48−) isolated from mice and CD34+/CD38− cells from human cord blood to determine the effects of the DOT1L inhibitors on normal stem and progenitor cells. Preclinical studies with the DOT1L inhibitor EPZ005676, which is being tested in a phase 1 clinical trial, did not show hematopoietic toxicity in mice or rats at a dose that was efficacious against human and murine MLL-translocated leukemia cells.

Example 5

Mouse Studies

Figures 12A, 12B:
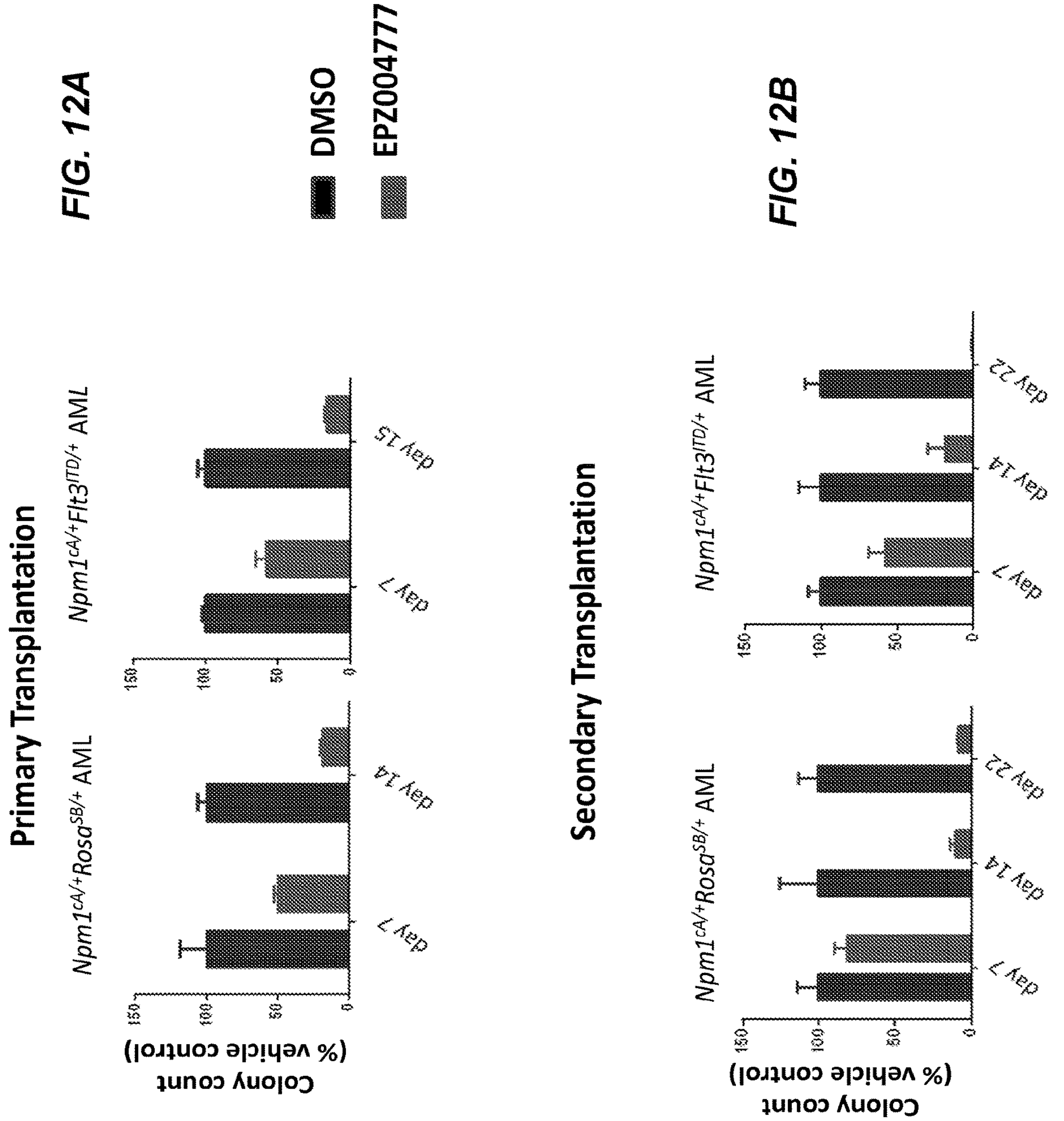
FIGS. 12A and 12B are graphs of AML cells isolated from $Npm1^{cA/+}Rosa^{SB/+}$ or $Npm1^{cA/+}Flt3^{ITD/+}$ mice, which were tested for their clonogenic potential following primary (FIG. 12A) and secondary (FIG. 12B) transplantation of cells into the recipients. AML cells isolated from $Npm1^{cA/+}Rosa^{SB/+}$ or $Npm1^{cA/+}Flt3^{ITD/+}$ mice were cultured for 6 days in the presence of 10 μM of DOT1L inhibitor prior to transplantation of cells into the recipients. Following the primary (FIG. 12A) and secondary (FIG. 12B) transplantations, $Npm1^{cA/+}Rosa^{SB/+}$ and $Npm1^{cA/+}Flt3^{ITD/+}$ AML cells were treated with vehicle control (DMSO) or 10 μM of EPZ00477 for indicated number of days (7, 14, and 15 for primary; 1, 14, and 22 for secondary transplantation) after which colony formation assay was performed. Treatment of AML mouse cell lines with 10 μM of DOT1L inhibitor resulted in significant reduction of the colony formation potential following both the primary and secondary transplantation.

Experiments using mouse models were performed to understand the consequences of DOT1L inhibition in vivo. Mouse models of AML were used to test the in vivo efficacy of DOT1L inhibitor EPZ004777. Animals engineered to contain NPM1c mutation in combination with an additional mutation such as $Npm1^{cA/+}Rosa^{SB/+}$ (Vassiliou G, Nature Genetics, 2011) or $Npm1^{cA/-}Flt3^{ITD/+}$ (Mupo A, Leukemia, 2013) develop AML within 1 year and 68 days, respectively. AML cells isolated from $Npm1^{cA/-}Rosa^{SB/+}$ or $Npm1^{cA/+}$ $Flt3^{ITD/+}$ mice and cultured for 6 days in the presence of 10 μM of DOT1L inhibitor were tested for their clonogenic potential following transplantation of cells into the recipients. Following the primary and secondary transplantations, $Npm1^{cA/+}$ $Rosa^{SB/+}$ and $Npm1^{cA/+}Flt3^{ITD/+}$ AML cells were treated with vehicle control (DMSO) or 10 μM of EPZ00477 for indicated number of days (7, 14, 15 or 22 as written) (FIGS. 12A and B) after which colony formation assay was performed. Culture of AML mouse cell lines in the presence of DOT1L inhibitor resulted in significant reduction of the colony formation potential following both the primary and secondary transplantation (FIGS. 12A and B). The effects of DOT1L inhibition on colony formation were more prominent at later time points (day 14, 15 and 22).

In order to assess the effects of DOT1L inhibition on leukemia initiating potential, syngeneic C57/BL6 mice were injected with Npm1$^{cA/+}$Rosa$^{SB/+}$ cells previously treated for 6 days with DMSO or 10 μM of EPZ004777. The Kaplan-Meier survival curves for the two groups (DMSO and EPZ004777) are illustrated in FIG. 13A and show extended survival time of animals injected with cells that received DOT1L inhibitor. Furthermore, peripheral blood smears stained with Wright-Giemsa stain indicate differentiation in EPZ00477 treated cells (and not in cells exposed to only DMSO) (FIG. 13B). Finally, complete blood counts were analyzed, showing a significant reduction in the number of white blood cells, which was accompanied by a parallel slight increase in the levels of hemoglobin and platelet counts (FIG. 13C). Collectively, these results demonstrate that DOT1L inhibitor abates leukemogenesis in vivo in a mouse model of AML driven by NPM1 and not by MLL mutation, translocation, or duplications.

Figure 14A:
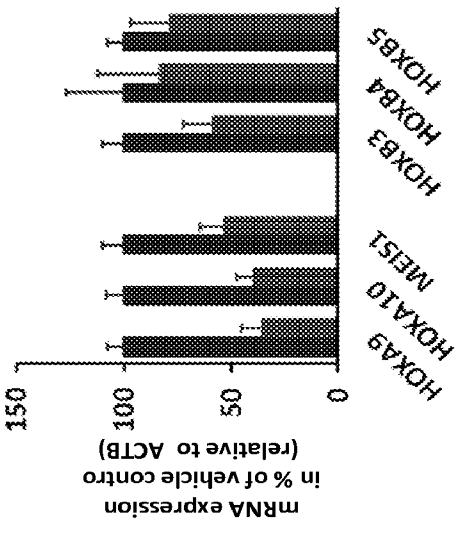
FIGS. 14A and 14B show bar graphs of relative expression of HOXA9, HOXA10, MEIS1, HOX3A, HOXA4, and HOXA5 relative to GAPDH (ddCT) in $Npm1^{cA/+}Rosa^{SB/+}$ (FIG. 14A) and $Npm1^{cA/+}Flt3^{ITD/+}$ (FIG. 14B) AML cells following the treatment of cells with DMSO or 10 μM EPZ004777.
Figure 14B:
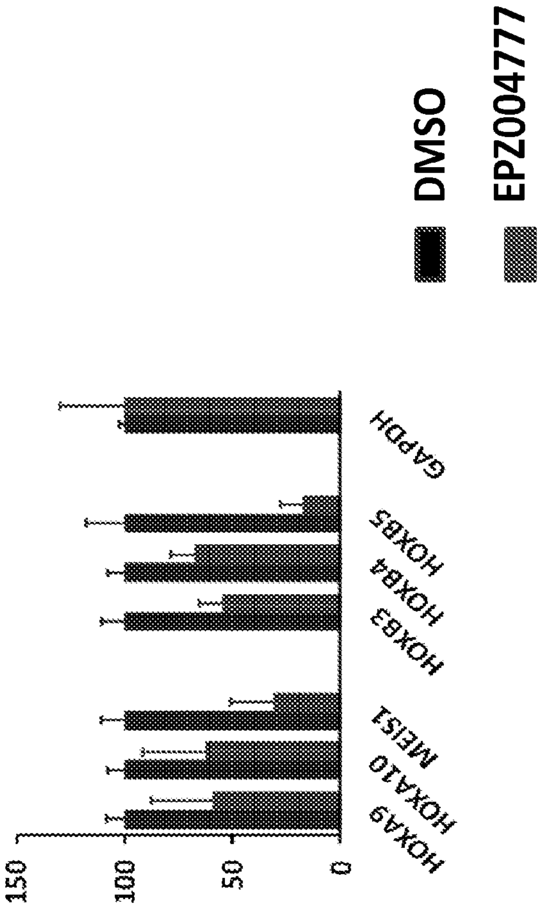

The effect of DOT1L inhibition on the levels of various HOX genes and HOX-associated genes was evaluated using qPCR. Treatment of Npm1$^{cA/+}$ Rosa$^{SB/+}$ and Npm1$^{cA/-}$ Flt3$^{ITD/+}$ murine AML cells with EPZ00477 led to a significant decrease of HOXA9, HOXA10, MEIS1, HOXB3, HOXB4 and HOXB5 mRNA levels (FIGS. 14A and B, wherein RNA level for each HOXA9, HOXA10, MEIS1, HOXB3, HOXB4 and HOXB5 are shown) further indicating HOX gene and HOX-associated gene expression is largely dependent on DOT1L activity.

Example 6

Mouse Studies (Prophetic)

This Example describes the generation of mice xenografted with leukemias, including leukemias associated with one or more mutation(s) in one or more of the NPM1, DNMT3A, IDH1, IDH2, RUNX1, TET2, and ASXL1 genes and/or an NUP98-NSD1 or other NUP98 translocation(s) and the testing of the resulting mouse models for the in vivo efficacy of DOT1L inhibitors.

Leukemia samples (pediatric and adult) are characterized for NPM1, DNMT3A, IDH1, IDH2, RUNX1, TET2, and ASXL1 mutations and NUP98-NSD1 and other NUP98 translocations. It is known that infusion, including continuous infusion, of EPZ005676 suppresses the growth of MLL-translocated leukemia cells in mice. Similar experiments are performed with NPM1, DNMT3A, IDH1, IDH2, RUNX1, TET2, and ASXL1 cell lines and cell lines exhibiting NUP98-NSD1 or other NUP98 translocations (and MLL-translocated and/or MLL-PTD cell lines as controls) to determine the activity of the small-molecule inhibitor in vivo.

Initial experiments are with cell lines where the growth kinetics and drug response characteristics are already known. Armstrong et al., Inhibition of FLT3 in MLL: Validation of a Therapeutic Target Identified by Gene Expression based Classification, *Cancer Cell* 3(2):173-83 (2003). Biomarker assessment, such as inhibition of H3K79me2, is defined in vitro in the same cell line studies as described above, and similar analysis is performed on the cells treated in vivo.

The in vivo efficacy of DOT1L inhibitors can be tested in immunodeficient rats xenografted with NPM1, DNMT3A, IDH1, IDH2, RUNX1, TET2, and/or ASXL1 cell lines and/or cell lines exhibiting NUP98-NSD1 or other NUP98 translocation(s) according to the methodology described in Daigle et al., Blood (2013, Jun. 25) [Epub ahead of print], which describes the in vivo efficacy of the DOT1L inhibitor EPZ005676 in immunodeficient rats xenografted with the MLL-translocation cell line MV4-11.

The in vivo efficacy of DOT1L inhibitors can be tested in immunodeficient mice xenografted with NPM1, DNMT3A, IDH1, IDH2, RUNX1, TET2, and/or ASXL1 cell lines and/or cell lines exhibiting NUP98-NSD1 or other NUP98 translocation(s) according to the methodology described in Wang et al., NUP98-NSD1 Links H3K36 Methylation to HOX-A Gene Activation and Leukaemogenesis, *Nature Cell Biology* 9(7):804-12 (2007)), which describes the generation of immunodeficient NSG mice engrafted with an NUP98-NSD1 murine leukemia. DOT1L inhibitors are then assessed against NPM1, DNMT3A, IDH1, IDH2, RUNX1, TET2, and/or ASXL1 leukemias and/or leukemias exhibiting NUP98-NSD1 or other NUP98 translocation(s) in those leukemia engrafted immunodeficient mice.

Biomarker assessment strategies are combined to assess the extent of inhibition of H3K79ME2. These biomarker assessment studies correlate enzyme inhibition and response that is relevant to clinical trial assessment of small molecule DOT1L inhibitors in patients. Group sizes of n=9 is sufficient to detect a 30% difference in tumor burden with a two-sided test at $\alpha$=0.05, with a power ≥80%. Group sizes of n=9-10 animals are, therefore, used for the in vivo efficacy studies.

These experiments will provide further support for the therapeutic efficacy of DOT1L inhibitors against NPM1, DNMT3A, IDH1, IDH2, RUNX1, TET2, and/or ASXL1 mediated leukemias and/or leukemias mediated by NUP98-NSD1 or other NUP98 translocation(s).

Example 7

Identification of Genes that Modulate Sensitivity to DOT1L Suppression in NPM1, DNMT3A, IDH1, IDH2, RUNX1, TET2, and/or ASXL1 Mediated Leukemias and/or Leukemias Mediated by NUP98-NSD1 or Other NUP98 Translocation(s) (Prophetic)

Given that DOT1L appears to be critical for NPM1, DNMT3A, IDH1, IDH2, RUNX1, TET2, ASXL1, and NUP98-NSD1 cell proliferation, other genes that are either enhancers or suppressors of this pathway are also identified. Modulators of the DOT1L complex are all potential therapeutic targets. Also, identification of genes that either suppress or enhance the DOT1L inhibitor mediated growth inhibition clarify the mechanism of action of both the inhibitor and the NPM1, DNMT3A, IDH1, IDH2, RUNX1, TET2, ASXL1, and NUP98-NSD1 genes.

Previous studies demonstrated that NUP98-NSD1 influences H3K36 methylation as part of its mechanism to induce HOX gene expression and transformation, but it is unclear how H3K79 methylation plays a role in this leukemia. ChIP-seq studies further define the changes in histone modifications that take place after DOT1L inhibition. The screens defined herein clarify the role that DOT1L plays in these leukemias.

High throughput, genome-scale shRNA screening (HT-shRNA) leads to the identification of new targets of drug sensitivity/resistance. Experiments are performed akin to genetic enhancer/suppressor screens using either small molecules or genetic loss of function models in mammalian systems.

Genome-wide pooled RNAi screens are performed in the presence or absence of a DOT1L inhibitor. MLL-AF9 transformed murine leukemia lines have been generated where DOT1L can be conditionally repressed via treatment of cells with tamoxifen and activation of Cre recombinase. The cell lines differentiate, stop proliferating, and start to undergo apoptosis approximately 6 days after Cre induction (FIG. 6). Furthermore, the recombination efficiency is such that outgrowth of cells is rarely seen where the DOT1L gene is not excised. Growth of the cells can be rescued by reintroduction of DOT1L or by expression of MLL-AF9 target genes, HOXA9 and MEIS1.

Similar cell lines are developed for NPM1, DNMT3A, IDH1, IDH2, RUNX1, TET2, ASXL1, and NUP98-NSD1 transformed cells. These cell lines are ideally suited for shRNA screens to identify shRNAs that select for or against growth in the absence of DOT1L.

NPM1, DNMT3A, IDH1, IDH2, RUNX1, TET2, ASXL1, and NUP98-NSD1 transformed cells are treated with 10 μM EP00Z4777 or DMSO. For each cell line, experiments are performed with 5 biologic replicates of untreated cells and replicates of tamoxifen treated cells. Cells are harvested 0, 3, 6, 9, and 12 days after induction of cre recombinase for isolation of genomic DNA. shRNA is amplified, barcoded, and sequenced using Illumina sequencing.

shRNAs that are depleted or enriched in the presence, but not the absence of a DOT1L inhibitor are identified, indicating that knockdown of these genes sensitizes or confers resistance to DOT1L inhibition. Genes for which two different shRNAs scored significantly, are designated as candidate genes. For candidate genes, the knockdown of shRNAs is validated by quantitative PCR and Western blot and additional cell lines are analyzed. Genes identified in the shRNA screen are validated by rescue of the phenotype through expression of non-targetable versions of the gene. These genes are investigated in additional cell lines not included in the primary screen, and particularly in MLL-translocated lines to confirm a similar effect. For candidate proteins with available small molecule inhibitors, phenotypic consequences are determined for DOT1L inhibitors in each cell line on viability, cell cycle, and apoptosis.

Example 8

Molecular Effects of DOT1L and Preclinical Activities of DOT1L and EZH2 Inhibitors (Prophetic)

Recent studies have demonstrated remarkable activity of DOT1L inhibitors against MLL-translocated human leukemia cell lines and murine models, and preliminary evidence suggests that other AML subtypes depend on DOT1L enzymatic activity.

Changes in histone methylation that occur after DOT1L inhibitor treatment of NPM1, DNMT3A, IDH1, IDH2, RUNX1, TET2, ASXL1, and NUP98-NSD1 leukemia cells are assessed. NUP98-NSD1 induces H3K36me3 at HOX genes because NSD1 is an H3K36 methyltransferase. Wang et al., *Nature Cell Biology* 9(7):804-12 (2007). To this date, it is not clear why dimethylation of H3K79 is important in this subtype of leukemia. Therefore, it is of great interest to examine how specific H3K79 modifications change following DOT1L inhibition.

MLL-fusion target genes have been defined. Target gene expression is more dependent on DOT1L than is gene expression more broadly. In order to use the same approach for the NPM1, DNMT34, IDH1, IDH2, RUNX1, TET2, ASXL1, and NUP98-NSD1 leukemias, the NPM1, DNMT3A, IDH1, IDH2, RUNX1, TET2, ASXL1, and NUP98-NSD1 target genes are determined as described with MLL-AF9. NPM1, DNMT3A, IDH1, IDH2, RUNX1, TET2, ASXL1, and NUP98-NSD1 proteins are generated that have a biotinylation sequence on the $NH_3$-terminus and expressed in mouse HSC. Upon cellular transformation, the cells are co-transfected with bacterial BirA, which biotinylates the $NH_3$-terminal sequence.

ChIPseq is performed using streptavidin beads and sites to which NPM1, DNMT3A, IDH1, IDH2, RUNX1, TET2, ASXL1, and NUP98-NSD1 is bound are determined. MLL-PTD, MLL-AF9, NPM1, DNMT3A, IDH1, IDH2, RUNX1, TET2, ASXL1, and NUP98-NSD1 mouse or human leukemia cell lines are treated with inhibitors and gene expression changes are assessed at 24, 48, and 72 hours after treatment. Expression changes with DOT1L inhibitor in the MLL-PTD and MLL-AF9 cells are compared to changes in other cell lines.

Standard gene expression algorithms such as gene set enrichment analysis are used to determine the extent of overlap in gene expression changes in MLL-fusion target genes and NPM1, DNMT3A, IDH1, IDH2, RUNX1, TET2, ASXL1, and NUP98-NSD1 target genes. This confirms whether the NPM1, DNMT3A, IDH1, IDH2, RUNX1, TET2, ASXL1, and NUP98-NSD1 driven gene expression program is reversed upon DOT1L inhibitor treatment.

Histone methylation is assessed by performing ChIP-seq for H3K79me2 as previously described [12]. H3K36me3 in the NPM1, DNMT3A, IDH1, IDH2, RUNX1, TET2, ASXL1, and NUP98-NSD1 transformed cells is assessed in order to determine if H3K36me3 profiles are aberrant in these cells. Changes in H3K79me2 and H3K36me3 are determined after DOT1L inhibitor treatment in order to determine how these modifications change in relation to one another. These experiments confirm that DOT1L inhibition reverses a leukemogeneic program as in MLL-fusion dependent leukemias.

Example 9

Anti-Leukemic Effects of DOT1L Inhibitors Combined with EZH2 Inhibitors In Vitro and In Vivo (Prophetic)

As disclosed herein, DOT1L inhibitors exhibit significant activity in NUP98-NSD1 and NPM1 leukemias. Combination approaches are assessed to effectively treat leukemias with targeted therapies in mouse model systems.

A number of different chromatin modifying enzymes and complexes have been shown to be important for MLL-translocated AML and other subtypes of AML. In particular, the histone H3K27 methyltransferase EZH2 is required for self-renewal of MLL-AF9 leukemia cells. Neff et al., Polycomb Repressive Complex 2 is Required for MLL-AF9 Leukemia, *Proc. Natl. Acad. Sci. U.S.A.* 109(13):5028-33 (2012). EZH2 works via a mechanism that is important for multiple subtypes of AML, namely suppression of p16/p19 and maintenance of a Myc-driven gene expression program. Wang et al., *Nature Cell Biology* 9(7):804-12 (2007).

The histone demethylase LSD1 has recently been shown to be important for continued AML cell proliferation and is tested as LSD1 inhibitors become available. Harris et al., The Histone Demethylase KDM1A Sustains the Oncogenic Potential of MLL-AF9 Leukemia Stem Cells, *Cancer Cell* 21(4:473-87 (2012). Combinations of DOT1L inhibitors and EZH2 inhibitors are tested in leukemia models, including NPM1, DNMT3A, IDH1, IDH2, RUNX1, TET2, ASXL1, and NUP98-NSD1 leukemia models. Other inhibitors are assessed in combination with DOT1L inhibition.

The combination of DOT1L and EZH2 inhibitors are assessed in vitro. Synergy in vitro in MLL-translocated and MLL-germline cells is assessed. Similar experiments are performed in NPM1, DNMT3A, IDH1, IDH2, RUNX1, TET2, ASXL1, and NUP98-NSD1 leukemia cells. A robotic pinning system has been established that allows titration of two different compounds at multiple concentrations. This provides detailed assessment of in vitro synergy that is used to assess DOT1L and EZH2 inhibitors.

Robotic liquid handling and an efficient library plate design allows the rapid, automated transfer of two compounds in combination to a 384-well plate of cultured cells. A 5×5 dose array of two compounds, in eight replicates, flanked by four replicates of each agent in dose-response format is generated. Following 7-10 day incubations, ATP content is determined as a surrogate for cell viability on a multi-label plate reader. These experiments are performed such that the cell lines are exposed to the DOT1L and EZH2 inhibitor compounds for 7-10 days prior to assessment of cell number. The prolonged period of incubation is necessary because both EZH2 and DOT1L inhibitors require up to one week to inhibit proliferation.

Results are plotted in the CompuSyn package according to the method of Chou and Talalay. The resulting dose-effect curves and isobolograms indicate whether there is an additive or synergistic effect. The combination index is obtained and compared to determine whether there is a significant synergy. Since the compounds induce differentiation, the effects of single agent and combinations of molecules are determined using microarray analyses to determine the extent of differentiation and whether a combination of expected gene expression changes is detected as expected based on previous studies with DOT1L and EZH2 loss of function models.

Combinations of inhibitors are tested in vivo. DOT1L inhibitors are assessed in mouse model systems from which appropriate dose and schedule for each of the compounds is determined. The dose and schedule of the EZH2 inhibitor has been published. McCabe et al., EZH2 Inhibition as a Therapeutic Strategy for Lymphoma with EZH2-activating Mutations, *Nature* 492(7427):108-12 (2012). Combination studies are performed to assess anti-leukemia activity by monitoring in vivo bioluminescence of luciferase expressing human and mouse MLL-fusion driven and MLL-PTD leukemias as well as NPM1, DNMT3A, IDH1, IDH2, RUNX1, TET2, ASXL1, and NUP98-NSD1 leukemia cells. Bernt et al., MLL-rearranged Leukemia is Dependent on Aberrant H3K79 Methylation by DOT1L, *Cancer Cell* 20(1):66-78 (2011) and Stubbs et al., MLL-AF9 and FLT3 Cooperation in Acute Myelogenous Leukemia: Development of a Model for Rapid Therapeutic Assessment, *Leukemia* 22(1):66-77 (2008).

Mice are treated daily with vehicle, individual inhibitors, or combinations of inhibitors until control animals reach institutional limits (i.e., onset of distress or tumor volume limits). Primary endpoints include tumor burden (as assessed by peripheral blood GFP positivity, % human CD45 in peripheral blood, and/or luminescent imaging). Time-to-sacrifice and secondary endpoints include full histopathological examination.

Efficacy is assessed against primary human MLL-translocated AMLs, of which samples are engrafted along with NPM1, DNMT3A, IDH1, IDH2, RUNX1, TET2, ASXL1, and NUP98-NSD1 leukemias. These studies provide important preclinical assessment of these compounds that support clinical translation of this combination.

Example 10

Dual Inhibition of NPM1 and FLT3 in a Mouse Model of ALM (Prophetic)

In leukemogenesis, more than one gene mutation is often required for the full development of the disease. Combinations of genetic alterations present in AML are major determinants of patient prognosis and response to therapy. Mutations in FLT3 and NPM1 genes represent the most frequent genetic aberrations in AML and serve as important prognostic indicators. While FLT3 is found in one third of AML cases (Thiede C, *Blood.* 2002 Jun. 15; 99 (12):4326-35) and is associated with poor prognosis and outcome, NPM1 mutation is present in 50-60% of patients with AML and generally confers increased response to chemotherapy and favorable prognosis (Schlenk R F, *N Engl J Med* 2008; 358: 1909-1918). However, approximately 40% of patients positive for NPM1 mutation also carry FLT3 mutation where the presence of FLT3 mutation negates the beneficial outcome of patients carrying only NPM1 mutation, (Gale, R E. *Blood.* Mar. 1, 2008; 111(5): 2776-84). Additionally, FLT3 receptor kinase has been shown to collaborate with NUP98-HOX fusions, inducing highly aggressive AML. Finally, elevated FLT3 levels have been observed in the subtype of AML characterized by high HOX gene expression (Palmqvist, L. *Blood.* Aug. 1; 2006; 108 (3)). Interestingly, current studies suggest that FLT3 mutations are most likely not causally connected to high HOX cluster gene expression, further validating the importance of dual inhibition of two separate pathways that contribute to leukemogenesis (Andreeff M, *Leukemia* 2008, 22, 2041-2047). Collectively, these observations suggest that use of FLT3 inhibitors in HOX-induced AML and ALL accompanied with high FLT3 expression and/or mutation can provide additional benefit to patients treated with DOT1L inhibitors.

To test the efficacy of DOT1L inhibition in combination with FLT3 inhibition in vivo, a mouse model of AML is administered the DOT1L inhibitor EPZ004777 together with the FLT3 inhibitor Quizartinib (AC220). Animals engineered to contain NPM1c mutation in combination with a FLT3 mutation, $Npm1^{cA/+}Flt3^{ITD/+}$ (Mupo A, *Leukemia* September 2013; 27(9): 1917-1920.) develop AML and die within 68 days. In order to assess whether dual combination therapy (inhibition of both DOT1L and FLT3) abates the leukemogenic potential of cells treated with the combination and provides additional survival benefit to the mice transplanted with pre-treated cells compared to the inhibition using either protein alone, the efficacy of both EPZ004777 and AC220 is evaluated in parallel. Because of technical difficulties of subjecting mice to continuous infusion, AML cells isolated from $Npm1^{cA/+}Flt3^{ITD/+}$ mice are cultured for 6 days in the presence of DOT1L inhibitor EPZ004777, or FLT3 inhibitor AC220, or both, in a dose dependent manner and tested for their clonogenic potential following transplantation of the cells into recipient mice in a manner paralleling that of Example 5. Both primary and secondary transplantations are performed. After each transplantation, Npm1$^{cA/+}$Flt3$^{ITD/+}$ AML cells are harvested and treated with vehicle control (DMSO), or EPZ00477, or AC220, or both EPZ004777 and C220 for 7, 14, and 22 of days after which a colony formation assay is performed. Culturing of AML mouse cells (Npm1$^{cA/+}$Flt3$^{ITD/+}$) in the presence of DOT1L inhibitor has already been shown to reduce the colony formation potential following both the primary and secondary transplantation (FIGS. 12A and B and Example 5). Thus, the ability of dual inhibition (DOT1L inhibition with FLT3 inhibition) to inhibit colony formation potential is compared to that of each of DOT1L inhibition alone and FLT3 inhibition alone. It is anticipated that the clonogenic potential of cells treated with the combination will be significantly lower than that of cells treated with either agent alone.

In order to further assess the effects of dual DOT1L and FLT3 inhibition on leukemia initiating potential, syngeneic C57/BL6 mice are injected with Npm1$^{cA/-}$Flt3$^{ITD/+}$ cells previously treated for 6 days with DMSO, or DOT1L inhibitor EPZ004777, or FLT3 inhibitor AC220, or both, in a dose dependent manner using 01, 1, and 10 μM of each compound. It has been demonstrated that the treatment of Npm1$^{cA/-}$Flt3$^{ITD/+}$ AML cells with the DOT1L inhibitor leads to prolonged survival time. While mice injected with cells treated with DMSO die at day 19, animals injected with cells treated with EP004777 (10 μM) start dying on day 31 (FIG. 13 A). Thus, treatment comprising both DOT1L and FLT3 inhibitors is assessed for the ability to delay the onset of dying (more than 31 days post-injection). Additionally, dose response curves are informative of minimum required dosage in dual inhibition experiments (EPZ004777 and AC220) versus either inhibitor alone. It is anticipated that these results will show increased efficacy of the combination using both DOT1L and FLT3 inhibitors in prolonging survival of a mouse model of AML driven by NPM1 and FLT3 mutations, which has implications for human therapy. FLT3 inhibitors are being used or currently developed as a first line treatment for AML. Availability of a drug combination as a second line treatment will substantially increase the available arsenal against leukemia.

What is claimed is:

1. A method for treating leukemia in a patient in need thereof, comprising:

administering to the patient a therapeutically effective amount of a DOT1L inhibitor, wherein the patient exhibits an elevated expression level of a HOX cluster gene or a HOX cluster-associated gene as compared to that observed in a healthy subject or a predetermined threshold, wherein the HOX cluster-associated gene is PBX3, MEIS1, or MEIS2, wherein the patient comprises a NPM1 mutation and does not comprise an MLL-translocation, an MLL-rearrangement, or an MLL-partial tandem duplication.

2. The method of claim 1, wherein the leukemia is selected from the group consisting of an acute lymphocytic leukemia (ALL) and an acute myeloid leukemia (AML).

3. The method of claim 1, wherein the HOX cluster gene is HOXA1, HOXA2, HOXA3, HOXA4, HOXA5, HOXA6, HOXA7, HOXA9, HOXA10, HOXA11, HOXA13, HOXB1, HOXB2, HOXB3, HOXB4, HOXB5, HOXB6, HOXB7, HOXB8, HOXB9, or HOXB13.

4. The method of claim 1, wherein the patient further comprises a mutation, or alteration in a gene selected from the group consisting of DNMT3A, IDH1, IDH2, RUNX1, TET2, ASXL1, and NUP98-NSD1.

5. The method of claim 1, wherein the DOT1L inhibitor inhibits DOT1L with an IC50 of from 100 nM to 10 μM or from 250 nM to 5 μM or from 500 nM to 1 μM.

6. The method of claim 5, wherein the DOT1L inhibitor is selected from the group consisting of a purine, a carbocycle-substituted purine, and a 7-deazapurine.

7. The method of claim 1, wherein administration of the DOT1L inhibitor results in decreased proliferation and/or increased apoptosis of leukemia cells.

8. The method of claim 1, further comprising administering an additional therapeutic agent to the patient.

9. The method of claim 8, wherein the additional agent is a FLT3 inhibitor and the patient possesses a genetic mutation in FLT3.

* * * * *